(12) United States Patent
Jia et al.

(10) Patent No.: US 10,968,200 B2
(45) Date of Patent: Apr. 6, 2021

(54) SALTS OF AN LSD1 INHIBITOR AND PROCESSES FOR PREPARING THE SAME

(71) Applicant: Incyte Corporation, Wilmington, DE (US)

(72) Inventors: Zhongjiang Jia, Kennett Square, PA (US); Wayne Han, West Chester, PA (US); Yongchun Pan, Wilmington, DE (US); Timothy Martin, Hockessin, DE (US); Jiacheng Zhou, Newark, DE (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/555,907

(22) Filed: Aug. 29, 2019

(65) Prior Publication Data

US 2020/0071289 A1 Mar. 5, 2020

Related U.S. Application Data

(60) Provisional application No. 62/725,961, filed on Aug. 31, 2018.

(51) Int. Cl.
*C07D 401/04* (2006.01)
*A61K 31/4523* (2006.01)
*A61K 9/00* (2006.01)

(52) U.S. Cl.
CPC .......... *C07D 401/04* (2013.01); *A61K 9/0053* (2013.01); *C07B 2200/13* (2013.01)

(58) Field of Classification Search
CPC .......................... C07D 401/04; A61K 31/4523
USPC .......................................... 546/208; 514/326
See application file for complete search history.

(56) References Cited

U.S. PATENT DOCUMENTS

| | | |
|---|---|---|
| 4,537,889 A | 8/1985 | Spitzer |
| 4,625,040 A | 11/1986 | Georgiev et al. |
| 5,658,857 A | 8/1997 | Andree et al. |
| 5,932,223 A | 8/1999 | Burke et al. |
| 7,759,386 B2 | 7/2010 | Benjain et al. |
| 7,858,609 B2 | 12/2010 | Shaw et al. |
| 8,115,000 B2 | 2/2012 | Rajagopalan et al. |
| 8,349,210 B2 | 1/2013 | Xu et al. |
| 8,383,154 B2 | 2/2013 | Bar-Shalom et al. |
| 8,546,394 B2 | 10/2013 | Li |
| 8,558,008 B2 | 10/2013 | Statler et al. |
| 8,568,782 B2 | 10/2013 | Viscomi et al. |
| 8,614,315 B2 | 12/2013 | Bilgic |
| 8,853,408 B2 | 10/2014 | Johnson |
| 9,493,442 B2 | 11/2016 | Wu et al. |
| 9,493,450 B2 | 11/2016 | Wu et al. |
| 9,527,835 B2 | 12/2016 | Wu et al. |
| 9,670,210 B2 | 6/2017 | Wu et al. |
| 9,695,167 B2 | 7/2017 | Wu et al. |
| 9,695,168 B2 | 7/2017 | Wu et al. |
| 9,695,180 B2 | 7/2017 | Wu et al. |
| 9,758,523 B2 | 9/2017 | Wu et al. |
| 9,790,169 B2 | 10/2017 | Balog et al. |
| 9,809,541 B2 | 11/2017 | Marx et al. |
| 9,944,647 B2 | 4/2018 | He et al. |
| 9,994,546 B2 | 6/2018 | Wu et al. |
| 10,112,950 B2 | 10/2018 | Wu et al. |
| 10,125,133 B2 | 11/2018 | Wu et al. |
| 10,138,249 B2 | 11/2018 | Wu et al. |
| 10,166,221 B2 | 1/2019 | Rocco et al. |
| 10,174,030 B2 | 1/2019 | Wu et al. |
| 10,300,051 B2 | 5/2019 | Wu et al. |
| 10,329,255 B2 | 6/2019 | Pan et al. |
| 10,556,908 B2 | 2/2020 | Wu et al. |
| 10,640,503 B2 | 5/2020 | Wu et al. |
| 10,676,457 B2 | 6/2020 | Wu et al. |
| 10,717,737 B2 | 7/2020 | Wu et al. |
| 10,723,700 B2 | 7/2020 | Pan et al. |
| 10,800,779 B2 | 10/2020 | He et al. |
| 2002/0151549 A1 | 10/2002 | Hayakawa et al. |
| 2004/0023972 A1 | 2/2004 | Sundermann et al. |
| 2004/0058938 A1 | 3/2004 | Cullmann et al. |
| 2004/0082635 A1 | 4/2004 | Hashimoto et al. |
| 2004/0082781 A1 | 4/2004 | Hibi et al. |
| 2004/0220189 A1 | 11/2004 | Sun et al. |
| 2005/0009832 A1 | 1/2005 | Sun et al. |
| 2005/0113283 A1 | 5/2005 | Solow-Cordero et al. |
| 2006/0178399 A1 | 8/2006 | Nishizawa et al. |
| 2006/0194842 A1 | 8/2006 | Uchida et al. |
| 2006/0276339 A1 | 12/2006 | Windsor et al. |
| 2007/0004772 A1 | 1/2007 | Sun et al. |
| 2007/0128276 A1 | 6/2007 | Jain et al. |

(Continued)

FOREIGN PATENT DOCUMENTS

| | | |
|---|---|---|
| BR | 2011-01013 | 6/2013 |
| CA | 2831143 | 10/2012 |

(Continued)

OTHER PUBLICATIONS

Chilean Office Action in Chilean Application No. 3040-2017, dated Jun. 15, 2020, 33 pages.
Colombian Office Action in Colombian Application No. NC 2018/0012482, dated Jun. 23, 2020, 20 pages.
Chilean Office Action in Chilean Application No. 2991-2018, dated Apr. 15, 2020, 14 pages.
Indian Office Action in Indian Application No. 201817043771, dated Jul. 15, 2020, 6 pages.

(Continued)

*Primary Examiner* — Charanjit Aulakh

(74) *Attorney, Agent, or Firm* — Fish & Richardson P.C.

(57) ABSTRACT

The present invention relates to processes and intermediates for preparing 3-(cyanomethyl)-3-(4-{[(1R,2S)-2-phenylcyclopropyl]amino}piperidin-1-yl)azetidine-1-sulfonamide, and salts and solid forms thereof, which selectively modulate demethylase. Particular embodiments contemplate compounds and disease indications amenable to treatment by modulation of lysine specific demethylase-1 (LSD1).

34 Claims, 39 Drawing Sheets

(56) References Cited

U.S. PATENT DOCUMENTS

| | | |
|---|---|---|
| 2007/0191395 A1 | 8/2007 | Kawakami |
| 2007/0191421 A1 | 8/2007 | Buettelmann et al. |
| 2008/0249154 A1 | 10/2008 | Ohmoto et al. |
| 2009/0004281 A1 | 1/2009 | Nghiem et al. |
| 2009/0047336 A1 | 2/2009 | Yang et al. |
| 2009/0203690 A1 | 8/2009 | Akritopoulou-Zanze et al. |
| 2009/0318436 A1 | 12/2009 | Albrecht et al. |
| 2010/0113441 A1 | 5/2010 | Siegel et al. |
| 2010/0143481 A1 | 6/2010 | Shenoy et al. |
| 2010/0209489 A1 | 8/2010 | Liang et al. |
| 2010/0316712 A1 | 12/2010 | Nangia et al. |
| 2011/0105457 A1 | 5/2011 | Taniyama et al. |
| 2011/0112067 A1 | 5/2011 | Hartmann et al. |
| 2012/0004262 A1 | 1/2012 | Guibourt et al. |
| 2012/0108500 A1 | 5/2012 | Sakane et al. |
| 2012/0220582 A1 | 8/2012 | Mitchell et al. |
| 2012/0283266 A1 | 11/2012 | Ortega Munoz et al. |
| 2012/0322877 A1 | 12/2012 | Casero et al. |
| 2013/0035377 A1 | 2/2013 | Minucci et al. |
| 2013/0040946 A1 | 2/2013 | Siegel et al. |
| 2013/0090386 A1 | 4/2013 | Ortega Munoz et al. |
| 2013/0095067 A1 | 4/2013 | Baker et al. |
| 2013/0109751 A1 | 5/2013 | Salvatore |
| 2013/0197013 A1 | 8/2013 | Fyfe et al. |
| 2013/0203754 A1 | 8/2013 | Yang et al. |
| 2013/0217878 A1 | 8/2013 | Lizuka et al. |
| 2013/0231342 A1 | 9/2013 | Munoz et al. |
| 2013/0303545 A1 | 11/2013 | Maes et al. |
| 2014/0011857 A1 | 1/2014 | Casero et al. |
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0064250 A1 | 3/2015 | Ghebre-Sellassie et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0232436 A1 | 8/2015 | Baker et al. |
| 2015/0265683 A1 | 9/2015 | Sahib et al. |
| 2015/0296852 A1 | 10/2015 | Penhasi et al. |
| 2016/0009711 A1 | 1/2016 | Wu et al. |
| 2016/0009712 A1 | 1/2016 | Wu et al. |
| 2016/0009720 A1 | 1/2016 | Wu et al. |
| 2016/0009721 A1 | 1/2016 | Wu et al. |
| 2016/0289238 A1 | 4/2016 | He et al. |
| 2017/0044101 A1 | 2/2017 | Pan et al. |
| 2017/0112816 A1 | 4/2017 | Wu et al. |
| 2017/0121302 A1 | 5/2017 | Wu et al. |
| 2017/0158633 A1 | 6/2017 | Wu et al. |
| 2017/0304282 A1 | 10/2017 | Rocco et al. |
| 2017/0342070 A1 | 11/2017 | Wu et al. |
| 2017/0362245 A1 | 12/2017 | Wu et al. |
| 2017/0369487 A1 | 12/2017 | Wu et al. |
| 2017/0369488 A1 | 12/2017 | Wu et al. |
| 2017/0369497 A1 | 12/2017 | Wu et al. |
| 2018/0118765 A1 | 5/2018 | Brias et al. |
| 2019/0040058 A1 | 2/2019 | Wu et al. |
| 2019/0055250 A1 | 2/2019 | He et al. |
| 2019/0062301 A1 | 2/2019 | Wu et al. |
| 2019/0106426 A1 | 4/2019 | Wu et al. |
| 2019/0119272 A1 | 4/2019 | Wu et al. |
| 2019/0152976 A1 | 5/2019 | Wu et al. |
| 2019/0211014 A1 | 7/2019 | Wu et al. |
| 2019/0307736 A1 | 10/2019 | Rocco et al. |
| 2019/0345106 A1 | 11/2019 | Pan et al. |
| 2020/0024277 A1 | 1/2020 | Wu et al. |
| 2020/0031835 A1 | 1/2020 | Wang et al. |
| 2020/0181077 A1 | 6/2020 | Wu et al. |
| 2020/0316041 A1 | 10/2020 | Rocco et al. |

FOREIGN PATENT DOCUMENTS

| | | |
|---|---|---|
| CA | 2844525 | 2/2013 |
| CA | 2849564 | 4/2013 |
| CA | 2887598 | 4/2014 |
| CL | 201400314 | 8/2014 |
| CL | 201400988 | 11/2014 |
| CL | 201702482 | 4/2018 |
| CL | 201702494 | 5/2018 |
| CL | 201800374 | 7/2019 |
| CN | 101848713 | 9/2010 |
| CN | 101987082 | 3/2011 |
| CN | 102247321 | 11/2011 |
| CN | 102397552 | 4/2012 |
| CN | 102579381 | 7/2012 |
| CN | 102772444 | 11/2012 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| CN | 104173313 | 12/2014 |
| CN | 105232488 | 1/2016 |
| DE | 102006041292 | 3/2008 |
| EP | 0179254 | 4/1986 |
| EP | 0404190 | 12/1990 |
| EP | 0430385 | 6/1991 |
| EP | 2168579 | 3/2010 |
| EP | 2524918 | 11/2012 |
| EP | 2740474 | 6/2014 |
| EP | 2743256 | 6/2014 |
| EP | 3105218 | 12/2016 |
| EP | 3277689 | 2/2018 |
| FR | 2662163 | 11/1991 |
| FR | 2920090 | 2/2009 |
| FR | 2920091 | 2/2009 |
| GB | 1277393 | 6/1972 |
| IN | 2007MU01698 | 3/2009 |
| JP | 2844351 | 1/1999 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |
| JP | 2008511668 | 4/2008 |
| JP | 2008531543 | 8/2008 |
| JP | 2009507843 | 2/2009 |
| JP | 2010070503 | 4/2010 |
| JP | 2010524953 | 7/2010 |
| JP | 2011500547 | 1/2011 |
| JP | 2011514363 | 5/2011 |
| JP | 2013530968 | 8/2013 |
| JP | 2014515013 | 6/2014 |
| JP | 2016044170 | 4/2016 |
| JP | 6602778 | 11/2019 |
| KR | 20090069703 | 7/2009 |
| WO | WO 1988/004298 | 6/1988 |
| WO | WO 1993/025553 | 12/1993 |
| WO | WO 1994/018198 | 8/1994 |
| WO | WO 1995/012594 | 5/1995 |
| WO | WO 1999/024434 | 5/1999 |
| WO | WO 01/25237 | 4/2001 |
| WO | WO 2001/027119 | 4/2001 |
| WO | WO 2001/083481 | 8/2001 |
| WO | WO 2002/000196 | 1/2002 |
| WO | WO 2002/006286 | 1/2002 |
| WO | WO 2002/034748 | 5/2002 |
| WO | WO 2002/038562 | 5/2002 |
| WO | WO 2002/038568 | 5/2002 |
| WO | WO 2002/051831 | 7/2002 |
| WO | WO 2002/072549 | 9/2002 |

(56) References Cited

FOREIGN PATENT DOCUMENTS

| | | |
|---|---|---|
| WO | WO 2003/006471 | 1/2003 |
| WO | WO 2003/044021 | 5/2003 |
| WO | WO 2003/062392 | 7/2003 |
| WO | WO 2004/017950 | 3/2004 |
| WO | WO 2004/021989 | 3/2004 |
| WO | WO 2004/058762 | 7/2004 |
| WO | WO 2004/072081 | 8/2004 |
| WO | WO 2004/074290 | 9/2004 |
| WO | WO 2004/089380 | 10/2004 |
| WO | WO 2004/089416 | 10/2004 |
| WO | WO 2004/096131 | 11/2004 |
| WO | WO 2004/108692 | 12/2004 |
| WO | WO 2005/007658 | 1/2005 |
| WO | WO 2005/025558 | 3/2005 |
| WO | WO 2005/035532 | 4/2005 |
| WO | WO 2005/042537 | 5/2005 |
| WO | WO 2005/044793 | 5/2005 |
| WO | WO 2005/097052 | 10/2005 |
| WO | WO 2006/015263 | 2/2006 |
| WO | WO 2006/018727 | 2/2006 |
| WO | WO 2006/038116 | 4/2006 |
| WO | WO 2006/057946 | 6/2006 |
| WO | WO 2006/058752 | 6/2006 |
| WO | WO 2006/073938 | 7/2006 |
| WO | WO 2006/074041 | 7/2006 |
| WO | WO 2006/113704 | 10/2006 |
| WO | WO 2006/131003 | 12/2006 |
| WO | WO 2006/135667 | 12/2006 |
| WO | WO 2006/135795 | 12/2006 |
| WO | WO 2006/138695 | 12/2006 |
| WO | WO 2006/138734 | 12/2006 |
| WO | WO 2007/022529 | 2/2007 |
| WO | WO 2007/028051 | 3/2007 |
| WO | WO 2007/058942 | 5/2007 |
| WO | WO 2007/074491 | 7/2007 |
| WO | WO 2007/095588 | 8/2007 |
| WO | WO 2007/113226 | 10/2007 |
| WO | WO 2007/145921 | 12/2007 |
| WO | WO 2007/149478 | 12/2007 |
| WO | WO 2008/005262 | 1/2008 |
| WO | WO 2008/005423 | 1/2008 |
| WO | WO 2008/005908 | 1/2008 |
| WO | WO 2008/008539 | 1/2008 |
| WO | WO 2008/011560 | 1/2008 |
| WO | WO 2008/027812 | 3/2008 |
| WO | WO 2008/037607 | 4/2008 |
| WO | WO 2008/045393 | 4/2008 |
| WO | WO 2008/056176 | 5/2008 |
| WO | WO 2008/064157 | 5/2008 |
| WO | WO 2008/065198 | 6/2008 |
| WO | WO 2008/110523 | 9/2008 |
| WO | WO 2008/113559 | 9/2008 |
| WO | WO 2008/125111 | 10/2008 |
| WO | WO 2008/130951 | 10/2008 |
| WO | WO 2008/141239 | 11/2008 |
| WO | WO 2008/154241 | 12/2008 |
| WO | WO 2008/156614 | 12/2008 |
| WO | WO 2008/157752 | 12/2008 |
| WO | WO 2009/010530 | 1/2009 |
| WO | WO 2009/017701 | 2/2009 |
| WO | WO 2009/017954 | 2/2009 |
| WO | WO 2009/023179 | 2/2009 |
| WO | WO 2009/028900 | 3/2009 |
| WO | WO 2009/045753 | 4/2009 |
| WO | WO 2009/047514 | 4/2009 |
| WO | WO 2009/047563 | 4/2009 |
| WO | WO 2009/048993 | 4/2009 |
| WO | WO 2009/085230 | 7/2009 |
| WO | WO 2009/085980 | 7/2009 |
| WO | WO 2009/091374 | 7/2009 |
| WO | WO 2009/114180 | 9/2009 |
| WO | WO 2009/114512 | 9/2009 |
| WO | WO 2009/128520 | 10/2009 |
| WO | WO 2009/138176 | 11/2009 |
| WO | WO 2010/010184 | 1/2010 |
| WO | WO 2010/010187 | 1/2010 |
| WO | WO 2010/010188 | 1/2010 |
| WO | WO 2010/010189 | 1/2010 |
| WO | WO 2010/019899 | 2/2010 |
| WO | WO 2010/021607 | 2/2010 |
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/090614 | 8/2010 |
| WO | WO 2010/091067 | 8/2010 |
| WO | WO 2010/091824 | 8/2010 |
| WO | WO 2010/101537 | 9/2010 |
| WO | WO 2010/104306 | 9/2010 |
| WO | WO 2010/107404 | 9/2010 |
| WO | WO 2010/108059 | 9/2010 |
| WO | WO 2010/113942 | 10/2010 |
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/149438 | 12/2011 |
| WO | WO 2011/160548 | 12/2011 |
| WO | WO 2012/003392 | 1/2012 |
| WO | WO 2012/006959 | 1/2012 |
| WO | WO 2012/007345 | 1/2012 |
| WO | WO 2012/009475 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/054698 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |

(56) References Cited

FOREIGN PATENT DOCUMENTS

| WO | WO 2013/025805 | 2/2013 |
|---|---|---|
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2011/136264 | 7/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/051698 | 3/2014 |
| WO | WO 2014/055955 | 4/2014 |
| WO | WO 2014/058071 | 4/2014 |
| WO | WO 2014/078479 | 5/2014 |
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/153001 | 9/2014 |
| WO | WO 2014/164867 | 10/2014 |
| WO | WO 2014/194280 | 12/2014 |
| WO | WO 2014/205213 | 12/2014 |
| WO | WO 2014/205223 | 12/2014 |
| WO | WO 2013/022047 | 3/2015 |
| WO | WO 2015/031564 | 3/2015 |
| WO | WO 2015/036512 | 3/2015 |
| WO | WO 2015/089192 | 6/2015 |
| WO | WO 2015/122187 | 8/2015 |
| WO | WO 2015/122188 | 8/2015 |
| WO | WO 2015/123424 | 8/2015 |
| WO | WO 2015/123465 | 8/2015 |
| WO | WO 2015/153720 | 10/2015 |
| WO | WO 2015/155281 | 10/2015 |
| WO | WO 2015/155297 | 10/2015 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |
| WO | WO 2016/055394 | 4/2016 |
| WO | WO 2016/055797 | 6/2016 |
| WO | WO 2016/161282 | 10/2016 |
| WO | WO 2017/027678 | 2/2017 |
| WO | WO 2017/130933 | 8/2017 |
| WO | WO 2017/184934 | 10/2017 |
| WO | WO 2018/136634 | 7/2018 |
| WO | WO 2018/166493 | 9/2018 |

OTHER PUBLICATIONS

Indian Office Action in Indian Application No. 201627030320, dated Aug. 21, 2020, 5 pages.
Israeli Office Action in Israeli Application No. 257,290, dated May 17, 2020, 10 pages.
Taiwan Office Action in Taiwan Application No. 108112023, dated Mar. 25, 2020, 7 pages (English Translation).
No Author, "LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.
Adamo et al., "LSD1 and pluripotency: a new player in the network," Cell Cycle, Oct. 2011, 10(19): 3215-6.
Adamo et al., "LSD1 regulates the balance between self-renewal and differentiation in human embryonic stem cells," Nat. Cell Biol, Jun. 2011, 13(6): 652-9.
Anand and Marmorstein, "Structure and mechanism of lysine-specific demethylase enzymes," J Biol Chem, Dec. 2007, 282(49): 35425-9.
Atzrodt et al.,"The Renaissance of H/D Exchange," Angew. Chem. Int. Ed., Spe. 21, 2007, 46:7744-7765.
Balamuth "Ewings sarcoma" Lancet Oncology (2010), 11(2):184-192.
Baron et al., "Molecular Mimicry and Ligand Recognition in Binding and Catalysis by the Histone Demethylase LSD1-CoREST Complex," Structure, Feb. 2011, 19: 212-220.
Bauer et al., "Reawakening fetal hemoglobin: prospects for new therapies for the β-globin disorders," Blood, Oct. 2012, 120(15): 3945-53.
Beck and Blanpain, "Unravelling cancer stem cell potential," Nat Rev Cancer, Oct. 2013, 13(10): 727-38.
Benelkebir et al., "Enantioselective synthesis of tranylcypromine analogues as lysine demethylase (LSD1) inhibitors," Bioorganic & Medicinal Chemistry, 2011, 19: 3709-3716.
Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.
Berge and Robiette, "Development of a Regioselective N-Methylation of (Benz)imidazoles Providing the More Sterically Hindered Isomer," The Journal of Organic Chemistry, 2013, pp. A-D, dx.doi.org/10.1021/jo401978b.
Berge et al., "Pharmaceutical salts," J Pharm Sci, 1977, 66(1): 1-19.
Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.
Binda et al., "Molecular Insights into Human Monoamine Oxidase B Inhibition by the Glitazone Antidiabetes Drugs," ACS Med. Chem. Lett., 2012, 3: 39-42.
Blom et al., "Optimizing Preparative LC/MS Configurations and Methods for Parallel Synthesis Purification," J. Comb. Chem., 2003, 5(5): 670-683.
Blom et al., "Preparative LC-MS Purification: Improved Compound-Specific Method Optimization," J. Comb. Chem., 2004, 6(6): 874-883.
Blom, "Two-Pump at-Column-Dilution Configuration for Preparative Liquid Chomratography-Mass Spectrometry," J. Comb. Chem, 2002, 4(4): 295-301.
Cain, "AML takes LSD1," SciBX, Apr. 2012, 1-3.
Carey, FA. Organic Chemistry 6th Ed. McGraw Hill. 2006, chapter 1, p. 9.
Cao et al., "One-Pot Regiospecific Synthesis of Imidazo[1,2-a]pyridines: A Novel, Metal-Free, Three-Component Reaction for the Formation of C—N, C—O, and C—S Bonds," Org. Lett., 2013, pp. A-D, dx.doi.org/10.1021/o14031414.
Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.
Chen et al., "Lysine-specific histone demethylase 1 (LSD1): A potential molecular target for tumor therapy," Crit Rev Eukaryot Gene Expre, 2012, 22(1): 53-9.
Chilean Opposition in Chilean Application No. 2021-2016, dated Dec. 23, 2016, 3 pages (English Translation).
Chilean Office Action in Chilean Application No. 2021-2016, dated Apr. 10, 2018, 13 pages (English Translation).
Chilean Office Action in Chilean Application No. 2021-2016, dated Oct. 19, 2018, 16 pages (English Translation).
Chinese Office Action in Chinese Application No. 201580017095, dated Mar. 30, 2018, 11 pages (English Translation).
Chinese Office Action in Chinese Application No. 201580017095, dated Dec. 17, 2018, 11 pages (English Translation).
Chinese Office Action in Chinese Application No. 201580019205.7, dated Nov. 27, 2019, 10 pages(English Translation).
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
ClinicalTrials.gov, "An Open-Label, Dose-Escalation/Dose-Expansion Safety Study of INC059872 in Subjects with Advanced

(56) References Cited

OTHER PUBLICATIONS

Malignancies," [retrieved on Nov. 5, 2018] retrieved from <https://clinicaltrials.gov/ct2/show/NCT02712905> 7 pages.
ClinicalTrials.gov, "IMG-7289, with and without ATRA, in patients with advanced myeloid malignancies," Jul. 25, 2016, [last update Feb. 26, 2019] retrieved from URL <https://clinicaltrials.gov/ct2/show/NCT02842827>, 6 pages.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, Jun. 1, 2015, 1-31.
Cui, Shuaiying, "Nuclear Receptors TR2 and TR4 Recruit Multiple Epigenetic Transcriptional Corepressors That Associate Specifically with the Embryonic-Type Globin Promoters in Differentiated Adult Erythroid Cells," Molecular and Cellular Biology, Aug. 31, 2011, 31(16): 3298-3311.
Culhane and Cole, "LSD1 and the chemistry of histone demethylation," Current Opinion in Chemical Biology, 2007, 11: 561-568.
Culhane et al., "A Mechanism-Based Inactivator for Histone Demethylase LSD1," J. Am. Chem. Soc., 2006, 128: 4536-4537.
Culhane et al., "Comparative Analysis of Small Molecules and Histone Substrate Analogues as LSD1 Lysine Demethylase Inhibitors," J. Am. Chem. Soc., 2010, 132: 3164-3176.
Colombian Office Action in Colombian Application No. NC20160001817, dated Mar. 20, 2018, 9 pages.
Dancy et al., "Azalysine Analogues as Probes for Protein Lysine Deacetylation and Demethylation," J. Am. Chem. Soc., 2012, 5138-5148.
Dawson and Kouzarides, "Cancer epigenetics: from mechanism to therapy," Cell, Jul. 2012, 150(1): 12-27.
Dhanak, "Cracking the Code: The Promise of Epigenetics," ACS Med. Chem. Lett., 2012, 3: 521-523.
Dhudshia and Thadani, "Diastereoselective allylation and crotylation of N-unsubstituted imines derived from ketones," Chem. Commun., 2005, 33 pages.
Dhudshia et al., "Diastereoselective allylation and crotylation of N-unsubstituted imines derived from ketones," Chem Commun, 2005, 5551-5553.
Ding et al., "LSD1-mediated epigenetic modification contributes to proliferation and metastasis of colon cancer," Br J Cancer, Aug. 2013, 109(4): 994-1003.
Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.
Eurasian Office Action in Eurasian Application No. 201691620, dated Mar. 16, 2017, 6 pages (English Translation).
Eurasian Office Action in Eurasian Application No. 201691594, dated Sep. 27, 2017, 4 pages (English Translation).
Eurasian Office Action in Eurasian Application No. 201792205, dated Apr. 4, 2018, 6 pages (English Translation).
European Search Report from European Application No. 18160157, dated Sep. 3, 2018, 6 pages.
European Extended Search Report in European Application No. 19190014.1, dated Jan. 23, 2020, 7 pages.
European Extended Search Report in European Application No. 19190494.5 dated Jan. 29, 2020, 10 pages.
European Examination Report in European Application No. 15707007.9, dated Feb. 27, 2018, 3 pages.
Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.
Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.

Forneris et al., "LSD1: oxidative chemistry for multifaceted functions in chormatin regulation," Cell Press, Mar. 2008, 181-189.
Forneris, F., et al., *Structural basis of LSD1-CoREST selectivity in histone H3 recognition.* J Biol Chem, 2007. 282(28): p. 20070-4.
Ganesan, "Targeting Epigenetic Demethylation," University of East Anglia (School of Pharmacy), PowerPoint presentation, Presented from the World Epigenetics Summit, London, Jul. 24, 2012, 26 pages.
Garson et al., "Models of ovarian cancer—are we there yet?," Mol Cell Endocrinol., Jul. 15, 2005, 239(1-2):15-26.
Ge et al., "Pd-Catalyzed $\alpha$-Arylation of $\alpha,\alpha$-Difluoroketones with Aryl Bromides and Chlorides. A Route to Difluoromethylarenes," J. Am. Chem. Soc., 2014, pp. A-D, dx.doi.org/10.1021/ja501117v.
George et al., "Soft Tissue and Uterine Lelomyosarcoma," J Clin Oncol., Dec. 8, 2017, 36(2):144-150.
Ghosh and Bank, "Formulation and in vitro evaluation of once daily sustained release formulation of aceclofenac," Tropical Journal of Pharmaceutical Research, 2010, 9(3):265-273.
Gonzalez et al., "Selective and Potent Morpholinone Inhibitors of the MDM2-p53 Protein-Protein Interaction," J. Med. Chem., 2013, pp. A-Q, dx.doi.org/10.1021/jm401767k.
Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.
Greaves and Gribben, "The role of B7 family molecules in hematologic malignancy," Blood, Jan. 2013, 121(5): 734-44.
Gui et al., "C—H Methylation of Heteroarenes Inspired by Radical SAM Methyl Transferase," J. Am. Chem. Soc., 2014, pp. A-D, dx.doi.org/10.1021/ja5007838.
Guiles et al. "preparation of triazolopyrimidine derivatives as P2T receptor antagonists," CA130:168386 (1999).
Hackam et al., "Translation of research evidence from animals to humans," JAMA, Oct. 2006, 296(14), 1731-1732.
Hakimi et al., "A core-BRAF35 complex containing histone deacetylase mediates repression of neuronal-specific genes," Proc Natl Acad Sci USA, May 2002, 99(11): 7420-5.
Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.
Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.
Han et al., "Synergistic re-activation of epigenetically silenced genes by combinatorial inhibition of DNMTs and LSD1 in cancer cells," pLoS One, Sep. 2013, 8(9): e75136.
Harris et al., "The histone demethylase KDM1A sustains the oncogenic potential of MLL-AF9 leukemia stem cells," Cancer Cell, Apr. 2012, 21(4): 473-87.
Hayami et al., "Overexpression of LSD1 contributes to human carcinogenesis through chromatin regulation in various cancers," Int J Cancer, Feb. 2011, 128(3): 574-86.
Hazeldine et al., "Low Molecular Weight Amidoximes that Act as Potent Inhibitors of Lysine-Specific Demethylase 1," J. Med. Chem., 2012, 55: 7378-7391.
Hesp et al., "Expedient Synthesis of $\alpha$-Heteroaryl Piperidines Using a Pd-Catalyzed Suzuki Cross-Coupling—Reduction Sequence," Org. Lett., 2013, pp. A-C, dx.doi.org/10.1021/o1403367b.
Hicken et al., "Discovery of a Novel Class of Imidazo[1,2-a]Pyridines with Potent PDGFR Activity and Oral Bioavailability," ACS Med. Chem. Lett., 2013, pp. A-F, dx.doi.org/10.1021/m14003953.
Hitchin et al., "Development and evaluation of selective, reversible LSD1 inhibitors derived from fragments," Med. Chem. Commun., 2013, 4: 1513-1522.
Hoffmann et al., "The role of histone demethylases in cancer therapy," Molecular Oncology, 2012, 6: 683-703.
Hou and Yu, "Structural insights into histone lysine demethylation," Current Opinion in Structural Biology, 2010, 20: 739-748.
Hruschka et al., "Fluorinated phenylcyclopropylamines. Part 5: Effects of electron-withdrawing or - donating aryl substituents on

(56) References Cited

OTHER PUBLICATIONS the inhibition of monoamine oxidases A and B by 2-aryl-2-fluoro-cyclopropylamines," Bioorganic & Medicinal Chemistry, 2008, 16: 7148-7166.
Huang et al., "p53 is regulated by the lysine demethylase LSD1," Nature, Sep. 2007, 449(7158): 105-8.
Huang et al., "Rhodium(III)-Catalyzed Direct Selective C(5)-H Oxidative Annulations of 2-Substituted Imidazoles and Alkynes by Double C—H Activation," Organic Letters, Feb. 2013, 15(8): 1878-1881.
Improper Markush Fed. Reg. 76(27) p. 7612-75, slide 1, 64-67 (2011).
International Preliminary Report on Patentability in International Application No. PCT/US2015/015600, dated Aug. 25, 2016, 7 pages.
International Preliminary Report on Patentability in International Application No. PCT/US2015/015635, dated Aug. 16, 2016, 8 pages.
International Preliminary Report on Patentability in International Application No. PCT/US2015/015663, dated Aug. 16, 2016, 7 pages.
International Preliminary Report on Patentability in International Application No. PCT/US2015/015706, dated Aug. 16, 2016, 10 pages.
International Preliminary Report on Patentability in International Application No. PCT/US2015/039734, dated Jan. 10, 2017, 10 pages.
International Preliminary Report on Patentability in International Application No. PCT/US2015/039706, dated Jan. 10, 2017, 10 pages.
International Preliminary Report on Patentability in International Application No. PCT/US2015/039724, dated Jan. 10, 2017, 10 pages.
International Preliminary Report on Patentability in International Application No. PCT/US2015/039718, dated Jan. 10, 2017, 9 pages.
International Preliminary Report on Patentability in International Application No. PCT/US2016/025550, dated Oct. 2, 2017, 8 pages.
International Preliminary Report on Patentability in International Application No. PCT/US2016/046497, dated Feb. 22, 2018, 8 pages.
International Preliminary Report on Patentability in International Application No. PCT/US2017/028756, dated Oct. 23, 2018, 8 pages.
International Search Report and Written Opinion in International Application No. PCT/US2015/015600, dated May 18, 2015, 9 pages.
International Search Report and Written Opinion in International Application No. PCT/US2015/015635, dated May 8, 2015, 10 pages.
International Search Report and Written Opinion in International Application No. PCT/US2015/015663, dated May 6, 2015, 10 pages.
International Search Report and Written Opinion in International Application No. PCT/US2015/015706, dated May 6, 2015, 16 pages.
International Search Report and Written Opinion in International Application No. PCT/US2015/039718, dated Sep. 15, 2015, 13 pages.
International Search Report and Written Opinion in International Application No. PCT/US2015/039724, dated Sep. 15, 2015, 14 pages.
International Search Report and Written Opinion in International Application No. PCT/US2015/039734, dated Sep. 18, 2015, 14 pages.
International Search Report and Written Opinion in International Application No. PCT/US2016/025550, dated Aug. 30, 2016, 12 pages.
International Search Report and Written Opinion in International Application No. PCT/US2016/046497, dated Oct. 21, 2016, 13 pages.
International Search Report and Written Opinion in International Application No. PCT/US2015/039706, dated Sep. 16, 2015, 12 pages.
International Search Report and Written Opinion in International Application No. PCT/US2017/028756, dated Jul. 3, 2017, 23 pages.
International Search Report and Written Opinion in International Application No. PCT/US2019/048725, dated Jan. 3, 2020, 19 pages.
Invitation to Pay Fees in International Application No. PCT/US2019/048725, dated Oct. 30, 2019, 12 pages.
Jalluri, Drug Analysis Table, LSD1 KDM1a Cortellis Update, retrieved on May 6, 2013, 3 pages.
Jordan, "Tamoxifen: A Most Unlikely Pioneering Medicine," Nature Reviews: Drug Discovery, Mar. 2003, 2:205-213.
Kahl et al., "Androgen Receptor Coactivators Lysine-Specific Histone Demethylase 1 and Four and a Half LIM Domain Protein 2 Predict Risk of Prostate Cancer Recurrence," Cancer Res., Dec. 2006, 66(23): 11341-11347.
Kakizawa et al., "Histone H3 peptide based LSD1-selective inhibitors," Bioorganic & Medicinal Chemistry Letters, 2015, 25: 1925-1928.
Karytinos et al., "A novel mammalian flavin-dependent histone demethylase," J Biol Chem, Jan. 2009, 284(26): 17775-82.
Kelly and Lipshutz, "Chemoselective Reductions of Nitroaromatics in Water at Room Temperature," Org. Lett., 2013, pp. A-D, dx.doi.org/10.1021/o1403079x.
Kerekes et al., "Aurora Kinase Inhibitors Based on the Imidazo[1,2-a]pyrazine Core: Fluorine and Deuterium Incorporation Improve Oral Absorption and Exposure," J. Med. Chem. Dec. 3, 2011, 54:201-210.
Kettle et al., "Diverse Heterocyclic Scaffolds as Allosteric Inhibitors of AKT," Journal of Medicinal Chemistry, Mar. 2012, 55(3): 1261-1273.
Khan et al., "An Overview of Phenylcyclopropylamine Derivatives: Biochemical and Biological Significance and Recent Developments," Medicinal Research Reviews, 2012, 874-910.
Khoury et al., "Efficient Assembly of Iminodicarboxamides by a "Truly" Four-Component Reaction," Angew. Chem. Int. Ed., 2012, 51: 10280-10283.
Kinzel et al., "Identification of MK-5710 ((8aS)-8a-methy1-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.
Kjer-Nielsen et al., "MR1 presents microbial vitamin B metabolites to MAIT cells," Nature, Nov. 2012, 491: 717-725.
Kocienski, PJ. Et al. Protecting Groups. Thieme. 2005, p. 52.
Kong et al., "Immunohistochemical expression of RBP2 and LSD1 in papillary thyroid carcinoma," Rom J Morphol Embryol, 2013, 54(3): 499-503.
Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.
Kontaki and Talianidis, "Lysine methylation regulates E2F1-induced cell death," Mol Cell, Jul. 2010, 39(1): 152-60.
Kooistra and Helin, "Molecular mechanisms and potential functions of histone demethylases," Nat Rev Mol Cell Biol, Apr. 2012, 13(5): 297-311.
Kuroyanagi et al., "Novel anti fungal agents: Triazolopyridines as inhibitors of beta-1,6-glucan synthesis," Bioorganic & Medicinal Chemistry, Aug. 2010, 18(16):5845-5854.
Kuroyanagi et al., "1,3-Benzoxazole-4-cathonitrile as a novel antifungal scaffold of beta-1,6-glucan synthesis inhibitors," Bioorganic & Medicinal Chemistry, Nov. 2010, 18(21):7593-7606.
Kutz et al., "3,5-Diamino-1,2,4-triazoles as a novel scaffold for potent, reversible LSD1 (KDM1A) inhibitors," Med. Chem. Commun., 2014, 5: 1863-1870.
Lan et al., "Recognition of unmethylated histone H3 lysine 4 links BHC80 to LSD1-mediated gene repression," Nature, 2007, 718-723.
Larsen and Hartwig, "Iridium-Catalyzed C—H Borylation of Heteroarenes: Scope, Regioselectivity, Application to Late-Stage

(56) References Cited

OTHER PUBLICATIONS

Functionalization, and Mechanism," J. Am. Chem. Soc., 2013, pp. A-M, dx.doi.org/10.1021/ja412563e.
Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.
Liang et al., "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS One, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Lynch et al., "LSD1 Inhibition: A therapeutic strategy in cancer?," Expert Opinion on Therapeutic Targets, 2012, 16(12): 1239-1249.
Masakatu et al., Medicinal Chemistry, 1995, 1:98-99.
Merck KGaA, "Product comparison—EMD4Biosciences," Comparison of LSD1 inhibitors, EMD Millipore USA, retrieved on May 6, 2013, 3 pages.
Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistry, 2010, 49: 6494-6503.
Moon et al., "Copper-Catalyzed Chan-Lam Coupling between Sulfonyl Azides and Boronic Acids at Room Temperature," Org. Lett., 2013, pp. A-D, dx.doi.org/10.1021/ol403717f.
Moormann et al., "Potential Antisecretory Antidiarrheals 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Muntean and Hess, "Biological Perspectives: Epigenetic Dysregulation in Cancer," Am J of Pathol., Oct. 2009, 175(4):1353-1361.
Neelamegam et al., "Brain-penetrant LSD1 inhibitors can block memory consolidation," Supplementary Data, 2012, 24 pages.
Neelamegam et al., "Brain-Penetrant LSD1 Inhibitors Can Block Memory Consolidation," ACS Chem. Neurosci., 2012, 3:120-128
No Author, "FS14 Myelofibrosis Facts," Leukemia & Lymphoma Society, [last updated Apr. 2012] retrieved from URL <http://www.lls.org/sites/default/files/file_assets/FS14_Myelofibrosis_Fact%20Sheet_Fina19.12.pdf>, 9 pages.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery Mechanism," Supporting Information, Angew. Chem. Int. Ed., 2013, 52: 8620-8624.
Patani et al., "Bioisosterism: A Rational Approach in Drug Design," Chemical Reviews, 1996, 96: 3147-3176.
Peturssion et al., "Protecting Groups in Carbohydrate Chemistry," J. Chem. Educ., Nov. 1, 1997, 74:1297.
Pitt "Heteroaromatic Rings of the Future" J. Med. Chem. 2009, 52, 2952-2963.
Portela and Esteller, "Epigenetic modifications and human disease," Nat Biotechnol, Oct. 2010, 28(10): 1057-68
Potts et al., "The mass spectra of somes-triazolo[4,3-a]pyrazines," Organic Mass Spectrometry, Jun. 1971, 5(6): 663-674.
Pozharskii et al., "Molecular Rings Studded with Jewels," Heterocycles in Life and Society, John Wiley & Sons Ltd., 1997, pp. 1-6.
Rambaldi et al., "From Palliation to Epigenetic Therapy in Myelofibrosis," Hematology Am Soc Hematol Educ Program., 2008, 83-91.
*Remington's Pharmaceutical Sciences*, 17th Ed., (Mack Publishing Company, Easton, 1985), p. 1418.
Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Rotilli and Mai, "Targeting Histone Demethylases: A New Avenue for the Fight against Cancer," Genes and Cancer, 2011, 2(6): 663-679.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.
Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Sale "Models of ovarian cancer metastasis: Murine models," Drug Discov Today Dis Models., Jun. 1, 2006, 3(2):149-154.
Samann et al., "Full Functionalization of the Imidazole Scaffold by Selective Metalation and Sulfoxide/Magnesium Exchange," Angew. Chem. Int. Ed., 2013, 52: 1-6.
Sankar et al., "Reversible LSD1 inhibition interferes with global EWS/ETS transcriptional activity and impedes Ewing sarcoma tumor growth," Clin Cancer Res., Sep. 1, 2014, 20(17):4584-4597.
Sankaran, "Anemia: progress in molecular mechanisms and therapies," Nature Medicine, 2015, 21(3): 221-230.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.
Schmitt et al., "Nonpeptidic Propargylamines as Inhibitors of Lysine Specific Demethylase 1 (LSD1) with Cellular Activity," J. Med. Chem., 2013, pp. A-I, dx.doi.org/10.1021/jm400792m.
Schulte et al., "Lysine-Specific Demethylase 1 Is Strongly Expressed in Poorly Differentiated Neuroblastoma: Implications for Therapy," Cancer Res, 2009, 69(5): 2065-71.
Search Report, Jun. 3, 2014, 7 pages.
Search Report, May 30, 2014, 109 pages.
Search Report, May 30, 2014, 6 pages.
Search Report, Feb. 12, 2016, 84 pages.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elecated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.

(56) References Cited

OTHER PUBLICATIONS

Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Shih et al., "The role of mutations in epigenetic regulators in myeloid malignancies," Nat Rev Cancer., Sep. 2012, 12(9):599-612.
Singh et al., "Inhibition of LSD1 sensitizes gliobastoma cells to histone deacetylase inhibitors," Neuro Oncol, Aug. 2011, 13(8): 894-903.
Son et al., "Structure of human monoamine oxidase A at 2.2-A resolution: The control of opening. The entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primary, Secondary, Tertiary) to Alcohols using $SmI_2$/Amine/$H_2O$ under Mild Conditions," J. Am. Chem. Soc., 2013, pp. A-D, dx.doi.org/10.1021/ja412578t.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.
Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.
Ueda et al., "Identification of Cell-Active Lysine Specific Demethylase 1-Selective Inhibitors," J. Am. Chem. Soc., 2009, 131: 17536-17537.
Ungerstedt, "Epigenetic Modifiers in Myeloid Malignancies: The Role of Histone Deacetylase Inhibitors," Int J Mol Sci., 2018, 19:3091, 18 pages.
Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.
Wakefield, Basil "Fluorinated Pharmaceuticals" Innovations in Pharmaceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).
Waldmann and Schneider, "Targeting histone modifications—epigenetics in cancer," Curr Opin Cell. Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.
Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.

Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Xu et al., "Design, synthesis and biological evaluation of deuterated nintedanib for improving pharmacokinetic properties," J. Label Compd. Radiopharm, May 26, 2015, 58:308-312.
Yang et al., "Reversible methylation of promoter-bound STAT3 by histone-modifying enzymes," Proc Natl Acad Sci USA, Dec. 2010, 107(50): 21499-504.
Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yuan et al., "6-Thioguanine Reactivates Epigenetically Silenced Genes in Acute Lymphoblastic Leukemia Cells by Facilitating Proteasome-Mediated Degradation of DNMT1," Cancer Res., Jan. 14, 2011, 71:1904-1911.
Yu et al., "Energetic factos determining the binding of type I inhibitors to c-Met kinase: experimental studies and quantum mechanical calculations," Acta Pharmacologica Sinica, Nov. 2013, 34(11): 1475-1783.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," Medicinal Research Reviews, 2015, pp. 1-40.
Zhu et al., "Preparation of imidazolidin-2-imines and their analogs as aspartyl protease inhibitors for treating various diseases," Pharmacopeia Drug Discovery, CA149: 307842, 2008, 4 pages.
Cancer, definition by Medical Dictionary, retrieved from URL<http://medical-dictionary.thefreedictionary.com/Cancer+(disease), p. 1 (2017).
SEER Training Modules, "Cancer Classification," [retrieved Dec. 26, 2005] retrieved from URL<http://training.seer.cancer.gov/module_ . . . ase/unit3_categories2_by_histology.html>, p. 1-3 (2005).
No Author, "Beta Thalassemia," Wikipedia, 2017 [retrieved on May 18, 2017], retrieved from URL<https://en.wikipedia.org/wiki/Beta_thalassemia>, 5 pages.
Pringle, "Overview of viruses" Merck Manual, Aug. 2013 [retrieved on May 18, 2017], retrieved from URL <http://merkmanuals.com/professional/infections-diseases/viruses/overview-of-viruses>, 5 pages.
Simone, Oncology: Introduction, Cecil Textbook of Medicine, 20th Edition, 1996 vol. 1, 1004-1010.
Vardiman, "The World Health Organization (WHO) classification of the myeloid neoplasms," Blood, 2002, 100(7): 2292-2302.
Estey, "New drug approvals in acute myeloid leukaemia: what's the best end point?" Leukemia, 2016, 30: 521-525.
Pui, "Treatment of Acute Lymphoblastic Leukemia," New England Journal of Medicine, 2006, 354: 166-78.
Krishnan, "Multiple myeloma and persistance of drug resistance in the age of novel drugs (Review)," International Journal of Oncology, 2016, 49: 33-50.
Stewart, "Novel therapeutics in multiple myeloma," Hematology, 2012, 17(S1): s105-s108.
Howington, "Treatment of Stage I and II Non-Small Cell Lung Cancer Diagnosis and Management of Lung Cancer 3rd Ed: Ameri-

(56) References Cited

OTHER PUBLICATIONS can College of Chest Physicians Evidence-Based Clinical Practice Guidelines," CHEST 2013, 143(5)(Suppl): e278S-e313S.
Socinski, "Treatment of Stage IV Non-small Cell Lung Cancer Diagnosis and Management of Lung Cancer, 3rd ed: American College of Chest Physicians Evidence-Based Clinical Practice Guideline," CHEST 2013, 143(5)(Suppl): e341S-e368S.
Sanz-Garcia, "Current and advancing treatments for metastatic colorectal cancer," Expert Opinion on Biological Therapy, 2016, 16:1, 93-110.
Boniface, "Multidisciplinary management for esophageal and gastric cancer," Cancer Management and Research, 2016, 39-44.
Yoo, "New drugs in prostate cancer," Prostate Int., 2016, 4: 37-42.
Jett, "Treatment of Small Cell Lung Cancer Diagnosis and Management of Lung Cancer, 3rd ed: American College of Chest Physicians Evidence-Based Clinical Practice Guidelines," CHEST 2013, 143(5)(Suppl): e400S-e419S.
Fattaneh and Devilee, "World Health Organization Classification of Tumours: Pathology and Genetics of Tumours of the Breast and Female Genital Organs," Online http://www.iarc.fr/en/publications/pdfs-online/pat-gen/bb4/BB4.pdf, accessed Nov. 4, 2016 IARCPress Lyon, 2003, 430 pages.
Hudis, "Triple-Negative Breast Cancer: An Unmet Medical Need," The Oncologist, 2011, 16(suppl 1): 1-11.
Gerratana, "Do platinum salts fit all triple negative breast cancers?" Cancer Treatment Reviews, 2016, 48: 34-41.
Gyawali, "Chemotherapy in locally advanced head and neck squamouscell carcinoma," Cancer Treatment Reviews, 2016, 44: 10-16.
Damia, "Contemporary pre-clinical development of anticancer agents—What are the optimal preclinical models?" European Journal of Cancer, 2009, 45: 2768-2781.
Sharma, "Cell-line based platforms to evaluate the therapeutic efficacy of candidate anticancer agents," Nature Reviews Cancer, Apr. 2010, 10: 241-253.
Ocana, "Preclinical development of molecular targeted agents for cancer," Nat. Rev. Clin. Oncol., 2011, 8: 200-209.
Ledford, "US cancer institute overhauls cell lines," Nature, Feb. 2016, 530: 391.
Johnson et al., "Relationships between drug activity in NCI preclinical in vitro and in vivo models and early clinical trials," British Journal of Cancer, 2001, 84: 1424-1431.
Muller and Krausslich, "Antiviral Strategies," Handbook of Experimental Pharmacology, 2009, 189(1): 1-24.
Wada et al., "Overexpression of the shortest isoform of histone demethylase LSD1 primes hematopoietic stem cells for malignant transformation," Blood, Jun. 2015, 125(24): 3731-3746.
WerMuth, The Practice of Medicinal Chemistry, Academic Press, 1998, p. 241-243, 253, 254 (with English Translation).
Yatim et al., "NOTCH1 Nuclear Intectome Reveals Key Regulators of Its Transcriptional Activity and Oncogenic Function," Molecular Cell, 2012, 48: 1-14.
Goossens et al., "Oncogenic ZEB2 activation drives sensitivy toward KDM1A inhibition in T-cell acute lymphoblastic leukemia," Blood, Feb. 2017, 129(8): 981-990.
Hu et al., "LSD1-mediated epigenetic modification is required for TAL1 function and hematopoiesis," PNAS, Jun. 2009, 106(25): 10141-10146.
Niebel et al., "Lysine-specific demethylase 1 (LSD1) in hematopoietic and lymhoid neoplasms," Blood, 2014, 124: 151-152.
Australian Examination Report in Australian Application No. 2015217073, dated Aug. 6, 2018, 4 pages.
Australian Examination Report in Australian Application No. 2015217119, dated Jun. 22, 2018, 4 pages.
Australian Office Action in Australian Application No. 2016306555, dated Jan. 17, 2020, 4 pages.
Australian Office Action in Australian Application No. 2019204244, dated Mar. 27, 2020, 4 pages.
Argentina Office Action in Argentina Application No. 20150100415, dated Jan. 27, 2020, 18 pages.
Argentina Office Action in Argentina Application No. 20150102198, dated Feb. 26, 2020, 6 pages.
Chilean Office Action in Chilean Application No. 2991-2018, dated Oct. 11, 2019, 15 pages (English Translation).
Chinese Office Action in Chinese Application No. 201580019205 dated May 22, 2018, 14 pages (English Translation).
Chinese Office Action in Chinese Application No. 201580019205.7, dated Mar. 15, 2019, 9 pages (English Translation).
Chinese Office Action in Chinese Application No. 201580021455.9, dated Oct. 17, 2019, 13 pages.
Colombian Office Action in Colombian Application No. NC2016/0001337, dated Jan. 9, 2019, 8 pages.
Colombian Office Action in Colombian Application No. NC2016/0001337, dated Jul. 10, 2018, 8 pages.
Colombian Office Action in Colombian Application No. NC2017/0011216, dated May 3, 2019, 9 pages.
Colombian Office Action in Colombian Application No. NC2019/0009689, dated Jan. 22, 2020, 10 pages.
Colombian Office Action in Colombian Application No. NC20180002354, dated Apr. 1, 2020, 14 pages.
Chilean Opposition in Chilean Application No. 3040-2017, dated Sep. 25, 2019, 20 pages.
Ecuador Opposition in Ecuador Application No. IEPI-2018-18869, dated Feb. 8, 2019, 34 pages (English Translation).
Eurasian Office Action in Eurasian Application No. 201691620, dated Jan. 18, 2019, 4 pages.
Eurasian Office Action in Eurasian Application No. 201892395, dated Oct. 28, 2019, 12 pages.
European Search Report in European Application No. 19190056.2 dated Feb. 7, 2020, 8 pages.
Indian Office Action in Indian Application No. 201627028454, dated Jun. 26, 2019, 6 pages.
Japanese Office Action in Japanese Application No. 2016-551815, dated Oct. 2, 2018, 6 pages.
Japanese Office Action in Japanese Application No. 2016-551710, dated Oct. 2, 2018, 7 pages.
Japanese Office Action in Japanese Application No. 2017-551636, dated Mar. 20, 2020, 8 pages.
New Zealand Office Action in New Zealand Application No. 723203, dated Jan. 15, 2020, 4 pages.
New Zealand Office Action in New Zealand Application No. 723817, dated Jan. 13, 2020, 4 pages.
Peruvian Office Action in Peruvian Application No. 1466, dated Feb. 13, 2020, 16 pages.
Philippine Office Action in Philippine Application No. 1/2017/501817, dated Mar. 12, 2020, 3 pages.
Taiwanese Office Action in Taiwan Application No. 104104830, dated Jul. 30, 2018, 8 pages (English Search Report).
Taiwanese Office Action in Taiwan Application No. 104104827, dated Dec. 18, 2018 11 pages (English Translation).
Taiwan Office Action in Taiwan Application No. 104122393, dated May 3, 2019, 6 pages (English Translation).
Ukrainian Office Action in Ukraine Application No. a 2016 09399, dated Sep. 26, 2019, 6 pages (English Translation).

SALTS OF AN LSD1 INHIBITOR AND PROCESSES FOR PREPARING THE SAME

CROSS-REFERENCE TO RELATED APPLICATIONS

The present application claims the benefit of U.S. Provisional Application No. 62/725,961, filed Aug. 31, 2018, which is incorporated herein by reference in its entirety.

FIELD OF THE INVENTION

The present invention relates to processes and intermediates for preparing 3-(cyanomethyl)-3-(4-{[(1R,2S)-2-phenylcyclopropyl]amino}piperidin-1-yl)azetidine-1-sulfonamide, and salts thereof, which selectively modulate demethylase. The present invention is further directed to solid forms of 3-(cyanomethyl)-3-(4-{[(1R,2S)-2-phenylcyclopropyl]amino}piperidin-1-yl)azetidine-1-sulfonamide and its salts, and hydrates and solvates thereof. The compounds and salts, solvates, and hydrates thereof as described herein are useful in the treatment of LSD1 diseases.

BACKGROUND OF THE INVENTION

Epigenetic modifications can impact genetic variation but, when dysregulated, can also contribute to the development of various diseases (Portela, A. and M. Esteller, *Epigenetic modifications anda3 human disease*. Nat Biotechnol, 2010. 28(10): p. 1057-68; Lund, A. H. and M. van Lohuizen, *Epigenetics and cancer*. Genes Dev, 2004. 18(19): p. 2315-35). Recently, in depth cancer genomics studies have discovered many epigenetic regulatory genes are often mutated or their own expression is abnormal in a variety of cancers (Dawson, M. A. and T. Kouzarides, *Cancer epigenetics: from mechanism to therapy*. Cell, 2012. 150(1): p. 12-27; Waldmann, T. and R. Schneider, *Targeting histone modifications—epigenetics in cancer*. Curr Opin Cell Biol, 2013. 25(2): p. 184-9; Shen, H. and P. W. Laird, *Interplay between the cancer genome and epigenome*. Cell, 2013. 153(1): p. 38-55). This implies epigenetic regulators function as cancer drivers or are permissive for tumorigenesis or disease progression. Therefore, deregulated epigenetic regulators are attractive therapeutic targets.

One particular enzyme which is associated with human diseases is lysine specific demethylase-1 (LSD1), the first discovered histone demethylase (Shi, Y., et al., *Histone demethylation mediated by the nuclear amine oxidase homolog LSD1*. Cell, 2004. 119(7): p. 941-53). It consists of three major domains: the N-terminal SWIRM which functions in nucleosome targeting, the tower domain which is involved in protein-protein interaction, such as transcriptional co-repressor, co-repressor of RE1-silencing transcription factor (CoREST), and lastly the C terminal catalytic domain whose sequence and structure share homology with the flavin adenine dinucleotide (FAD)-dependent monoamine oxidases (i.e., MAO-A and MAO-B) (Forneris, F., et al., *Structural basis of LSD1-CoREST selectivity in histone H3 recognition*. J Biol Chem, 2007. 282(28): p. 20070-4; Anand, R. and R. Marmorstein, *Structure and mechanism of lysine-specific demethylase enzymes*. J Biol Chem, 2007. 282(49): p. 35425-9; Stavropoulos, P., G. Blobel, and A. Hoelz, *Crystal structure and mechanism of human lysine-specific demethylase-1*. Nat Struct Mol Biol, 2006. 13(7): p. 626-32; Chen, Y., et al., *Crystal structure of human histone lysine-specific demethylase 1 (LSD1)*. Proc Natl Acad Sci USA, 2006. 103(38): p. 13956-61). LSD1 also shares a fair degree of homology with another lysine specific demethylase (LSD2) (Karytinos, A., et al., *A novel mammalian flavin-dependent histone demethylase*. J Biol Chem, 2009. 284(26): p. 17775-82). Although the biochemical mechanism of action is conserved in two isoforms, the substrate specificities are thought to be distinct with relatively small overlap. The enzymatic reactions of LSD1 and LSD2 are dependent on the redox process of FAD and the requirement of a protonated nitrogen in the methylated lysine is thought to limit the activity of LSD1/2 to mono- and di-methylated at the position of 4 or 9 of histone 3 (H3K4 or H3K9). These mechanisms make LSD1/2 distinct from other histone demethylase families (i.e. Jumonji domain containing family) that can demethylate mono-, di-, and tri-methylated lysines through alpha-ketoglutarate dependent reactions (Kooistra, S. M. and K. Helin, *Molecular mechanisms and potential functions of histone demethylases*. Nat Rev Mol Cell Biol, 2012. 13(5): p. 297-311; Mosammaparast, N. and Y. Shi, *Reversal of histone methylation: biochemical and molecular mechanisms of histone demethylases*. Annu Rev Biochem, 2010. 79: p. 155-79).

Methylated histone marks on K3K4 and H3K9 are generally coupled with transcriptional activation and repression, respectively. As part of corepressor complexes (e.g., CoREST), LSD1 has been reported to demethylate H3K4 and repress transcription, whereas LSD1, in nuclear hormone receptor complex (e.g., androgen receptor), may demethylate H3K9 to activate gene expression (Metzger, E., et al., *LSD1 demethylates repressive histone marks to promote androgen-receptor-dependent transcription*. Nature, 2005. 437(7057): p. 436-9; Kahl, P., et al., *Androgen receptor coactivators lysine-specific histone demethylase 1 and four and a half LIM domain protein 2 predict risk of prostate cancer recurrence*. Cancer Res, 2006. 66(23): p. 11341-7). This suggests the substrate specificity of LSD1 can be determined by associated factors, thereby regulating alternative gene expressions in a context dependent manner. In addition to histone proteins, LSD1 may demethylate non-histone proteins. These include p53 (Huang, J., et al., *p53 is regulated by the lysine demethylase LSD1*. Nature, 2007. 449(7158): p. 105-8.), E2F (Kontaki, H. and I. Talianidis, *Lysine methylation regulates E2F1-induced cell death*. Mol Cell, 2010. 39(1): p. 152-60), STAT3 (Yang, J., et al., *Reversible methylation of promoter-bound STAT3 by histone-modifying enzymes*. Proc Natl Acad Sci USA, 2010. 107(50): p. 21499-504), Tat (Sakane, N., et al., *Activation of HIV transcription by the viral Tat protein requires a demethylation step mediated by lysine-specific demethylase 1 (LSD1/KDM1)*. PLoS Pathog, 2011. 7(8): p. e1002184), and myosin phosphatase target subunit 1 (MYPT1) (Cho, H. S., et al., *Demethylation of RB regulator MYPT1 by histone demethylase LSD1 promotes cell cycle progression in cancer cells*. Cancer Res, 2011. 71(3): p. 655-60). The lists of non-histone substrates are growing with technical advances in functional proteomics studies. These suggest additional oncogenic roles of LSD1 beyond in regulating chromatin remodeling. LSD1 also associates with other epigenetic regulators, such as DNA methyltransferase 1 (DNMT1) (Wang, J., et al., *The lysine demethylase LSD1 (KDM1) is required for maintenance of global DNA methylation*. Nat Genet, 2009. 41(1): p. 125-9) and histone deacetylases (HDACs) complexes (Hakimi, M. A., et al., *A core-BRAF35 complex containing histone deacetylase mediates repression of neuronal-specific genes*. Proc Natl Acad Sci USA, 2002. 99(11): p. 7420-5; Lee, M. G., et al., *Functional interplay between histone demethylase and deacetylase enzymes*. Mol Cell Biol, 2006. 26(17): p. 6395-402; You, A., et al., CoREST is an integral component of the CoREST-human histone deacetylase complex. Proc Natl Acad Sci USA, 2001. 98(4): p. 1454-8). These associations augment the activities of DNMT or HDACs. LSD1 inhibitors may therefore potentiate the effects of HDAC or DNMT inhibitors. Indeed, preclinical studies have shown such potential already (Singh, M. M., et al., Inhibition of LSD1 sensitizes glioblastoma cells to histone deacetylase inhibitors. Neuro Oncol, 2011. 13(8): p. 894-903; Han, H., et al., Synergistic re-activation of epigenetically silenced genes by combinatorial inhibition of DNMTs and LSD1 in cancer cells. PLoS One, 2013. 8(9): p. e75136).

LSD1 has been reported to contribute to a variety of biological processes, including cell proliferation, epithelial-mesenchymal transition (EMT), and stem cell biology (both embryonic stem cells and cancer stem cells) or self-renewal and cellular transformation of somatic cells (Chen, Y., et al., Lysine-specific histone demethylase 1 (LSD1): A potential molecular target for tumor therapy. Crit Rev Eukaryot Gene Expr, 2012. 22(1): p. 53-9; Sun, G., et al., Histone demethylase LSD1 regulates neural stem cell proliferation. Mol Cell Biol, 2010. 30(8): p. 1997-2005; Adamo, A., M. J. Barrero, and J. C. Izpisua Belmonte, LSD1 and pluripotency: a new player in the network. Cell Cycle, 2011. 10(19): p. 3215-6; Adamo, A., et al., LSD1 regulates the balance between self-renewal and differentiation in human embryonic stem cells. Nat Cell Biol, 2011. 13(6): p. 652-9). In particular, cancer stem cells or cancer initiating cells have some pluripotent stem cell properties that contribute the heterogeneity of cancer cells. This feature may render cancer cells more resistant to conventional therapies, such as chemotherapy or radiotherapy, and then develop recurrence after treatment (Clevers, H., The cancer stem cell: premises, promises and challenges. Nat Med, 2011. 17(3): p. 313-9; Beck, B. and C. Blanpain, Unravelling cancer stem cell potential. Nat Rev Cancer, 2013. 13(10): p. 727-38). LSD1 was reported to maintain an undifferentiated tumor initiating or cancer stem cell phenotype in a spectrum of cancers (Zhang, X., et al., Pluripotent Stem Cell Protein Sox2 Confers Sensitivity to LSD1 Inhibition in Cancer Cells. Cell Rep, 2013. 5(2): p. 445-57; Wang, J., et al., Novel histone demethylase LSD1 inhibitors selectively target cancer cells with pluripotent stem cell properties. Cancer Res, 2011. 71(23): p. 7238-49). Acute myeloid leukemias (AMLs) are an example of neoplastic cells that retain some of their less differentiated stem cell like phenotype or leukemia stem cell (LSC) potential. Analysis of AML cells including gene expression arrays and chromatin immunoprecipitation with next generation sequencing (ChIP-Seq) revealed that LSD1 may regulate a subset of genes involved in multiple oncogenic programs to maintain LSC (Harris, W. J., et al., The histone demethylase KDM1A sustains the oncogenic potential of MLL-AF9 leukemia stem cells. Cancer Cell, 2012. 21(4): p. 473-87; Schenk, T., et al., Inhibition of the LSD1 (KDM1A) demethylase reactivates the all-trans-retinoic acid differentiation pathway in acute myeloid leukemia. Nat Med, 2012. 18(4): p. 605-11). These findings suggest potential therapeutic benefit of LSD1 inhibitors targeting cancers having stem cell properties, such as AMLs.

Overexpression of LSD1 is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., Overexpression of LSD1 contributes to human carcinogenesis through chromatin regulation in various cancers. Int J Cancer, 2011. 128(3): p. 574-86; Lv, T., et al., Over-expression of LSD1 promotes proliferation, migration and invasion in non-small cell lung cancer. PLoS One, 2012. 7(4): p. e35065; Serce, N., et al., Elevated expression of LSD1 (Lysine-specific demethylase 1) during tumour progression from pre-invasive to invasive ductal carcinoma of the breast. BMC Clin Pathol, 2012. 12: p. 13; Lim, S., et al., Lysine-specific demethylase 1 (LSD1) is highly expressed in ER-negative breast cancers and a biomarker predicting aggressive biology. Carcinogenesis, 2010. 31(3): p. 512-20; Konovalov, S. and I. Garcia-Bassets, Analysis of the levels of lysine-specific demethylase 1 (LSD1) mRNA in human ovarian tumors and the effects of chemical LSD1 inhibitors in ovarian cancer cell lines. J Ovarian Res, 2013. 6(1): p. 75; Sareddy, G. R., et al., KDM1 is a novel therapeutic target for the treatment of gliomas. Oncotarget, 2013. 4(1): p. 18-28; Ding, J., et al., LSD1-mediated epigenetic modification contributes to proliferation and metastasis of colon cancer. Br J Cancer, 2013. 109(4): p. 994-1003; Bennani-Baiti, I. M., et al., Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma. Hum Pathol, 2012. 43(8): p. 1300-7; Schulte, J. H., et al., Lysine-specific demethylase 1 is strongly expressed in poorly differentiated neuroblastoma: implications for therapy. Cancer Res, 2009. 69(5): p. 2065-71; Crea, F., et al., The emerging role of histone lysine demethylases in prostate cancer. Mol Cancer, 2012. 11: p. 52; Suikki, H. E., et al., Genetic alterations and changes in expression of histone demethylases in prostate cancer. Prostate, 2010. 70(8): p. 889-98; Yu, Y., et al., High expression of lysine-specific demethylase 1 correlates with poor prognosis of patients with esophageal squamous cell carcinoma. Biochem Biophys Res Commun, 2013. 437(2): p. 192-8; Kong, L., et al., Immunohistochemical expression of RBP2 and LSD1 in papillary thyroid carcinoma. Rom J Morphol Embryol, 2013. 54(3): p. 499-503.

Recently, the induction of CD86 expression by inhibiting LSD1 activity was reported (Lynch, J. T., et al., CD86 expression as a surrogate cellular biomarker for pharmacological inhibition of the histone demethylase lysine-specific demethylase 1. Anal Biochem, 2013. 442(1): p. 104-6). CD86 expression is a marker of maturation of dendritic cells (DCs) which are involved in antitumor immune response. Notably, CD86 functions as a co-stimulatory factor to activate T cell proliferation (Greaves, P. and J. G. Gribben, The role of B7 family molecules in hematologic malignancy. Blood, 2013. 121(5): p. 734-44; Chen, L. and D. B. Flies, Molecular mechanisms of T cell co-stimulation and co-inhibition. Nat Rev Immunol, 2013. 13(4): p. 227-42).

In addition to playing a role in cancer, LSD1 activity has also been associated with viral pathogenesis. Particularly, LSD1 activity appears to be linked with viral replications and expressions of viral genes. For example, LSD1 functions as a co-activator to induce gene expression from the viral immediate early genes of various type of herpes virus including herpes simplex virus (HSV), varicella zoster virus (VZV), and β-herpesvirus human cytomegalovirus (Liang, Y., et al., *Targeting the JMJD2 histone demethylases to epigenetically control herpesvirus infection and reactivation from latency*. Sci Transl Med, 2013. 5(167): p. 167ra5; Liang, Y., et al., *Inhibition of the histone demethylase LSD1 blocks alpha-herpesvirus lytic replication and reactivation from latency*. Nat Med, 2009. 15(11): p. 1312-7). In this setting, a LSD1 inhibitor showed antiviral activity by blocking viral replication and altering virus associated gene expression.

Recent studies have also shown that the inhibition of LSD1 by either genetic depletion or pharmacological intervention increased fetal globin gene expression in erythroid cells (Shi, L., et al., *Lysine-specific demethylase 1 is a therapeutic target for fetal hemoglobin induction*. Nat Med, 2013. 19(3): p. 291-4; Xu, J., et al., *Corepressor-dependent silencing of fetal hemoglobin expression by BCL11A*. Proc Natl Acad Sci USA, 2013. 110(16): p. 6518-23). Inducing fetal globin gene would be potentially therapeutically beneficial for the disease of β-globinopathies, including β-thalassemia and sickle cell disease where the production of normal β-globin, a component of adult hemoglobin, is impaired (Sankaran, V. G. and S. H. Orkin, *The switch from fetal to adult hemoglobin*. Cold Spring Harb Perspect Med, 2013. 3(1): p. a011643; Bauer, D. E., S. C. Kamran, and S. H. Orkin, *Reawakening fetal hemoglobin: prospects for new therapies for the beta-globin disorders*. Blood, 2012. 120 (15): p. 2945-53). Moreover, LSD1 inhibition may potentiate other clinically used therapies, such as hydroxyurea or azacitidine. These agents may act, at least in part, by increasing γ-globin gene expression through different mechanisms.

In summary, LSD1 contributes to tumor development by altering epigenetic marks on histones and non-histone proteins. Accumulating data have validated that either genetic depletion or pharmacological intervention of LSD1 normalizes altered gene expressions, thereby inducing differentiation programs into mature cell types, decreasing cell proliferation, and promoting apoptosis in cancer cells. Therefore, LSD1 inhibitors alone or in combination with established therapeutic drugs would be effective to treat the diseases associated with LSD1 activity.

SUMMARY OF THE INVENTION

The present disclosure provides, inter alia, salts of 3-(cyanomethyl)-3-(4-{[(1R,2S)-2-phenylcyclopropyl]amino}piperidin-1-yl)azetidine-1-sulfonamide (Compound 1):

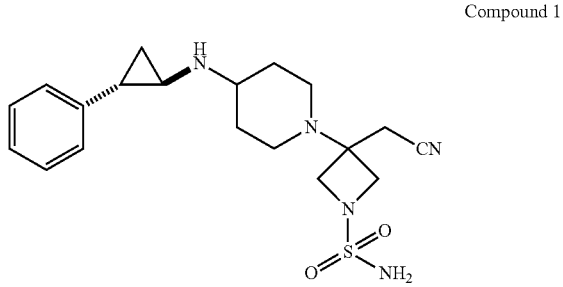

Compound 1 or a hydrate or solvate thereof. The present disclosure also provides processes and intermediates for preparing Compound 1 and its salts.

Provided herein are solid forms of Compound 1 and its salts.

The present disclosure is further directed to the hydrochloric acid salt of Compound 1 (e.g., the mono-hydrochloric acid salt of Compound 1 or the di-hydrochloric acid salt of Compound 1), methanesulfonic acid salt of Compound 1 (e.g., the mono-methanesulfonic acid salt of Compound 1 or the di-methanesulfonic acid salt of Compound 1), malonic acid salt of Compound 1, ethanesulfonic acid salt of Compound 1, maleic acid salt of Compound 1, camphorsulfonic acid salt of Compound 1, isethionic acid salt of Compound 1, and the 1,2-ethanedisulfonic acid salt of Compound 1.

The present disclosure is further directed to crystalline forms of the salts described herein.

Provided herein are also pharmaceutical compositions, which include Compound 1 and its salts, and solid forms thereof as described herein, and one or more pharmaceutically acceptable carriers or excipients.

The present disclosure also provides methods of inhibiting LSD1 enzymes using Compound 1 and its salts, and solid forms thereof as described herein.

The present disclosure also provides therapeutic methods of using Compound 1 and its salts, and solid forms thereof as described herein. The present disclosure also provides uses of Compound 1 and its salts, and solid forms thereof as described herein in the manufacture of a medicament for use in therapy. The present disclosure also Compound 1 and its salts, and solid forms thereof as described herein for use in therapy.

DETAILED DESCRIPTION

Figure 1:
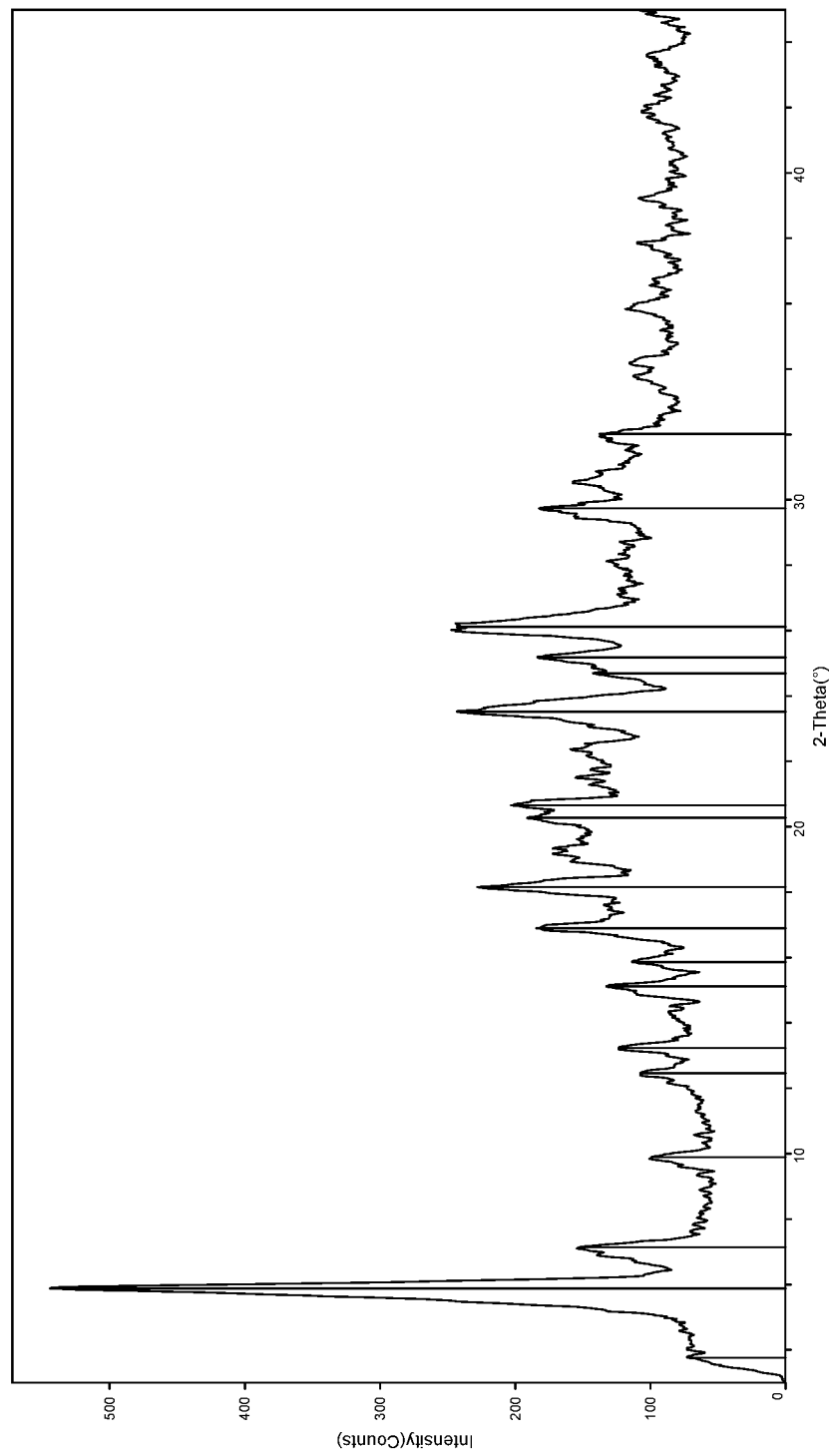
FIG. 1 shows an X-ray powder diffraction (XRPD) pattern of Compound 1 di-HCl, Form I.

This disclosure provides salts of an LSD-1 inhibitor and processes and intermediates for preparing the same. LSD-1 inhibitors are described in U.S. Pat. No. 9,493,450, filed Feb. 2, 2015, which is incorporated herein by reference in its entirety, including 3-(cyanomethyl)-3-(4-{[(1R,2S)-2-phenylcyclopropyl]amino}piperidin-1-yl)azetidine-1-sulfonamide, which is depicted below as Compound 1.

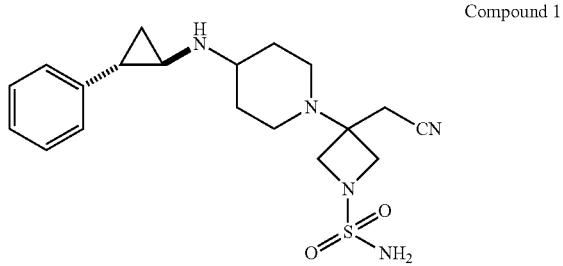

Compound 1

Provided herein is an acid salt of Compound 1, or a hydrate or solvate thereof. The salt can be substantially crystalline. In some embodiments, the salt is a solid form. In some embodiments, the salt is crystalline.

In some embodiments, the acid is selected from hydrochloric acid, methanesulfonic acid, malonic acid, ethanesulfonic acid, maleic acid, camphorsulfonic acid, the isethionic acid, 1,2-ethanedisulfonic acid, and methanesulfonic acid.

In some embodiments, the salt of Compound 1 is a hydrochloric acid salt. In some embodiments, the salt of Compound 1 is a di-hydrochloric acid salt. The di-hydrochloric acid salt can be represented by its chemical name: 3-(cyanomethyl)-3-(4-{[(1R,2S)-2-phenylcyclopropyl]amino}piperidin-1-yl)azetidine-1-sulfonamide dihydrochloride; or 3-(cyanomethyl)-3-(4-{[(1R,2S)-2-phenylcyclopropyl]amino}piperidin-1-yl)azetidine-1-sulfonamide di-hydrochloric acid salt. The dihydrochloric acid salt of Compound 1 is referred to herein as "Compound 1 di-HCl," and "Compound 1 di-hydrochloride." In some embodiments, the dihydrochloric acid salt has Form I, Form II, Form III, Form IV, or Form V. In some embodiments, the salt of Compound 1 is a mono-hydrochloric acid salt. The mono-hydrochloric acid salt can be represented by its chemical name: 3-(cyanomethyl)-3-(4-{[(1R,2S)-2-phenylcyclopropyl]amino}piperidin-1-yl)azetidine-1-sulfonamide hydrochloride; or 3-(cyanomethyl)-3-(4-{[(1R,2S)-2-phenyl cyclopropyl]amino}piperidin-1-yl)azetidine-1-sulfonamide mono-hydrochloric acid salt. The mono-hydrochloric acid salt of Compound 1 is referred to herein as "Compound 1 HCl" or "Compound 1 mono-HCl."

In some embodiments, the salt of Compound 1 is a di-methanesulfonic acid salt. The di-methanesulfonic acid salt can be represented by its chemical name: 3-(cyanomethyl)-3-(4-{[(1R,2S)-2-phenylcyclopropyl]amino}piperidin-1-yl)azetidine-1-sulfonamide dimesylate; or 3-(cyanomethyl)-3-(4-{[(1R,2S)-2-phenylcyclopropyl]amino}piperidin-1-yl)azetidine-1-sulfonamide di-methanesulfonic acid salt. The di-methanesulfonic acid salt of Compound 1 is referred to herein as "Compound 1 di-mesylate." In some embodiments, the salt of Compound 1 is a mono-methanesulfonic acid salt. The mono-methanesulfonic acid salt can be represented by its chemical name: 3-(cyanomethyl)-3-(4-{[(1R,2S)-2-phenylcyclopropyl]amino}piperidin-1-yl)azetidine-1-sulfonamide mesylate; or 3-(cyanomethyl)-3-(4-{[(1R,2S)-2-phenylcyclopropyl]amino}piperidin-1-yl)azetidine-1-sulfonamide mono-methanesulfonic acid salt. The methanesulfonic acid salt of Compound 1 is referred to herein as "Compound 1 mesylate" or "Compound 1 mono-mesylate."

In some embodiments, the salt of Compound 1 is a malonic acid salt. The malonic acid salt can be represented by its chemical name: 3-(cyanomethyl)-3-(4-{[(1R,2S)-2-phenylcyclopropyl]amino}piperidin-1-yl)azetidine-1-sulfonamide malonate; or 3-(cyanomethyl)-3-(4-{[(1R,2S)-2-phenylcyclopropyl]amino}piperidin-1-yl)azetidine-1-sulfonamide mono-malonic acid salt. The malonic acid salt of Compound 1 is referred to herein as "Compound 1 malonate."

In some embodiments, the salt of Compound 1 is an ethanesulfonic acid salt. The ethanesulfonic acid salt can be represented by its chemical name: 3-(cyanomethyl)-3-(4-{[(1R,2S)-2-phenylcyclopropyl]amino}piperidin-1-yl)azetidine-1-sulfonamide esylate; or 3-(cyanomethyl)-3-(4-{[(1R,2S)-2-phenylcyclopropyl]amino}piperidin-1-yl)azetidine- 1-sulfonamide mono-ethanesulfonic acid salt. The ethanesulfonic acid salt of Compound 1 is referred to herein as "Compound 1 esylate."

In some embodiments, the salt of Compound 1 is a maleic acid salt. The maleic acid salt can be represented by its chemical name: 3-(cyanomethyl)-3-(4-{[(1R,2S)-2-phenylcyclopropyl]amino}piperidin-1-yl)azetidine-1-sulfonamide maleate; or 3-(cyanomethyl)-3-(4-{[(1R,2S)-2-phenylcyclopropyl]amino}piperidin-1-yl)azetidine-1-sulfonamide mono-maleic acid salt. The maleic acid salt of Compound 1 is referred to herein as "Compound 1 maleate."

In some embodiments, the salt of Compound 1 is a camphorsulfonic acid salt. The camphorsulfonic acid salt can be represented by its chemical name: 3-(cyanomethyl)-3-(4-{[(1R,2S)-2-phenylcyclopropyl]amino}piperidin-1-yl) azetidine-1-sulfonamide camsylate; or 3-(cyanomethyl)-3-(4-{[(1R,2S)-2-phenylcyclopropyl]amino}piperidin-1-yl) azetidine-1-sulfonamide mono-camphorsulfonic acid salt. The camphorsulfonic acid salt of Compound 1 is referred to herein as "Compound 1 camsylate."

In some embodiments, the salt of Compound 1 is an isethionic acid salt. The isethionic acid salt can be represented by its chemical name: 3-(cyanomethyl)-3-(4-{[(1R,2S)-2-phenylcyclopropyl]amino}piperidin-1-yl)azetidine-1-sulfonamide isethionate; or 3-(cyanomethyl)-3-(4-{[(1R,2S)-2-phenylcyclopropyl]amino}piperidin-1-yl)azetidine-1-sulfonamide mono-isethionic acid salt. The isethionic acid salt of Compound 1 is referred to herein as "Compound 1 isethionate."

In some embodiments, the salt of Compound 1 is a 1,2-ethanedisulfonic acid salt. The 1,2-ethanedisulfonic acid salt can be represented by its chemical name: 3-(cyanomethyl)-3-(4-{[(1R,2S)-2-phenylcyclopropyl]amino}piperidin-1-yl)azetidine-1-sulfonamide ethanedisulfonate; or 3-(cyanomethyl)-3-(4-{[(1R,2S)-2-phenylcyclopropyl]amino}piperidin-1-yl)azetidine-1-sulfonamide mono-1,2-ethanedisulfonic acid salt. The 1,2-ethanedisulfonic acid salt of Compound 1 is referred to herein as "Compound 1 1,2-ethanedisulfonate."

In some embodiments, the salt of Compound 1 is a sulfuric acid salt. The sulfuric acid salt can be represented by its chemical name: 3-(cyanomethyl)-3-(4-{[(1R,2S)-2-phenylcyclopropyl]amino}piperidin-1-yl)azetidine-1-sulfonamide sulfate. The sulfuric acid salt of Compound 1 is referred to herein as "Compound 1 sulfate."

Compound 1 and its salts can be isolated as one or more solid forms. The solid forms (e.g., crystalline forms) described herein can have certain advantages, for example, they may have desirable properties, such as ease of handling, ease of processing, storage stability, and ease of purification. Moreover, the crystalline forms can be useful for improving the performance characteristics of a pharmaceutical product such as dissolution profile, shelf-life and bioavailability.

As used herein, the phrase "solid form" refers to a salt of the invention in either an amorphous state or a crystalline state ("crystalline form" or "crystalline solid"), whereby a salt of the invention in a crystalline state may optionally include solvent or water within the crystalline lattice, for example, to form a solvated or hydrated crystalline form. In some embodiments, the salt of the present invention is in a crystalline state as described herein. The term "hydrated," as used herein, is meant to refer to a crystalline form that includes one or more water molecules in the crystalline lattice. Example "hydrated" crystalline forms include hemihydrates, monohydrates, dihydrates, and the like. Other hydrated forms such as channel hydrates and the like are also included within the meaning of the term.

In some embodiments, salts of the invention can be prepared by any suitable method for the preparation of acid addition salts. For example, the free base Compound 1 can be combined with the desired acid in a solvent or in a melt. Alternatively, an acid addition salt of Compound 1 can be converted to a different acid addition salt by anion exchange. Salts of the invention which are prepared in a solvent system can be isolated by precipitation from the solvent. Precipitation and/or crystallization can be induced, for example, by evaporation, reduction of temperature, addition of antisolvent, or combinations thereof.

In some embodiments, the salts of the invention are crystalline, including crystalline forms which are anhydrous, hydrated, non-solvated, or solvated. Example hydrates include hemihydrates, monohydrates, dihydrates, and the like. In some embodiments, the crystalline salts are anhydrous and non-solvated. By "anhydrous" is meant that the crystalline salt contains no bound water in the crystal lattice structure, i.e., the compound does not form a crystalline hydrate.

In some embodiments, the salts of the invention are substantially isolated. By "substantially isolated" is meant that the salt is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the salt.

Salts of the invention also include all isotopes of atoms occurring in the salts. Isotopes include those atoms having the same atomic number but different mass numbers. For example, isotopes of hydrogen include tritium and deuterium.

The salt forms of the invention were found to be highly crystalline, a desirable property which can facilitate, for example, purification of the drug such as by crystallization and recrystallization as necessary. Further, a crystalline form tends to be more stable and can be easier to mill or micronize when formulating a drug. Crystalline salts also tend have excellent properties with respect to solubility and can be more suitable to be manufactured reproducibly in a clear acid/base ratio, facilitating the preparation of liquid formulations for oral as well as for intravenous applications.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystals. As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

As used herein, the term "substantially crystalline," means a majority of the weight of a sample or preparation of a salt (or hydrate or solvate thereof) of the invention is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±3° C. Accordingly, a crystalline form reported herein having a DSC thermogram "substantially" as shown in any of the Figures is understood to accommodate such variation.

The salts and compounds disclosed herein can include all isotopes of atoms occurring within them. Isotopes include those atoms having the same atomic number but different mass numbers. For example, isotopes of hydrogen include tritium and deuterium. Salts and compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}$C NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. When used with respect to XRPD values, the term "about" means that the peak assignments can vary by ±0.2° (2-theta). When used in reference to DSC thermogram values, the term "about" means that the temperature assignments can vary by ±3° C.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "melting point" refers to an endothermic event or endothermal event observed in e.g., a DSC experiment. An endothermic event is a process or reaction in which a sample absorbs energy from its surrounding in the form of e.g., heat as in a DSC experiment. An exothermic event is a process or reaction in which a sample releases energy. The process of heat absorption and release can be detected by DSC. In some embodiments, the term "melting point" is used to describe the major endothermic event revealed on a particular DSC thermogram.

The term "room temperature" as used herein, is understood in the art, and refers generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

Compound 1 Di-HCl Form I

Provided herein is a solid form of Compound 1 di-HCl which is crystalline, referred to as Form I, which is described below in the Examples. In some embodiments, Form I has a molar ratio of Compound 1 to HCl that is about 1:2.

In some embodiments, Form I has an X-ray diffraction pattern comprising at least one characteristic peak in degrees 2θ selected from about 5.9°, about 7.1°, and about 9.9°. In some embodiments, Form I has an X-ray diffraction pattern comprising a characteristic peak in degrees 2θ at about 5.9°.

In some embodiments, Form I has an X-ray diffraction pattern comprising a characteristic peak in degrees 2θ at about 7.1°. In some embodiments, Form I has an X-ray diffraction pattern comprising a characteristic peak in degrees 2θ at about 9.9°.

In some embodiments, Form I has an X-ray diffraction pattern comprising at least two characteristic peak in degrees 2θ selected from about 5.9°, about 7.1°, and about 9.9°.

In some embodiments, Form I has an X-ray diffraction pattern comprising characteristic peaks in degrees 2θ at about 5.9°, about 7.1°, and about 9.9°.

In some embodiments, Form I has an X-ray diffraction pattern comprising at least four characteristic peaks in degrees 2θ selected from about 5.9°, about 7.1°, about 9.9°, about 13.2°, about 15.1°, and about 18.2°. In some embodiments, Form I has an X-ray diffraction pattern comprising at least three characteristic peaks in degrees 2θ selected from about 5.9°, about 7.1°, about 9.9°, about 13.2°, about 15.1°, and about 18.2°. In some embodiments, Form I has an X-ray diffraction pattern comprising at least two characteristic peaks in degrees 2θ selected from about 5.9°, about 7.1°, about 9.9°, about 13.2°, about 15.1°, and about 18.2°. In some embodiments, Form I has an X-ray diffraction pattern comprising at least one characteristic peaks in degrees 2θ selected from about 5.9°, about 7.1°, about 9.9°, about 13.2°, about 15.1°, and about 18.2°.

In some embodiments, Form I has an X-ray diffraction pattern comprising at least four characteristic peaks in degrees 2θ selected from about 3.8°, about 5.9°, about 7.1°, about 9.9°, about 13.2°, about 15.1°, about 16.9°, about 18.2°, about 23.5°, and about 26.1°. In some embodiments, Form I has an X-ray diffraction pattern comprising at least three characteristic peaks in degrees 2θ selected from about 3.8°, about 5.9°, about 7.1°, about 9.9°, about 13.2°, about 15.1°, about 16.9°, about 18.2°, about 23.5°, and about 26.1°. In some embodiments, Form I has an X-ray diffraction pattern comprising at least two characteristic peaks in degrees 2θ selected from about 3.8°, about 5.9°, about 7.1°, about 9.9°, about 13.2°, about 15.1°, about 16.9°, about 18.2°, about 23.5°, and about 26.1°. In some embodiments, Form I has an X-ray diffraction pattern comprising at least one characteristic peaks in degrees 2θ selected from about 3.8°, about 5.9°, about 7.1°, about 9.9°, about 13.2°, about 15.1°, about 16.9°, about 18.2°, about 23.5°, and about 26.1°.

In some embodiments, Form I has an XRPD pattern with characteristic peaks as substantially shown in FIG. 1.

Figure 2:
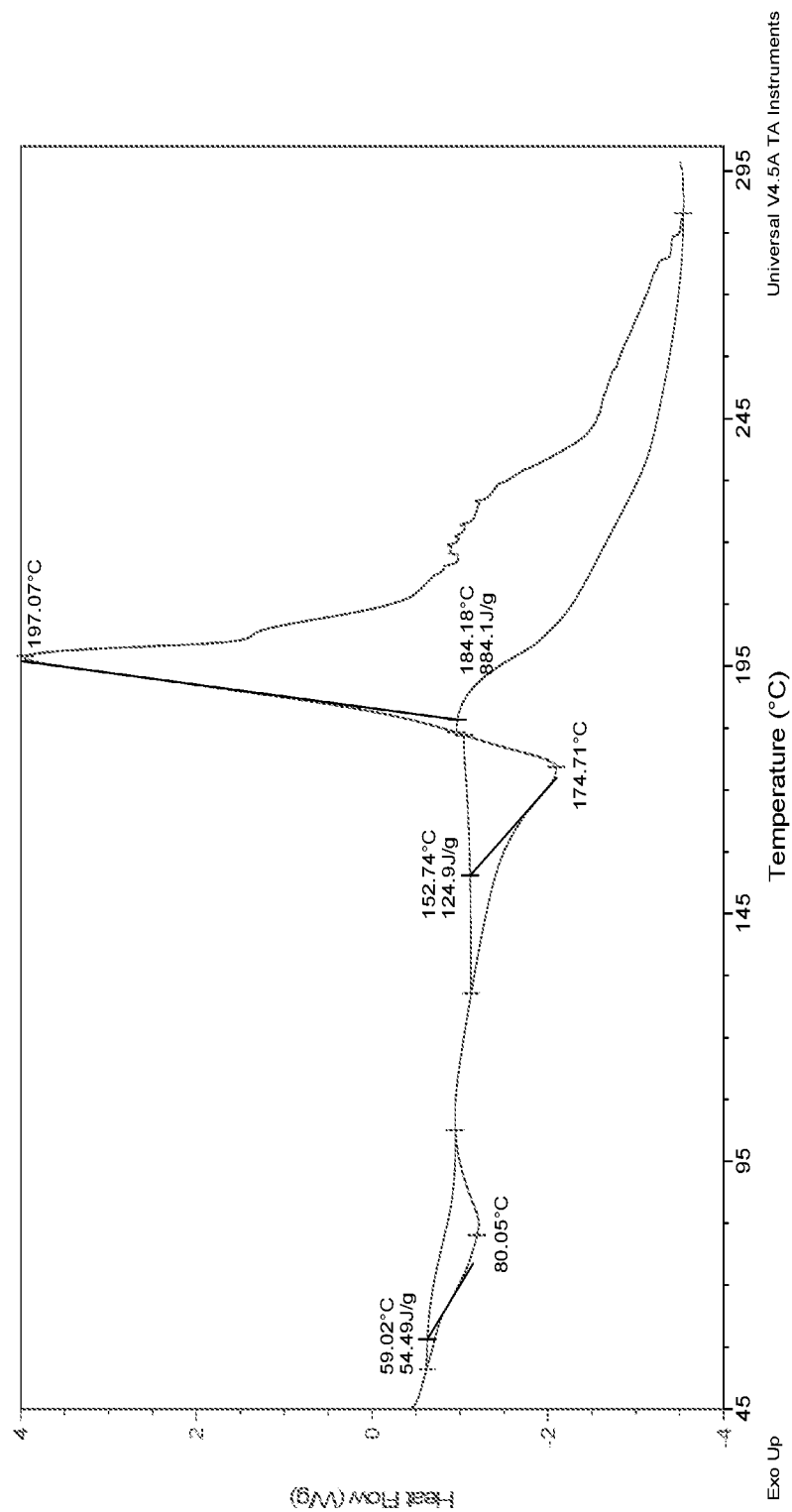
FIG. 2 shows a differential scanning calorimetry (DSC) thermogram of Compound 1 di-HCl, Form I.
Figure 3:
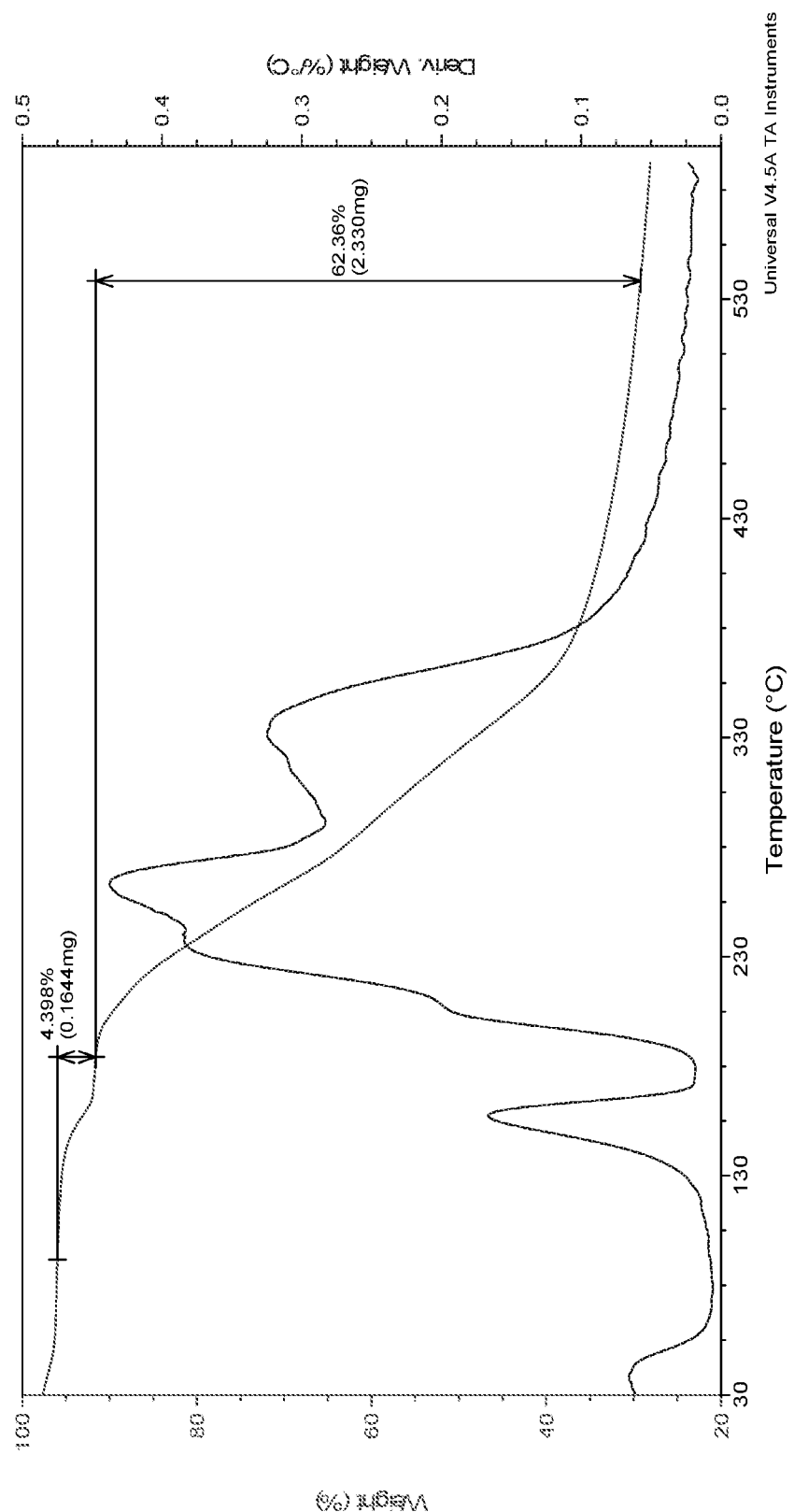
FIG. 3 shows a thermogravimetric analysis (TGA) thermogram of Compound 1 di-HCl, Form I.

In some embodiments, Form I has a DSC thermogram characterized by endotherm peaks at temperatures of about 80° C. and about 175° C. In some embodiments, Form I has a DSC thermogram characterized by an exotherm peak at a temperature of about 197° C. In some embodiments, Form I has a DSC thermogram characterized by an endotherm peak at a temperature of about 80° C. In some embodiments, Form I has a DSC thermogram characterized by an endotherm peak at a temperature of about 175° C. In some embodiments, Form I has a DSC thermogram substantially as shown in FIG. 2. In some embodiments, Form I has a TGA thermogram substantially as shown in FIG. 3.

In some embodiments, Form I has an X-ray diffraction pattern comprising at least four characteristic peaks in degrees 2θ selected from about 5.9°, about 7.1°, about 9.9°, about 13.2°, about 15.1°, and about 18.2°; and Form I has a DSC thermogram characterized by endotherm peaks at temperatures of about 80° C. and 175° C. In some embodiments, Form I has an X-ray diffraction pattern comprising at least four characteristic peaks in degrees 2θ selected from about 5.9°, about 7.1°, about 9.9°, about 13.2°, about 15.1°, and about 18.2°; and Form I has a DSC thermogram characterized by an endotherm peak at a temperature of about 80° C. In some embodiments, Form I has an X-ray diffraction pattern comprising at least four characteristic peaks in degrees 2θ selected from about 5.9°, about 7.1°, about 9.9°, about 13.2°, about 15.1°, and about 18.2°; and Form I has a DSC thermogram characterized by an endotherm peak at a temperature of about 175° C.

Provided herein are also processes for preparing Form I of Compound 1 comprising precipitating Compound 1 di-HCl from a solvent. In some embodiments, the solvent is a mixture of a polar and a hydrocarbon solvent. In some embodiments, the solvent is a mixture of methanol and 2-methoxy-2-methylpropane. In some embodiments, the precipitating comprises a) heating a solution of Compound 1 di-HCl in methanol to an elevated temperature, b) cooling to a reduced temperature, and c) adding 2-methoxy-2-methylpropane. In some embodiments, the elevated temperature is at least about 50° C., at least about 55° C., at least about 60° C., or at least about 65° C. In some embodiments, the reduced temperature is ambient temperature. In some embodiments, the reduced temperature is about 23° C.

In some embodiments, Form I can be isolated with a purity of at least about 80%, about 85%, about 90%, about 95%, about 96%, about 97%, about 98%, or about 99%. In some embodiments, Form I can be isolated with a purity greater than about 99%.

Compound 1 Di-HCl Form II

Provided herein is a solid form of Compound 1 di-HCl, which is crystalline, referred to as Form II, which is described below in the Examples. In some embodiments, Form II has a molar ratio of Compound 1 to HCl that is about 1:2.

In some embodiments, Form II has an X-ray diffraction pattern comprising at least one characteristic peak in degrees 2θ selected from about 5.8°, about 13.2°, and about 15.1°. In some embodiments, Form II has an X-ray diffraction pattern comprising a characteristic peak in degrees 2θ at about 5.8°. In some embodiments, Form II has an X-ray diffraction pattern comprising a characteristic peak in degrees 2θ at about 13.2°. In some embodiments, Form II has an X-ray diffraction pattern comprising a characteristic peak in degrees 2θ at about 15.1°.

In some embodiments, Form II has an X-ray diffraction pattern comprising at least two characteristic peaks in degrees 2θ selected from about 5.8°, about 13.2°, and about 15.1°.

In some embodiments, Form II has an X-ray diffraction pattern comprising characteristic peaks in degrees 2θ selected from about 5.8°, about 13.2°, and about 15.1°.

In some embodiments, Form II has an X-ray diffraction pattern comprising at least four characteristic peaks in degrees 2θ selected from about 5.8°, about 13.2°, about 15.1°, about 17.1°, about 20.1° and about 20.8°. In some embodiments, Form II has an X-ray diffraction pattern comprising at least three characteristic peaks in degrees 2θ selected from about 5.8°, about 13.2°, about 15.1°, about 17.1°, about 20.1° and about 20.8°. In some embodiments, Form II has an X-ray diffraction pattern comprising at least two characteristic peaks in degrees 2θ selected from about 5.8°, about 13.2°, about 15.1°, about 17.1°, about 20.1° and about 20.8°. In some embodiments, Form II has an X-ray diffraction pattern comprising at least one characteristic peak in degrees 2θ selected from about 5.8°, about 13.2°, about 15.1°, about 17.1°, about 20.1° and about 20.8°.

In some embodiments, Form II has an X-ray diffraction pattern comprising at least four characteristic peaks in degrees 2θ selected from about 5.8°, about 13.2°, about 15.1°, about 17.1°, about 20.1° about 20.8°, about 22.5°, about 25.4°, about 28.0°, and about 29.1°. In some embodiments, Form II has an X-ray diffraction pattern comprising at least three characteristic peaks in degrees 2θ selected from about 5.8°, about 13.2°, about 15.1°, about 17.1°, about 20.1° about 20.8°, about 22.5°, about 25.4°, about 28.0°, and about 29.1°. In some embodiments, Form II has an X-ray diffraction pattern comprising at least two characteristic peaks in degrees 2θ selected from about 5.8°, about 13.2°, about 15.1°, about 17.1°, about 20.1° about 20.8°, about 22.5°, about 25.4°, about 28.0°, and about 29.1°. In some embodiments, Form II has an X-ray diffraction pattern comprising at least one characteristic peak in degrees 2θ selected from about 5.8°, about 13.2°, about 15.1°, about 17.1°, about 20.1° about 20.8°, about 22.5°, about 25.4°, about 28.0°, and about 29.1°.

Figure 4:
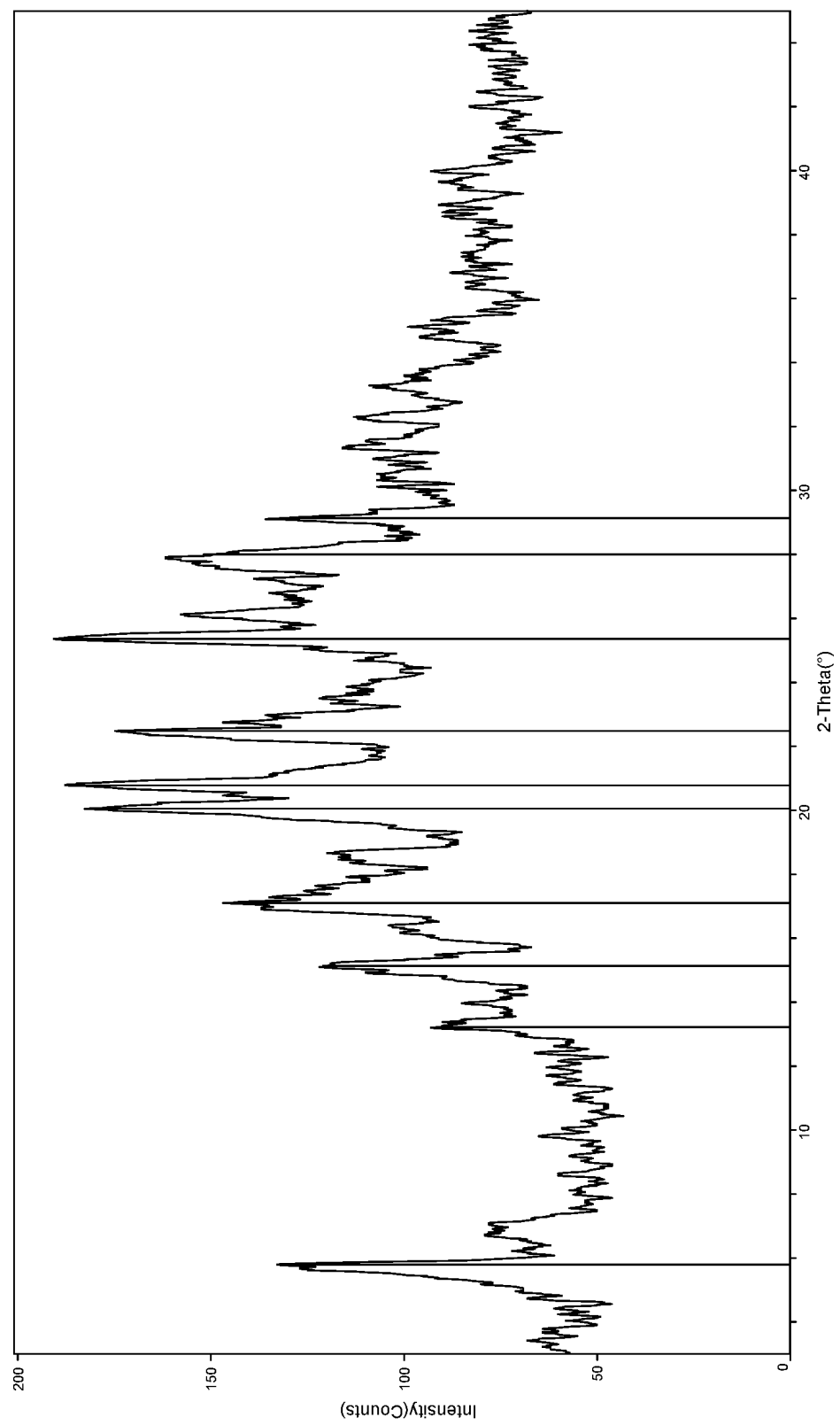
FIG. 4 shows an XRPD pattern of Compound 1 di-HCl, Form II.

In some embodiments, Form II has an XRPD pattern with characteristic peaks as substantially shown in FIG. 4.

Figure 5:
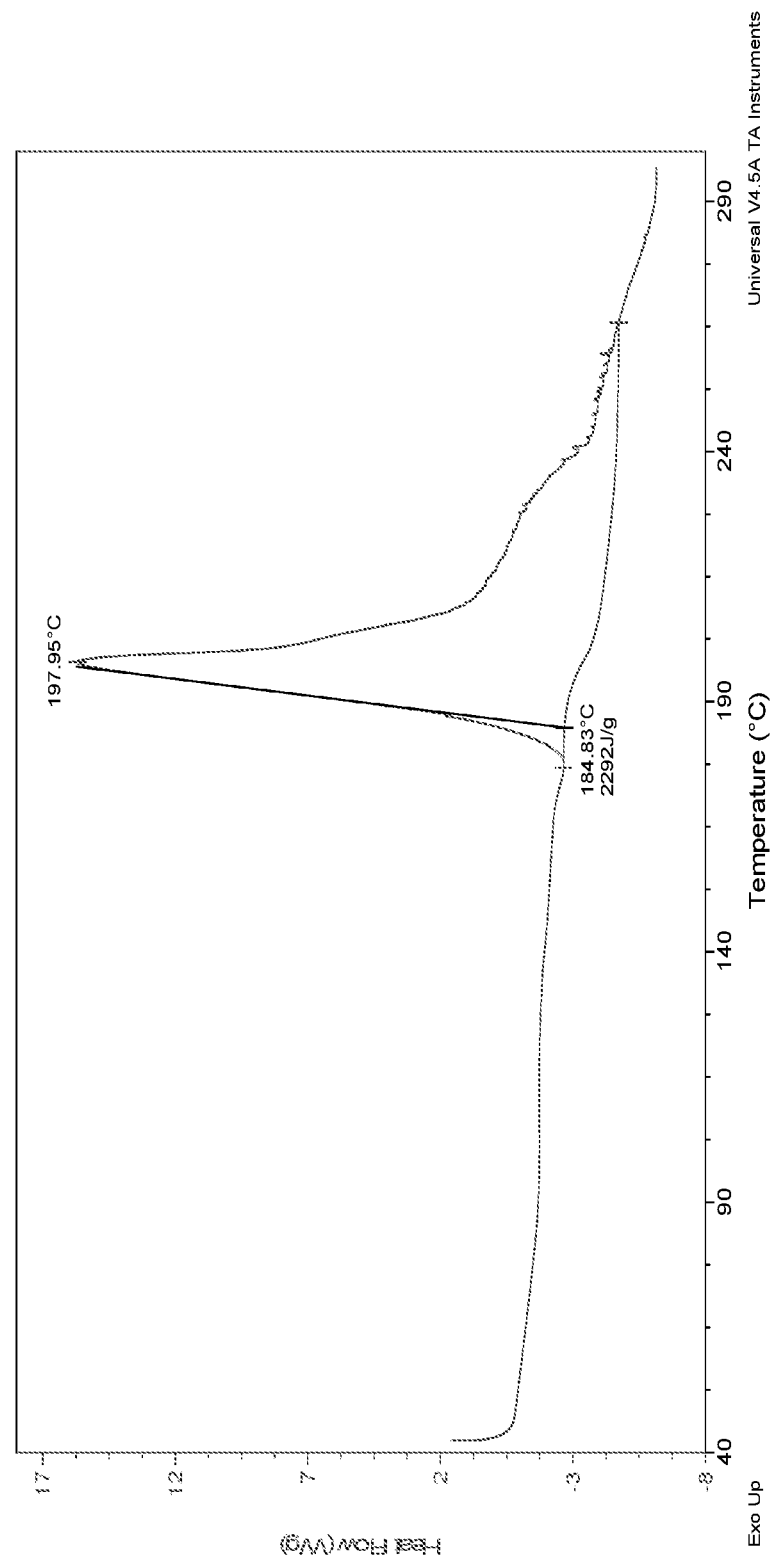
FIG. 5 shows a DSC thermogram of Compound 1 di-HCl, Form II.
Figure 6:
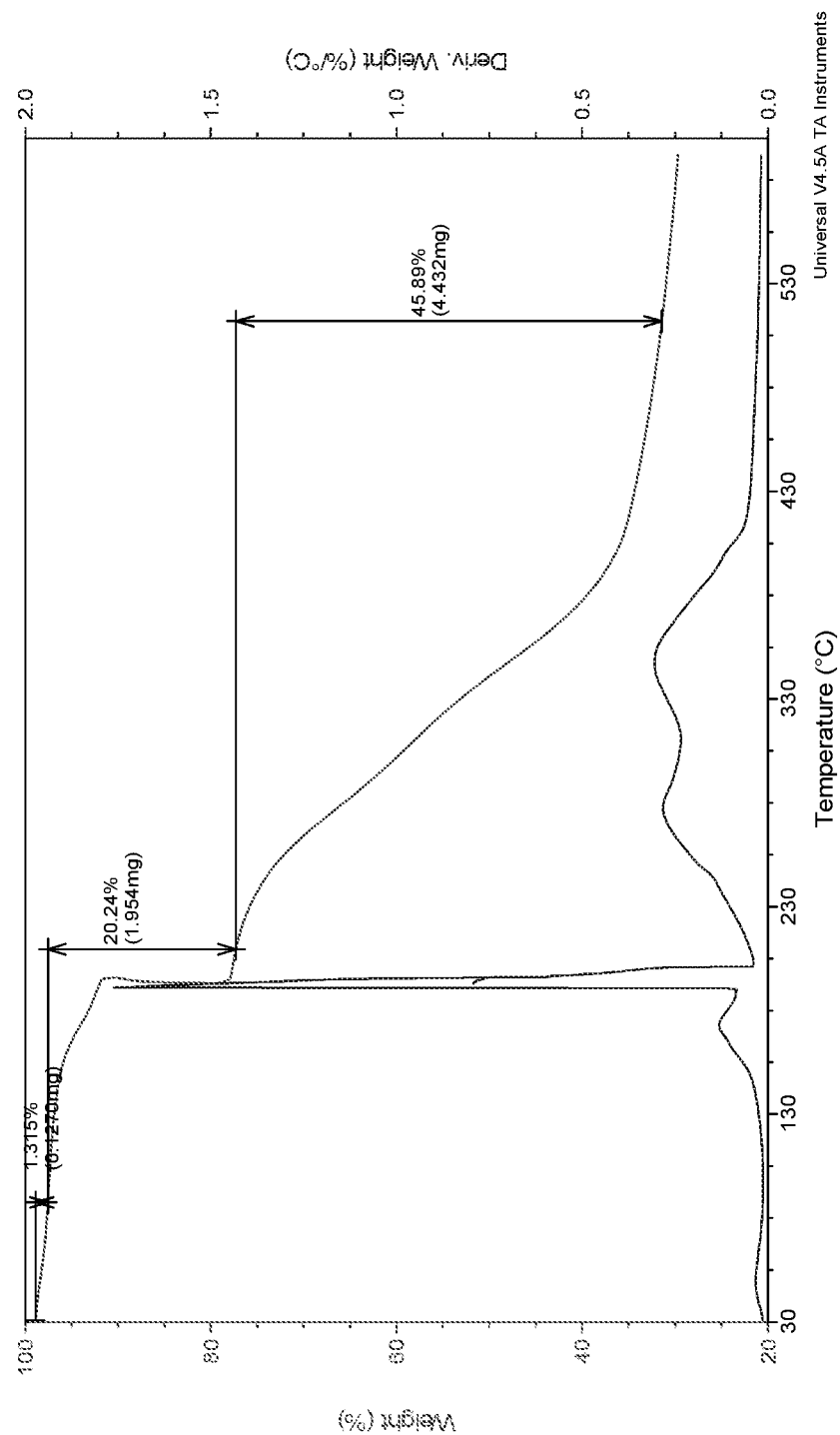
FIG. 6 shows a TGA thermogram of Compound 1 di-HCl, Form II.

In some embodiments, Form II has a DSC thermogram characterized by an exotherm peak at a temperature of about 198° C. In some embodiments, Form II has a DSC thermogram substantially as shown in FIG. 5. In some embodiments, Form II has a TGA thermogram substantially as shown in FIG. 6.

In some embodiments, Form II has an X-ray diffraction pattern comprising at least four characteristic peaks in degrees 2θ selected from about 5.8°, about 13.2°, about 15.1°, about 17.1°, about 20.1° and about 20.8°; and Form II has a DSC thermogram characterized by an exotherm peak at a temperature of about 198° C.

Provided herein are also processes for preparing Form II of Compound 1 comprising precipitating Compound 1 di-HCl from a solvent. In some embodiments, the solvent is a mixture of a polar and a hydrocarbon solvent. In some embodiments, the solvent is a mixture of 2-butanone and heptane. In some embodiments, the precipitating comprises a) heating a solution of Compound 1 in a mixture of 2-butanone and heptane to an elevated temperature for a first period of time and b) cooling to a reduced temperature for a second period of time. In some embodiments, the elevated temperature is at least about 40° C., at least about 45° C., at least about 50° C., or at least about 55° C. In certain embodiments, the first period of time is between about 3 and 5 h (e.g., about 4 h). In some embodiments, the reduced temperature is ambient temperature. In some embodiments, the reduced temperature is about 23° C. In some embodiments, the second period of time is between 12 and 16 hours. In some embodiments, the second period of time is longer than 6, 12, or 18 hours.

In some embodiments, Form II can be isolated with a purity of at least about 80%, about 85%, about 90%, about 95%, about 96%, about 97%, about 98%, or about 99%. In some embodiments, Form II can be isolated with a purity greater than about 99%.

Compound 1 Di-HCl Form III

Provided herein is a solid form of Compound 1 di-HCl which is crystalline, referred to as Form III, which is described below in the Examples. In some embodiments, Form III has a molar ratio of Compound 1 to HCl that is about 1:2.

In some embodiments, Form III has an X-ray diffraction pattern comprising at least one characteristic peak in degrees 2θ selected from about 5.4°, about 16.8°, and about 21.9°. In some embodiments, Form III has an X-ray diffraction pattern comprising a characteristic peak in degrees 2θ at about 5.4°. In some embodiments, Form III has an X-ray diffraction pattern comprising a characteristic peak in degrees 2θ at about 16.8°. In some embodiments, Form III has an X-ray diffraction pattern comprising a characteristic peak in degrees 2θ at about 21.9°.

In some embodiments, Form III has an X-ray diffraction pattern comprising at least two characteristic peaks in degrees 2θ selected from about 5.4°, about 16.8°, and about 21.9°.

In some embodiments, Form III has an X-ray diffraction pattern comprising characteristic peaks in degrees 2θ at about 5.4°, about 16.8°, and about 21.9°.

In some embodiments, Form III has an X-ray diffraction pattern comprising at least four characteristic peaks in degrees 2θ selected from about 5.4°, about 16.8°, about 21.9°, about 27.7°, and about 28.6°. In some embodiments, Form III has an X-ray diffraction pattern comprising at least three characteristic peaks in degrees 2θ selected from about 5.4°, about 16.8°, about 21.9°, about 27.7°, and about 28.6°. In some embodiments, Form III has an X-ray diffraction pattern comprising at least two characteristic peaks in degrees 2θ selected from about 5.4°, about 16.8°, about 21.9°, about 27.7°, and about 28.6°. In some embodiments, Form III has an X-ray diffraction pattern comprising at least one characteristic peak in degrees 2θ selected from about 5.4°, about 16.8°, about 21.9°, about 27.7°, and about 28.6°.

In some embodiments, Form III has an X-ray diffraction pattern comprising at least four characteristic peaks in degrees 2θ selected from about 5.4°, about 6.7°, about 16.4°, about 16.8°, about 18.2°, about 19.5°, about 21.9°, about 22.2°, about 23.3°, about 27.4°, and about 28.6°. In some embodiments, Form III has an X-ray diffraction pattern comprising at least three characteristic peaks in degrees 2θ selected from about 5.4°, about 6.7°, about 16.4°, about 16.8°, about 18.2°, about 19.5°, about 21.9°, about 22.2°, about 23.3°, about 27.4°, and about 28.6°. In some embodiments, Form III has an X-ray diffraction pattern comprising at least two characteristic peaks in degrees 2θ selected from about 5.4°, about 6.7°, about 16.4°, about 16.8°, about 18.2°, about 19.5°, about 21.9°, about 22.2°, about 23.3°, about 27.4°, and about 28.6°. In some embodiments, Form III has an X-ray diffraction pattern comprising at least one characteristic peak in degrees 2θ selected from about 5.4°, about 6.7°, about 16.4°, about 16.8°, about 18.2°, about 19.5°, about 21.9°, about 22.2°, about 23.3°, about 27.4°, and about 28.6°.

Figure 7:
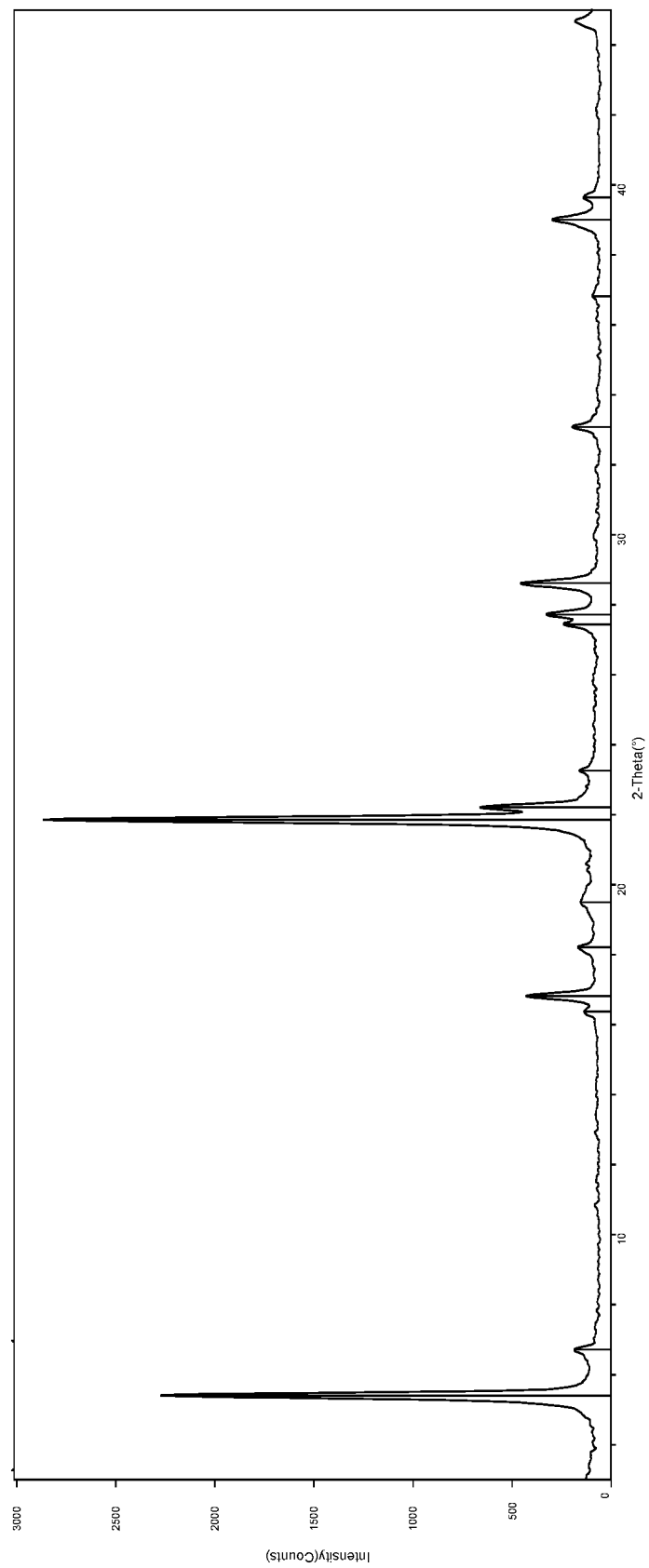
FIG. 7 shows an XRPD pattern of Compound 1 di-HCl, Form III.

In some embodiments, Form III has an XRPD pattern with characteristic peaks as substantially shown in FIG. 7.

Provided herein are also processes for preparing Form III comprising precipitating Compound 1 di-HCl from a solvent. In some embodiments, the solvent is a polar solvent. In some embodiments, the solvent is 1,4-dioxane. In some embodiments, the precipitating comprises stirring a solution of Compound 1 di-HCl in 1,4-dioxane for a period of time and filtering the mixture. In some embodiments, the period of time is greater than 12 h. In some embodiments, the period of time is greater than about 1 day. In some embodiments, the period of time is greater than about two days. In some embodiments, the period of time is about 2 days. In some embodiments, Form III can be isolated with a purity of at least about 80%, about 85%, about 90%, about 95%, about 96%, about 97%, about 98%, or about 99%. In some embodiments, Form III can be isolated with a purity greater than about 99%.

Compound 1 Di-HCl Form IV

Provided herein is a solid form of Compound 1 di-HCl which is crystalline, referred to as Form IV, which is described below in the Examples. In some embodiments, Form IV has a molar ratio of Compound 1 to HCl that is about 1:2.

In some embodiments, Form IV has an X-ray diffraction pattern comprising at least one characteristic peak in degrees 2θ selected from about 5.8°, about 17.4°, and about 18.3°. In some embodiments, Form IV has an X-ray diffraction pattern comprising a characteristic peak in degrees 2-theta at about 5.8°. In some embodiments, Form IV has an X-ray diffraction pattern comprising a characteristic peak in degrees 2-theta at about 17.4°. In some embodiments, Form IV has an X-ray diffraction pattern comprising a characteristic peak in degrees 2-theta at about 18.3°.

In some embodiments, Form IV has an X-ray diffraction pattern comprising at least two characteristic peaks in degrees 2θ selected from about 5.8°, about 17.4°, and about 18.3°.

In some embodiments, Form IV has an X-ray diffraction pattern comprising characteristic peaks in degrees 2θ selected from about 5.8°, about 17.4°, and about 18.3°.

In some embodiments, Form IV has an X-ray diffraction pattern comprising at least four characteristic peaks in degrees 2θ selected from about 5.8°, about 17.4°, about 18.3°, about 20.9°, about 22.5°, and about 26.9°. In some embodiments, Form IV has an X-ray diffraction pattern comprising at least three characteristic peaks in degrees 2θ selected from about 5.8°, about 17.4°, about 18.3°, about 20.9°, about 22.5°, and about 26.9°. In some embodiments, Form IV has an X-ray diffraction pattern comprising at least two characteristic peaks in degrees 2θ selected from about 5.8°, about 17.4°, about 18.3°, about 20.9°, about 22.5°, and about 26.9°. In some embodiments, Form IV has an X-ray diffraction pattern comprising at least one characteristic peak in degrees 2θ selected from about 5.8°, about 17.4°, about 18.3°, about 20.9°, about 22.5°, and about 26.9°.

In some embodiments, Form IV has an X-ray diffraction pattern comprising at least four characteristic peaks in degrees 2θ selected from about 5.8°, about 17.4°, about 18.3°, about 20.9°, about 21.4°, about 22.5°, about 24.2°, about 25.6°, and about 26.9°. In some embodiments, Form IV has an X-ray diffraction pattern comprising at least three characteristic peaks in degrees 2θ selected from about 5.8°, about 17.4°, about 18.3°, about 20.9°, about 21.4°, about 22.5°, about 24.2°, about 25.6°, and about 26.9°. In some embodiments, Form IV has an X-ray diffraction pattern comprising at least two characteristic peaks in degrees 2θ selected from about 5.8°, about 17.4°, about 18.3°, about 20.9°, about 21.4°, about 22.5°, about 24.2°, about 25.6°, and about 26.9°. In some embodiments, Form IV has an X-ray diffraction pattern comprising at least one characteristic peak in degrees 2θ selected from about 5.8°, about 17.4°, about 18.3°, about 20.9°, about 21.4°, about 22.5°, about 24.2°, about 25.6°, and about 26.9°.

Figure 8:
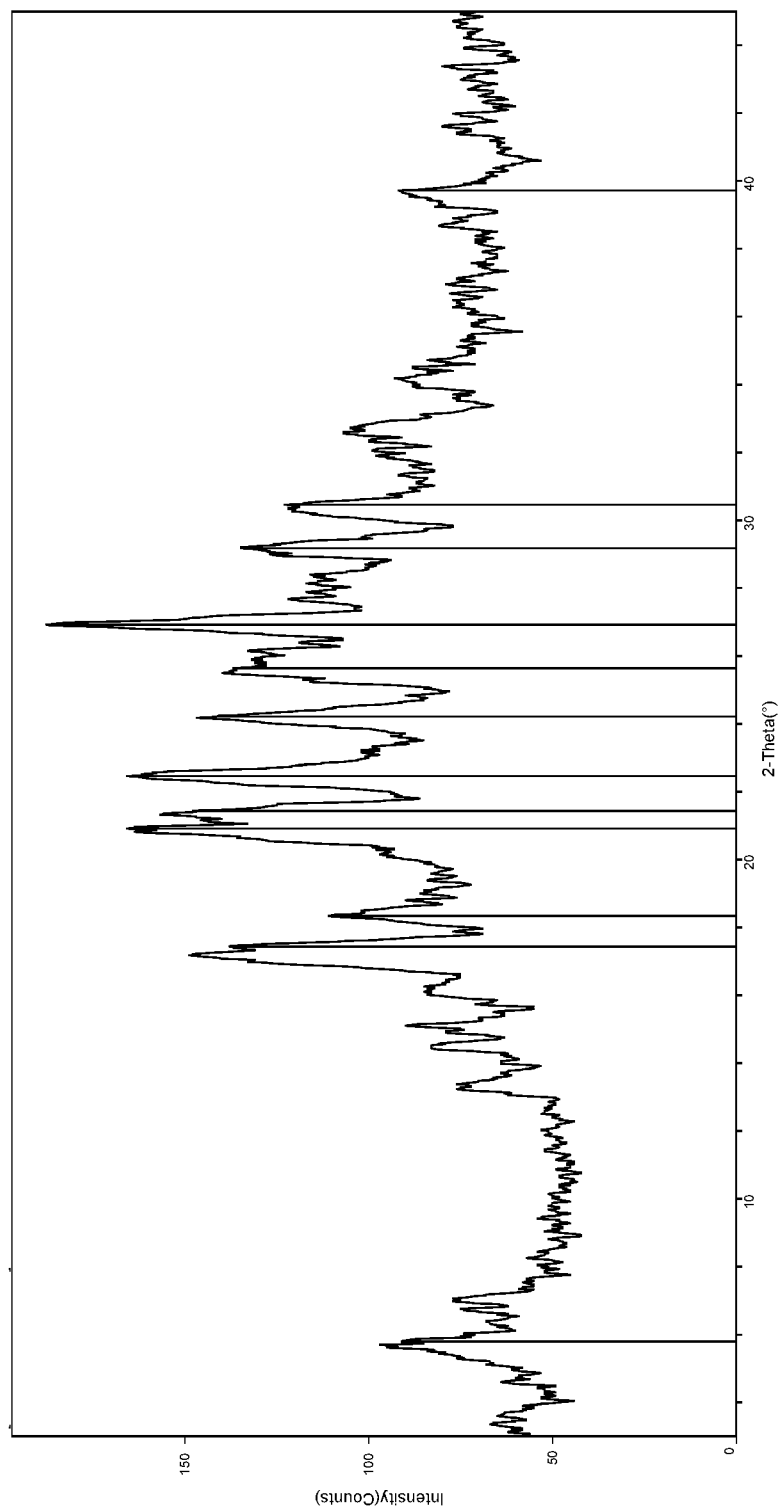
FIG. 8 shows an XRPD pattern of Compound 1 di-HCl, Form IV.

In some embodiments, Form IV has an XRPD pattern with characteristic peaks as substantially shown in FIG. 8.

Provided herein are also processes for preparing Form IV comprising precipitating Compound 1 di-HCl from a solvent. In some embodiments, the solvent is a non-polar aromatic solvent. In some embodiments, the solvent is toluene. In some embodiments, the precipitating comprises stirring a solution of Compound 1 di-HCl in toluene for a period of time and filtering the mixture. In some embodiments, the period of time is greater than 12 h. In some embodiments, the period of time is greater than about 1 day. In some embodiments, the period of time is greater than about two days. In some embodiments, the period of time is about 2 days.

In some embodiments, Form IV can be isolated with a purity of at least about 80%, about 85%, about 90%, about 95%, about 96%, about 97%, about 98%, or about 99%. In some embodiments, Form IV can be isolated with a purity greater than about 99%.

Compound 1 Di-HCl Form V

Provided herein is a solid form of Compound 1 di-HCl which is crystalline, referred to as Form V, which is described below in the Examples. In some embodiments, Form V has a molar ratio of Compound 1 to HCl that is about 1:2.

In some embodiments, Form V has an X-ray diffraction pattern comprising at least one characteristic peak in degrees 2θ selected from about 5.4°, about 6.8°, and about 13.1°. In some embodiments, Form V has an X-ray diffraction pattern comprising a characteristic peak in degrees 2-theta at about 5.4°. In some embodiments, Form V has an X-ray diffraction pattern comprising a characteristic peak in degrees 2-theta at about 6.8°. In some embodiments, Form V has an X-ray diffraction pattern comprising a characteristic peak in degrees 2-theta at about 13.1°.

In some embodiments, Form V has an X-ray diffraction pattern comprising at least two characteristic peaks in degrees 2θ selected from about 5.4°, about 6.8°, and about 13.1°.

In some embodiments, Form V has an X-ray diffraction pattern comprising characteristic peaks in degrees 2θ at about 5.4°, about 6.8°, and about 13.1°.

In some embodiments, Form V has an X-ray diffraction pattern comprising at least four characteristic peaks in degrees 2θ selected from about 5.4°, about 6.8°, about 13.1°, about 15.2, and about 21.7°. In some embodiments, Form V has an X-ray diffraction pattern comprising at least three characteristic peaks in degrees 2θ selected from about 5.4°, about 6.8°, about 13.1°, about 15.2, and about 21.7°. In some embodiments, Form V has an X-ray diffraction pattern comprising at least two characteristic peaks in degrees 2θ selected from about 5.4°, about 6.8°, about 13.1°, about 15.2, and about 21.7°. In some embodiments, Form V has an X-ray diffraction pattern comprising at least one characteristic peak in degrees 2θ selected from about 5.4°, about 6.8°, about 13.1°, about 15.2, and about 21.7°.

In some embodiments, Form V has an X-ray diffraction pattern comprising at least four characteristic peaks in degrees 2θ selected from about 4.1°, about 5.4°, about 6.8°, about 13.1°, about 15.2°, about 16.7°, about 17.3°, about 20.5°, about 21.7°, and about 25.6°. In some embodiments, Form V has an X-ray diffraction pattern comprising at least three characteristic peaks in degrees 2θ selected from about 4.1°, about 5.4°, about 6.8°, about 13.1°, about 15.2°, about 16.7°, about 17.3°, about 20.5°, about 21.7°, and about 25.6°. In some embodiments, Form V has an X-ray diffraction pattern comprising at least two characteristic peaks in degrees 2θ selected from about 4.1°, about 5.4°, about 6.8°, about 13.1°, about 15.2°, about 16.7°, about 17.3°, about 20.5°, about 21.7°, and about 25.6°. In some embodiments, Form V has an X-ray diffraction pattern comprising at least one characteristic peak in degrees 2θ selected from about 4.1°, about 5.4°, about 6.8°, about 13.1°, about 15.2°, about 16.7°, about 17.3°, about 20.5°, about 21.7°, and about 25.6°.

Figure 9:
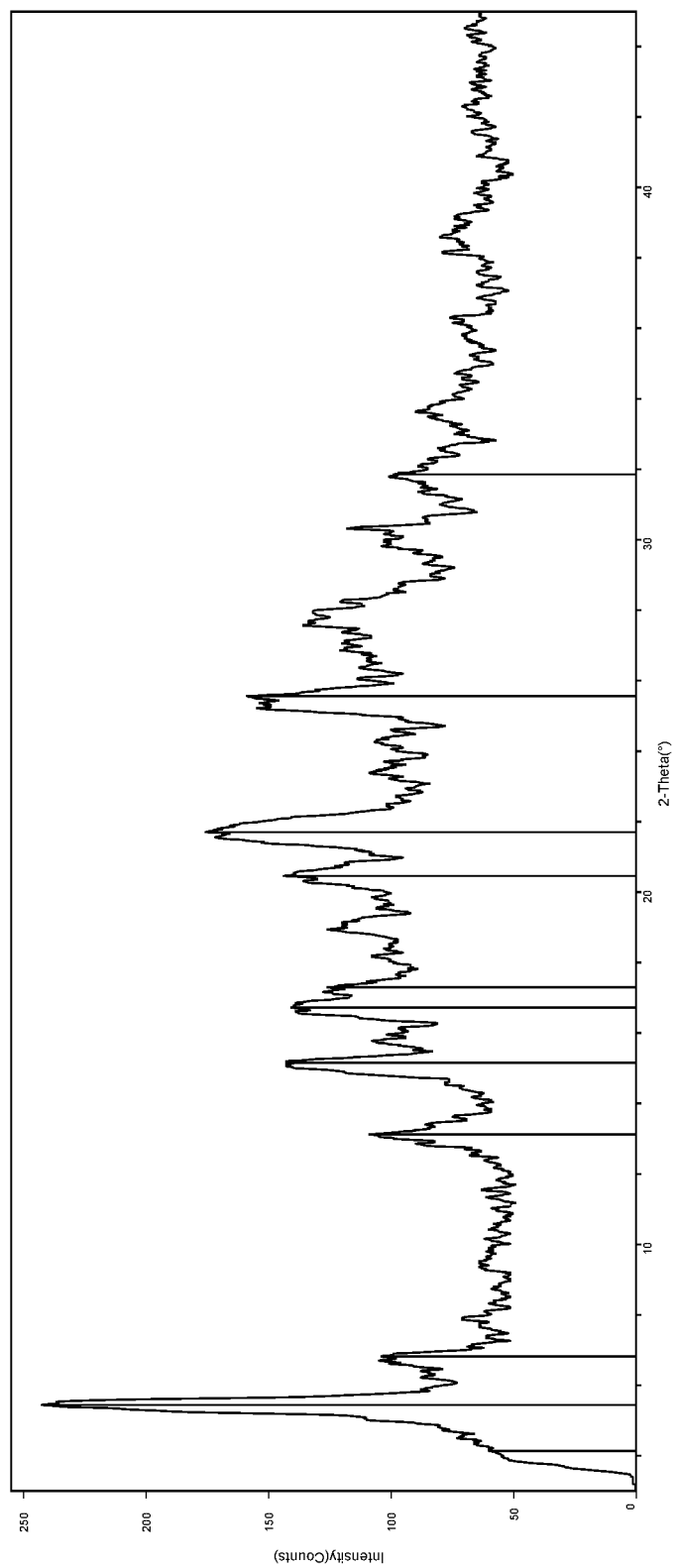
FIG. 9 shows an XRPD pattern of Compound 1 di-HCl, Form V.

In some embodiments, Form V has an XRPD pattern with characteristic peaks as substantially shown in FIG. 9.

Figure 10:
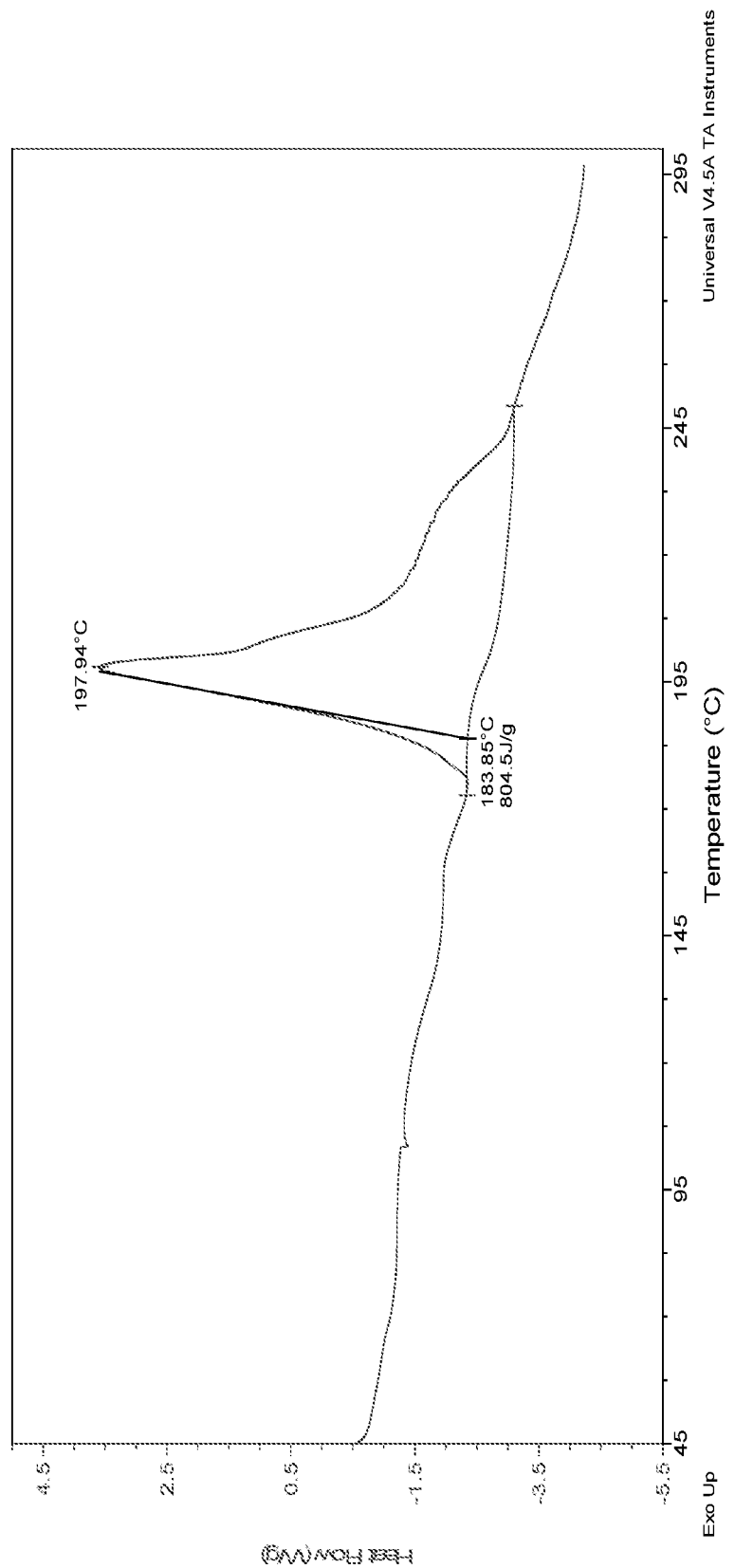
FIG. 10 shows a DSC thermogram of Compound 1 di-HCl, Form V.
Figure 11:
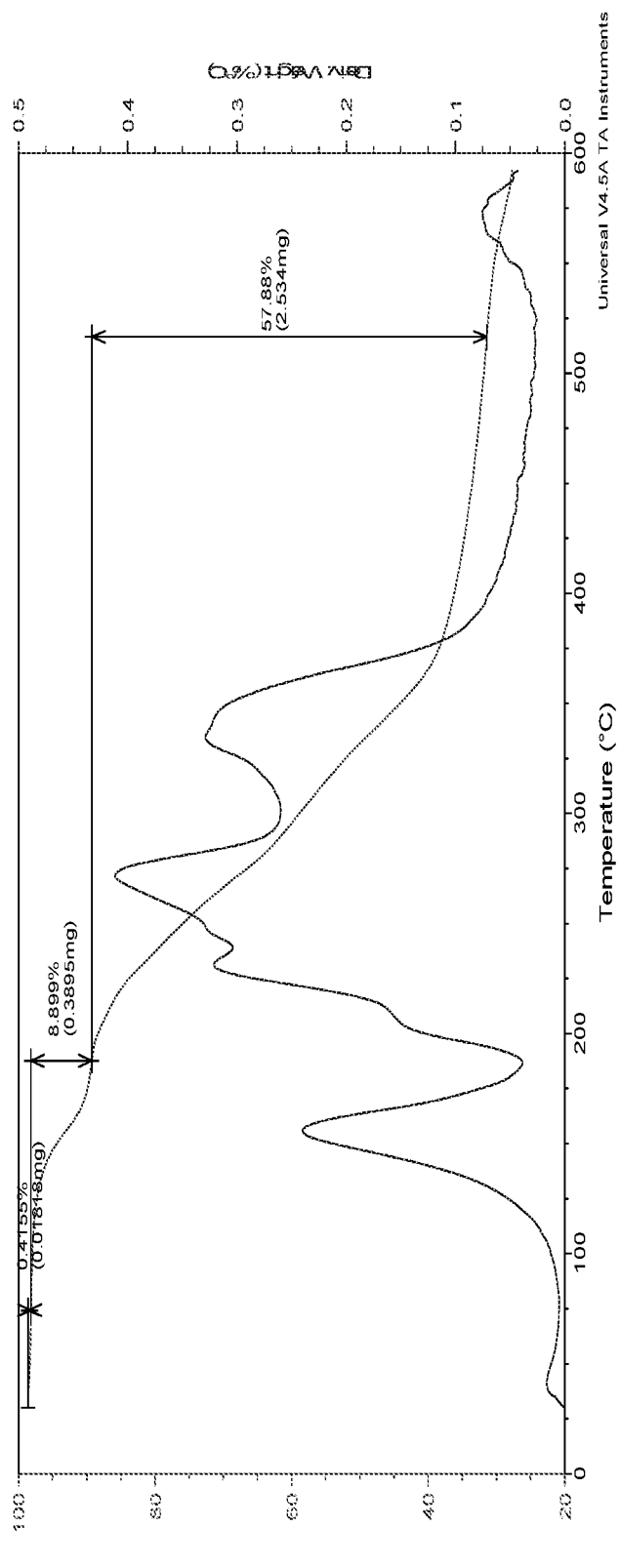
FIG. 11 shows a TGA thermogram of Compound 1 di-HCl, Form V.

In some embodiments, Form V has a DSC thermogram characterized by an exotherm peak at a temperature of about 198° C. In some embodiments, Form V has a DSC thermogram substantially as shown in FIG. 10. In some embodiments, Form V has a TGA thermogram substantially as shown in FIG. 11.

In some embodiments, Form V has an X-ray diffraction pattern comprising at least four characteristic peaks in degrees 2θ selected from about 5.4°, about 6.8°, about 13.1°, about 15.2, and about 21.7°; and Form V has a DSC thermogram characterized by an exotherm peak at a temperature of about 198° C.

Provided herein are also processes for preparing Form V comprising precipitating Compound 1 di-HCl from a solvent. In some embodiments, the solvent is an ether. In some embodiments, the solvent is MTBE. In some embodiments, the precipitating comprises stirring a solution of Compound 1 di-HCl in MTBE for a period of time and filtering the mixture. In some embodiments, the period of time is greater than 12 h. In some embodiments, the period of time is greater than about 1 day. In some embodiments, the period of time is greater than about two days. In some embodiments, the period of time is about 2 days.

In some embodiments, Form V can be isolated with a purity of at least about 80%, about 85%, about 90%, about 95%, about 96%, about 97%, about 98%, or about 99%. In some embodiments, Form V can be isolated with a purity greater than about 99%.

Compound 1 Mono-HCl

Provided herein is a solid form of Compound 1 mono-HCl which is crystalline and is described below in the Examples. In some embodiments, Compound 1 mono-HCl has a molar ratio of Compound 1 to HCl that is about 1:1.

Compound 1 mono-HCl can be prepared by any suitable method for the preparation of HCl acid addition salts. For example, Compound 1 can be combined with HCl (e.g., about 1.0 equiv or more) in a first solvent. In some embodiments, the first solvent is a mixture of dichloromethane and isopropanol. In certain embodiments, Compound 1 is combined with about 1 to about 2 molar equivalents of HCl. In certain embodiments, Compound 1 is combined with about 1.0 to about 1.1 molar equivalents of HCl. In certain embodiments, Compound 1 is combined with about 1.05 molar equivalents of HCl.

Compound 1 mono-HCl can then be isolated by partially evaporating the first solvent and then precipitating Compound 1 mono-HCl from a solution comprising Compound 1 mono-HCl and a second solvent. In some embodiments, the second solvent is isopropanol. In some embodiments, the second solvent is a mixture of isopropanol and dichloromethane. In some embodiments, precipitation is completed within about 2 hours, but longer and shorter periods are possible depending on the choice of solvent and temperature.

In some embodiments, Compound 1 mono-HCl has an X-ray diffraction pattern comprising at least one characteristic peak in degrees 2θ selected from about 10.3°, about 12.8°, and about 15.6°. In some embodiments, Compound 1 mono-HCl has an X-ray diffraction pattern in degrees 2θ comprising a characteristic peak at about 10.3°. In some embodiments, Compound 1 mono-HCl has an X-ray diffraction pattern comprising a characteristic peak in degrees 2θ at about 12.8°. In some embodiments, Compound 1 mono-HCl has an X-ray diffraction pattern comprising a characteristic peak in degrees 2θ at about 15.6°.

In some embodiments, Compound 1 mono-HCl has an X-ray diffraction pattern comprising at least two characteristic peaks in degrees 2θ selected from about 10.3°, about 12.8°, and about 15.6°.

In some embodiments, Compound 1 mono-HCl has an X-ray diffraction pattern comprising characteristic peaks in degrees 2θ selected from about 10.3°, about 12.8°, and about 15.6°.

In some embodiments, Compound 1 mono-HCl has an X-ray diffraction pattern comprising at least four characteristic peaks in degrees 2θ selected from about 10.3°, about 12.8°, about 15.6°, about 16.4°, about 21.5°, and about 25.7°. In some embodiments, Compound 1 mono-HCl has an X-ray diffraction pattern comprising at least three characteristic peaks in degrees 2θ selected from about 10.3°, about 12.8°, about 15.6°, about 16.4°, about 21.5°, and about 25.7°. In some embodiments, Compound 1 mono-HCl has an X-ray diffraction pattern comprising at least two characteristic peaks in degrees 2θ selected from about 10.3°, about 12.8°, about 15.6°, about 16.4°, about 21.5°, and about 25.7°. In some embodiments, Compound 1 mono-HCl has an X-ray diffraction pattern comprising at least one characteristic peak in degrees 2θ selected from about 10.3°, about 12.8°, about 15.6°, about 16.4°, about 21.5°, and about 25.7°.

In some embodiments, Compound 1 mono-HCl has an X-ray diffraction pattern comprising at least four characteristic peaks in degrees 2θ selected from about 10.3°, about 11.4°, about 12.1°, about 12.8°, about 14.2°, about 15.6°, about 16.4°, about 18.4°, about 21.5°, about 22.8°, about 23.5°, about 24.2°, and about 27.5°. In some embodiments, Compound 1 mono-HCl has an X-ray diffraction pattern comprising at least three characteristic peaks in degrees 2θ selected from about 10.3°, about 11.4°, about 12.1°, about 12.8°, about 14.2°, about 15.6°, about 16.4°, about 18.4°, about 21.5°, about 22.8°, about 23.5°, about 24.2°, and about 27.5°. In some embodiments, Compound 1 mono-HCl has an X-ray diffraction pattern comprising at least two characteristic peaks in degrees 2θ selected from about 10.3°, about 11.4°, about 12.1°, about 12.8°, about 14.2°, about 15.6°, about 16.4°, about 18.4°, about 21.5°, about 22.8°, about 23.5°, about 24.2°, and about 27.5°. In some embodiments, Compound 1 mono-HCl has an X-ray diffraction pattern comprising at least one characteristic peak in degrees 2θ selected from about 10.3°, about 11.4°, about 12.1°, about 12.8°, about 14.2°, about 15.6°, about 16.4°, about 18.4°, about 21.5°, about 22.8°, about 23.5°, about 24.2°, and about 27.5°.

Figure 18:
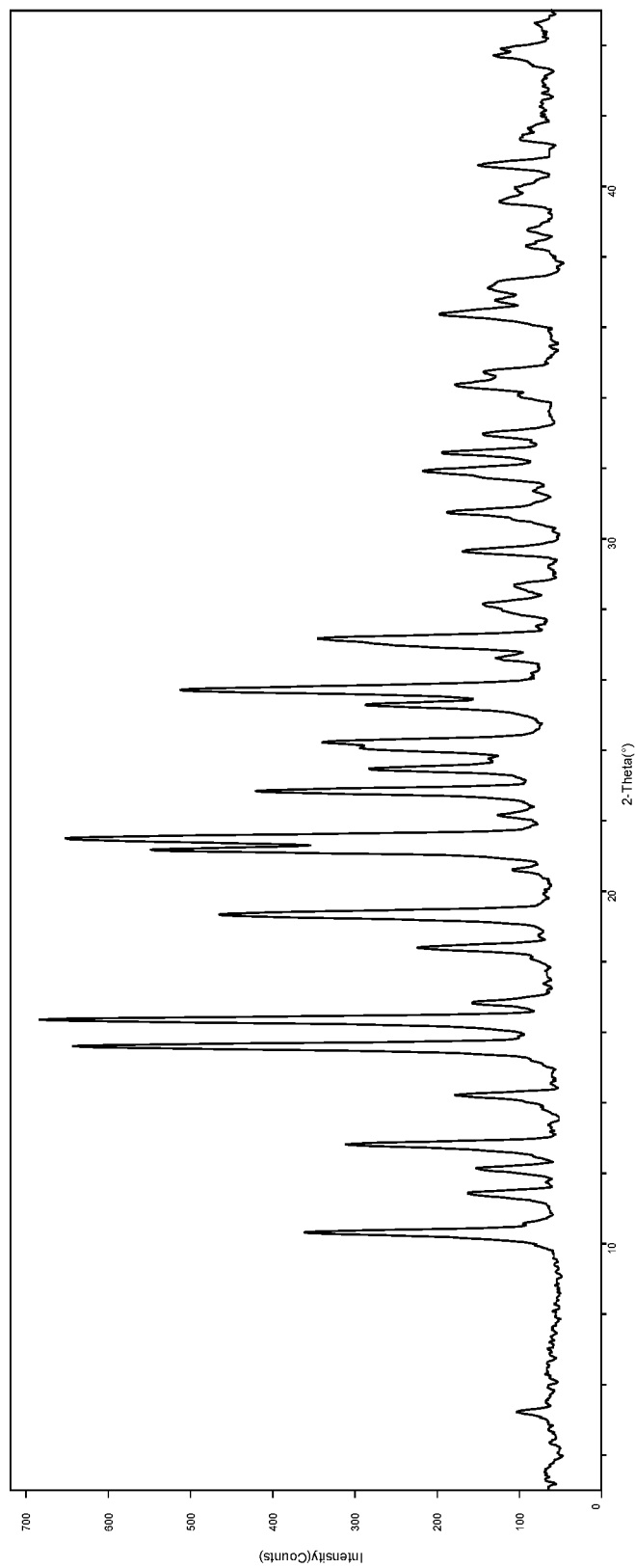
FIG. 18 shows an XRPD pattern of Compound 1 mono-HCl.

In some embodiments, Compound 1 mono-HCl has an XRPD pattern with characteristic peaks as substantially shown in FIG. 18.

Figure 19:
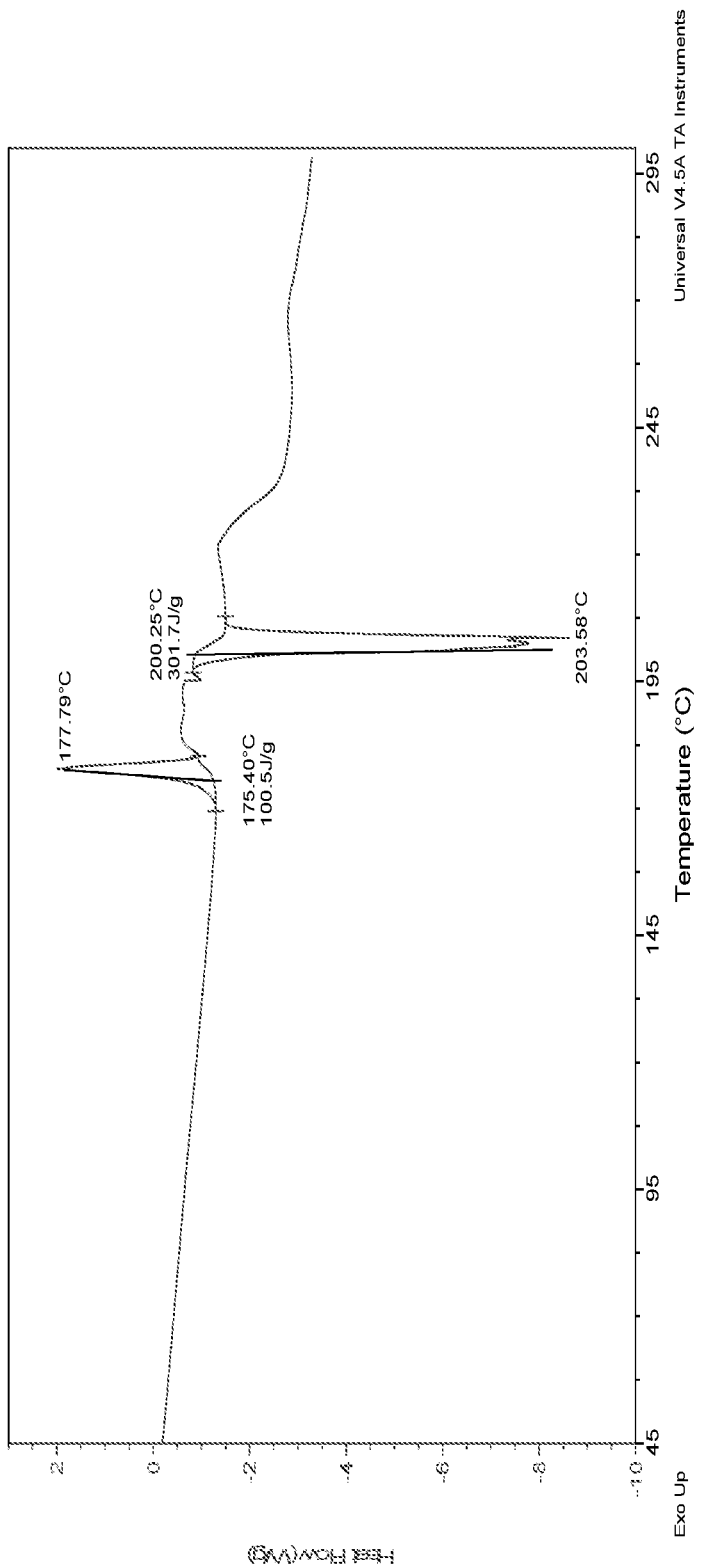
FIG. 19 shows a DSC thermogram of Compound 1 mono-HCl.
Figure 20:
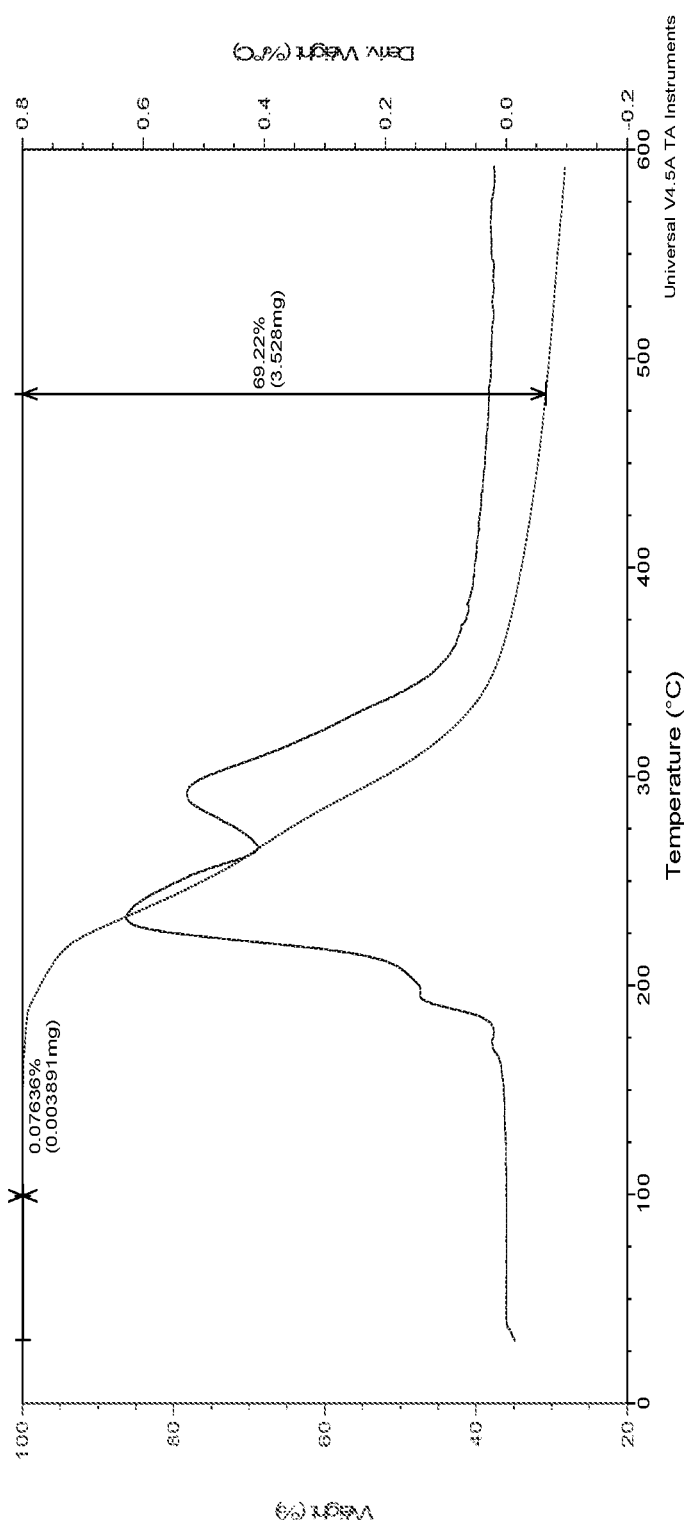
FIG. 20 shows a TGA thermogram of Compound 1 mono-HCl.

In some embodiments, Compound 1 mono-HCl has a DSC thermogram characterized by an exotherm peak at a temperature of about 178° C. and an endotherm peak at a temperature of about 204° C. In some embodiments, Compound 1 mono-HCl has a DSC thermogram characterized by an exotherm peak at a temperature of about 178° C. In some embodiments, Compound 1 mono-HCl has a DSC thermogram characterized by an endotherm peak at a temperature of about 200° C. In some embodiments, Compound 1 mono-HCl has a DSC thermogram substantially as shown in FIG. 19. In some embodiments, Compound 1 mono-HCl has a TGA thermogram substantially as shown in FIG. 20.

In some embodiments, Compound 1 mono-HCl has an X-ray diffraction pattern comprising at least four characteristic peaks in degrees 2θ selected from about 10.3°, about 12.8°, about 15.6°, about 16.4°, about 21.5°, and about 25.7°; and Compound 1 mono-HCl has a DSC thermogram characterized by an exotherm peak at a temperature of about 178° C. In some embodiments, Compound 1 mono-HCl has an X-ray diffraction pattern comprising at least four characteristic peaks in degrees 2θ selected from about 10.3°, about 12.8°, about 15.6°, about 16.4°, about 21.5°, and about 25.7°; and Compound 1 mono-HCl has a DSC thermogram characterized by an endotherm peak at a temperature of about 204° C.

In some embodiments, Compound 1 mono-HCl can be isolated with a purity of at least about 80%, about 85%, about 90%, about 95%, about 96%, about 97%, about 98%, or about 99%. In some embodiments, Compound 1 mono-HCl can be isolated with a purity greater than about 99%.

Compound 1 Di-Mesylate

Provided herein is a solid form of Compound 1 di-mesylate, which is crystalline and is described below in the Examples. In some embodiments, Compound 1 di-mesylate has a molar ratio of Compound 1 to methanesulfonic acid that is about 1:2.

Compound 1 di-mesylate can be prepared by any suitable method for the preparation of methanesulfonic acid addition salts. For example, Compound 1 can be combined with methanesulfonic acid (e.g., about 2 equiv or more) in a first solvent. In certain embodiments, Compound 1 is combined with about 2 to about 5 molar equivalents of methanesulfonic acid. In certain embodiments, Compound 1 is combined with about 2 to about 3 molar equivalents of methanesulfonic acid. In certain embodiments, Compound 1 is combined with about 2.5 molar equivalents of methanesulfonic acid. In some embodiments, the first solvent is a mixture of alcohols and dichloromethane. In some embodiments, the first solvent is a mixture of methanol and dichloromethane. In some embodiments, the first solvent is a mixture of methanol, isopropanol, and dichloromethane.

Compound 1 di-mesylate can then be isolated by partially evaporating the first solvent and then precipitating Compound 1 di-mesylate from a solution comprising Compound 1 di-mesylate and a second solvent. In some embodiments, the second solvent is methanol. In some embodiments, the second solvent is isopropanol. In some embodiments, the second solvent is a mixture of isopropanol and methanol. In some embodiments, the second solvent is a mixture of isopropanol, methanol, and dichloromethane. In some embodiments, precipitation is completed within about 2 hours, but longer and shorter periods are possible depending on the choice of solvent and temperature.

In some embodiments, Compound 1 di-mesylate has an X-ray diffraction pattern comprising at least one characteristic peak in degrees 2θ selected from about 3.9°, about 5.8°, and about 11.8°. In some embodiments, Compound 1 di-mesylate has an X-ray diffraction pattern comprising a characteristic peak in degrees 2θ at about 3.9°. In some embodiments, Compound 1 di-mesylate has an X-ray diffraction pattern comprising a characteristic peak in degrees 2θ at about 5.8°. In some embodiments, Compound 1 di-mesylate has an X-ray diffraction pattern comprising a characteristic peak in degrees 2θ at about 11.8°.

In some embodiments, Compound 1 di-mesylate has an X-ray diffraction pattern comprising at least two characteristic peaks in degrees 2θ selected from about 3.9°, about 5.8°, and about 11.8°.

In some embodiments, Compound 1 di-mesylate has an X-ray diffraction pattern comprising characteristic peaks in degrees 2θ selected from about 3.9°, about 5.8°, and about 11.8°.

In some embodiments, Compound 1 di-mesylate has an X-ray diffraction pattern comprising at least four characteristic peaks in degrees 2θ selected from about 3.9°, about 5.8°, about 11.8°, about 14.3°, about 15.8° and about 19.1°. In some embodiments, Compound 1 di-mesylate has an X-ray diffraction pattern comprising at least three characteristic peaks in degrees 2θ selected from about 3.9°, about 5.8°, about 11.8°, about 14.3°, about 15.8° and about 19.1°. In some embodiments, Compound 1 di-mesylate has an X-ray diffraction pattern comprising at least two characteristic peaks in degrees 2θ selected from about 3.9°, about 5.8°, about 11.8°, about 14.3°, about 15.8° and about 19.1°. In some embodiments, Compound 1 di-mesylate has an X-ray diffraction pattern comprising at least one characteristic peak in degrees 2θ selected from about 3.9°, about 5.8°, about 11.8°, about 14.3°, about 15.8° and about 19.1°.

In some embodiments, Compound 1 di-mesylate has an X-ray diffraction pattern comprising at least four characteristic peaks in degrees 2θ selected from about 3.9°, about 5.8°, about 11.8°, about 14.3°, about 15.8°, about 19.1°, about 20.2°, about 21.9°, about 22.8°, about 25.2°, and about 25.9°. In some embodiments, Compound 1 di-mesylate has an X-ray diffraction pattern comprising at least three characteristic peaks in degrees 2θ selected from about 3.9°, about 5.8°, about 11.8°, about 14.3°, about 15.8°, about 19.1°, about 20.2°, about 21.9°, about 22.8°, about 25.2°, and about 25.9°. In some embodiments, Compound 1 di-mesylate has an X-ray diffraction pattern comprising at least two characteristic peaks in degrees 2θ selected from about 3.9°, about 5.8°, about 11.8°, about 14.3°, about 15.8°, about 19.1°, about 20.2°, about 21.9°, about 22.8°, about 25.2°, and about 25.9°. In some embodiments, Compound 1 di-mesylate has an X-ray diffraction pattern comprising at least one characteristic peak in degrees 2θ selected from about 3.9°, about 5.8°, about 11.8°, about 14.3°, about 15.8°, about 19.1°, about 20.2°, about 21.9°, about 22.8°, about 25.2°, and about 25.9°.

Figure 12:
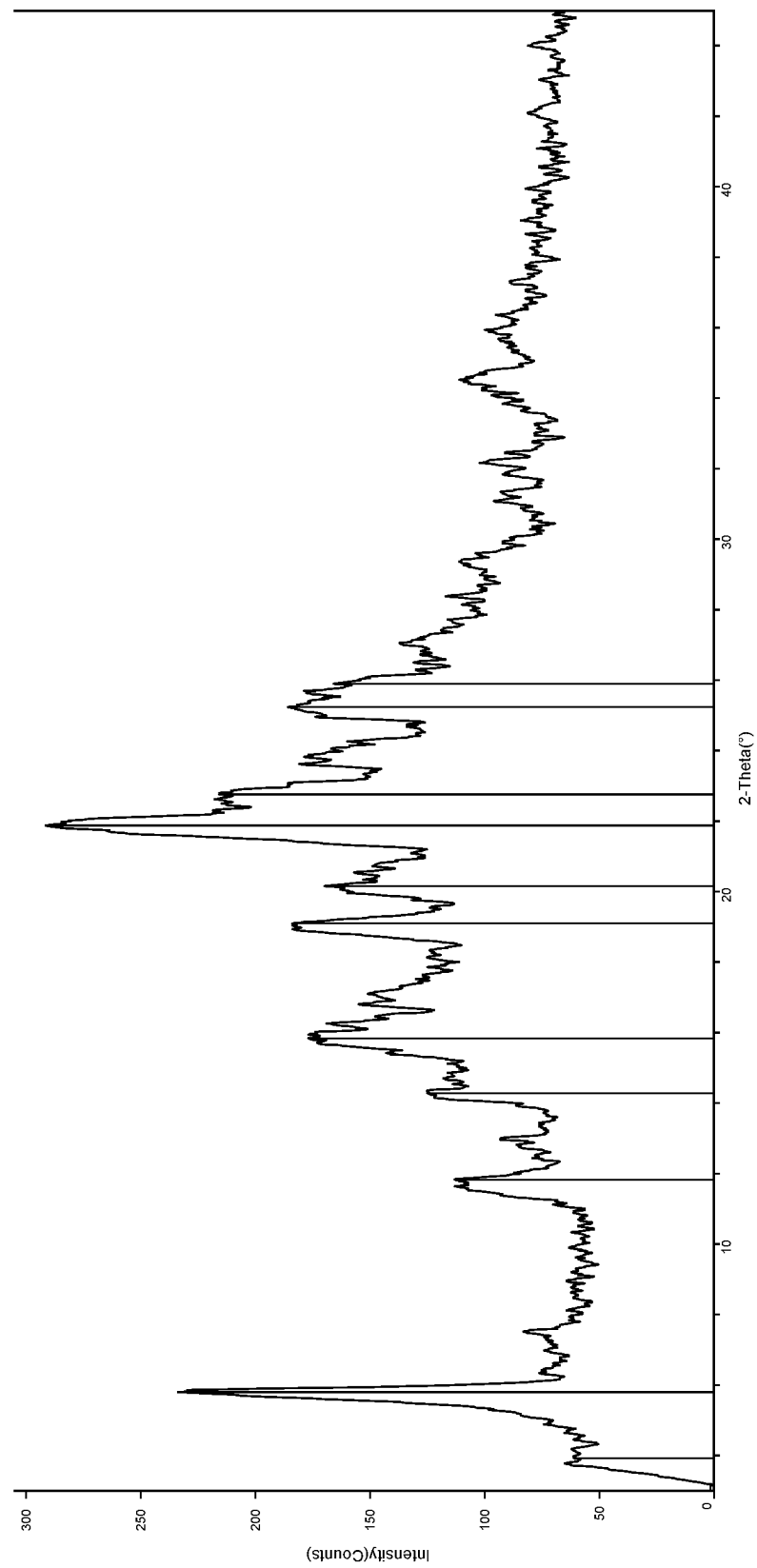
FIG. 12 shows an XRPD pattern of Compound 1 di-mesylate.

In some embodiments, Compound 1 di-mesylate has an XRPD pattern with characteristic peaks as substantially shown in FIG. 12.

Figure 13:
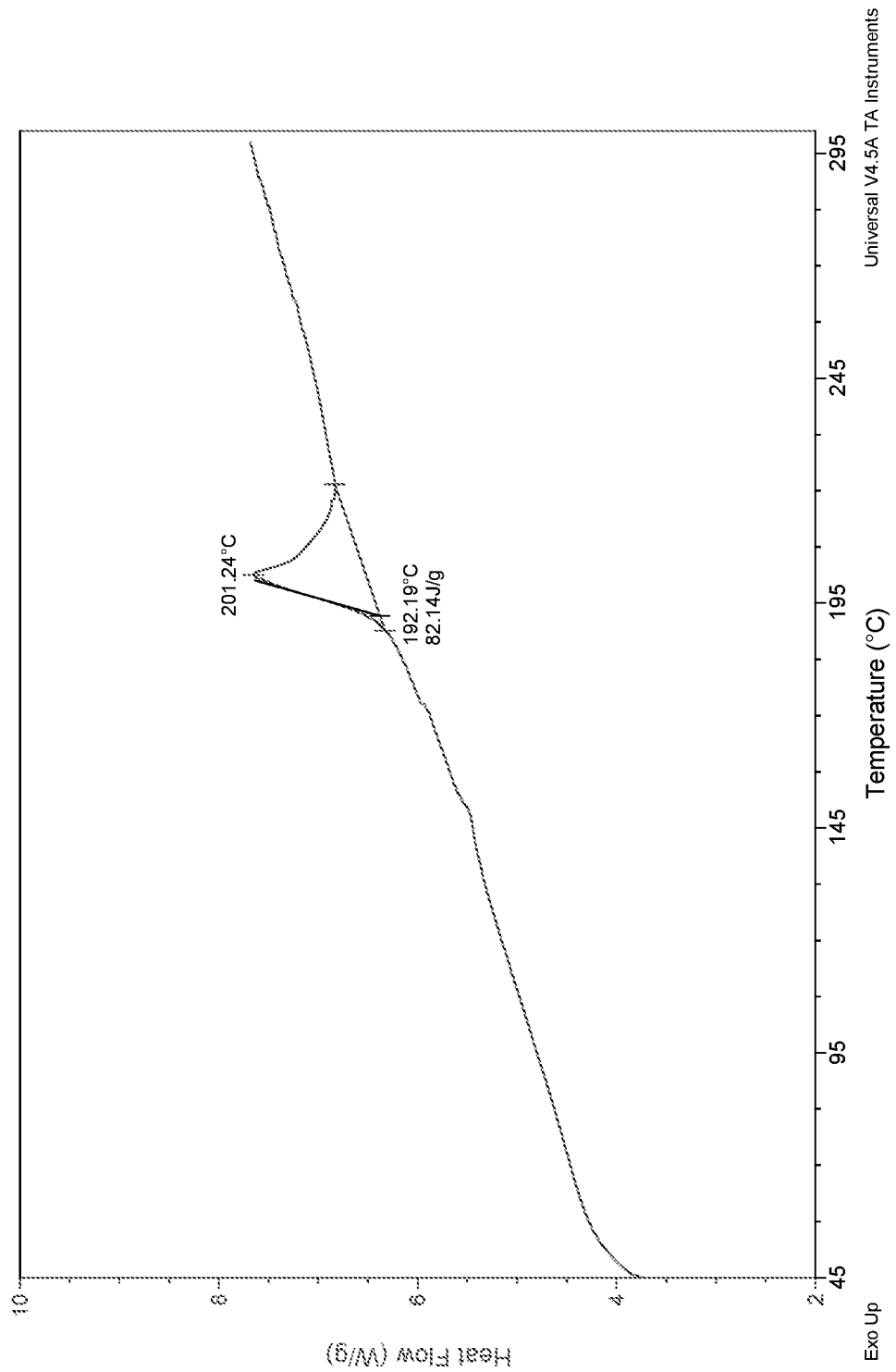
FIG. 13 shows a DSC thermogram of Compound 1 di-mesylate.
Figure 14:
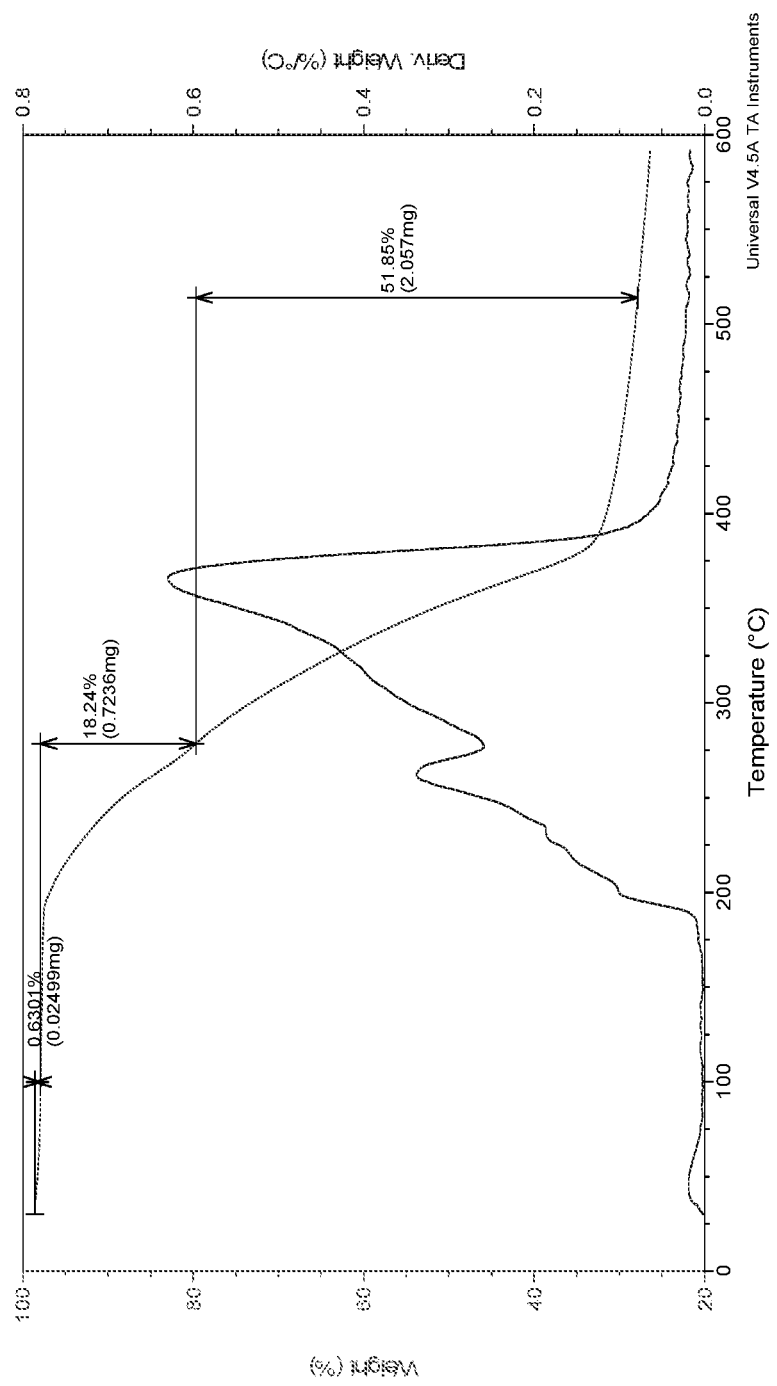
FIG. 14 shows a TGA thermogram of Compound 1 di-mesylate.

In some embodiments, Compound 1 di-mesylate has a DSC thermogram characterized by an exotherm peak at a temperature of about 201° C. In some embodiments, Compound 1 di-mesylate has a DSC thermogram substantially as shown in FIG. 13. In some embodiments, Compound 1 di-mesylate has a TGA thermogram substantially as shown in FIG. 14.

In some embodiments, Compound 1 di-mesylate has an X-ray diffraction pattern comprising at least four characteristic peaks in degrees 2θ selected from about 3.9°, about 5.8°, about 11.8°, about 14.3°, about 15.8° and about 19.1°; and Compound 1 di-mesylate has a DSC thermogram characterized by an exotherm peak at a temperature of about 201° C.

In some embodiments, Compound 1 di-mesylate can be isolated with a purity of at least about 80%, about 85%, about 90%, about 95%, about 96%, about 97%, about 98%, or about 99%. In some embodiments, Compound 1 di-mesylate can be isolated with a purity greater than about 99%.

Compound 1 Mono-Mesylate

Provided herein is a solid form of Compound 1 mono-mesylate, which is crystalline and is described below in the Examples. In some embodiments, Compound 1 mono-mesylate has a molar ratio of Compound 1 to methanesulfonic acid that is about 1:1.

Compound 1 mono-mesylate can be prepared by any suitable method for the preparation of methanesulfonic acid addition salts. For example, Compound 1 can be combined with methanesulfonic acid (e.g., about 1.0 equiv or more) in a solvent and the resulting salt can be isolated by filtering the salt from solution. In some embodiments, the resulting salt is isolated as crystalline Compound 1 mono-mesylate. In certain embodiments, Compound 1 is combined with about 1 to about 3 molar equivalents of methanesulfonic acid. In some embodiments, Compound 1 is combined with about 1 to about 2 molar equivalents of methanesulfonic acid. In certain embodiments, Compound 1 is combined with about 1.5 to about 2.5 molar equivalents of methanesulfonic acid. In certain embodiments, Compound 1 is combined with about 2.1 molar equivalents of methanesulfonic acid. In some embodiments, the solvent contains dichloromethane, methanol, ethanol, 1-propanol, or isopropanol. In some embodiments, the solvent is methanol. In some embodiments, the solvent is isopropanol. In some embodiments, the solvent is a mixture of methanol, isopropanol, and dichloromethane.

In some embodiments, Compound 1 mono-mesylate has an X-ray diffraction pattern comprising at least one characteristic peak in degrees 2θ selected from about 4.7°, about 9.5°, and about 14.5°. In some embodiments, Compound 1 mono-mesylate has an X-ray diffraction pattern comprising a characteristic peak in degrees 2θ at about 4.7°. In some embodiments, Compound 1 mono-mesylate has an X-ray diffraction pattern comprising a characteristic peak in degrees 2θ at about 9.5°. In some embodiments, Compound 1 mono-mesylate has an X-ray diffraction pattern comprising a characteristic peak in degrees 2θ at about 14.5°.

In some embodiments, Compound 1 mono-mesylate has an X-ray diffraction pattern comprising at least two characteristic peaks in degrees 2θ selected from about 4.7°, about 9.5°, and about 14.5°.

In some embodiments, Compound 1 mono-mesylate has an X-ray diffraction pattern comprising characteristic peaks in degrees 2θ selected from about 4.7°, about 9.5°, and about 14.5°.

In some embodiments, Compound 1 mono-mesylate has an X-ray diffraction pattern comprising at least four characteristic peaks in degrees 2θ selected from about 4.7°, about 9.5°, about 12.4°, about 14.5°, about 15.9°, about 16.6°, and about 18.6°, and about 21.8°. In some embodiments, Compound 1 mono-mesylate has an X-ray diffraction pattern comprising at least three characteristic peaks in degrees 2θ selected from about 4.7°, about 9.5°, about 12.4°, about 14.5°, about 15.9°, about 16.6°, about 18.6°, and about 21.8°. In some embodiments, Compound 1 mono-mesylate has an X-ray diffraction pattern comprising at least two characteristic peaks in degrees 2θ selected from about 4.7°, about 9.5°, about 12.4°, about 14.5°, about 15.9°, about 16.6°, about 18.6°, and about 21.8°. In some embodiments, Compound 1 mono-mesylate has an X-ray diffraction pattern comprising at least one characteristic peak in degrees 2θ selected from about 4.7°, about 9.5°, about 12.4°, about 14.5°, about 15.9°, about 16.6°, about 18.6°, and about 21.8°.

In some embodiments, Compound 1 mono-mesylate has an X-ray diffraction pattern comprising at least four characteristic peaks in degrees 2θ selected from about 4.7°, about 9.5°, about 12.4°, about 14.5°, about 15.9°, about 16.6°, about 17.8°, about 18.6°, about 19.2°, about 20.8°, about 21.8°, and about 22.6°. In some embodiments, Compound 1 mono-mesylate has an X-ray diffraction pattern comprising at least three characteristic peaks in degrees 2θ selected from about 4.7°, about 9.5°, about 12.4°, about 14.5°, about 15.9°, about 16.6°, about 17.8°, about 18.6°, about 19.2°, about 20.8°, about 21.8°, and about 22.6°. In some embodiments, Compound 1 mono-mesylate has an X-ray diffraction pattern comprising at least two characteristic peaks in degrees 2θ selected from about 4.7°, about 9.5°, about 12.4°, about 14.5°, about 15.9°, about 16.6°, about 17.8°, about 18.6°, about 19.2°, about 20.8°, about 21.8°, and about 22.6°. In some embodiments, Compound 1 mono-mesylate has an X-ray diffraction pattern comprising at least one characteristic peak in degrees 2θ selected from about 4.7°, about 9.5°, about 12.4°, about 14.5°, about 15.9°, about 16.6°, about 17.8°, about 18.6°, about 19.2°, about 20.8°, about 21.8°, and about 22.6°.

Figure 35:
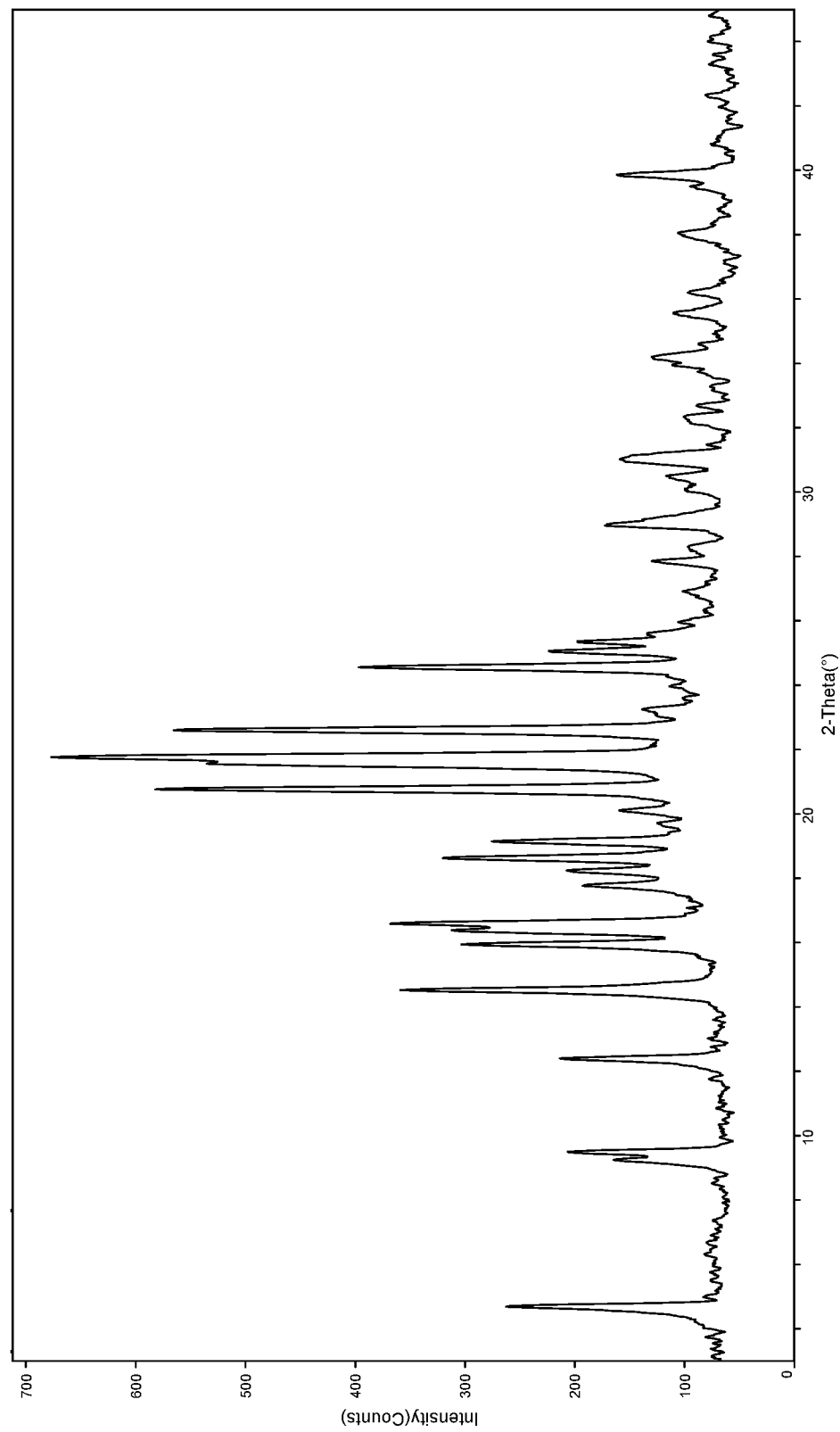
FIG. 35 shows an XRPD pattern of Compound 1 mono-mesylate.

In some embodiments, Compound 1 mono-mesylate has an XRPD pattern with characteristic peaks as substantially shown in FIG. 35.

Figure 36:
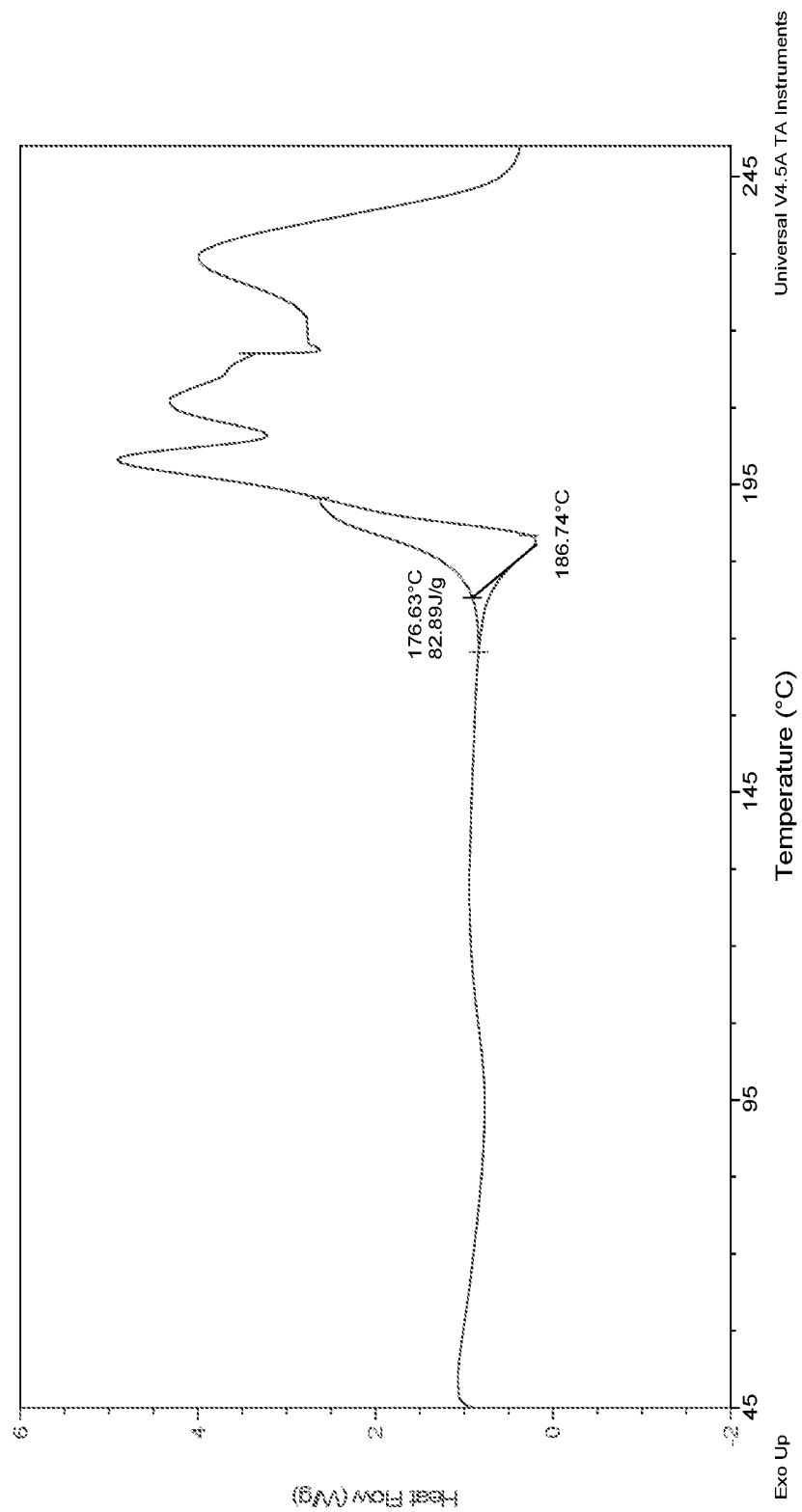
FIG. 36 shows a DSC thermogram of Compound 1 mono-mesylate.

In some embodiments, Compound 1 mono-mesylate has a DSC thermogram characterized by an endotherm peak at a temperature of about 187° C. In some embodiments, Compound 1 mono-mesylate has a DSC thermogram substantially as shown in FIG. 36.

In some embodiments, Compound 1 mono-mesylate has an X-ray diffraction pattern comprising at least four characteristic peaks in degrees 2θ selected from about 4.7°, about 9.5°, about 12.4°, about 14.5°, about 15.9°, about 16.6°, about 18.6°, and about 21.8°; and Compound 1 mono-mesylate has a DSC thermogram exhibiting an endotherm peak at a temperature of about 187° C.

In some embodiments, Compound 1 mono-mesylate can be isolated with a purity of at least about 80%, about 85%, about 90%, about 95%, about 96%, about 97%, about 98%, or about 99%. In some embodiments, Compound 1 mono-mesylate can be isolated with a purity greater than about 99%.

Compound 1 Malonate

Provided herein is a solid form of Compound 1 malonate which is crystalline and is described below in the Examples. In some embodiments, the solid form has a molar ratio of Compound 1 to malonic acid that is about 1:1.

Compound 1 malonate can be prepared by any suitable method for the preparation of malonic acid addition salts. For example, Compound 1 can be combined with malonic acid (e.g., about 1.0 equiv or more) in a first solvent. In some embodiments, Compound 1 is combined with about 1 to about 2 molar equivalents of malonic acid. In certain embodiments, Compound 1 is combined with about 2 to about 3 molar equivalents of malonic acid. In certain embodiments, Compound 1 is combined with about 2.5 molar equivalents of malonic acid. In some embodiments, the first solvent is a mixture of isopropanol and dichloromethane. In some embodiments, the first solvent is isopropanol. In some embodiments, the first solvent is dichloromethane.

Compound 1 malonate can then be isolated by partially evaporating the first solvent and then precipitating Compound 1 malonate from a solution comprising Compound 1 malonate and a second solvent. In some embodiments, the second solvent is isopropanol. In some embodiments, the second solvent is a mixture of isopropanol and dichloromethane. In some embodiments, precipitation is completed within about 2 hours, but longer and shorter periods are possible depending on the choice of solvent and temperature.

In some embodiments, Compound 1 malonate has an X-ray diffraction pattern comprising at least one characteristic peak in degrees 2θ selected from about 4.9°, about 13.1°, and about 14.8°. In some embodiments, Compound 1 malonate has an X-ray diffraction pattern comprising a characteristic peak in degrees 2θ at about 4.9°. In some embodiments, Compound 1 malonate has an X-ray diffraction pattern comprising a characteristic peak in degrees 2θ at about 13.1°. In some embodiments, Compound 1 malonate has an X-ray diffraction pattern comprising a characteristic peak in degrees 2θ at about 14.8°.

In some embodiments, Compound 1 malonate has an X-ray diffraction pattern comprising at least two characteristic peaks in degrees 2θ selected from about 4.9°, about 13.1°, and about 14.8°.

In some embodiments, Compound 1 malonate has an X-ray diffraction pattern comprising characteristic peaks in degrees 2θ selected from about 4.9°, about 13.1°, and about 14.8°.

In some embodiments, Compound 1 malonate has an X-ray diffraction pattern comprising at least four characteristic peaks in degrees 2θ selected from about 4.9°, about 13.1°, about 14.8°, about 16.1°, about 16.8°, about 17.7°, about 20.0°, and about 22.2°. In some embodiments, Compound 1 malonate has an X-ray diffraction pattern comprising at least three characteristic peaks in degrees 2θ selected from about 4.9°, about 13.1°, about 14.8°, about 16.1°, about 16.8°, about 17.7°, about 20.0°, and about 22.2°. In some embodiments, Compound 1 malonate has an X-ray diffraction pattern comprising at least two characteristic peaks in degrees 2θ selected from about 4.9°, about 13.1°, about 14.8°, about 16.1°, about 16.8°, about 17.7°, about 20.0°, and about 22.2°. In some embodiments, Compound 1 malonate has an X-ray diffraction pattern comprising at least one characteristic peak in degrees 2θ selected from about 4.9°, about 13.1°, about 14.8°, about 16.1°, about 16.8°, about 17.7°, about 20.0°, and about 22.2°.

In some embodiments, Compound 1 malonate has an X-ray diffraction pattern comprising at least four characteristic peaks in degrees 2θ selected from about 4.9°, about 13.1°, about 14.8°, about 15.4°, about 16.1°, about 16.8°, about 17.7°, about 18.3°, about 20.0°, about 22.2°, about 24.5°, and about 25.0°. In some embodiments, Compound 1 malonate has an X-ray diffraction pattern comprising at least three characteristic peaks in degrees 2θ selected from about 4.9°, about 13.1°, about 14.8°, about 15.4°, about 16.1°, about 16.8°, about 17.7°, about 18.3°, about 20.0°, about 22.2°, about 24.5°, and about 25.0°. In some embodiments, Compound 1 malonate has an X-ray diffraction pattern comprising at least two characteristic peaks in degrees 2θ selected from about 4.9°, about 13.1°, about 14.8°, about 15.4°, about 16.1°, about 16.8°, about 17.7°, about 18.3°, about 20.0°, about 22.2°, about 24.5°, and about 25.0°. In some embodiments, Compound 1 malonate has an X-ray diffraction pattern comprising at least one characteristic peak in degrees 2θ selected from about 4.9°, about 13.1°, about 14.8°, about 15.4°, about 16.1°, about 16.8°, about 17.7°, about 18.3°, about 20.0°, about 22.2°, about 24.5°, and about 25.0°. In some embodiments, Compound 1 malonate has an XRPD pattern with characteristic peaks as substantially shown in FIG. 15.

Figure 16:
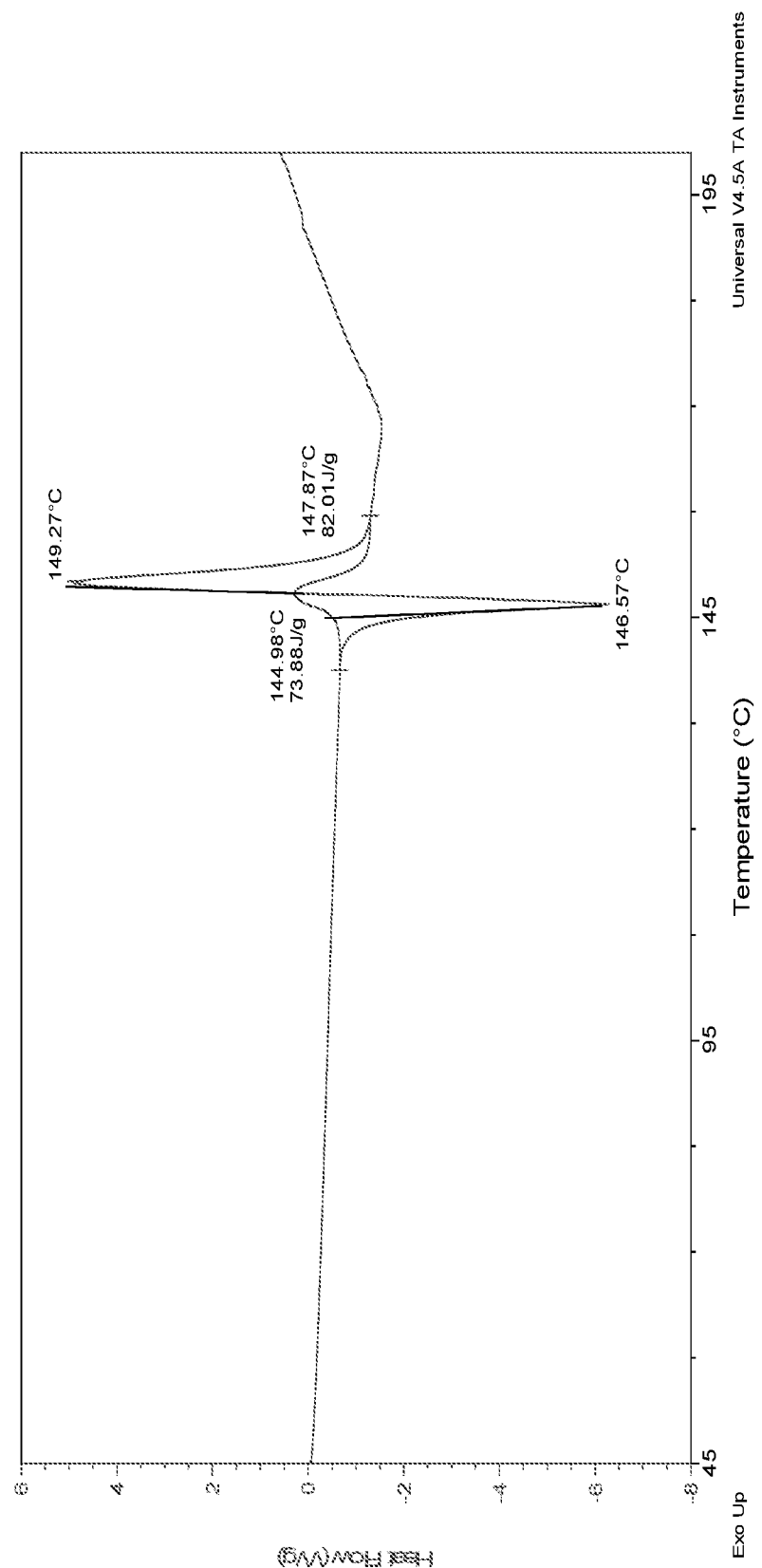
FIG. 16 shows a DSC thermogram of Compound 1 malonate.
Figure 17:
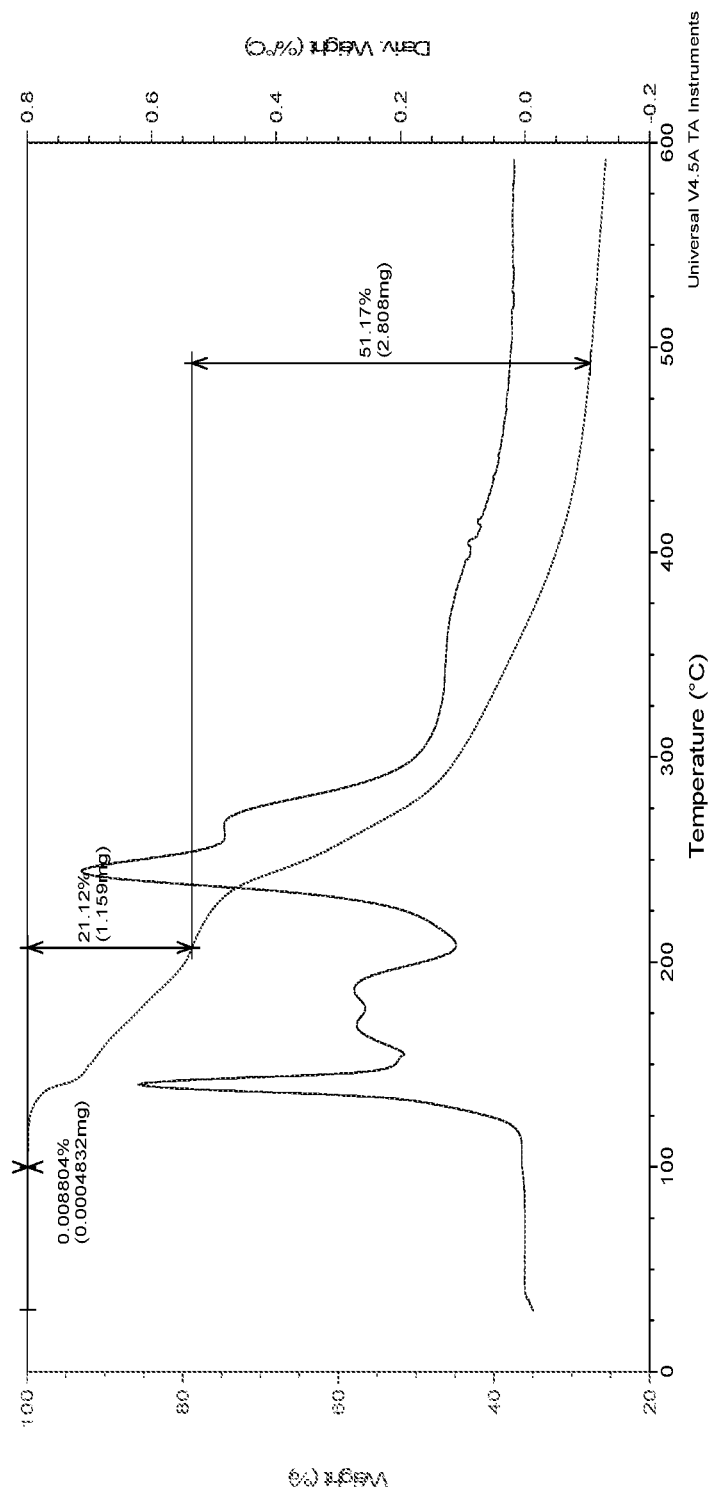
FIG. 17 shows a TGA thermogram of Compound 1 malonate.

In some embodiments, Compound 1 malonate has a DSC thermogram characterized by an endotherm peak at a temperature of about 147° C. and an exotherm peak at a temperature of about 149° C. In some embodiments, Compound 1 malonate has a DSC thermogram characterized by an endotherm peak at a temperature of about 147° C. In some embodiments, Compound 1 malonate has a DSC thermogram characterized by an exotherm peak at a temperature of about 149° C. In some embodiments, Compound 1 malonate has a DSC thermogram substantially as shown in FIG. 16. In some embodiments, Compound 1 malonate has a TGA thermogram substantially as shown in FIG. 17.

In some embodiments, Compound 1 malonate has an X-ray diffraction pattern comprising at least four characteristic peaks in degrees 2θ selected from about 4.9°, about 13.1°, about 14.8°, about 16.1°, about 16.8°, about 17.7°, about 20.0°, and about 22.2°; and Compound 1 malonate has a DSC thermogram characterized by an endotherm peak at a temperature of about 147° C. In some embodiments, Compound 1 malonate has an X-ray diffraction pattern comprising at least four characteristic peaks in degrees 2θ selected from about 4.9°, about 13.1°, about 14.8°, about 16.1°, about 16.8°, about 17.7°, about 20.0°, and about 22.2°; and Compound 1 malonate has a DSC thermogram characterized by an exotherm peak at a temperature of about 149° C.

In some embodiments, Compound 1 malonate can be isolated with a purity of at least about 80%, about 85%, about 90%, about 95%, about 96%, about 97%, about 98%, or about 99%. In some embodiments, Compound 1 malonate can be isolated with a purity greater than about 99%.

Compound 1 Esylate

Provided herein is a solid form of Compound 1 esylate which is crystalline and is described below in the Examples. In some embodiments, the solid form has a molar ratio of Compound 1 to ethanesulfonic acid that is about 1:1.

Compound 1 esylate can be prepared by any suitable method for the preparation of ethanesulfonic acid addition salts. For example, Compound 1 can be combined with ethanesulfonic acid (e.g., about 1.0 equiv or more) in a solvent and the resulting salt can be isolated by filtering the salt from solution. In some embodiments, the resulting salt is isolated as crystalline Compound 1 esylate. In certain embodiments, Compound 1 is combined with about 1 to about 2 molar equivalents of ethanesulfonic acid. In certain embodiments, Compound 1 is combined with about 1.0 to about 1.5 molar equivalents of ethanesulfonic acid. In certain embodiments, Compound 1 is combined with about 1.35 molar equivalents of ethanesulfonic acid. In some embodiments, the solvent is methanol. In some embodiments, the solvent is isopropanol. In some embodiments, the solvent is a mixture of methanol and isopropanol. In some embodiments, the solution is allowed to stir for about three hours before filtering.

In some embodiments, Compound 1 esylate has an X-ray diffraction pattern comprising at least one characteristic peak in degrees 2θ selected from about 4.7°, about 9.4°, and about 12.3°. In some embodiments, Compound 1 esylate has an X-ray diffraction pattern comprising a characteristic peak in degrees 2θ at about 4.7°. In some embodiments, Compound 1 esylate has an X-ray diffraction pattern comprising a characteristic peak in degrees 2θ at about 9.4°. In some embodiments, Compound 1 esylate has an X-ray diffraction pattern comprising a characteristic peak in degrees 2θ at about 12.3°.

In some embodiments, Compound 1 esylate has an X-ray diffraction pattern comprising at least two characteristics peak in degrees 2θ selected from about 4.7°, about 9.4°, and about 12.3°.

In some embodiments, Compound 1 esylate has an X-ray diffraction pattern comprising characteristic peaks in degrees 2θ at about 4.7°, about 9.4°, and about 12.3°.

In some embodiments, Compound 1 esylate has an X-ray diffraction pattern comprising at least four characteristics peaks in degrees 2θ selected from about 4.7°, about 9.4°, about 12.3°, about 16.1°, about 16.7°, about 18.9°, about 20.5°, and about 21.7°. In some embodiments, Compound 1 esylate has an X-ray diffraction pattern comprising at least three characteristics peaks in degrees 2θ selected from about 4.7°, about 9.4°, about 12.3°, about 16.1°, about 16.7°, about 18.9°, about 20.5°, and about 21.7°. In some embodiments, Compound 1 esylate has an X-ray diffraction pattern comprising at least two characteristics peaks in degrees 2θ selected from about 4.7°, about 9.4°, about 12.3°, about 16.1°, about 16.7°, about 18.9°, about 20.5°, and about 21.7°. In some embodiments, Compound 1 esylate has an X-ray diffraction pattern comprising at least one characteristics peak in degrees 2θ selected from about 4.7°, about 9.4°, about 12.3°, about 16.1°, about 16.7°, about 18.9°, about 20.5°, and about 21.7°.

In some embodiments, Compound 1 esylate has an X-ray diffraction pattern comprising at least four characteristics peaks in degrees 2θ selected from about 4.7°, about 9.4°, about 12.3°, about 14.7°, about 16.1°, about 16.7°, about 18.0°, about 18.9°, about 20.5°, about 21.7°, about 22.8°, and about 24.6°. In some embodiments, Compound 1 esylate has an X-ray diffraction pattern comprising at least three characteristics peaks in degrees 2θ selected from about 4.7°, about 9.4°, about 12.3°, about 14.7°, about 16.1°, about 16.7°, about 18.0°, about 18.9°, about 20.5°, about 21.7°, about 22.8°, and about 24.6°. In some embodiments, Compound 1 esylate has an X-ray diffraction pattern comprising at least two characteristics peaks in degrees 2θ selected from about 4.7°, about 9.4°, about 12.3°, about 14.7°, about 16.1°, about 16.7°, about 18.0°, about 18.9°, about 20.5°, about 21.7°, about 22.8°, and about 24.6°. In some embodiments, Compound 1 esylate has an X-ray diffraction pattern comprising at least one characteristics peak in degrees 2θ selected from about 4.7°, about 9.4°, about 12.3°, about 14.7°, about 16.1°, about 16.7°, about 18.0°, about 18.9°, about 20.5°, about 21.7°, about 22.8°, and about 24.6°.

Figure 21:
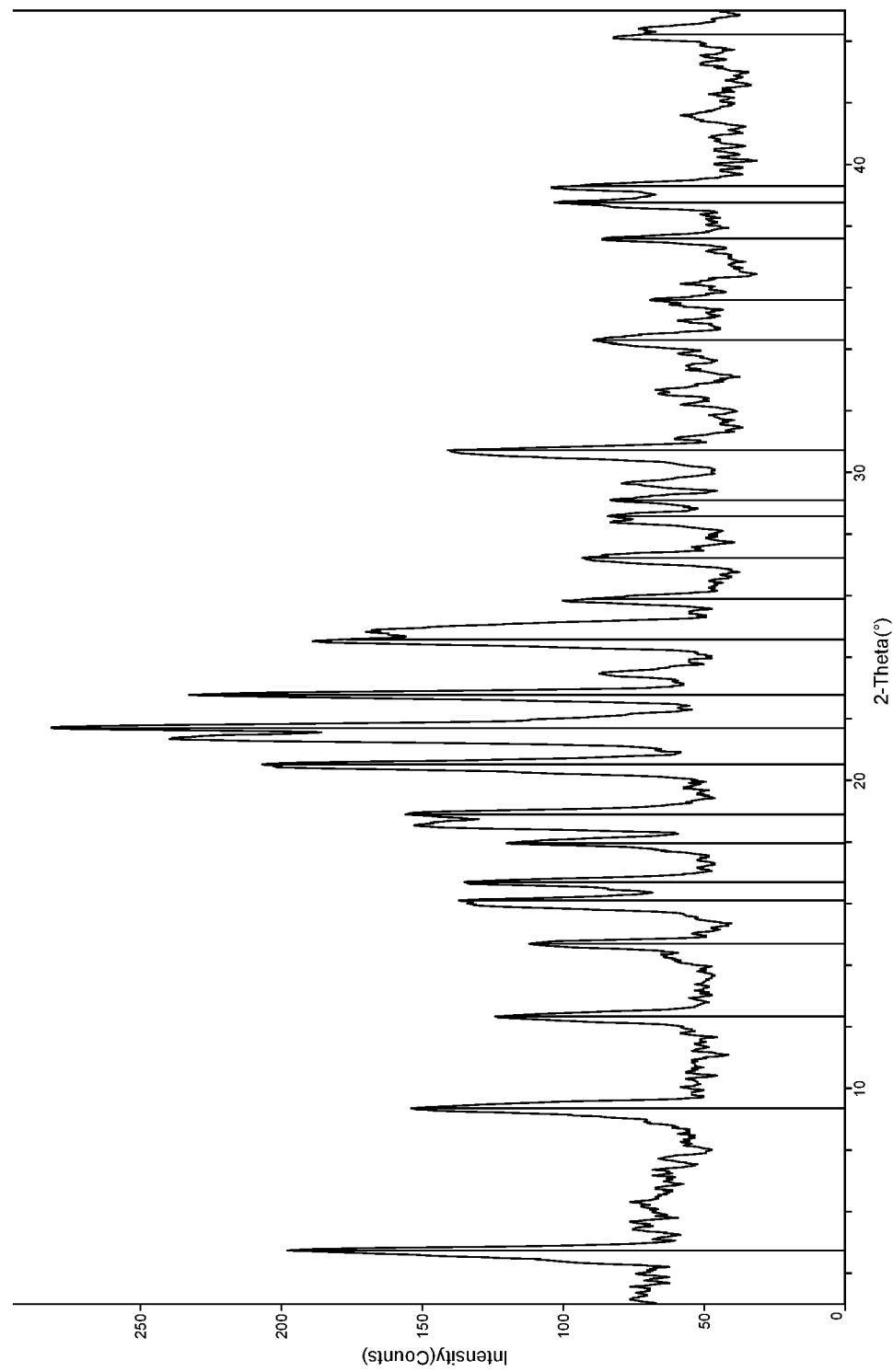
FIG. 21 shows an XRPD pattern of Compound 1 esylate.

In some embodiments, Compound 1 esylate has an XRPD pattern with characteristic peaks as substantially shown in FIG. 21.

Figure 22:
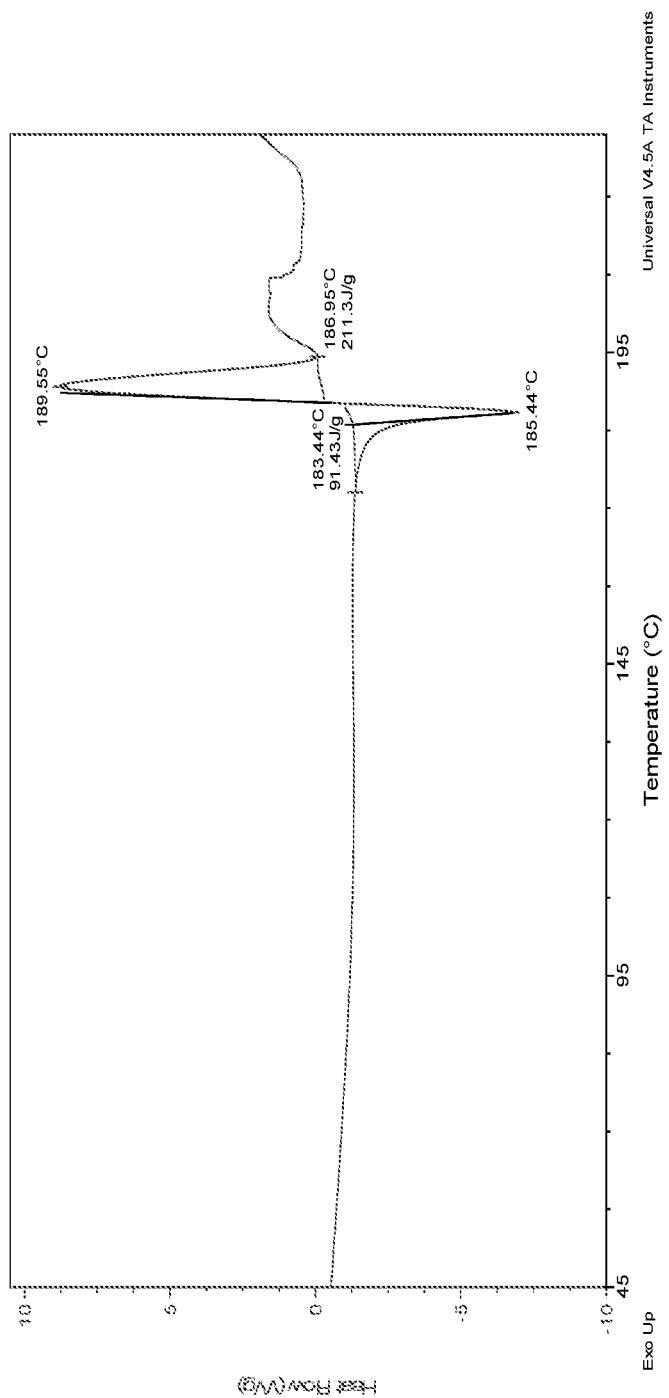
FIG. 22 shows a DSC thermogram of Compound 1 esylate.
Figure 23:
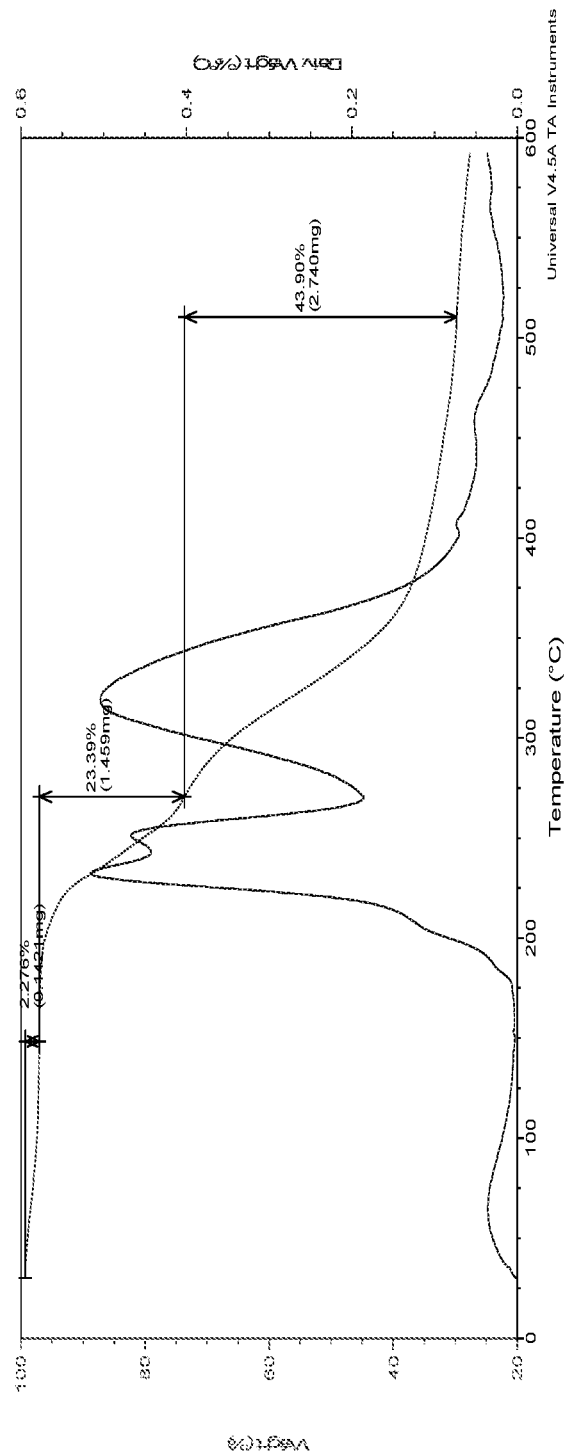
FIG. 23 shows a TGA thermogram of Compound 1 esylate.

In some embodiments, Compound 1 esylate has a DSC thermogram characterized by an endotherm peak at a temperature of about 185° C. and an exotherm peak at a temperature of about 190° C. In some embodiments, Compound 1 esylate has a DSC thermogram characterized by an endotherm peak at a temperature of about 185° C. In some embodiments, Compound 1 esylate has a DSC thermogram characterized by an exotherm peak at a temperature of about 190° C. In some embodiments, Compound 1 esylate has a DSC thermogram substantially as shown in FIG. 22. In some embodiments, Compound 1 esylate has a TGA thermogram substantially as shown in FIG. 23.

In some embodiments, Compound 1 esylate has an X-ray diffraction pattern comprising at least four characteristics peaks in degrees 2θ selected from about 4.7°, about 9.4°, about 12.3°, about 16.1°, about 16.7°, about 18.9°, about 20.5°, and about 21.7°; and Compound 1 esylate has a DSC thermogram characterized by an endotherm peak at a temperature of about 185° C. In some embodiments, Compound 1 esylate has an X-ray diffraction pattern comprising at least four characteristics peaks in degrees 2θ selected from about 4.7°, about 9.4°, about 12.3°, about 16.1°, about 16.7°, about 18.9°, about 20.5°, and about 21.7°; and Compound 1 esylate has a DSC thermogram characterized by an exotherm peak at a temperature of about 190° C.

In some embodiments, Compound 1 esylate can be isolated with a purity of at least about 80%, about 85%, about 90%, about 95%, about 96%, about 97%, about 98%, or about 99%. In some embodiments, Compound 1 esylate can be isolated with a purity greater than about 99%.

Compound 1 Maleate

Provided herein is a solid form of Compound 1 maleate which is crystalline and is described below in the Examples. In some embodiments, the solid form has a molar ratio of Compound 1 to maleic acid that is about 1:1.

Compound 1 maleate can be prepared by any suitable method for the preparation of maleic acid addition salts. For example, Compound 1 can be combined with maleic acid (e.g., about 1.0 equiv or more) in a first solvent. In certain embodiments, Compound 1 is combined with about 1 to about 2 molar equivalents of maleic acid. In certain embodiments, Compound 1 is combined with about 1.0 to about 1.5 molar equivalents of maleic acid. In certain embodiments, Compound 1 is combined with about 1.35 molar equivalents of maleic acid. In some embodiments, the first solvent is methanol. In some embodiments, the first solvent is isopropanol. In some embodiments, the first solvent is a mixture of methanol and isopropanol.

Compound 1 maleate can then be isolated by partially evaporating the first solvent and then precipitating Compound 1 maleate from a solution comprising Compound 1 maleate and a second solvent. In some embodiments, the second solvent is isopropanol. In some embodiments, the second solvent is a mixture of isopropanol and methanol. In some embodiments, precipitation is completed within about 2 hours, but longer and shorter periods are possible depending on the choice of solvent and temperature.

In some embodiments, Compound 1 maleate has an X-ray diffraction pattern comprising at least one characteristic peak in degrees 2θ selected from about 3.8°, about 11.5°, and about 15.3°. In some embodiments, Compound 1 maleate has an X-ray diffraction pattern comprising a characteristic peak in degrees 2θ at about 3.8°. In some embodiments, Compound 1 maleate has an X-ray diffraction pattern comprising a characteristic peak in degrees 2θ at about 11.5°. In some embodiments, Compound 1 maleate has an X-ray diffraction pattern comprising a characteristic peak in degrees 2θ at about 15.3°.

In some embodiments, Compound 1 maleate has an X-ray diffraction pattern comprising at least two characteristic peaks in degrees 2θ selected from about 3.8°, about 11.5°, and about 15.3°.

In some embodiments, Compound 1 maleate has an X-ray diffraction pattern comprising characteristic peaks in degrees 2θ at about 3.8°, about 11.5°, and about 15.3°.

In some embodiments, Compound 1 maleate has an X-ray diffraction pattern comprising at least four characteristic peaks in degrees 2θ selected from about 3.8°, about 9.9°, about 11.5°, about 15.3°, about 16.3°, about 18.4°, about 19.0°, about 19.6°, and about 20.7°. In some embodiments, Compound 1 maleate has an X-ray diffraction pattern comprising at least three characteristic peaks in degrees 2θ selected from about 3.8°, about 9.9°, about 11.5°, about 15.3°, about 16.3°, about 18.4°, about 19.0°, about 19.6°, and about 20.7°. In some embodiments, Compound 1 maleate has an X-ray diffraction pattern comprising at least two characteristic peaks in degrees 2θ selected from about 3.8°, about 9.9°, about 11.5°, about 15.3°, about 16.3°, about 18.4°, about 19.0°, about 19.6°, and about 20.7°. In some embodiments, Compound 1 maleate has an X-ray diffraction pattern comprising at least one characteristic peak in degrees 2θ selected from about 3.8°, about 9.9°, about 11.5°, about 15.3°, about 16.3°, about 18.4°, about 19.0°, about 19.6°, and about 20.7°. In some embodiments, Compound 1 maleate has an X-ray diffraction pattern comprising at least four characteristic peaks in degrees 2θ selected from about 3.8°, about 9.9°, about 11.5°, about 15.3°, about 16.3°, about 18.4°, about 19.0°, about 19.6°, about 20.7°, about 21.5°, about 22.9°, about 24.7°, and about 25.2°. In some embodiments, Compound 1 maleate has an X-ray diffraction pattern comprising at least three characteristic peaks in degrees 2θ selected from about 3.8°, about 9.9°, about 11.5°, about 15.3°, about 16.3°, about 18.4°, about 19.0°, about 19.6°, about 20.7°, about 21.5°, about 22.9°, about 24.7°, and about 25.2°. In some embodiments, Compound 1 maleate has an X-ray diffraction pattern comprising at least two characteristic peaks in degrees 2θ selected from about 3.8°, about 9.9°, about 11.5°, about 15.3°, about 16.3°, about 18.4°, about 19.0°, about 19.6°, about 20.7°, about 21.5°, about 22.9°, about 24.7°, and about 25.2°. In some embodiments, Compound 1 maleate has an X-ray diffraction pattern comprising at least one characteristic peak in degrees 2θ selected from about 3.8°, about 9.9°, about 11.5°, about 15.3°, about 16.3°, about 18.4°, about 19.0°, about 19.6°, about 20.7°, about 21.5°, about 22.9°, about 24.7°, and about 25.2°. In some embodiments, Compound 1 maleate has an XRPD pattern with characteristic peaks as substantially shown in FIG. 24.

Figure 25:
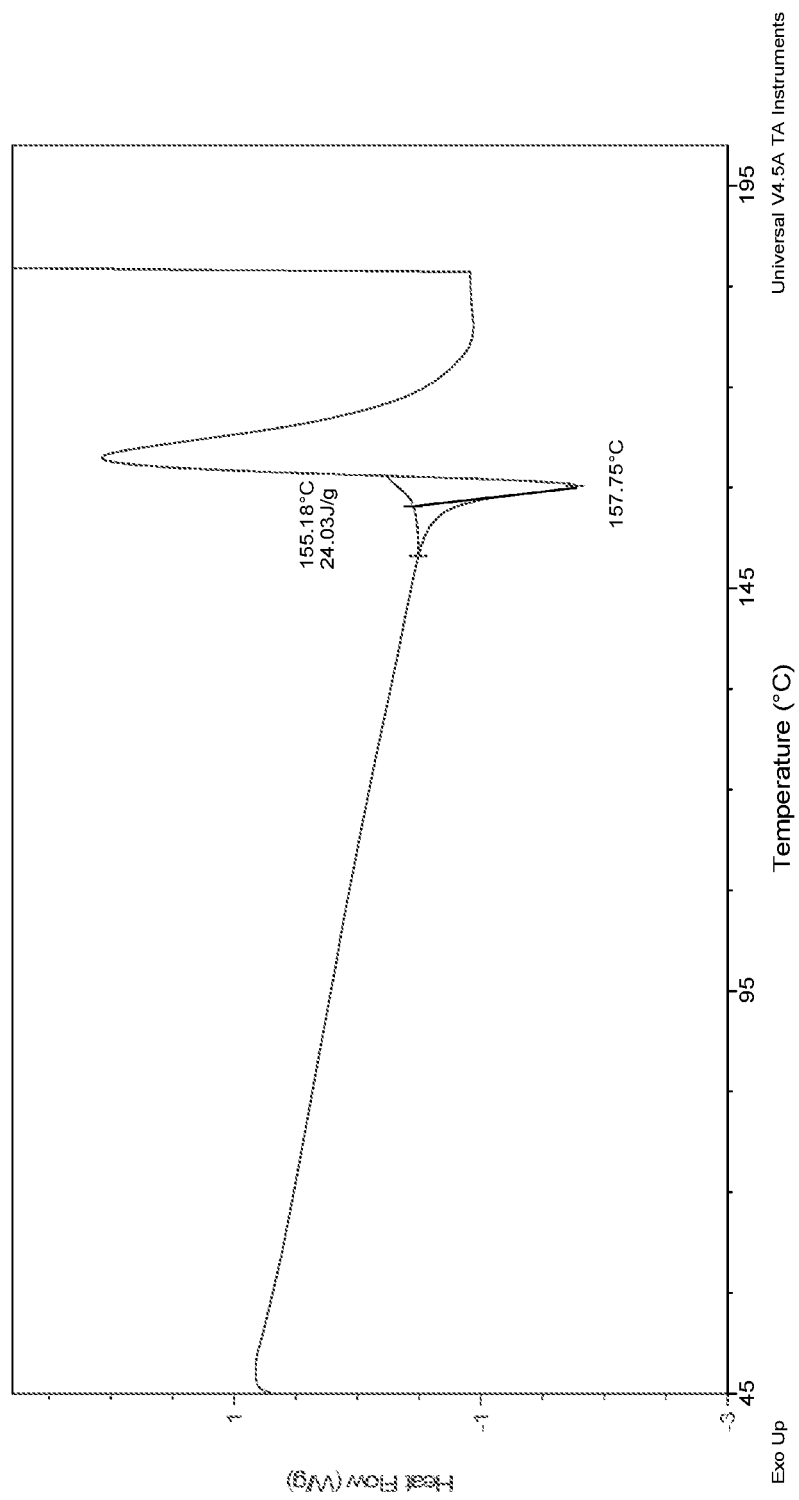
FIG. 25 shows a DSC thermogram of Compound 1 maleate.
Figure 26:
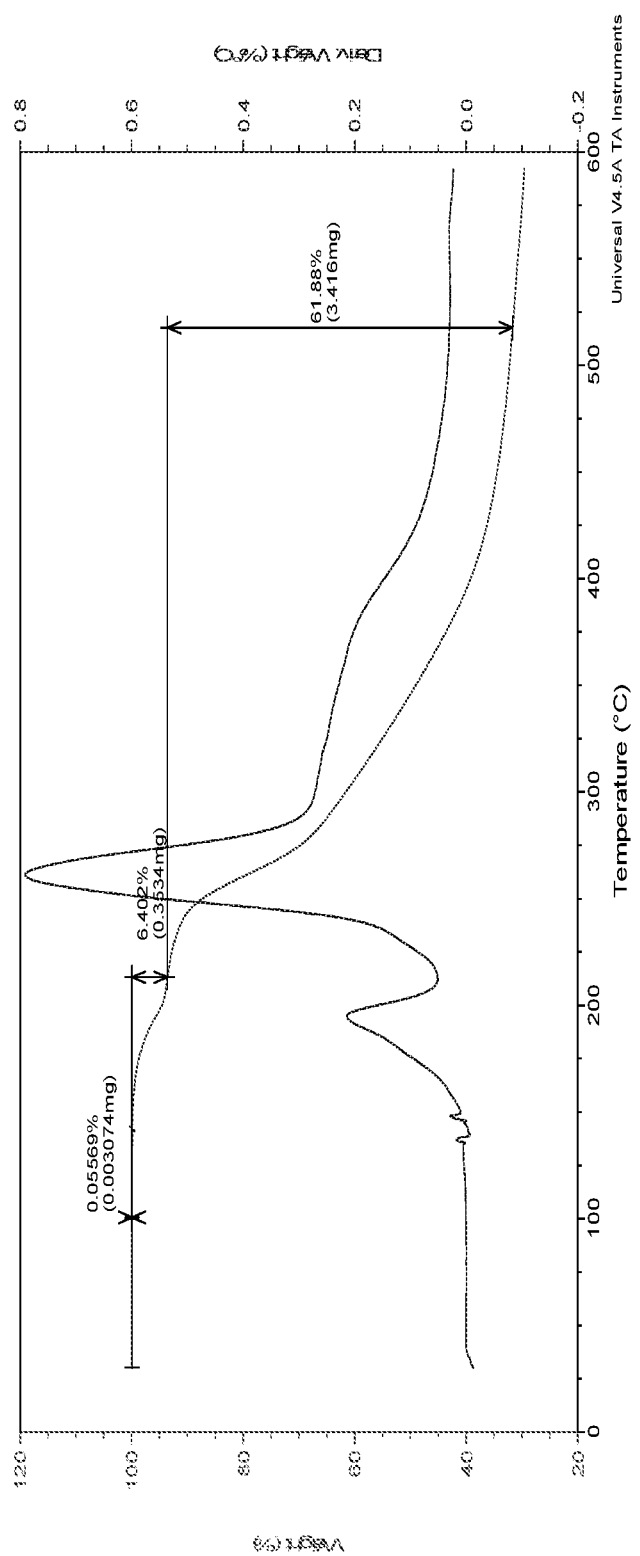
FIG. 26 shows a TGA thermogram of Compound 1 maleate.

In some embodiments, Compound 1 maleate has a DSC thermogram characterized by an endotherm peak at a temperature of about 158° C. In some embodiments, Compound 1 maleate has a DSC thermogram characterized by an endotherm peak at a temperature of about 158° C. In some embodiments, Compound 1 maleate has a DSC thermogram substantially as shown in FIG. 25. In some embodiments, Compound 1 maleate has a TGA thermogram substantially as shown in FIG. 26.

In some embodiments, Compound 1 maleate has an X-ray diffraction pattern comprising at least four characteristic peaks in degrees 2θ selected from about 3.8°, about 9.9°, about 11.5°, about 15.3°, about 16.3°, about 18.4°, about 19.0°, about 19.6°, and about 20.7°; and Compound 1 maleate has a DSC thermogram characterized by an endotherm peak at a temperature of about 158° C.

In some embodiments, Compound 1 maleate can be isolated with a purity of at least about 80%, about 85%, about 90%, about 95%, about 96%, about 97%, about 98%, or about 99%. In some embodiments, Compound 1 maleate can be isolated with a purity greater than about 99%.

Compound 1 Camsylate

Provided herein is a solid form of Compound 1 camsylate which is crystalline and is described below in the Examples. In some embodiments, the solid form has a molar ratio of Compound 1 to camphorsulfonic acid that is about 1:1.

Compound 1 camsylate can be prepared by any suitable method for the preparation of camphorsulfonic acid addition salts. For example, Compound 1 can be combined with camphorsulfonic acid (e.g., about 1.0 equiv or more) in a solvent and the resulting salt can be isolated by filtering the salt from solution. In some embodiments, the resulting salt is isolated as crystalline Compound 1 camsylate. In certain embodiments, Compound 1 is combined with about 1 to about 3 molar equivalents of camphorsulfonic acid. In some embodiments, Compound 1 is combined with about 1 to about 2 molar equivalents of camphorsulfonic acid. In certain embodiments, Compound 1 is combined with about 1.5 to about 2.5 molar equivalents of camphorsulfonic acid. In certain embodiments, Compound 1 is combined with about 2 molar equivalents of camphorsulfonic acid. In certain embodiments, the solvent is a mixture of water, methanol, and dichloromethane. In some embodiments, the solvent is a mixture of methanol and dichloromethane. In some embodiments, the solvent is methanol. In some embodiments, the solvent is dichloromethane.

In some embodiments, Compound 1 camsylate has an X-ray diffraction pattern comprising at least one characteristic peak in degrees 2θ selected from about 4.0°, about 7.8°, and about 8.5°. In some embodiments, Compound 1 camsylate has an X-ray diffraction pattern comprising a characteristic peak in degrees 2θ at about 4.0°. In some embodiments, Compound 1 camsylate has an X-ray diffraction pattern comprising a characteristic peak in degrees 2θ at about 7.8°. In some embodiments, Compound 1 camsylate has an X-ray diffraction pattern comprising a characteristic peak in degrees 2θ at about 8.5°.

In some embodiments, Compound 1 camsylate has an X-ray diffraction pattern comprising at least two characteristic peaks in degrees 2θ selected from about 4.0°, about 7.8°, and about 8.5°.

In some embodiments, Compound 1 camsylate has an X-ray diffraction pattern comprising characteristic peaks in degrees 2θ at about 4.0°, about 7.8°, and about 8.5°.

In some embodiments, Compound 1 camsylate has an X-ray diffraction pattern comprising at least four characteristic peaks in degrees 2θ selected from about 4.0°, about 7.8°, about 8.5°, about 11.4°, about 12.8°, about 14.2°, about 16.1°, and about 19.5°. In some embodiments, Compound 1 camsylate has an X-ray diffraction pattern comprising at least three characteristic peaks in degrees 2θ selected from about 4.0°, about 7.8°, about 8.5°, about 11.4°, about 12.8°, about 14.2°, about 16.1°, and about 19.5°. In some embodiments, Compound 1 camsylate has an X-ray diffraction pattern comprising at least two characteristic peaks in degrees 2θ selected from about 4.0°, about 7.8°, about 8.5°, about 11.4°, about 12.8°, about 14.2°, about 16.1°, and about 19.5°. In some embodiments, Compound 1 camsylate has an X-ray diffraction pattern comprising at least one characteristic peak in degrees 2θ selected from about 4.0°, about 7.8°, about 8.5°, about 11.4°, about 12.8°, about 14.2°, about 16.1°, and about 19.5°.

In some embodiments, Compound 1 camsylate has an X-ray diffraction pattern comprising at least four characteristic peaks in degrees 2θ selected from about 4.0°, about 7.8°, about 8.5°, about 11.4°, about 12.8°, about 14.2°, about 16.1°, about 16.7°, about 17.3°, about 19.5°, about 21.2°, and about 22.5°. In some embodiments, Compound 1 camsylate has an X-ray diffraction pattern comprising at least three characteristic peaks in degrees 2θ selected from about 4.0°, about 7.8°, about 8.5°, about 11.4°, about 12.8°, about 14.2°, about 16.1°, about 16.7°, about 17.3°, about 19.5°, about 21.2°, and about 22.5°. In some embodiments, Compound 1 camsylate has an X-ray diffraction pattern comprising at least two characteristic peaks in degrees 2θ selected from about 4.0°, about 7.8°, about 8.5°, about 11.4°, about 12.8°, about 14.2°, about 16.1°, about 16.7°, about 17.3°, about 19.5°, about 21.2°, and about 22.5°. In some embodiments, Compound 1 camsylate has an X-ray diffraction pattern comprising at least one characteristic peak in degrees 2θ selected from about 4.0°, about 7.8°, about 8.5°, about 11.4°, about 12.8°, about 14.2°, about 16.1°, about 16.7°, about 17.3°, about 19.5°, about 21.2°, and about 22.5°.

Figure 27:
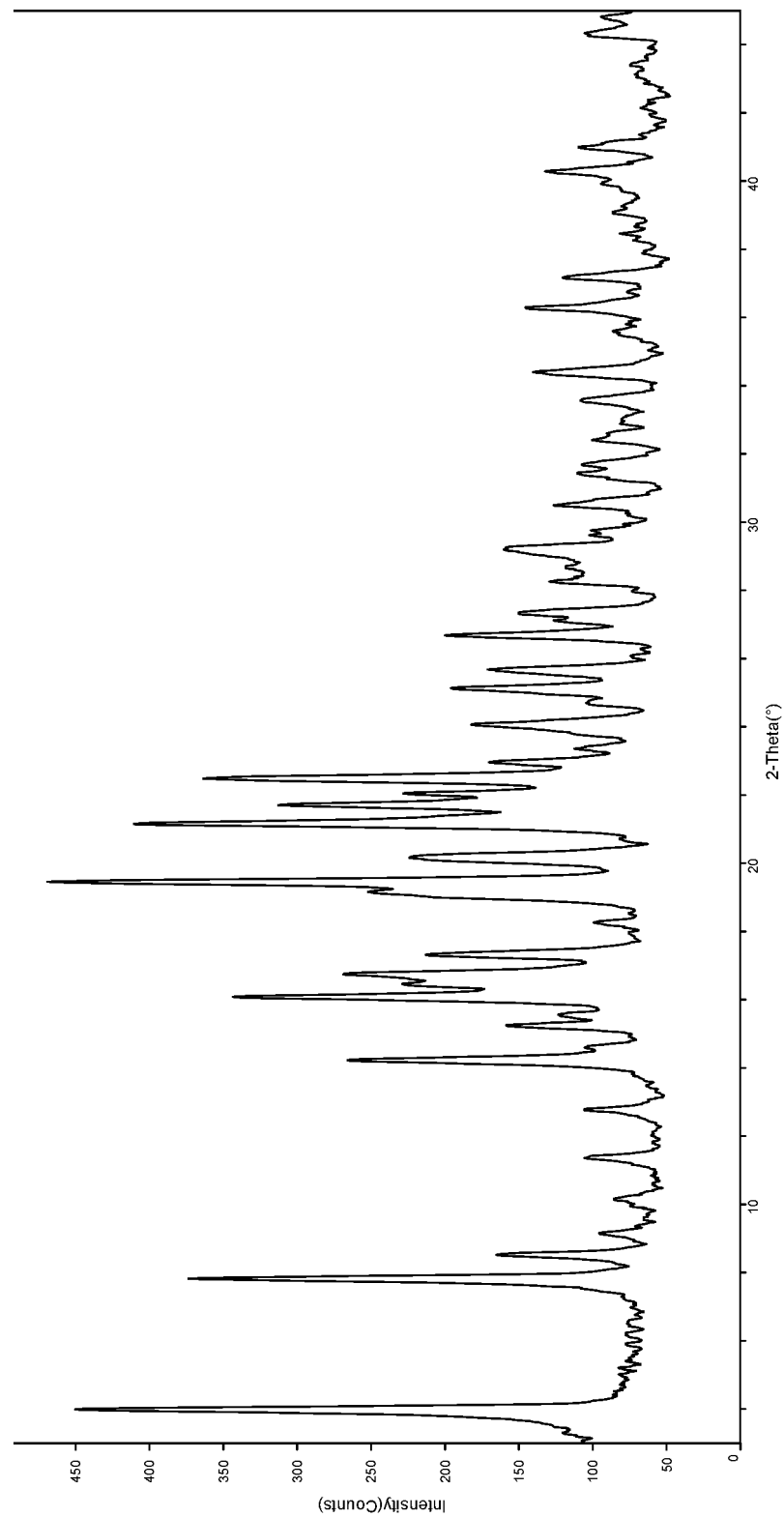
FIG. 27 shows an XRPD pattern of Compound 1 camsylate.

In some embodiments, Compound 1 camsylate has an XRPD pattern with characteristic peaks as substantially shown in FIG. 27.

Figure 28:
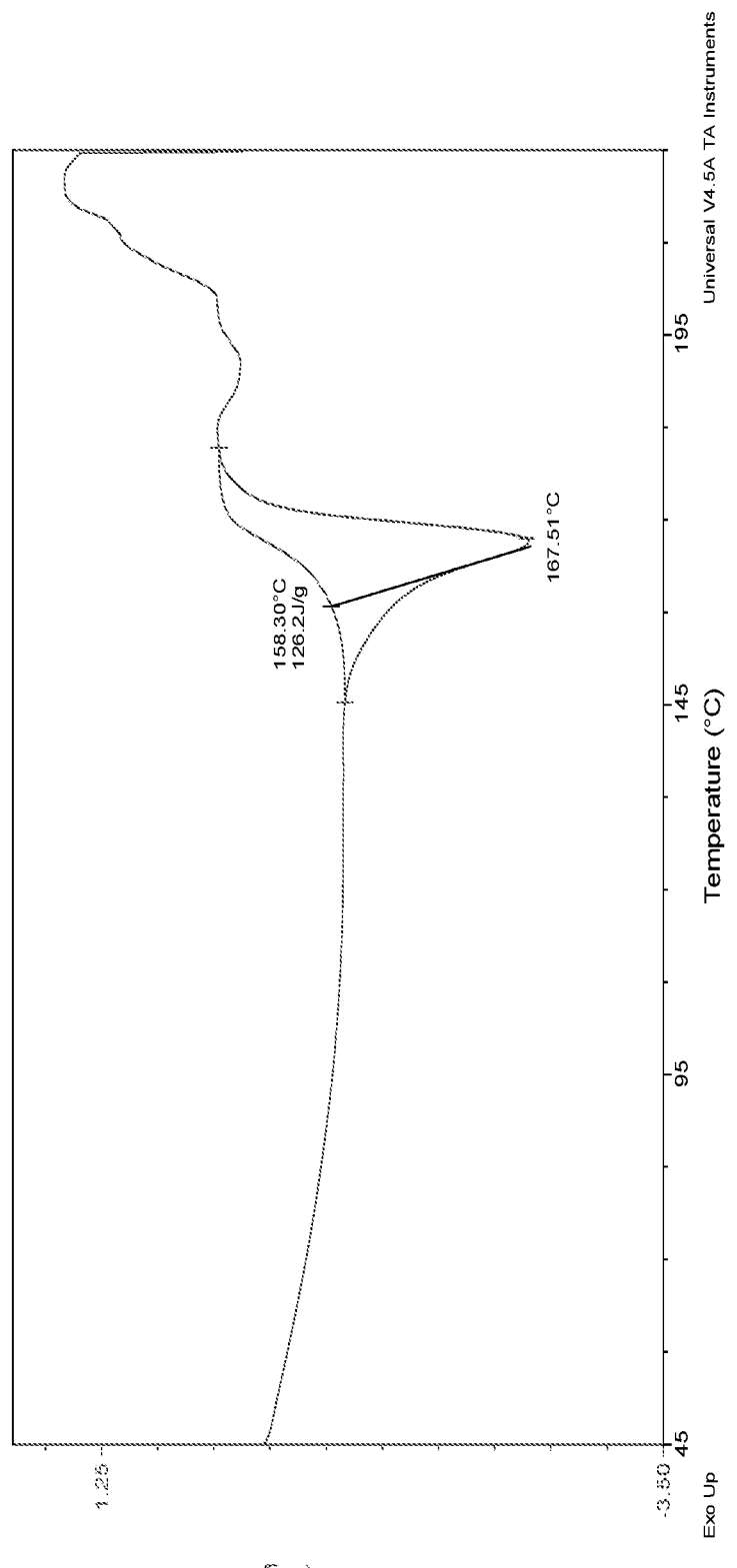
FIG. 28 shows a DSC thermogram of Compound 1 camsylate.
Figure 29:
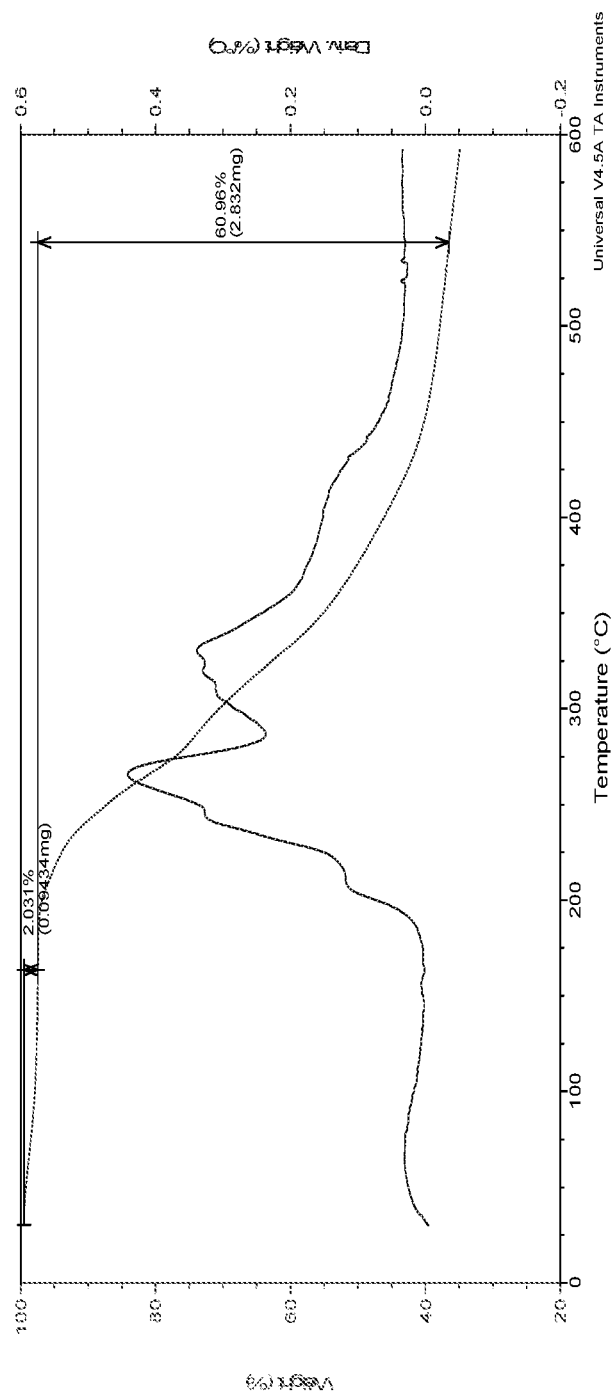
FIG. 29 shows a TGA thermogram of Compound 1 camsylate.

In some embodiments, Compound 1 camsylate has a DSC thermogram characterized by an endotherm peak at a temperature of about 168° C. In some embodiments, Compound 1 camsylate has a DSC thermogram substantially as shown in FIG. 28. In some embodiments, Compound 1 camsylate has a TGA thermogram substantially as shown in FIG. 29.

In some embodiments, Compound 1 camsylate has an X-ray diffraction pattern comprising at least four characteristic peaks in degrees 2θ selected from about 4.0°, about 7.8°, about 8.5°, about 11.4°, about 12.8°, about 14.2°, about 16.1°, and about 19.5°; and Compound 1 camsylate has a DSC thermogram characterized by an endotherm peak at a temperature of about 168° C.

In some embodiments, Compound 1 camsylate can be isolated with a purity of at least about 80%, about 85%, about 90%, about 95%, about 96%, about 97%, about 98%, or about 99%. In some embodiments, Compound 1 camsylate can be isolated with a purity greater than about 99%.

Compound 1 Isethionate

Provided herein is a solid form of Compound 1 isethionate which is crystalline and is described below in the Examples. In some embodiments, the solid form has a molar ratio of Compound 1 to isethionic acid that is about 1:1.

Compound 1 isethionate can be prepared by any suitable method for the preparation of isethionic acid addition salts. For example, Compound 1 can be combined with isethionic acid (e.g., about 1.0 equiv or more) in a solvent and the resulting salt can be isolated by filtering the salt from solution. In some embodiments, the resulting salt is isolated as crystalline Compound 1 isethionate. In certain embodiments, Compound 1 is combined with about 1 to about 3 molar equivalents of isethionic acid. In some embodiments, Compound 1 is combined with about 1 to about 2 molar equivalents of isethionic acid. In certain embodiments, Compound 1 is combined with about 1.5 to about 2.5 molar equivalents of isethionic acid. In certain embodiments, Compound 1 is combined with about 2.2 molar equivalents of isethionic acid. In certain embodiments, the solvent is a mixture of dichloromethane and methanol. In certain embodiments, the solvent is dichloromethane. In certain embodiments, the solvent is methanol.

In some embodiments, Compound 1 isethionate has an X-ray diffraction pattern comprising at least one characteristic peak in degrees 2θ selected from about 6.7°, about 14.9°, and about 18.2°. In some embodiments, Compound 1 isethionate has an X-ray diffraction pattern comprising a characteristic peak in degrees 2θ at about 6.7°. In some embodiments, Compound 1 isethionate has an X-ray diffraction pattern comprising a characteristic peak in degrees 2θ at about 14.9°. In some embodiments, Compound 1 isethionate has an X-ray diffraction pattern comprising a characteristic peak in degrees 2θ at about 18.2°.

In some embodiments, Compound 1 isethionate has an X-ray diffraction pattern comprising at least two characteristic peaks in degrees 2θ selected from about 6.7°, about 14.9°, and about 18.2°.

In some embodiments, Compound 1 isethionate has an X-ray diffraction pattern comprising characteristics peak in degrees 2θ at about 6.7°, about 14.9°, and about 18.2°.

In some embodiments, Compound 1 isethionate has an X-ray diffraction pattern comprising at least four characteristic peaks in degrees 2θ selected from about 6.7°, about 14.9°, about 15.5°, about 16.7°, about 17.7°, about 18.2°, and about 19.1°. In some embodiments, Compound 1 isethionate has an X-ray diffraction pattern comprising at least three characteristic peaks in degrees 2θ selected from about 6.7°, about 14.9°, about 15.5°, about 16.7°, about 17.7°, about 18.2°, and about 19.1°. In some embodiments, Compound 1 isethionate has an X-ray diffraction pattern comprising at least two characteristic peaks in degrees 2θ selected from about 6.7°, about 14.9°, about 15.5°, about 16.7°, about 17.7°, about 18.2°, and about 19.1°. In some embodiments, Compound 1 isethionate has an X-ray diffraction pattern comprising at least one characteristic peak in degrees 2θ selected from about 6.7°, about 14.9°, about 15.5°, about 16.7°, about 17.7°, about 18.2°, and about 19.1°.

In some embodiments, Compound 1 isethionate has an X-ray diffraction pattern comprising at least four characteristic peaks in degrees 2θ selected from about 6.7°, about 14.9°, about 15.5°, about 16.7°, about 17.7°, about 18.2°, about 19.1°, about 19.9°, about 20.8°, about 22.6°, and about 24.8°. In some embodiments, Compound 1 isethionate has an X-ray diffraction pattern comprising at least three characteristic peaks in degrees 2θ selected from about 6.7°, about 14.9°, about 15.5°, about 16.7°, about 17.7°, about 18.2°, about 19.1°, about 19.9°, about 20.8°, about 22.6°, and about 24.8°. In some embodiments, Compound 1 isethionate has an X-ray diffraction pattern comprising at least two characteristic peaks in degrees 2θ selected from about 6.7°, about 14.9°, about 15.5°, about 16.7°, about 17.7°, about 18.2°, about 19.1°, about 19.9°, about 20.8°, about 22.6°, and about 24.8°. In some embodiments, Compound 1 isethionate has an X-ray diffraction pattern comprising at least one characteristic peak in degrees 2θ selected from about 6.7°, about 14.9°, about 15.5°, about 16.7°, about 17.7°, about 18.2°, about 19.1°, about 19.9°, about 20.8°, about 22.6°, and about 24.8°. In some embodiments, Compound 1 isethionate has an XRPD pattern with characteristic peaks as substantially shown in FIG. 30.

Figure 31:
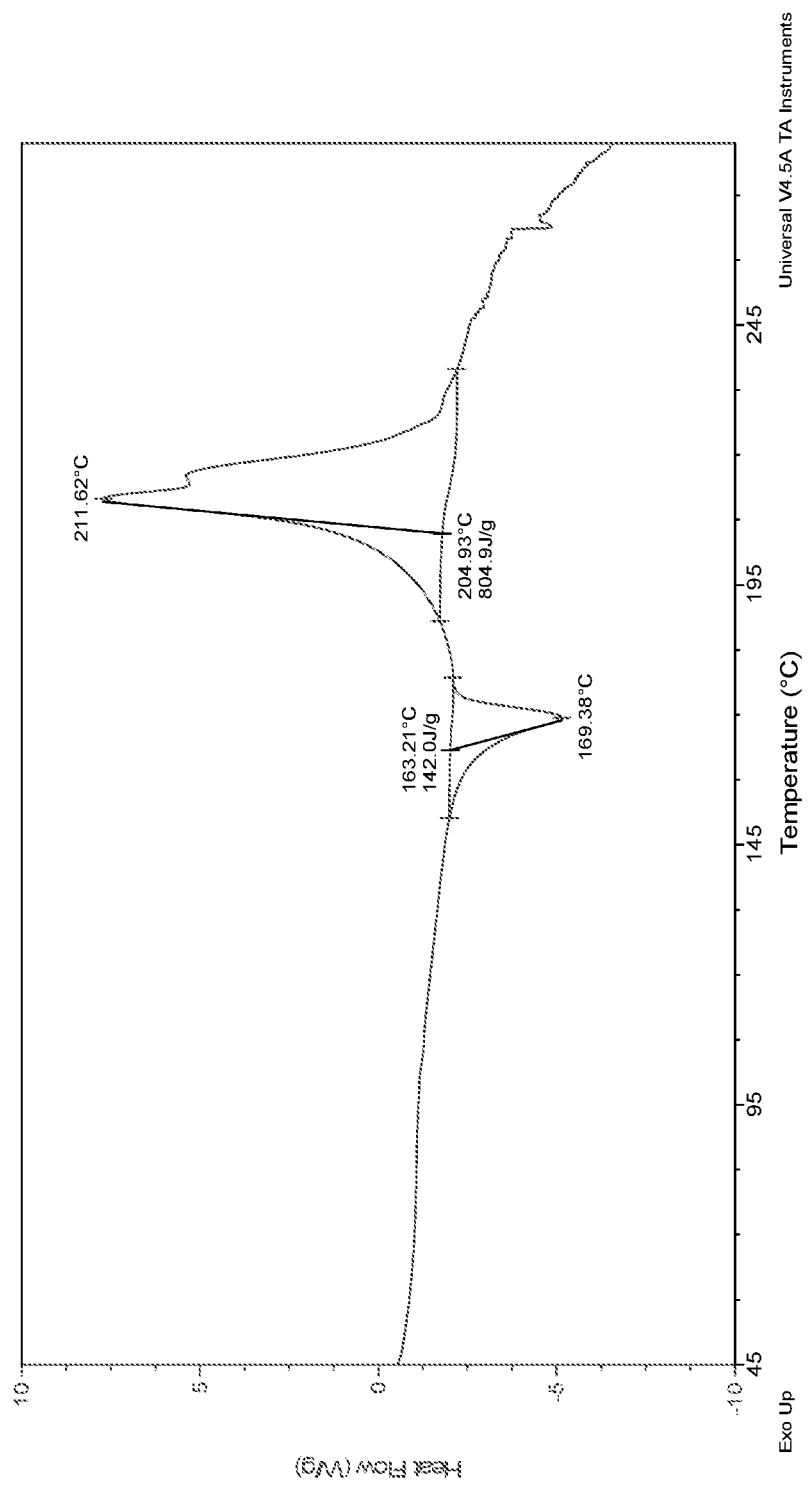
FIG. 31 shows a DSC thermogram of Compound 1 isethionate.
Figure 32:
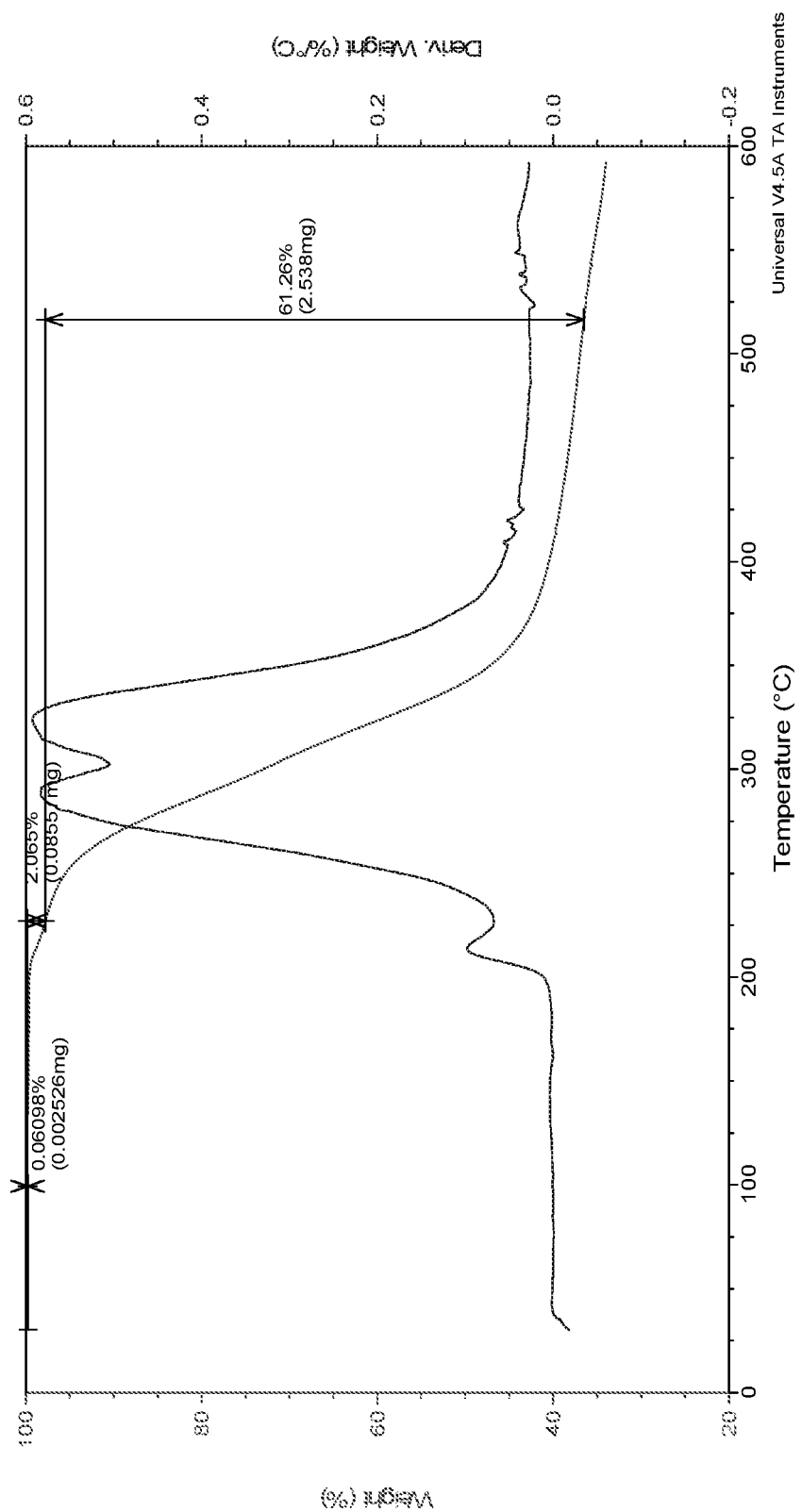
FIG. 32 shows a TGA thermogram of Compound 1 isethionate.

In some embodiments, Compound 1 isethionate has a DSC thermogram characterized by endotherm peaks at a temperature of about 169° C. and an exotherm peak at a temperature of about 212° C. In some embodiments, Compound 1 isethionate has a DSC thermogram characterized by an endotherm peak at a temperature of about 169° C. In some embodiments, Compound 1 isethionate has a DSC thermogram characterized by an exotherm peak at a temperature of about 212° C. In some embodiments, Compound 1 isethionate has a DSC thermogram substantially as shown in FIG. 31. In some embodiments, Compound 1 isethionate has a TGA thermogram substantially as shown in FIG. 32.

In some embodiments, Compound 1 isethionate has an X-ray diffraction pattern comprising at least four characteristic peaks in degrees 2θ selected from about 6.7°, about 14.9°, about 15.5°, about 16.7°, about 17.7°, about 18.2°, and about 19.1°; and Compound 1 isethionate has a DSC thermogram characterized by an endotherm peak at a temperature of about 169° C. In some embodiments, Compound 1 isethionate has an X-ray diffraction pattern comprising at least four characteristic peaks in degrees 2θ selected from about 6.7°, about 14.9°, about 15.5°, about 16.7°, about 17.7°, about 18.2°, and about 19.1°; and Compound 1 isethionate has a DSC thermogram characterized by an exotherm peak at a temperature of about 212° C.

In some embodiments, Compound 1 isethionate can be isolated with a purity of at least about 80%, about 85%, about 90%, about 95%, about 96%, about 97%, about 98%, or about 99%. In some embodiments, Compound 1 isethionate can be isolated with a purity greater than about 99%.

Compound 1 1,2-Ethanedisulfonate

Provided herein is a solid form of Compound 1 1,2-ethanedisulfonate which is crystalline and is described below in the Examples. In some embodiments, the solid form has a molar ratio of Compound 1 to 1,2-ethanedisulfonic acid that is about 1:1.

Compound 1 1,2-ethanedisulfonate can be prepared by any suitable method for the preparation of 1,2-ethanedisulfonic acid addition salts. For example, Compound 1 can be combined with 1,2-ethanedisulfonic acid (e.g., about 1.0 equiv or more) in a solvent and the resulting salt can be isolated by filtering the salt from solution. In some embodiments, the resulting salt is isolated as crystalline Compound 1 1,2-ethanedisulfonate. In certain embodiments, Compound 1 is combined with about 1 to about 3 molar equivalents of 1,2-ethanedisulfonic acid. In some embodiments, Compound 1 is combined with about 1 to about 2 molar equivalents of 1,2-ethanedisulfonic acid. In certain embodiments, Compound 1 is combined with about 1.5 to about 2.5 molar equivalents of 1,2-ethanedisulfonic acid. In certain embodiments, Compound 1 is combined with about 2.1 molar equivalents of 1,2-ethanedisulfonic acid. In certain embodiments, the solvent is a mixture of isopropanol, methanol, and dichloromethane. In certain embodiments, the solvent is a mixture of methanol and dichloromethane. In some embodiments, the solvent is a mixture of isopropanol and dichloromethane. In some embodiments, the solvent is methanol. In some embodiments, the solvent is isopropanol. In some embodiments, the solvent is dichloromethane.

In some embodiments, Compound 1 1,2-ethanedisulfonate has an X-ray diffraction pattern comprising at least one characteristic peak in degrees 2θ selected from about 7.9°, about 10.5°, and about 12.9°. In some embodiments, Compound 1 1,2-ethanedisulfonate has an X-ray diffraction pattern comprising a characteristic peak in degrees 2θ at about 7.9°. In some embodiments, Compound 1 1,2-ethanedisulfonate has an X-ray diffraction pattern comprising a characteristic peak in degrees 2θ at about 10.5°. In some embodiments, Compound 1 1,2-ethanedisulfonate has an X-ray diffraction pattern comprising a characteristic peak in degrees 2θ at about 12.9°.

In some embodiments, Compound 1 1,2-ethanedisulfonate has an X-ray diffraction pattern comprising at least one characteristic peak in degrees 2θ selected from about 7.9°, about 10.5°, and about 12.9°.

In some embodiments, Compound 1 1,2-ethanedisulfonate has an X-ray diffraction pattern comprising characteristic peaks in degrees 2θ selected from about 7.9°, about 10.5°, and about 12.9°.

In some embodiments, Compound 1 1,2-ethanedisulfonate has an X-ray diffraction pattern comprising at least four characteristic peaks in degrees 2θ selected from about 7.9°, about 10.5°, about 12.9°, about 15.7°, about 17.6°, about 18.4°, about 20.3°, about 21.0°, and about 23.7°. In some embodiments, Compound 1 1,2-ethanedisulfonate has an X-ray diffraction pattern comprising at least three characteristic peaks in degrees 2θ selected from about 7.9°, about 10.5°, about 12.9°, about 15.7°, about 17.6°, about 18.4°, about 20.3°, about 21.0°, and about 23.7°. In some embodiments, Compound 1 1,2-ethanedisulfonate has an X-ray diffraction pattern comprising at least two characteristic peaks in degrees 2θ selected from about 7.9°, about 10.5°, about 12.9°, about 15.7°, about 17.6°, about 18.4°, about 20.3°, about 21.0°, and about 23.7°. In some embodiments, Compound 1 1,2-ethanedisulfonate has an X-ray diffraction pattern comprising at least one characteristic peak in degrees 2θ selected from about 7.9°, about 10.5°, about 12.9°, about 15.7°, about 17.6°, about 18.4°, about 20.3°, about 21.0°, and about 23.7°.

In some embodiments, Compound 1 1,2-ethanedisulfonate has an X-ray diffraction pattern comprising at least four characteristic peaks in degrees 2θ selected from about 7.9°, about 10.5°, about 11.9°, about 12.9°, about 15.7°, about 16.8°, about 17.6°, about 18.4°, about 19.4°, about 20.3°, about 21.0°, about 21.9°, about 23.7°, about 25.0°, and about 25.8°. In some embodiments, Compound 1 1,2-ethanedisulfonate has an X-ray diffraction pattern comprising at least three characteristic peaks in degrees 2θ selected from about 7.9°, about 10.5°, about 11.9°, about 12.9°, about 15.7°, about 16.8°, about 17.6°, about 18.4°, about 19.4°, about 20.3°, about 21.0°, about 21.9°, about 23.7°, about 25.0°, and about 25.8°. In some embodiments, Compound 1 1,2-ethanedisulfonate has an X-ray diffraction pattern comprising at least two characteristic peaks in degrees 2θ selected from about 7.9°, about 10.5°, about 11.9°, about 12.9°, about 15.7°, about 16.8°, about 17.6°, about 18.4°, about 19.4°, about 20.3°, about 21.0°, about 21.9°, about 23.7°, about 25.0°, and about 25.8°. In some embodiments, Compound 1 1,2-ethanedisulfonate has an X-ray diffraction pattern comprising at least one characteristic peak in degrees 2θ selected from about 7.9°, about 10.5°, about 11.9°, about 12.9°, about 15.7°, about 16.8°, about 17.6°, about 18.4°, about 19.4°, about 20.3°, about 21.0°, about 21.9°, about 23.7°, about 25.0°, and about 25.8°.

Figure 33:
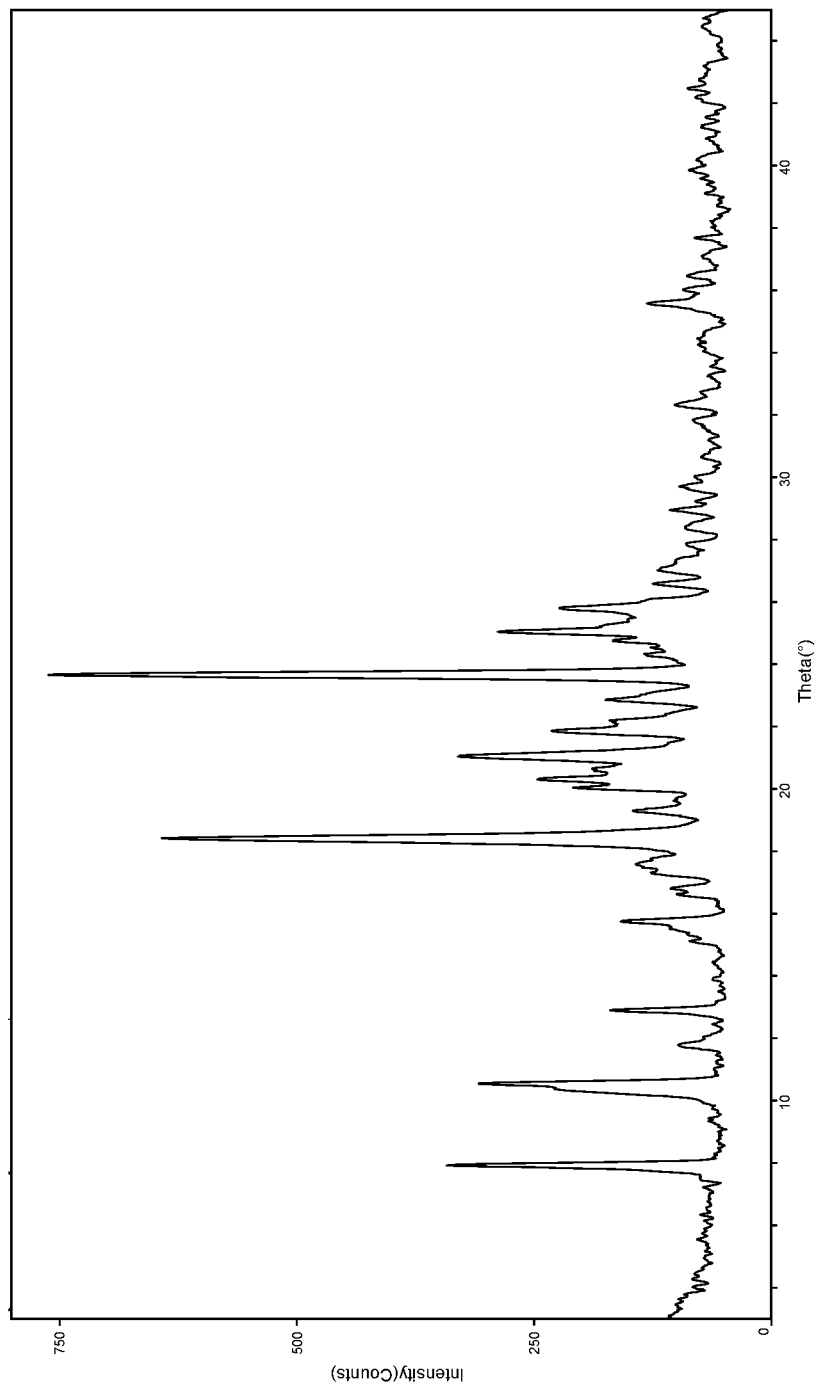
FIG. 33 shows an XRPD pattern of Compound 1 1,2-ethanedisulfonate.

In some embodiments, Compound 1 1,2-ethanedisulfonate has an XRPD pattern with characteristic peaks as substantially shown in FIG. 33.

Figure 34:
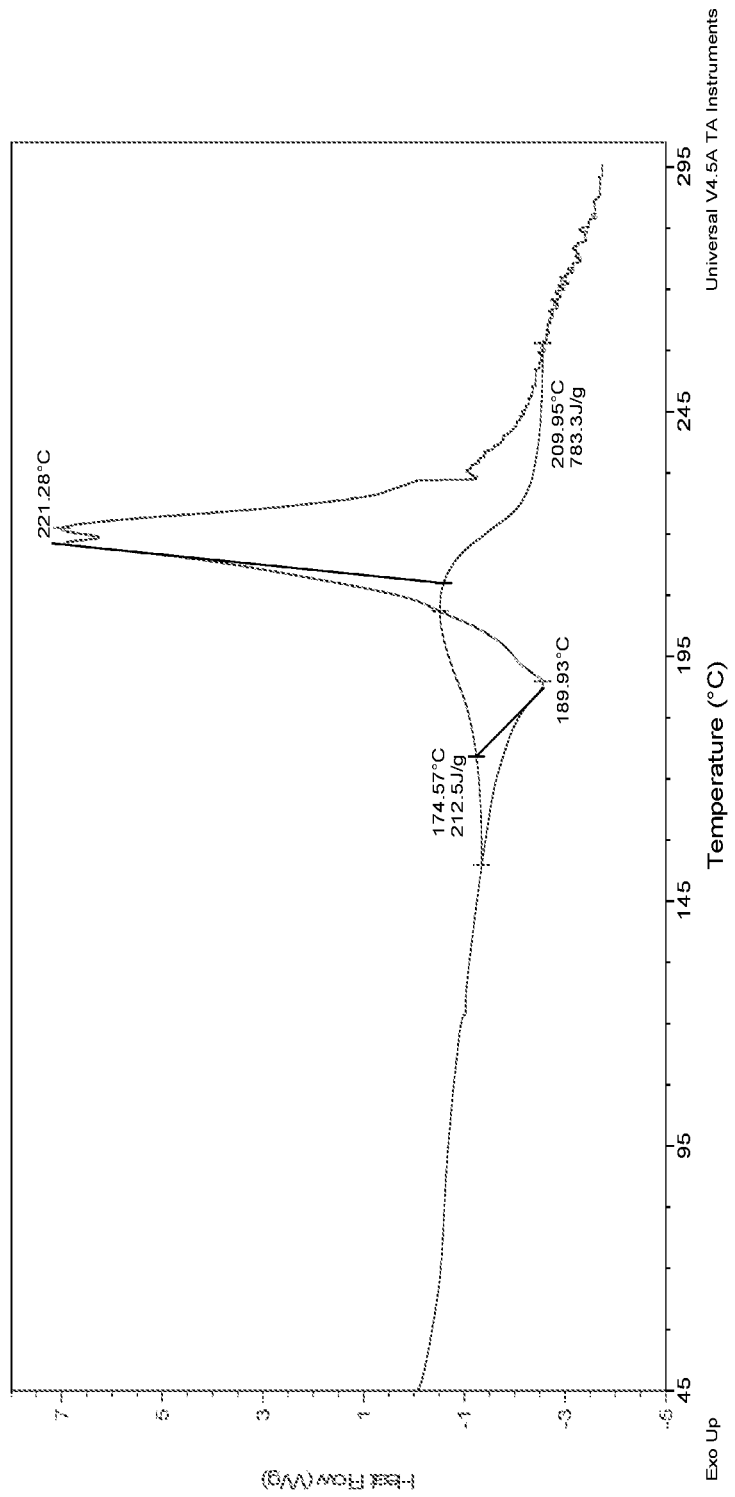
FIG. 34 shows a DSC thermogram of Compound 1 1,2-ethanedisulfonate.

In some embodiments, Compound 1 1,2-ethanedisulfonate has a DSC thermogram characterized by an endotherm peak at a temperature of about 190° C. and an exotherm peak at a temperature of about 221° C. In some embodiments, Compound 1 1,2-ethanedisulfonate has a DSC thermogram characterized by an endotherm peak at a temperature of about 190° C. In some embodiments, Compound 1 1,2-ethanedisulfonate has a DSC thermogram characterized by an exotherm peak at a temperature of about 221° C. In some embodiments, Compound 1 1,2-ethanedisulfonate has a DSC thermogram substantially as shown in FIG. 34.

In some embodiments, Compound 1 1,2-ethanedisulfonate has an X-ray diffraction pattern comprising at least four characteristic peaks in degrees 2θ selected from about 7.9°, about 10.5°, about 12.9°, about 15.7°, about 17.6°, about 18.4°, about 20.3°, about 21.0°, and about 23.7°; and Compound 1 1,2-ethanedisulfonate has a DSC thermogram characterized by an endotherm peak at a temperature of about 190° C. In some embodiments, Compound 1 1,2-ethanedisulfonate has an X-ray diffraction pattern comprising at least four characteristic peaks in degrees 2θ selected from about 7.9°, about 10.5°, about 12.9°, about 15.7°, about 17.6°, about 18.4°, about 20.3°, about 21.0°, and about 23.7°; and Compound 1 1,2-ethanedisulfonate has a DSC thermogram characterized by an endotherm peak at a temperature of about 221° C.

In some embodiments, Compound 1 1,2-ethanedisulfonate can be isolated with a purity of at least about 80%, about 85%, about 90%, about 95%, about 96%, about 97%, about 98%, or about 99%. In some embodiments, Compound 1 1,2-ethanedisulfonate can be isolated with a purity greater than about 99%.

Compound 1 Sulfate

Provided herein is a solid form of Compound 1 sulfate, which is described below in the Examples. In some embodiments, Compound 1 sulfate is amorphous.

Compound 1 sulfate can be prepared by any suitable method for the preparation of sulfuric acid addition salts. For example, Compound 1 can be combined with sulfuric acid (e.g., about 1.0 equiv or more) in a solvent and the resulting salt can be isolated by filtering the salt from solution. In some embodiments, the resulting salt is isolated as crystalline Compound 1 sulfate. In certain embodiments, Compound 1 is combined with about 1 to about 3 molar equivalents of sulfuric acid. In some embodiments, Compound 1 is combined with about 1 to about 2 molar equivalents of sulfuric acid. In certain embodiments, Compound 1 is combined with about 1.5 to about 2.5 molar equivalents of sulfuric acid. In certain embodiments, Compound 1 is combined with about 2.1 molar equivalents of sulfuric acid. In certain embodiments, the solvent is a mixture of isopropanol, methanol, and dichloromethane. In certain embodiments, the solvent is a mixture of methanol and dichloromethane. In some embodiments, the solvent is a mixture of isopropanol and dichloromethane. In some embodiments, the solvent is methanol. In some embodiments, the solvent is isopropanol. In some embodiments, the solvent is dichloromethane.

In some embodiments, Compound 1 sulfate can be isolated with a purity of at least about 80%, about 85%, about 90%, about 95%, about 96%, about 97%, about 98%, or about 99%. In some embodiments, Compound 1 sulfate can be isolated with a purity greater than about 99%.

Compound 1 (Free Base)

Provided herein is a solid form of Compound 1.

Compound 1 can be prepared by treating an acid addition salt of Compound 1 with a base. For example, Compound 1 di-HCl in a solvent be combined with sodium bicarbonate (e.g., about 2.0 equiv or more) and the resulting Compound 1 can be isolated by filtering the compound from the solution. In certain embodiments, the acid addition salt is combined with about 2 to about 10 molar equivalents of sodium bicarbonate. In certain embodiments, Compound 1 is combined with about 4 to about 8 molar equivalents of sodium bicarbonate. In certain embodiments, Compound 1 is combined with about 5.5 molar equivalents of sodium bicarbonate. In some embodiments, the solvent is a polar protic solvent. In some embodiments, the solvent is water.

In some embodiments, Compound 1 has an X-ray diffraction pattern comprising two characteristic peaks in degrees 2θ selected from about 4.1° and about 21.7°. In some embodiments, Compound 1 has a characteristic XRPD peak in degrees 2θ at about 4.1°. In some embodiments, Compound 1 has a characteristic XRPD peak in degrees 2θ at about 21.7°. In some embodiments, Compound 1 has an X-ray diffraction pattern comprising two characteristic peaks in degrees 2θ selected from about 4.1° and about 21.7°.

Figure 37:
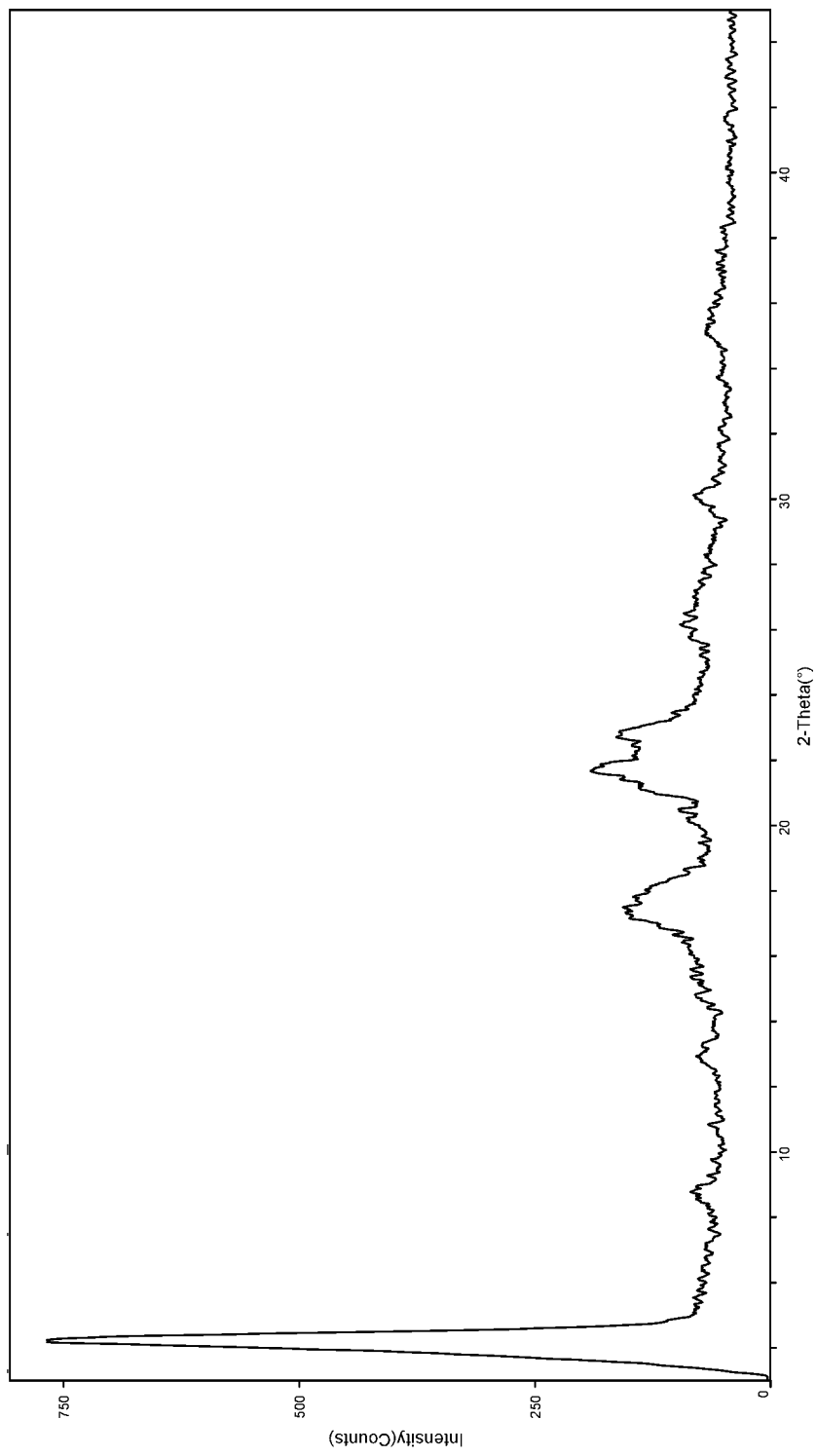
FIG. 37 shows an XRPD pattern of Compound 1 (free base).

In some embodiments, Compound 1 has an XRPD pattern with characteristic peaks as substantially shown in FIG. 37.

Figure 38:
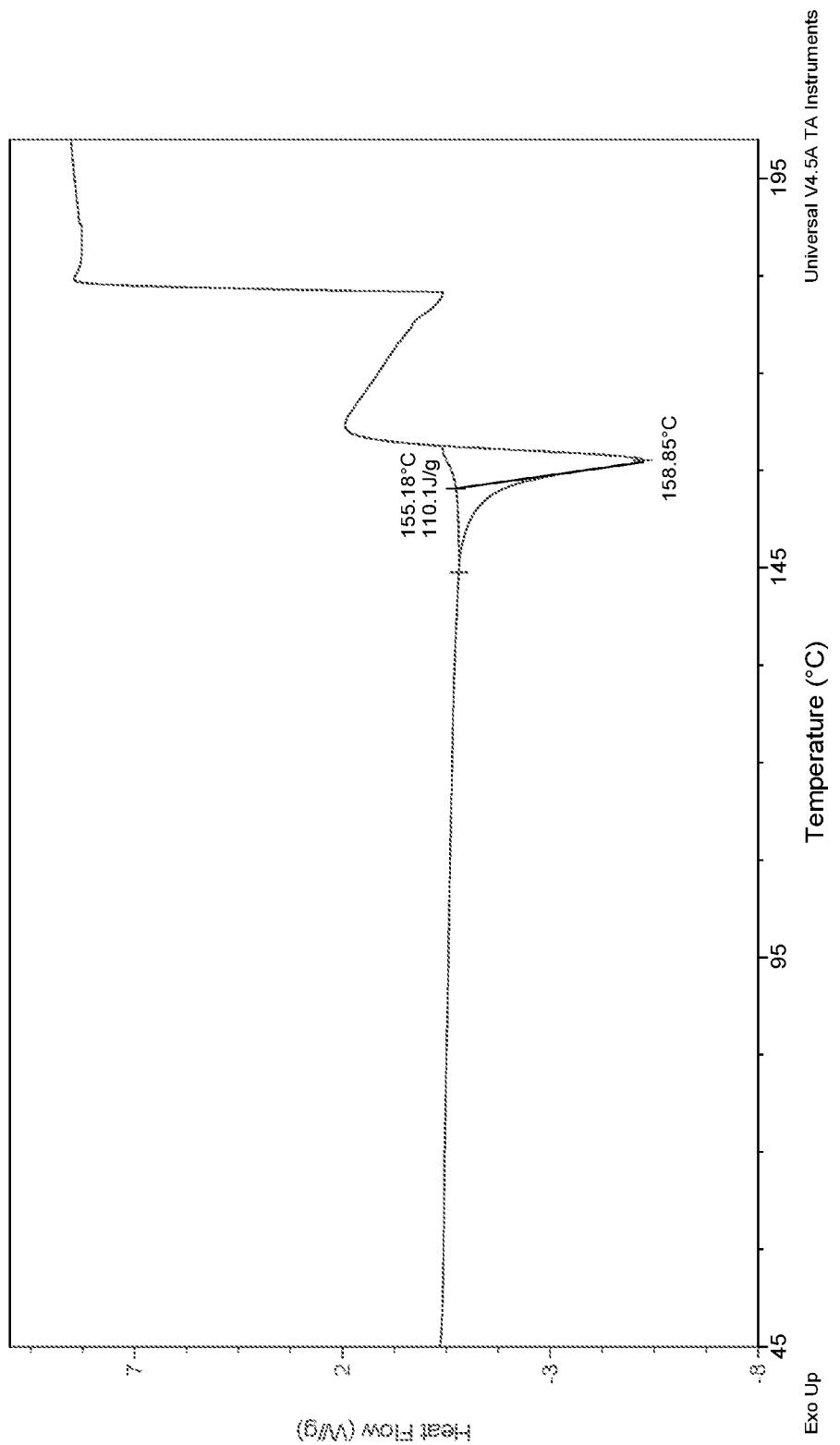
FIG. 38 shows a DSC thermogram of Compound 1 (free base).
Figure 39:
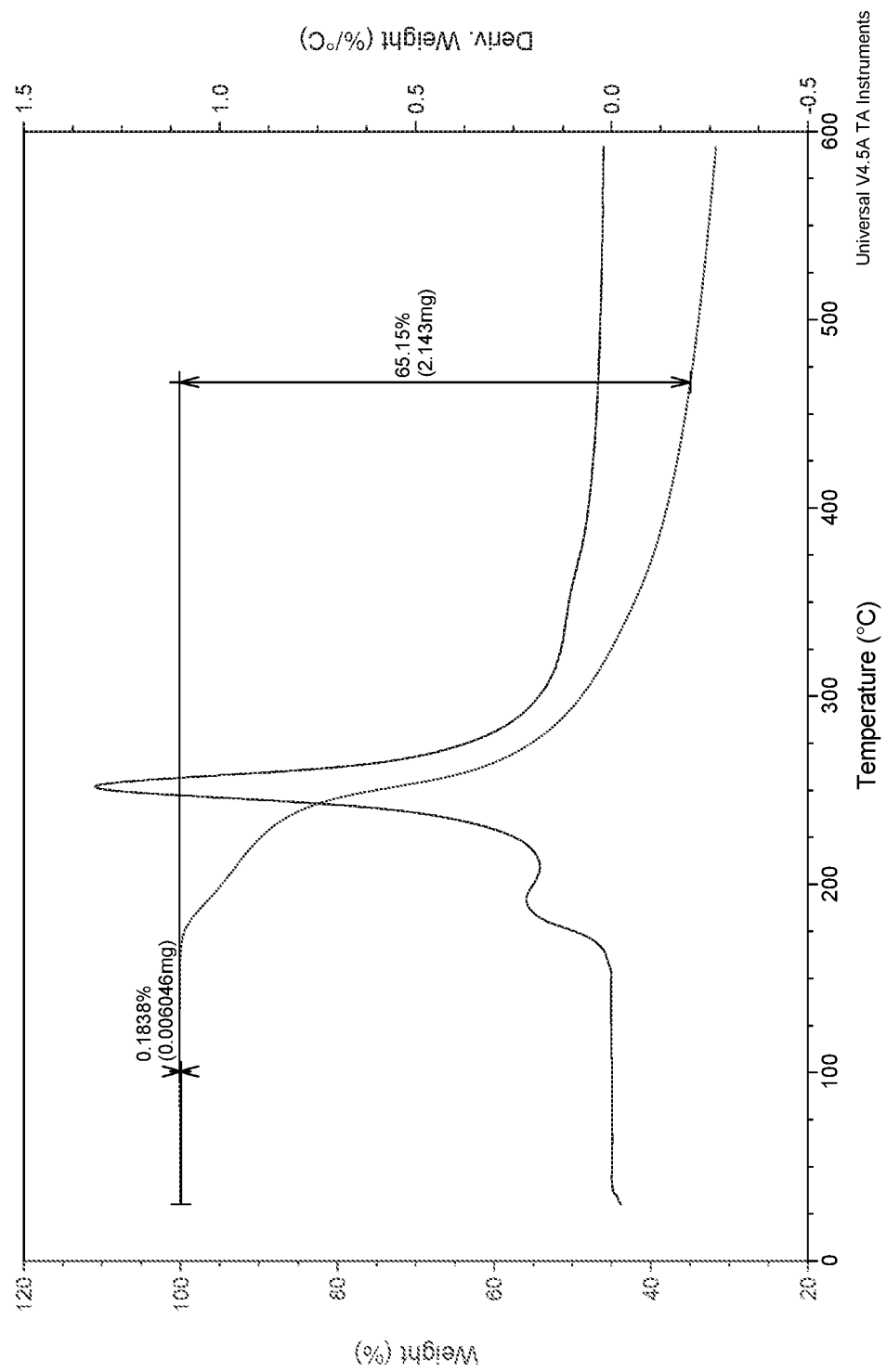
FIG. 39 shows a TGA thermogram of Compound 1 (free base).

In some embodiments, Compound 1 has a DSC thermogram characterized by an endotherm peak at a temperature of about 159° C. In some embodiments, Compound 1 has a DSC thermogram substantially as shown in FIG. 38. In some embodiments, Compound 1 has a TGA thermogram substantially as shown in FIG. 39.

In some embodiments, Compound 1 has an X-ray diffraction pattern comprising two characteristic peaks in degrees 2θ selected from about 4.1° and about 21.7°; and Compound 1 has a DSC thermogram characterized by an endotherm peak at a temperature of about 159° C.

In some embodiments, Compound 1 can be isolated with a purity of at least about 80%, about 85%, about 90%, about 95%, about 96%, about 97%, about 98%, or about 99%. In some embodiments, Compound 1 can be isolated with a purity greater than about 99%.

Processes for Preparing Compound 1 or a Salt Thereof

Provided herein are also processes for preparing Compound 1 or a salt thereof. The processes for preparing Compound 1 or a salt thereof provided herein have certain advantages over the processes currently disclosed in the art. For example, the processes described herein demonstrate good scalability and yields. In addition, the key intermediates of the disclosed processes contain chromophores, and their reaction progresses are easily monitored by HPLC.

The processes for preparing Compound 1 or a salt thereof can comprise:

a) treating Compound 11 having the formula:

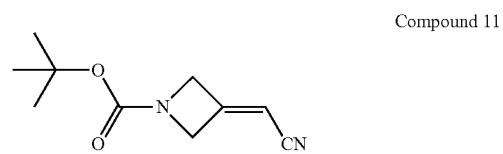

Compound 11 with HCl to form Compound 10 having the formula:

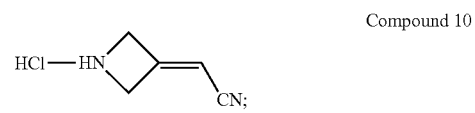

Compound 10 b) treating Compound 10 with B3 and by tert-butyl chlorosulfonylcarbamate, wherein B3 is a base, to form Compound 9 having the formula:

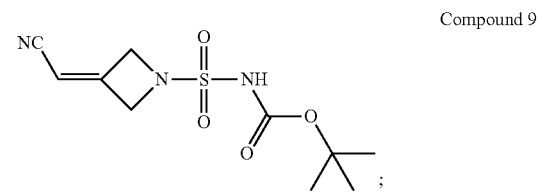 [SMILES: CC(C)(C)OC(=O)NS(=O)(=O)N1CC(=CC#N)C1]

Compound 9 c) treating Compound 9 with A3, wherein A3 is an acid, to form Compound 4 having the formula:

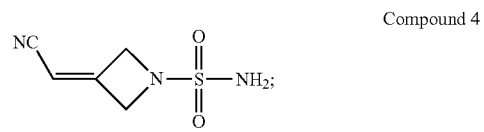 [SMILES: N#CC=C1CN(S(N)(=O)=O)C1]

Compound 4 d) contacting piperidin-4-one hydrochloride hydrate with 2,2,2-trifluoroacetic anhydride in the presence of B2, wherein B2 is a base, to form Compound 7 having the formula:

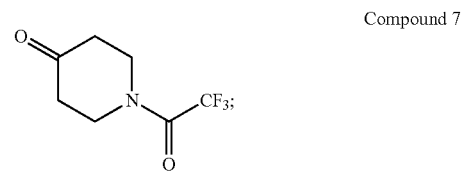 [SMILES: O=C1CCN(C(=O)C(F)(F)F)CC1]

Compound 7 e) contacting Compound 7 with Compound 8 having the formula:

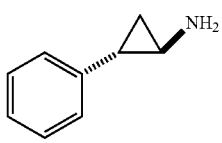
Compound 8 in the presence of A2 and RA1, wherein A2 is an acid, and RA1 is a reducing agent, to provide Compound 6 having the formula:

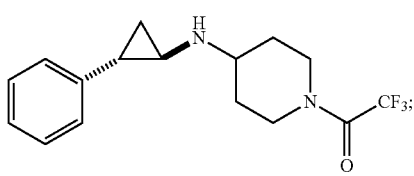
Compound 6 f) reacting Compound 6 with di-tert-butyl dicarbonate to produce Compound 5 having the formula:

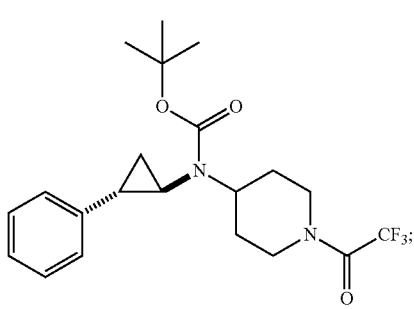
Compound 5 g) treating Compound 5 with B1, wherein B1 is a base, to produce Compound 3 having the formula:

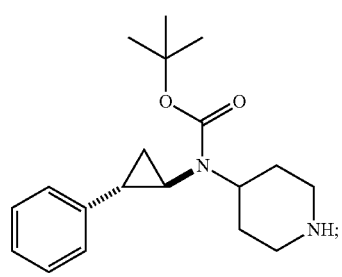
Compound 3 h) contacting Compound 3 with Compound 4 to form Compound 2 having the formula:

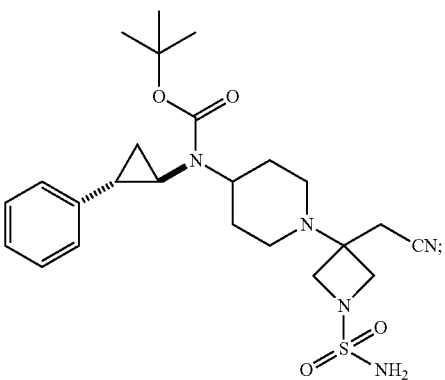
Compound 2 and i) deprotecting Compound 2 with A1, wherein A1 is an acid, to form Compound 1.

The process to prepare Compound 1 can include deprotecting Compound 2 with A1, wherein A1 is an acid. The acid can be a mineral acid. In some embodiments, A1 is HCl. The salt of Compound 1 can be a hydrochloric acid salt. The salt of Compound 1 can be a dihydrochloric acid salt. The deprotecting can be performed in the presence of S1, wherein S1 is a protic solvent. In some embodiments, S1 is an alcohol, e.g., methanol. In some embodiments, the deprotecting is performed at a temperature between about 30° C. to about 50° C. In some embodiments, the deprotecting is performed at a temperature of about 35° C. to about 45° C., e.g., about 40° C. In some embodiments, the deprotecting comprises using about 1 to about 15 molar equivalents of A1 to Compound 2. In some embodiments, the protecting comprises using about 5 to about 10 molar equivalents of A1 to Compound 2. In some embodiments, the protecting comprises using about 8 to about 9 molar equivalents of A1 to Compound 2.

The process of preparing Compound 1 can further include precipitating Compound 1 from a solution comprising Compound 1 and S2, wherein S2 comprises a solvent and an anti-solvent. The solvent can be a polar aprotic solvent, e.g., 2-butanone. The anti-solvent can be a hydrocarbon solvent, e.g., heptane.

Compound 2 can be prepared by a process that includes contacting Compound 3 with Compound 4. The contacting of Compound 3 and Compound 4 can be performed in the presence of S3, wherein S3 is a polar protic solvent. In some embodiments, S3 is an alcohol, e.g., methanol. In some embodiments, the contacting of Compound 3 and Compound 4 is performed at a temperature of about 55° C. to about 65° C. For example, the temperature is about 60° C. In some embodiments, the contacting of Compound 3 and Compound 4 comprises using about 1 to about 2 molar equivalents of Compound 4 per molar equivalent of Compound 3. In some embodiments, the contacting of Compound 3 and Compound 4 comprises using about 1.1 to about 1.5 molar equivalents of Compound 4 per molar equivalent of Compound 3. In some embodiments, the contacting of Compound 3 and Compound 4 comprises using about 1.15 molar equivalents of Compound 4 per molar equivalent of Compound 3.

Compound 3 can be produced by a process that includes treating Compound 5 with B1, wherein B1 is a base. In some embodiments, B1 is a metal hydroxide base, e.g., KOH. The treating of Compound 5 can be performed at a temperature of about 50° C. to about 60° C., e.g., about 55° C. In some embodiments, the treating of Compound 5 is performed in the presence of S4, wherein S4 is a polar protic solvent. In some embodiments, S4 is an alcohol, e.g., methanol. In some embodiments, the treating of Compound 5 comprises using about 1 to about 5 molar equivalents of B1 per molar equivalent of Compound 5. In some embodiments, the treating of Compound 5 comprises using about 3 molar equivalents of B1 per molar equivalent of Compound 5.

Compound 5 can be produced by a process comprising reacting Compound 6 with di-tert-butyl dicarbonate. The reacting of Compound 6 can be performed in the presence of S5, wherein S5 is a polar aprotic solvent. In some embodiments, S5 is dichloromethane. In some embodiments, the reacting of Compound 6 is performed at about 35° C. to about 45° C. In some embodiments, the reacting of Compound 6 is performed at about 40° C. In some embodiments, the reacting of Compound 6 comprises using about 1 to about 1.5 molar equivalents of di-tert-butyl dicarbonate per molar equivalent of Compound 6. In some embodiments, the reacting of Compound 6 comprises using about 1 to about 1.25 molar equivalents of di-tert-butyl dicarbonate per molar equivalent of Compound 6. In some embodiments, the reacting of Compound 6 comprises using about 1 (e.g., about 1.1) molar equivalents of di-tert-butyl dicarbonate per molar equivalent of Compound 6.

Compound 6 can be produced by a process comprising contacting a Compound 7 with Compound 8. In some embodiments, in the presence of A2 and RA1, wherein A2 is an acid and RA1 is a reducing agent. A2 can be an organic acid, e.g., acetic acid. In some embodiments, about 0.75 to 1.25 molar equivalents of Compound 8 are used per molar equivalent of Compound 7. In some embodiments, about 1.1 molar equivalents of Compound 8 are used per molar equivalent of Compound 7. In some embodiments, about 1 to about 3 molar equivalents of A2 are used per molar equivalent of Compound 7. In some embodiments, about 1.5 to about 2.5 molar equivalents of A2 are used per molar equivalent of Compound 7. In some embodiments, about 2 (e.g., about 2.1) molar equivalents of A2 are used per molar equivalent of Compound 7. In some embodiments, RA1 is a borohydride reducing agent. In some embodiments, RA1 is sodium triacetoxyborohydride. In some embodiments, about 1 to about 2 molar equivalents of RA1 are used per molar equivalent of Compound 7. In some embodiments, about 1.2 molar equivalents of RA1 are used per molar equivalent of Compound 7. In some embodiments, the contacting of Compound 7 with Compound 8 is performed in the presence of S6, wherein S6 is a polar aprotic solvent. In some embodiments, S6 is dichloromethane. In some embodiments, the contacting of Compound 7 with Compound 8 is performed at first temperature and then cooled to second temperature. In some embodiments, the first temperature is about 20° C. to about 30° C. In some embodiments, the first temperature is room temperature. In some embodiments, the second temperature is between about −5° C. and about 5° C. In some embodiments, the second temperature is about 5° C.

Compound 7 can be produced by a process comprising contacting piperidin-4-one hydrochloride hydrate with 2,2,2-trifluoroacetic anhydride in the presence of B2, wherein B2 is a base. In some embodiments, B2 is an amine base. In some embodiments, B2 is triethylamine. In some embodiments, the contacting of piperidin-4-one hydrochloride hydrate with 2,2,2-trifluoroacetic anhydride is performed in the presence of S7, wherein S7 is a polar aprotic solvent. In some embodiments, S7 is dichloromethane. In some embodiments, between about 1 to about 2 molar equivalents of B2 are used per molar equivalent of piperidin-4-one hydrochloride hydrate. In some embodiments, about 1 (e.g., about 1.1) molar equivalents of B2 are used per molar equivalent of piperidin-4-one hydrochloride hydrate. In some embodiments, between about 1 to about 3 molar equivalents of 2,2,2-trifluoroacetic anhydride are used per molar equivalent of piperidin-4-one hydrochloride hydrate. In some embodiments, about 2 molar equivalents of 2,2,2-trifluoroacetic anhydride are used per molar equivalent of piperidin-4-one hydrochloride hydrate. In some embodiments, the contacting of piperidin-4-one hydrochloride hydrate with 2,2,2-trifluoroacetic anhydride is performed at a temperature between about 0° C. and about 30° C.

Compound 4 can be produced by a process comprising treating Compound 9 with A3, wherein A3 is an acid. In some embodiments, A3 is an organic acid such as trifluoroacetic acid. In some embodiments, the treating of Compound 9 is performed in the presence of S8, wherein S8 is a polar aprotic solvent, e.g., dichloromethane. In some embodiments, between about 2 to about 10 molar equivalents of A3 are used per molar equivalent of Compound 9. In some embodiments, between about 3 to about 6 molar equivalents of A3 are used per molar equivalent of Compound 9. In some embodiments, about 4 molar equivalents of A3 are used per molar equivalent of Compound 9. In some embodiments, the treating of Compound 9 is performed at a temperature between about 25° C. and about 45° C. In some embodiments, the treating of Compound 9 is performed at a temperature between about 30° C. and 40° C.

Compound 9 can be produced by a process comprising treating Compound 10 with B3 and tert-butyl chlorosulfonylcarbamate, wherein B3 is a base. In some embodiments, B3 is an amine base, e.g., triethylamine. In some embodiments, between about 1 and about 5 molar equivalents of B3 are used per molar equivalent of Compound 10. In some embodiments, between about 2 and about 3 molar equivalents of B3 are used per molar equivalent of Compound 10. In some embodiments, wherein the treating of Compound 10 is performed in the presence of S9, wherein S9 is a polar aprotic solvent. In some embodiments, S9 is dichloromethane. In some embodiments, the treating of Compound 10 is performed at a first temperature and then cooled to a second temperature. In some embodiments, the first temperature is between about 15° C. and about 30° C. In some embodiments, the first temperature is room temperature. In some embodiments, the second temperature is between about −5° C. and about 5° C. In some embodiments, the second temperature is about 0° C.

Compound 10 can be produced by a process comprising treating Compound 11 with HCl. In some embodiments, the treating of Compound 11 is performed in the presence of S10, wherein S10 is a polar aprotic solvent, e.g., dichloromethane. In some embodiments, between about 1 and about 20 molar equivalents of HCl are used per molar equivalent of Compound 11. In some embodiments, between about 5 and about 15 molar equivalents of HCl are used per molar equivalent of Compound 11. In some embodiments, about 10 molar equivalents of HCl are used per molar equivalent of Compound 11.

Compound 1 or a salt thereof can also be prepared by a process that includes:

a) contacting Compound 16 having the formula:

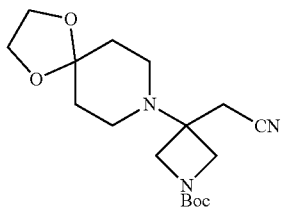

Compound 16 with A6 and water, wherein A6 is an acid, to produce Compound 15 having the formula:

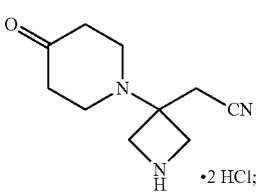

Compound 15 b) treating Compound 15 with B5 and tert-butyl chlorosulfonylcarbamate, wherein B5 is a base, to produce Compound 14 having the formula:

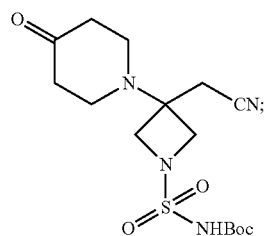

Compound 14 c) contacting a Compound 14 with Compound 8 having the formula:

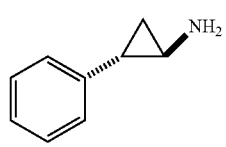

Compound 8 in the presence of A5 and RA2, wherein A5 is an acid, and RA2 is a reducing agent to produce Compound 13 having the formula:

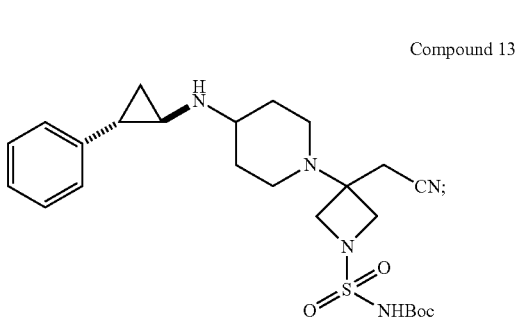

Compound 13 d) contacting Compound 13 with di-tert-butyl dicarbonate to produce Compound 12 having the formula:

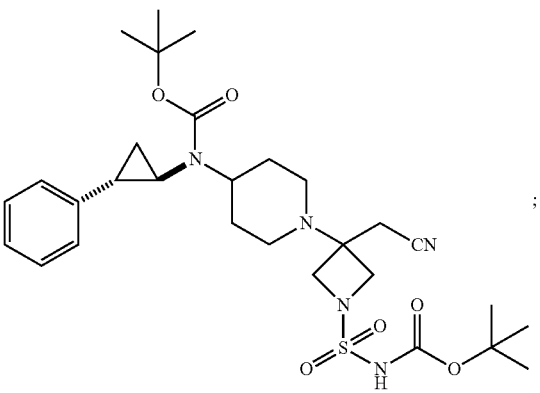

Compound 12 and e) deprotecting Compound 12 with A4, wherein A4 is an acid, to form Compound 1.

Compound 1 or a salt thereof can be prepared by a process that includes deprotecting Compound 12 with A4, wherein A4 is an acid. In some embodiments, A4 is a mineral acid. For example, A4 is HCl. The salt of Compound 1 can be a hydrochloric acid salt. In some embodiments, the deprotecting of Compound 12 is performed in the presence of S11, wherein S11 is a polar protic solvent. In some embodiments, S11 is an alcohol, e.g., methanol. In some embodiments, the deprotecting of Compound 12 is performed at a temperature between about 35° C. and about 45° C. In some embodiments, the deprotecting of Compound 12 is performed at a temperature of about 40° C. In some embodiments, the process of preparing Compound 1 further comprises precipitating Compound 1 from a solution comprising Compound 1 and S12, wherein S12 comprises a solvent and an anti-solvent. In some embodiments, the solvent of S12 is a polar aprotic solvent, e.g., 2-butanone. In some embodiments, the anti-solvent of S12 is a hydrocarbon solvent, e.g., heptane. In some embodiments, the deprotecting of Compound 12 comprises using about 1 to about 15 molar equivalents of A4 per molar equivalent of Compound 12. In some embodiments, the deprotecting of Compound 12 comprises using about 5 to about 10 molar equivalents of A4 per molar equivalent of Compound 12. In some embodiments, the deprotecting of Compound 12 comprises using about 8 to about 9 molar equivalents of A4 per molar equivalent of Compound 12.

Compound 12 can be prepared by a process comprising contacting Compound 3 with Compound 9 in the presence of B4, wherein B4 is a base. In some embodiments, B4 is an amine base. In some embodiments, B4 is 1,8-diazabicyclo[5.4.0]undec-7-ene. In some embodiments, the contacting of Compound 3 with Compound 9 is performed in the presence of S13, wherein S13 is a polar aprotic solvent. In some embodiments, S13 is acetonitrile. In some embodiments, the contacting of Compound 3 with Compound 9 is performed at a temperature between about 50° C. and about 60° C. In some embodiments, the contacting of Compound 3 with Compound 9 is performed at a temperature of about 55° C. In some embodiments, the contacting of Compound 3 with Compound 9 comprises using between about 1 and about 5 molar equivalents of Compound 3 per molar equivalent of Compound 9. In some embodiments, the contacting of Compound 3 with Compound 9 comprises using between about 1 and about 2 molar equivalents of Compound 3 per molar equivalent of Compound 9. In some embodiments, the contacting of Compound 3 with Compound 9 comprises using about 1.5 equivalents of Compound 3 per equivalent of molar Compound 9. In some embodiments, the contacting of Compound 3 with Compound 9 comprises using between about 1 and about 1.5 molar equivalents of B4 per molar equivalent of Compound 9. In some embodiments, the contacting of Compound 3 with Compound 9 comprises using about 1 (e.g., about 1.1) molar equivalents of B4 per molar equivalent of Compound 9.

Alternatively, Compound 12 can be prepared by a process comprising contacting Compound 13 with di-tert-butyl dicarbonate. In some embodiments, the reacting of Compound 13 is performed in the presence of S14, wherein S14 is a polar aprotic solvent, e.g., dichloromethane. In some embodiments, the reacting of Compound 13 is performed at a temperature between about 35° C. and about 45° C. In some embodiments, the reacting of Compound 13 is performed at about 40° C. In some embodiments, the reacting of Compound 13 comprises using between about 1 and about 2 molar equivalents of di-tert-butyl dicarbonate per molar equivalent of Compound 13. In some embodiments, the reacting of Compound 13 comprises using about 1 and about 1.25 molar equivalents of di-tert-butyl dicarbonate per molar equivalent of Compound 13. In some embodiments, the reacting of Compound 13 comprises using about 1 molar equivalent of di-tert-butyl dicarbonate per molar equivalent of Compound 13.

Compound 13 can be prepared by a process comprising contacting a Compound 14 with Compound 8 in the presence of A5 and RA2, wherein A5 is an acid, and RA2 is a reducing agent. In some embodiments, A5 is an organic acid. In some embodiments, A5 is acetic acid. In some embodiments, the contacting of Compound 14 with Compound 8 comprises using between about 1 and about 3 molar equivalents of A5 per molar equivalent Compound 14. In some embodiments, the contacting of Compound 14 with Compound 8 comprises using about 1.2 molar equivalents of A5 per molar equivalent of Compound 14. In some embodiments, the contacting of Compound 14 with Compound 8 is performed in the presence of S15, wherein S15 is a polar aprotic solvent. In some embodiments, S15 is dichloromethane. In some embodiments, the contacting of Compound 14 with Compound 8 is performed at a first temperature and then cooled to a second temperature. In some embodiments, the first temperature is between about 20° C. and about 30° C. In some embodiments, the first temperature is room temperature. In some embodiments, the second temperature is between about −5° C. and about 5° C. In some embodiments, the second temperature is about 0° C. In some embodiments, RA2 is a borohydride reducing agent. In some embodiments, RA2 is sodium triacetoxyborohydride. In some embodiments, the contacting of Compound 14 with Compound 8 comprises using between about 1 and about 3 molar equivalents of RA2 per molar equivalent of Compound 14. In some embodiments, the contacting of Compound 14 with Compound 8 comprises using about 1.2 molar equivalents of RA2 per molar equivalent of Compound 14.

Compound 14 can be prepared by a process comprising: treating Compound 15 with B5 and tert-butyl chlorosulfonylcarbamate, wherein B5 is a base. In some embodiments, B5 is an amine base. In some embodiments, B5 is triethylamine. In some embodiments, between about 1 and about 5 molar equivalents of B5 are used per molar equivalent of Compound 15. In some embodiments, between about 2 and about 3 molar equivalents of B5 are used per molar equivalent of Compound 15. In some embodiments, the treating of Compound 15 is performed in the presence of S16, wherein S16 is a polar aprotic solvent. In some embodiments, S16 is dichloromethane. In some embodiments, the treating of Compound 15 is performed at a first temperature and then cooled to a second temperature. In some embodiments, the first temperature is between about 15° C. and about 30° C. In some embodiments, the first temperature is room temperature. In some embodiments, the second temperature is between about −5° C. and about 5° C. In some embodiments, the second temperature is about 0° C.

Compound 15 can be prepared by a process comprising: contacting Compound 16 with A6 and water, wherein A6 is an acid. In some embodiments, A6 is a mineral acid. In some embodiments, A6 is HCl. In some embodiments, A6 is a solution of HCl in isopropanol. In some embodiments, the contacting of Compound 16 is performed in the presence of S17, wherein S17 is a polar protic solvent. In some embodiments, S17 is an alcohol. In some embodiments, S17 is isopropanol. In some embodiments, the contacting of Compound 16 is performed at a temperature between about 55° C. and about 65° C. In some embodiments, the contacting of Compound 16 is performed at about 60° C.

Compound 16 can be prepared by a process comprising: contacting tert-butyl 3-(cyanomethylene) azetidine-1-carboxylate with 1,4-dioxa-8-azaspiro[4.5]decane. In some embodiments, the contacting of tert-butyl 3-(cyanomethylene) azetidine-1-carboxylate with 1,4-dioxa-8-azaspiro[4.5]decane is performed in the presence of S18, wherein S18 is a polar protic solvent. In some embodiments, S18 is an alcohol. In some embodiments, S18 is methanol. In some embodiments, the contacting of tert-butyl 3-(cyanomethylene) azetidine-1-carboxylate with 1,4-dioxa-8-azaspiro[4.5]decane is performed at a temperature between about 60° C. and about 70° C. In some embodiments, the contacting of tert-butyl 3-(cyanomethylene) azetidine-1-carboxylate with 1,4-dioxa-8-azaspiro[4.5]decane is performed at a temperature of about 65° C.

In some embodiments, provided herein is a process for preparing Compound 1 comprising deprotecting Compound 2 with A1, wherein A1 is an acid, to form Compound 1. In some embodiments, provided herein is a process for preparing Compound 1 comprising:
a) contacting Compound 3 with Compound 4 to form Compound 2; and
b) deprotecting Compound 2 with A1, wherein A1 is an acid, to form Compound 1.

In some embodiments, provided herein is a process for preparing Compound 1 comprising contacting deprotecting Compound 12 with A4, wherein A4 is an acid to form Compound 1. In some embodiments, provided herein is a process for preparing Compound 1 comprising:
   a) contacting Compound 3 with Compound 9 in the presence of B4, wherein B4 is a base, to form Compound 12; and
   b) deprotecting Compound 12 with A4, wherein A4 is an acid to form Compound 1.

In some embodiments, provided herein is a process for preparing Compound 1 comprising:
   a) contacting Compound 13 with di-tert-butyl dicarbonate to form Compound 12; and
   b) deprotecting Compound 12 with A4, wherein A4 is an acid.

In some embodiments, provided herein is a process for preparing Compound 1 comprising:
   a) contacting Compound 14 with Compound 8 in the presence of A5 and RA2, wherein A5 is an acid, and RA2 is a reducing agent to produce Compound 13;
   b) contacting Compound 13 with di-tert-butyl dicarbonate to form Compound 12; and
   c) deprotecting Compound 12 with A4, wherein A4 is an acid.

In some embodiments, provided herein is a process for preparing Compound 2, comprising contacting Compound 3 with Compound 4. In some embodiments, provided herein is a process for preparing Compound 2, comprising:
   a) treating Compound 11 with HCl to form Compound 10;
   b) treating Compound 10 with B3 and tert-butyl chlorosulfonylcarbamate, wherein B3 is a base, to form Compound 9;
   c) treating Compound 9 with A3, wherein A3 is an acid, to form Compound 4;
   d) contacting piperidin-4-one hydrochloride hydrate with 2,2,2-trifluoroacetic anhydride in the presence of B2, wherein B2 is a base, to form Compound 7;
   e) contacting Compound 7 with Compound 8 in the presence of A2 and RA1, wherein A2 is an acid, and RA1 is a reducing agent, to provide Compound 6;
   f) reacting Compound 6 with di-tert-butyl dicarbonate to produce Compound 5;
   g) treating Compound 5 with B1, wherein B1 is a base, to produce Compound 3; and
   h) contacting Compound 3 with Compound 4 to form Compound 2.

In some embodiments, provided herein is a process for preparing Compound 12 comprising contacting Compound 13 with di-tert-butyl dicarbonate. In some embodiments, provided herein is a process for preparing Compound 12 comprising contacting Compound 3 with Compound 9 in the presence of B4, wherein B4 is a base.

In some embodiments, provided herein is a process for preparing Compound 9 comprising treating Compound 10 with B3 and tert-butyl chlorosulfonylcarbamate, wherein B3 is a base. In some embodiments, provided herein is a process for preparing Compound 9 comprising:
   a) treating Compound 11 with HCl to form Compound 10; and
   b) treating Compound 10 with B3 and tert-butyl chlorosulfonylcarbamate, wherein B3 is a base, to form Compound 9.

Also provided herein is also a process for preparing Compound 4 comprising:
   a) treating Compound 10 with B3 and tert-butyl chlorosulfonylcarbamate, wherein B3 is a base, to form Compound 9; and
   b) treating Compound 9 with A3, wherein A3 is an acid, to form Compound 4.

In some embodiments, Compound 4 is prepared by a process comprising:
   c) treating Compound 11 with HCl to form Compound 10;
   d) treating Compound 10 with B3 and tert-butyl chlorosulfonylcarbamate, wherein B3 is a base, to form Compound 9; and
   e) treating Compound 9 with A3, wherein A3 is an acid, to form Compound 4.

Also provided herein is a process for preparing Compound 3 comprising treating Compound 5 with B1, wherein B1 is a base, to produce Compound 3. In some embodiments, Compound 3 is prepared by a process comprising:
   a) reacting Compound 6 with di-tert-butyl dicarbonate to produce Compound 5; and
   b) treating Compound 5 with B1, wherein B1 is a base, to produce Compound 3.

In some embodiments, Compound 3 is prepared by a process comprising:
   a) contacting Compound 7 with Compound 8 in the presence of A2 and RA1, wherein A2 is an acid, and RA1 is a reducing agent, to provide Compound 6;
   b) reacting Compound 6 with di-tert-butyl dicarbonate to produce Compound 5; and
   c) treating Compound 5 with B1, wherein B1 is a base, to produce Compound 3.

Also provided herein is a process for preparing Compound 3 comprising:
   a) contacting piperidin-4-one hydrochloride hydrate with 2,2,2-trifluoroacetic anhydride in the presence of B2, wherein B2 is a base, to form Compound 7;
   b) contacting Compound 7 with Compound 8 in the presence of A2 and RA1, wherein A2 is an acid, and RA1 is a reducing agent, to provide Compound 6;
   c) reacting Compound 6 with di-tert-butyl dicarbonate to produce Compound 5; and
   d) treating Compound 5 with B1, wherein B1 is a base, to produce Compound 3.

In some embodiments, provided herein is a process for preparing Compound 14 comprising treating Compound 15 with B5 and tert-butyl chlorosulfonylcarbamate, wherein B5 is a base, to provide Compound 14. In some embodiments, provided herein is a process for preparing Compound 14 comprising:
   a) contacting tert-butyl 3-(cyanomethyl ene) azetidine-1-carboxylate with 1,4-dioxa-8-azaspiro[4.5]decane to provide Compound 16; and
   b) contacting Compound 16 with A6, wherein A6 is an acid, and water to provide Compound 15.

In some embodiments, provided herein is a process for preparing Compound 14 comprising:
   a) contacting tert-butyl 3-(cyanomethylene) azetidine-1-carboxylate with 1,4-dioxa-8-azaspiro[4.5]decane to provide Compound 16;
   b) contacting Compound 16 with A6, wherein A6 is an acid, and water to provide Compound 15;
   c) treating Compound 15 with B5 and tert-butyl chlorosulfonylcarbamate, wherein B5 is a base, to provide Compound 14.

In some embodiments, provided herein is a compound having the formula:

Compound 2

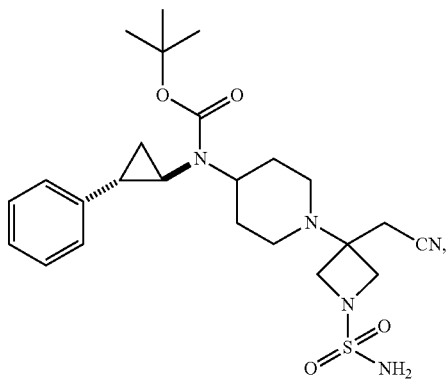

or a salt thereof.

In some embodiments, provided herein is a compound having the formula:

Compound 3

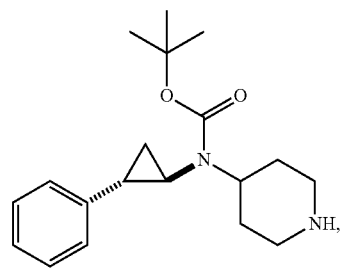

or a salt thereof.

In some embodiments, provided herein is a compound having the formula:

Compound 4

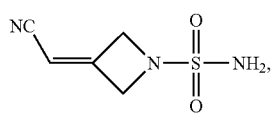

or a salt thereof.

In some embodiments, provided herein is a compound having the formula:

Compound 5

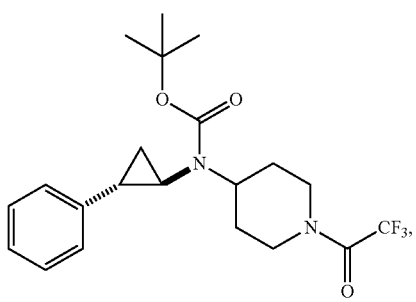

or a salt thereof.

In some embodiments, provided herein is a compound having the formula:

Compound 6

or a salt thereof.

In some embodiments, provided herein is a compound having the formula:

Compound 9

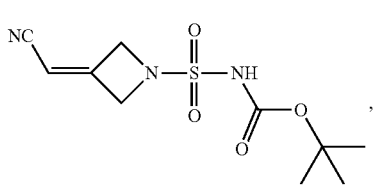

or a salt thereof.

In some embodiments, provided herein is a compound having the formula:

Compound 12

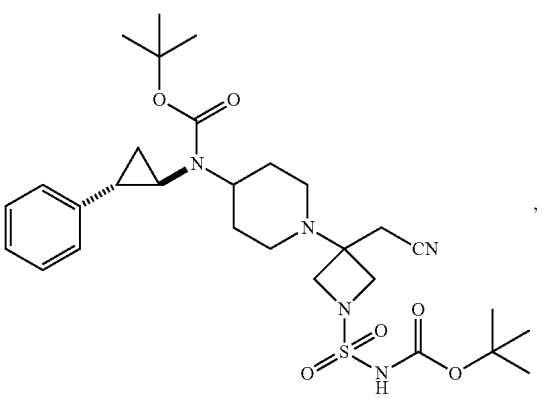

or a salt thereof.

In some embodiments, provided herein is a compound having the formula:

Compound 13

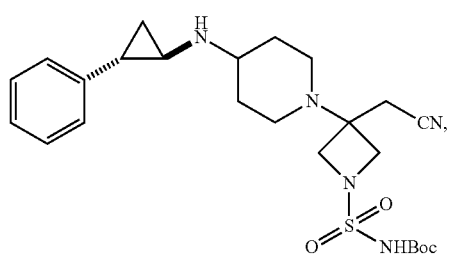

or a salt thereof.

In some embodiments, provided herein is a compound having the formula:

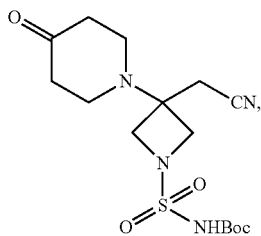

Compound 14 or a salt thereof.

In some embodiments, provided herein is a compound having the formula:

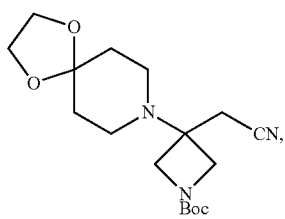

Compound 16 or a salt thereof.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

As used herein, the term "reacting," "contacting" or "treating" when describing a certain process is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The terms "protecting" and "deprotecting" as used herein in a chemical reaction refer to inclusion of a chemical group in a process and such group is removed in a later step in the process. The term preparation of Compound 1 and its salts can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006). Examples of protecting groups include amino protecting groups. As used herein, "amino protecting group" refers to any protecting group for the protection of amines. Example amino protecting groups include, but are not limited to, phenylsulfonyl, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl) ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM).

As used herein, the phrase "metal hydroxide base," employed alone or in combination with other terms, refers to a base having formula MOH, wherein M refers to a metal such as an alkali metal (e.g. lithium, sodium, or potassium). Example alkali metal hydroxide bases include, but are not limited to lithium hydroxide, sodium hydroxide, and potassium hydroxide.

The term "amine base" refers to a base that has an amine group. The amine can be a primary, secondary, or tertiary amine. Examples of an amine base include methylamine, dimethylamine, diphenyl amine, trimethylamine, triethylamine, 1,8-diazabicyclo[5.4.0]undec-7-ene, and the like.

The term "mineral acid" refers to an acid that is formed from inorganic compound and can form hydrogen ions and conjugate base ions in an aqueous solution. Mineral acids can be a strong acid or strong acid. Examples of mineral acids include but not limited to hydrochloric acid, perchloric acid, sulfuric acid, nitric acid, boric acid, phosphoric acid, and the like.

The term "organic acid" refers to an acid with an organic moiety. Examples of organic acid include but not limited to acetic acid, trifluoroacetic acid, formic acid, benzoic acid, toluenesulfonic acid, triflic acid, and the like.

In some embodiments, anti-solvent as described herein refers to a solvent where Compound 1 or its salts are less soluble relative to another solvent or solvent mixture in the solution. For example, anti-solvent can include but not limited to benzene, cyclohexane, pentane, hexane, heptane (e.g., n-heptane), toluene, cycloheptane, methylcyclohexane, heptane, ethylbenzene, m-, o-, or p-xylene, octane, indane, nonane, or naphthalene.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable polar protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol. The polar protic solvent can be an alcohol such as methanol, ethanol, 1-propanol, 2-propanol, and the like.

Suitable aprotic solvents can include, by way of example and without limitation, 2-butanone, acetonitrile, dichloromethane, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, and the like.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The term "reducing agent" as used herein refers to a compound that donates an electron to another compound in a redox reaction. The reducing agent would be oxidized after it loses its electrons. Examples of reducing agents include, but not limited to, borohydride, triacetoxyborohydride, sodium borohydride, lithium aluminium hydride, hydrogen on palladium, and the like.

The reactions of the processes described herein can be carried out in air or under an inert atmosphere. Typically, reactions containing reagents or products that are substantially reactive with air can be carried out using air-sensitive synthetic techniques that are well known to the skilled artisan.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

Methods of Use

Compounds and solid forms of the invention, e.g., Compound 1 and salts thereof, are LSD1 inhibitors and, thus, are useful in treating diseases and disorders associated with activity of LSD1. For the uses described herein, any of the compounds and solid forms of the invention, including any of the embodiments thereof, may be used.

In some embodiments, the compounds of the invention are selective for LSD1 over LSD2, meaning that the compounds bind to or inhibit LSD1 with greater affinity or potency, compared to LSD2. In general, selectivity can be at least about 5-fold, at least about 10-fold, at least about 20-fold, at least about 50-fold, at least about 100-fold, at least about 200-fold, at least about 500-fold or at least about 1000-fold.

As inhibitors of LSD1, the compounds and solid forms of the invention are useful in treating LSD1-mediated diseases and disorders. The term "LSD1-mediated disease" or "LSD1-mediated disorder" refers to any disease or condition in which LSD1 plays a role, or where the disease or condition is associated with expression or activity of LSD1. The compounds of the invention can therefore be used to treat or lessen the severity of diseases and conditions where LSD1 is known to play a role.

Diseases and conditions treatable using the compounds and solid forms of the invention include generally cancers, inflammation, autoimmune diseases, viral induced pathogenesis, beta-globinopathies, and other diseases linked to LSD1 activity.

Cancers treatable using compounds according to the present invention include, for example, hematological cancers, sarcomas, lung cancers, gastrointestinal cancers, genitourinary tract cancers, liver cancers, bone cancers, nervous system cancers, gynecological cancers, and skin cancers.

Example hematological cancers include, for example, lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Example sarcomas include, for example, chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Example lung cancers include, for example, non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Example gastrointestinal cancers include, for example, cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Example genitourinary tract cancers include, for example, cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Example liver cancers include, for example, hepatoma (hepatocellular carcinoma), cholangiocarcinoma, hepatoblastoma, angiosarcoma, hepatocellular adenoma, and hemangioma.

Example bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Example nervous system cancers include, for example, cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Example gynecological cancers include, for example, cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Example skin cancers include, for example, melanoma, basal cell carcinoma, squamous cell carcinoma, Kaposi's sarcoma, moles dysplastic nevi, lipoma, angioma, dermatofibroma, and keloids.

The compounds and solid forms of the invention can further be used to treat cancer types where LSD1 may be overexpressed including, for example, breast, prostate, head and neck, laryngeal, oral, and thyroid cancers (e.g., papillary thyroid carcinoma).

The compounds and solid forms of the invention can further be used to treat genetic disorders such as Cowden syndrome and Bannayan-Zonana syndrome.

The compounds and solid forms of the invention can further be used to treat viral diseases such as herpes simplex virus (HSV), varicella zoster virus (VZV), human cytomegalovirus, hepatitis B virus (HBV), and adenovirus.

The compounds and solid forms of the invention can further be used to treat beta-globinopathies including, for example, beta-thalassemia and sickle cell anemia.

The term "contacting" as used in the context of in vitro and in vivo system, refers to the bringing together of indicated moieties in an in vitro system or an in vivo system. For example, "contacting" a LSD1 protein with a compound of the invention includes the administration of a compound of the present invention to an individual or patient, such as a human, having a LSD1 protein, as well as, for example, introducing a compound of the invention into a sample containing a cellular or purified preparation containing the LSD1 protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

The term "treating" or "treatment" as used in the context of treating diseases, condition or disorders refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds and solid forms of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, JAK, PIM, PI3K inhibitors for treatment of LSD1-mediated diseases, disorders or conditions. The one or more additional pharmaceutical agents can be administered to a patient simultaneously or sequentially.

In some embodiments, the compounds and solid forms of the invention can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

The compounds and solid forms described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the compounds as described herein can be combined with inhibitors of kinases associated with the PIK3/Akt/mTOR signaling pathway, such as PI3K, Akt (including Akt1, Akt2 and Akt3) and mTOR kinases.

The compounds and solid forms as described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

One or more of the following agents may be used in combination with the compounds and solid forms of the present disclosure and are presented as a non-limiting list: a cytostatic agent, taxotere, taxol, camptostar, epothilones, 5-fluorouracil, SCH 66336, R115777, L778,123, BMS 214662, IRESSA™ (gefitinib), TARCEVA™ (erlotinib), antibodies to EGFR, GLEEVEC™ (imatinib mesylate), intron, ara-C, adriamycin, cytoxan, chlormethine, triethylenemelamine, triethylenethiophosphoramine, busulfan, 6-mercaptopurine, 6-thioguanine, fludarabine phosphate, ELOXATIN™ (oxaliplatin), vindesine, mithramycin, deoxycoformycin, L-asparaginase, 17 alpha-ethinylestradiol, diethylstilbestrol, testosterone, prednisone, fluoxymesterone, methylprednisolone, methyltestosterone, prednisolone, triamcinolone, chlortrianisene, hydroxyprogesterone, aminoglutethimide, medroxyprogesteroneacetate, leuprolide, flutamide, goserelin, hydroxyurea, amsacrine, navelbene, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), aphidicolon, rituxan, Sml1, triapine, didox, trimidox, amidox, 3-AP, and MDL-101, 731.

For treating cancer and other proliferative diseases, the compounds and solid forms of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, baricitinib, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, niraparib, nofetumomab, olaparib, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, rucaparib, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, veliparib, talazoparib, and zoledronate.

For treating cancer and other proliferative diseases, the compounds and solid forms of the invention can be used in combination with ruxolitinib.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include the compounds, and pharmaceutically acceptable salts.

Example suitable Flt-3 inhibitors include compounds, and their pharmaceutically acceptable salts.

Example suitable RAF inhibitors include compounds, and their pharmaceutically acceptable salts.

Example suitable FAK inhibitors include compounds, and their pharmaceutically acceptable salts.

In some embodiments, the compounds and solid forms of the disclosure can be used in combination with one or more other kinase inhibitors including imatinib, particularly for treating patients resistant to imatinib or other kinase inhibitors.

The compounds and solid forms can be used in combination with tumor vaccines and CAR (Chimeric antigen receptor) T cell treatment as a booster for T cell activation (21). In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds and solid forms of the present disclosure can be used in combination with tumor specific antigen such as heat shock proteins isolated from tumor tissue itself. In some embodiments, the compounds and solid forms can be combined with dendritic cells immunization to activate potent anti-tumor responses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

For treating cancer and other proliferative diseases, the compounds and solid forms of the invention can be used in combination with targeted therapies, including JAK kinase inhibitors (Ruxolitinib, additional JAK1/2 and JAK1-selective, baricitinib or INCB39110), Pim kinase inhibitors (e.g., INCB53914), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors, TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors INCB54329 or INCB57643), LSD1 inhibitors (INCB59872), arginase inhibitors (INCB1158), indoleamine 2,3-dioxygenase inhibitors (epacadostat, NLG919 or BMS-986205), and PARP inhibitors (e.g., olaparib or rucaparib).

For treating autoimmune or inflammatory conditions, the compounds and solid forms of the invention can be administered in combination with a corticosteroid such as triamcinolone, dexamethasone, fluocinolone, cortisone, prednisolone, or flumetholone.

For treating autoimmune or inflammatory conditions, the compounds and solid forms of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compounds and solid forms of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101 (T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S, 3S, 4R, 5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compounds and solid forms of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastine; naphazoline; antazoline; pheniramine; or azalide antibiotic.

Other examples of agents, one or more of which a provided compound or solid form may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Biological drugs, such as antibodies and cytokines, used as anticancer angents, can be combined with the compounds of the invention. In addition, drugs modulating microenvironment or immune responses can be combined with the compounds of the invention. Examples of such drugs are anti-Her2 antibodies, anti-CD20 antibodies, anti-CTLA1, anti-PD-1, anti-PDL1, and other immunotherapeutic drugs.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

Formulation, Dosage Forms and Administration

When employed as pharmaceuticals, the compounds and solid forms of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound and solid forms of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound or solid form can be milled to provide the appropriate particle size prior to combining with the other ingredients. If the active compound or solid form is substantially insoluble, it can be milled to a particle size of less than 200 mesh. If the active compound or solid form is substantially water soluble, the particle size can be adjusted by milling to provide a substantially uniform distribution in the formulation, e.g., about 40 mesh.

The compounds and solid forms of the invention may be milled using known milling procedures such as wet milling to obtain a particle size appropriate for tablet formation and for other formulation types. Finely divided (nanoparticulate) preparations of the compounds and solid forms of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound or solid form of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound or solid form of the invention. The topical formulations can be suitably packaged in tubes of, for example, 100 g which are optionally associated with instructions for the treatment of the select indication, e.g., psoriasis or other skin condition.

The amount of compound or solid form or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds and solid forms of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating LSD1 in tissue samples, including human, and for identifying LSD1 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes LSD1 assays that contain such labeled or substituted compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium) $^{11}C$, $^{13}C$, $^{14}C$, $^{13}N$, $^{15}N$, $^{15}O$, $^{17}O$, $^{18}F$, $^{35}S$, $^{36}Cl$, $^{82}Br$, $^{75}Br$, $^{76}Br$, $^{77}B$, $^{123}I$, $^{124}I$, $^{125}I$ and $^{131}I$. For example, one or more hydrogen atoms in a compound of the present invention can be replaced by deuterium atoms (e.g., one or more hydrogen atoms of a $C_{1-6}$ alkyl group of a compound provided herein can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-", "alkylene", "alkenylene" and "alkynylene" linking groups, as described herein, are optionally replaced by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro LSD1 and competition assays, compounds that incorporate $^{3}H$, $^{14}C$, $^{82}Br$, $^{125}I$, $^{131}I$ or $^{35}S$ can be useful. For radioimaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind LSD1 by monitoring its concentration variation when contacting with LSD1, through tracking of the labeling. For example, a test compound (labeled) can be evaluated for its ability to reduce binding of another compound which is known to bind to LSD1 (i.e., standard compound). Accordingly, the ability of a test compound to compete with the standard compound for binding to LSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of LSD1 as described below.

EXAMPLES

Experimental procedures for compounds of the invention are provided below.

Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

The following abbreviations may be used herein: AcOH (acetic acid); Ac₂O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N,N-diisopropylethylamine); DIBAL (diisobutylaluminium hydride); DMF (N,N-dimethylformamide); Et (ethyl); EtOAc (ethyl acetate); FCC (flash column chromatography); g (gram(s)); h (hour(s)); HATU (N,N,N',N'-tetramethyl-O-(7-azabenzotriazol-1-yl) uronium hexafluorophosphate); HCl (hydrochloric acid); HPLC (high performance liquid chromatography); Hz (hertz); J (coupling constant); LCMS (liquid chromatography-mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); (microliter(s)); μM (micromolar); wt % (weight percent).

Intermediate 1.
3-(cyanomethylene)azetidine-1-sulfonamide

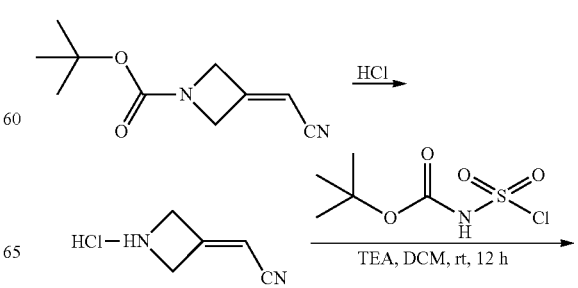

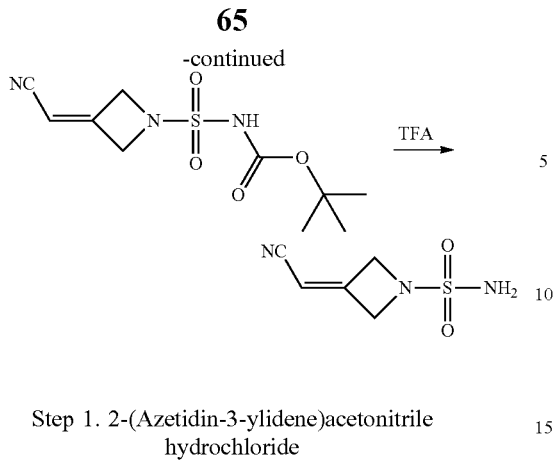
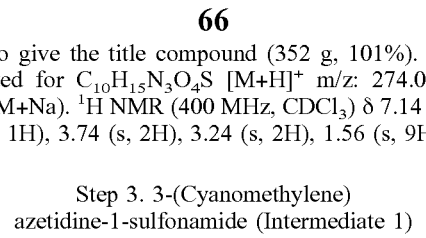

Step 1. 2-(Azetidin-3-ylidene)acetonitrile hydrochloride

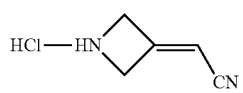

To a solution of tert-butyl 3-(cyanomethylene) azetidine-1-carboxylate (150.0 g, 772 mmol) in dichloromethane (1.48 L) was added a 5.25 M solution of HCl in isopropyl alcohol (1.47 L, 7723 mmol) with an addition funnel. After the reaction mixture was stirred at room temperature for 4 h, heptane (3.0 L) was added. The mixture was stirred for 1 hour, filtered and dried by pulling air through the resulting cake to give 89.5 g of the title compound (yield: 89%, white solid). $^1$H NMR (400 MHz, DMSO) δ 9.96 (s, 2H), 6.25-5.66 (m, 1H), 5.13-4.47 (m, 4H).

Step 2. Tert-butyl ((3-(cyanomethylene)azetidin-1-yl)sulfonyl)carbamate

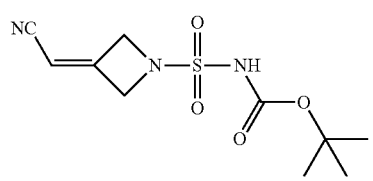 [SMILES: CC(C)(C)OC(=O)NS(=O)(=O)N1CC(=CC#N)C1]

A solution of tert-butyl alcohol (123 g, 1660 mmol) in dichloromethane (660 mL, 6V) was allowed to stir and cooled via a salt/ice bath. To this solution, sulfurisocyanatidic chloride (128 mL, 1468 mmol) dissolved in dichloromethane (660 mL, 6V) was added slowly via addition funnel, as the temperature of the solution was held from 1.2° C. to 5.5° C.). The solution was stirred for 1 h at 3° C., providing a solution of tert-butyl chlorosulfonylcarbamate.

To a suspension of 2-(azetidin-3-ylidene) acetonitrile hydrochloride (Step 1, 166.7 g, 1277 mmol) in dichloromethane (1660 mL, 10V) was added triethylamine (445 mL, 3192 mmol). After stirring for 30 minutes, the reaction mixture was cooled down to 0° C. To this mixture was slowly added the prepared solution of tert-butyl chlorosulfonylcarbamate with an addition funnel, holding the temperature between 2 and 13° C. The reaction mixture was then stirred at 0° C. for 1 h. The reaction mixture was diluted with dichloromethane (300 mL). The reaction mixture was partitioned between dichloromethane and 0.2N HCl in water (3.55 L). The organics were dried over MgSO$_4$ and concentrated to give the title compound (352 g, 101%). LC-MS calculated for C$_{10}$H$_{15}$N$_3$O$_4$S [M+H]$^+$ m/z: 274.0; found 296.0 (M+Na). $^1$H NMR (400 MHz, CDCl$_3$) δ 7.14 (s, 1H), 5.46 (s, 1H), 3.74 (s, 2H), 3.24 (s, 2H), 1.56 (s, 9H).

Step 3. 3-(Cyanomethylene)azetidine-1-sulfonamide (Intermediate 1)

To a solution of tert-butyl ((3-(cyanomethylene)azetidin-1-yl)sulfonyl)carbamate (Step 2, 349 g, 1277 mmol) in dichloromethane (3.85 L) was added trifluoroacetic acid (582 g, 394 mL, 5108 mmol) via an addition funnel at room temperature. The reaction mixture was stirred at 30-38° C. (internal) for 3 h. The reaction mixture was concentrated to remove dichloromethane, and then dissolved in EtOAc (2.0 L). To the solution was added 7% NaHCO$_3$/water solution to reach pH 8. The aqueous layer was extracted with EtOAc (800 mL each) twice and the organic layers were combined, dried and concentrated to give crude 3-(cyanomethylene)azetidine-1-sulfonamide (203.4 g, 92%).

The crude product was dissolved in EtOAc (6V) and MeOH (1V) at 55° C. (oil bath temperature). Heptane was added (10V) at 55° C., and the solution became cloudy. The mixture was stirred at room temperature for 5 h. Filtration gave the desired product. LC-MS calculated for C$_5$H$_7$N$_3$O$_2$S [M+H]$^+$ m/z: 174.0; found 174.0 (weak ionization). $^1$H NMR (400 MHz, MeOD) δ 5.69 (s, 1H), 4.76-4.41 (m, 4H).

Example 1

Synthesis of 3-(cyanomethyl)-3-(4-{[(1R,2S)-2-phenylcyclopropyl]amino}piperidin-1-yl)azetidine-1-sulfonamide (Compound 1)

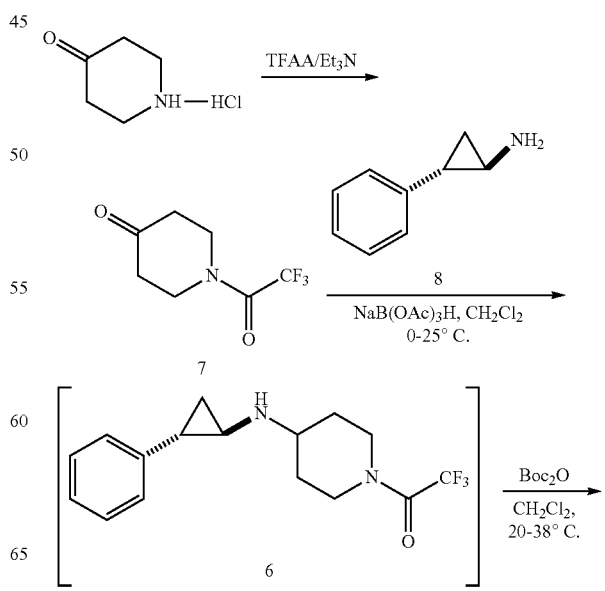

-continued

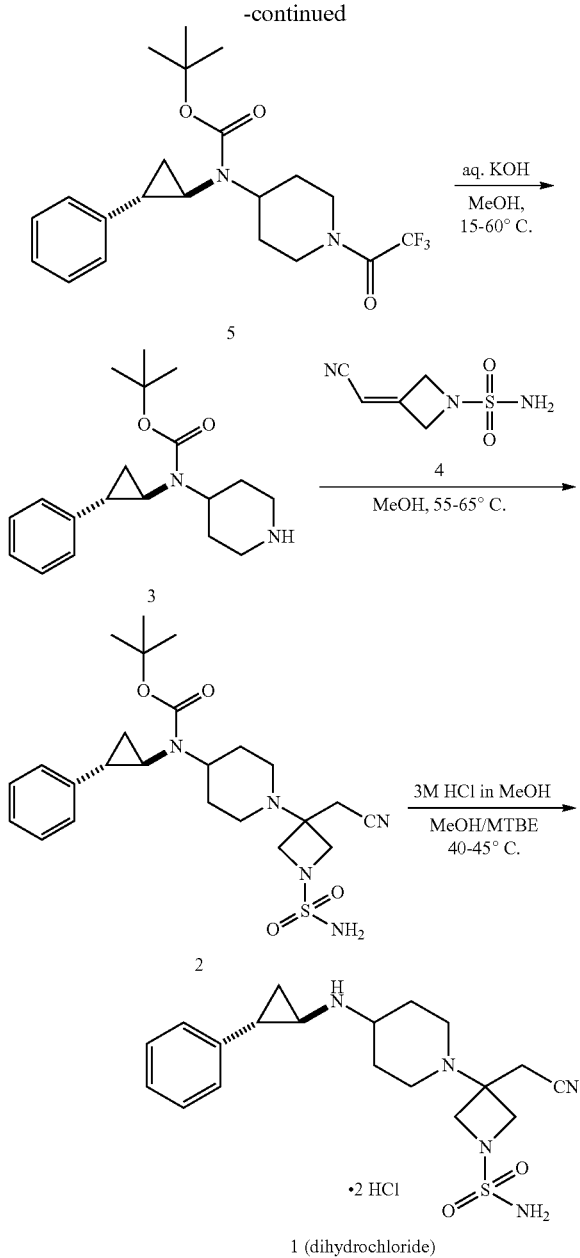

Step 1. 1-(2,2,2-Trifluoroacetyl)piperidin-4-one (7)

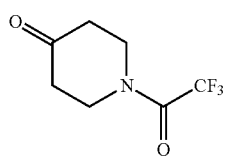 [SMILES: O=C1CCN(C(=O)C(F)(F)F)CC1]

To a suspension of piperidin-4-one hydrochloride hydrate (248 g, 1615 mmol) in dichloromethane (2.48 L, 10V) was added triethylamine (248 ml, 1776 mmol) at 0° C. The mixture was stirred for 5 min, then 2,2,2-trifluoroacetic anhydride (471 ml, 3390 mmol) in dichloromethane (940 mL) was added via addition funnel (over 1 h) at 0° C. After addition was complete, the cooling bath was removed and the reaction mixture was warmed to room temperature. After 2.5 h, the reaction was complete. The reaction mixture was poured into 900 mL of 0.2 M HCl in water. The reaction mixture was partitioned between dichloromethane and water. After separation, the water layer was back extracted with dichloromethane (600 mL). The combined organic layers were washed with 1 L water, twice, then 1 L brine. The organic phase was dried with 150 g magnesium sulfate, filtered, and concentrated. The resulting solid was dried under high vacuum. 1-(2,2,2-trifluoroacetyl)piperidin-4-one (303 g, 1615 mmol) was obtained as a solid in 96% yield. LC-MS calculated for $C_7H_8F_3NO_2$ [M+H]$^+$ m/z: 196.0; found 196.0. $^1$H NMR (400 MHz, CDCl$_3$) δ 4.06-3.77 (dt, J=23.1, 6.4 Hz, 4H), 2.76-2.46 (q, J=6.6 Hz, 4H).

Step 2. Tert-butyl((1R,2S)-2-phenylcyclopropyl)(1-(2,2,2-trifluoroacetyl)piperidin-4-yl)carbamate (5)

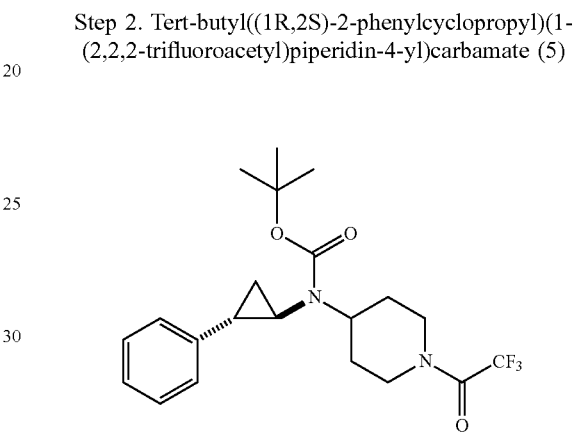

1-(2,2,2-Trifluoroacetyl)piperidin-4-one (24.96 g, 128 mmol) and (1R,2S)-2-phenylcyclopropan-1-amine (19.94 g, 141 mmol) were dissolved in dichloromethane (340 ml). Acetic acid (15.38 ml, 269 mmol) was added and the reaction mixture was stirred at room temperature for 1 h. The reaction mixture was then cooled to 0° C. Sodium triacetoxyhydroborate (32.5 g, 153 mmol) was added in six 5.4 g portions over 30 minutes. The reaction mixture was stirred at 0° C. for 4 h, until the reaction was complete. 7% NaHCO$_3$ in water (200 mL) was added. The mixture was stirred for 30 min, after which time the organic and aqueous phases were separated. The organic phase was dried with sodium sulfate, filtered, and returned to a 1 L round bottom flask. Di-tert-butyl dicarbonate (30.7 g, 141 mmol) was added, and the reaction mixture was heated to 38° C. The reaction mixture was stirred at 38° C. until complete. The reaction mixture was then cooled to room temperature, and water (200 mL) was added. The organic and aqueous phases were separated. The organic phase was dried with sodium sulfate, filtered, and concentrated to provide 50.8 g of oil that was used as is in the subsequent step. LC-MS calculated for $C_{21}H_{27}F_3N_2O_3$ [M+H]$^+$ m/z: 413.2; found 413.2. $^1$H NMR (400 MHz, CDCl$_3$) δ 7.34-7.26 (m, 2H), 7.26-7.16 (m, 1H), 7.12-7.05 (m, 2H), 4.71-4.60 (m, 1H), 4.16-4.02 (td, J=15.4, 12.9, 4.1 Hz, 1H), 4.01-3.88 (tt, J=11.9, 4.1 Hz, 1H), 3.20-3.08 (m, 1H), 2.83-2.70 (tt, J=13.3, 3.6 Hz, 1H), 2.63-2.53 (dtd, J=8.0, 4.5, 3.3 Hz, 1H), 2.20-1.85 (m, 5H), 1.49-1.42 (d, J=1.6 Hz, 9H), 1.40-1.22 (m, 2H).

Step 3. Tert-butyl((1S,2S)-2-phenylcyclopropyl)(piperidin-4-yl)carbamate (3)

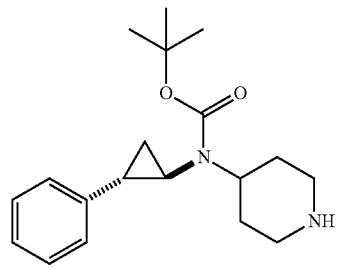

In a 1 L flask, tert-butyl ((1R,2S)-2-phenylcyclopropyl)(1-(2,2,2-trifluoroacetyl)piperidin-4-yl)carbamate (50.8 g, 118 mmol) was dissolved in methanol (500 ml). Potassium hydroxide (19.78 g, 353 mmol) in water (20 ml) was added slowly. The reaction mixture was heated to 55° C. and stirred for 2 h, at which time the starting material was consumed and the reaction mixture was cooled to room temperature. The methanol was removed via rotavap. The crude residue was dissolved in MTBE (500 mL) and washed with 250 mL water. The aqueous layer was back extracted by MTBE (500 mL). The organic phase was dried and the solvent was removed under reduced pressure to give 34.5 g of crude product.

To the product tert-butyl ((1R,2S)-2-phenylcyclopropyl)(piperidin-4-yl)carbamate (34.5 g, 109 mmol) in 2-propanol (415 ml, 12 V) was added a solution of L-Tartaric acid (18.00 g, 120 mmol) in MeOH (25 ml, 1.5 V). The mixture was stirred at room temperature for 14 h, after which time heptane (520 mL, 15 V) was added. The slurry was stirred for 2 h, after which time the white solid was collected by filtration and dried to afford tert-butyl ((1S,2S)-2-phenylcyclopropyl)(piperidin-4-yl) carbamate Tartrate (40 g, 85 mmol) in 78% yield.

To a suspension of tert-butyl ((1R,2S)-2-phenylcyclopropyl)(piperidin-4-yl) carbamate Tartrate (30 g, 64.2 mmol) in MTBE (300 mL, 10V) was added sodium bicarbonate (17.27 g, 206 mmol) as a solution in 300 mL water (10V). The reaction mixture was stirred for 1 h, then partitioned between MTBE and water. The organic layer was separated and washed with additional saturated NaHCO$_3$ (100 mL). The organic phase was separated, dried with sodium sulfate, and filtered into a round bottom flask. MTBE was removed under reduced pressure to afford tert-butyl ((1R,2S)-2-phenylcyclopropyl)(piperidin-4-yl) carbamate (19.2 g, 60.6 mmol) in 94% yield. LC-MS calculated for C$_{19}$H$_{28}$N$_2$O$_2$ [M+H]$^+$ m/z: 317.2; found 317.2. $^1$H NMR (600 MHz, MeOD) δ 7.31-7.22 (m, 2H), 7.21-7.10 (m, 3H), 3.82-3.73 (tt, J=12.1, 3.7 Hz, 1H), 3.15-3.05 (dddt, J=23.7, 12.5, 4.1, 2.0 Hz, 2H), 2.67-2.58 (m, 3H), 2.19-2.10 (ddd, J=9.9, 6.5, 3.5 Hz, 1H), 2.08-1.99 (m, 1H), 1.94-1.86 (m, 1H), 1.84-1.77 (ddt, J=15.0, 4.8, 2.4 Hz, 1H), 1.79-1.71 (m, 1H), 1.48 (s, 10H), 1.30-1.21 (dt, J=7.3, 6.1 Hz, 1H).

Step 4: Tert-butyl(1-(3-(cyanomethyl)-1-sulfamoylazetidin-3-yl)piperidin-4-yl)((1R,2S)-2-phenylcyclopropyl)carbamate (2)

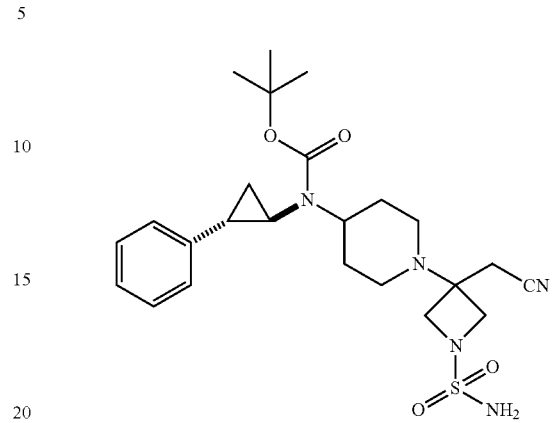

tert-butyl ((1R,2S)-2-phenylcyclopropyl)(piperidin-4-yl) carbamate (11.6 g, 36.7 mmol) and 3-(cyanomethylene) azetidine-1-sulfonamide (Intermediate 1, 7.30 g, 42.2 mmol) were dissolved in methanol (30 ml, 4 V). The reaction mixture was heated to 60° C. and stirred for 8 h, after which time the reaction was judged complete by HPLC. The reaction mixture was cooled to room temperature. Water (60.0 ml, 8 V) was added dropwise. After a milky solution formed, addition was stopped, and the mixture was stirred for 5 min until a beige solid was observed. The remaining water was added. The mixture was stirred at room temperature for 14 h. The solid was isolated via filtration and washed with water (60 mL). The solid was dried to a constant weight. The solid was then dissolved in methanol (80 mL) at 45° C. The solution was cooled to room temperature, at which time precipitate formed. Water (70 mL) was added dropwise while stirring at room temperature. The mixture was stirred for 1 h after addition. The solid was isolated via filtration and dried to afford tert-butyl (1-(3-(cyanomethyl)-1-sulfamoylazetidin-3-yl)piperidin-4-yl)((1R,2S)-2-phenylcyclopropyl)carbamate (17 g, 34.5 mmol) in 94% yield. LC-MS calculated for C$_{24}$H$_{35}$N$_5$O$_4$S [M+H]$^+$ m/z: 490.2; found 490.1. $^1$H NMR (500 MHz, MeOD) δ 7.31-7.24 (m, 2H), 7.21-7.10 (m, 3H), 3.83-3.76 (dd, J=8.0, 6.9 Hz, 2H), 3.69-3.59 (m, 3H), 3.02 (s, 2H), 2.88-2.76 (m, 2H), 2.66-2.59 (ddd, J=7.8, 4.6, 3.5 Hz, 1H), 2.41-2.31 (tdd, J=11.5, 4.6, 2.4 Hz, 2H), 2.19-2.08 (m, 2H), 2.05-1.94 (m, 1H), 1.86-1.73 (dddd, J=25.5, 12.1, 4.3, 2.5 Hz, 2H), 1.46 (s, 10H), 1.29-1.21 (dt, J=7.3, 6.2 Hz, 1H).

Step 5. 3-(Cyanomethyl)-3-(4-{[(1R,2S)-2-phenylcyclopropyl]amino}piperidin-1-yl)azetidine-1-sulfonamide dihydrochloride (1)

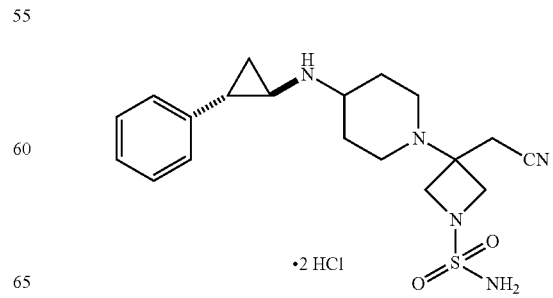

Tert-butyl (1-(3-(cyanomethyl)-1-sulfamoylazetidin-3-yl)piperidin-4-yl)((1R,2S)-2-phenylcyclopropyl) carbamate (2.0 g, 4.08 mmol) was dissolved in methanol (6 mL, 3 V) and methanolic HCl (3.0 M, 12.0 mL). The reaction mixture was heated to 40° C. and stirred for 3 h, at which time the reaction was judged complete by HPLC. After cooling to room temperature, a white precipitate formed. MTBE (36 mL, 18 V) was added and the mixture was stirred at room temperature. Filtration provided the desired product (1.7 g) in 90% yield. LC-MS calculated for $C_{19}H_{29}Cl_2N_5O_2S$ [M+H]$^+$ m/z: 390.1; found 390.1. $^1$H NMR (400 MHz, D$_2$O) δ 7.43-7.27 (m, 3H), 7.25-7.17 (m, 2H), 4.20-4.13 (d, J=9.8 Hz, 2H), 4.09-4.01 (d, J=9.8 Hz, 2H), 3.71-3.58 (tt, J=11.9, 4.2 Hz, 1H), 3.48-3.33 (m, 4H), 3.12-2.95 (dddt, J=23.8, 11.8, 8.0, 3.4 Hz, 3H), 2.59-2.39 (m, 3H), 2.08-1.96 (m, 2H), 1.60-1.43 (m, 2H).

Example 2

Alternative Preparation of 3-(cyanomethyl)-3-(4-{[(1R,2S)-2-phenylcyclopropyl]amino}piperidin-1-yl)azetidine-1-sulfonamide (Compound 1)

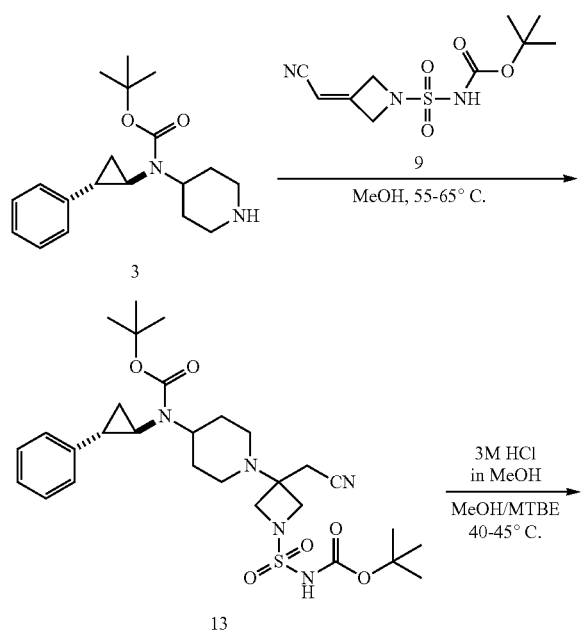

Step 1. Tert-butyl(1-(1-(N-(tert-butoxycarbonyl)sulfamoyl)-3-(cyanomethyl)azetidin-3-yl)piperidin-4-yl)((1R,2S)-2-phenylcyclopropyl)carbamate (13)

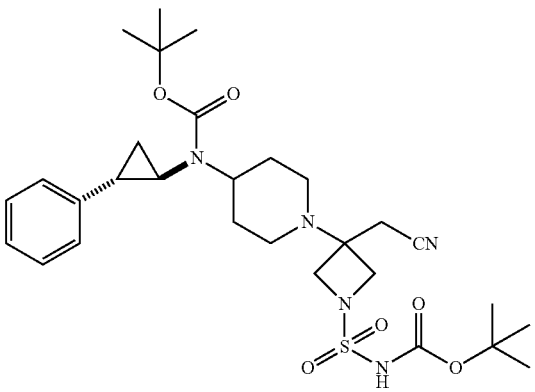

tert-butyl ((1R,2S)-2-phenylcyclopropyl)(piperidin-4-yl)carbamate (from Example 1, Step 3; 1.74 g, 5.47 mmol) and tert-butyl 3-(cyanomethylene)azetidin-1-ylsulfonylcarbamate (from Intermediate 1, Step 2; 1.0 g, 3.65 mmol) and DBU (1.1 eq.) were dissolved in acetonitrile (3.0 ml, 3 V). The reaction mixture was heated to 55° C. and stirred for 18 h, after which time the reaction was judged complete by HPLC. The reaction mixture was cooled to room temperature. Aqueous 0.3N HCl solution (6.0 ml, 6 V) was added dropwise. The mixture was partitioned between EtOAc (10.0 mL) and water. The organics were washed with 0.3N HCl and water, dried and concentrated to provide crude product. The crude material was dissolved in THF (5V). Heptane was added slowly to provide a beige solid. The mixture was stirred at room temperature for 6 h. The solid was isolated via filtration and washed with heptane. The solid was dried to afford the title compound in 94% yield. LC-MS calculated for $C_{29}H_{43}N_5O_6S$ [M+H]$^+$ m/z: 590.7; found 590.3. $^1$H NMR (400 MHz, CDCl$_3$) δ 7.35-7.26 (m, 2H), 7.18-7.08 (m, 3H), 4.18-4.09 (t, J=8.1 Hz, 2H), 3.98-3.88 (dd, J=7.7, 5.1 Hz, 2H), 3.77-3.63 (tq, J=12.5, 4.8, 4.4 Hz, 1H), 2.83-2.71 (m, 4H), 2.62-2.53 (m, 1H), 2.44-2.30 (tdd, J=11.0, 8.5, 2.4 Hz, 2H), 2.18-1.99 (m, 2H), 2.00-1.77 (m, 3H), 1.53 (s, 9H), 1.48-1.18 (m, 12H).

Step 2. 3-(Cyanomethyl)-3-(4-{[(1R,2S)-2-phenylcyclopropyl]amino}piperidin-1-yl)azetidine-1-sulfonamide dihydrochloride (1)

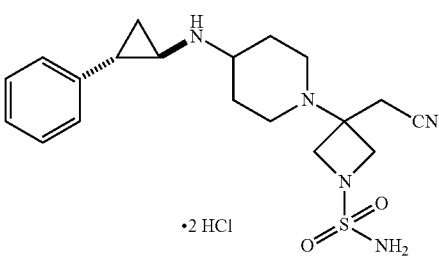

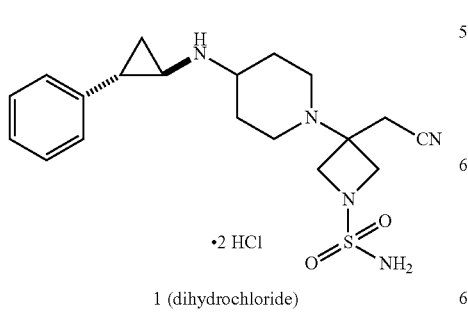

1 (dihydrochloride)

tert-butyl (1-(1-(N-(tert-butoxycarbonyl)sulfamoyl)-3-(cyanomethyl)azetidin-3-yl)piperidin-4-yl)((1R,2S)-2-phenylcyclopropyl)carbamate (2.0 g, 4.08 mmol) was dissolved in methanolic HCl (3.0 M, 12.0 mL). The reaction mixture was heated to 40° C. and stirred for 3 h, at which time the reaction was judged complete by HPLC. After cooling to room temperature, a white precipitate formed. MTBE (36 mL, 18 V) was added and the mixture was stirred at room temperature. Filtration provided the desired product (1.44 g) in 92% yield. LC-MS calculated for $C_{19}H_{129}Cl_2N_5O_2S$ [M+H]$^+$ m/z: 390.1; found 390.1. $^1$H NMR (400 MHz, D$_2$O) δ 7.43-7.27 (m, 3H), 7.25-7.17 (m, 2H), 4.20-4.13 (d, J=9.8 Hz, 2H), 4.09-4.01 (d, J=9.8 Hz, 2H), 3.71-3.58 (tt, J=11.9, 4.2 Hz, 1H), 3.48-3.33 (m, 4H), 3.12-2.95 (dddt, J=23.8, 11.8, 8.0, 3.4 Hz, 3H), 2.59-2.39 (m, 3H), 2.08-1.96 (m, 2H), 1.60-1.43 (m, 2H).

Example 3

Alternative Preparation of 3-(cyanomethyl)-3-(4-{[(1R,2S)-2-phenylcyclopropyl]amino}piperidin-1-yl)azetidine-1-sulfonamide (Compound 1)

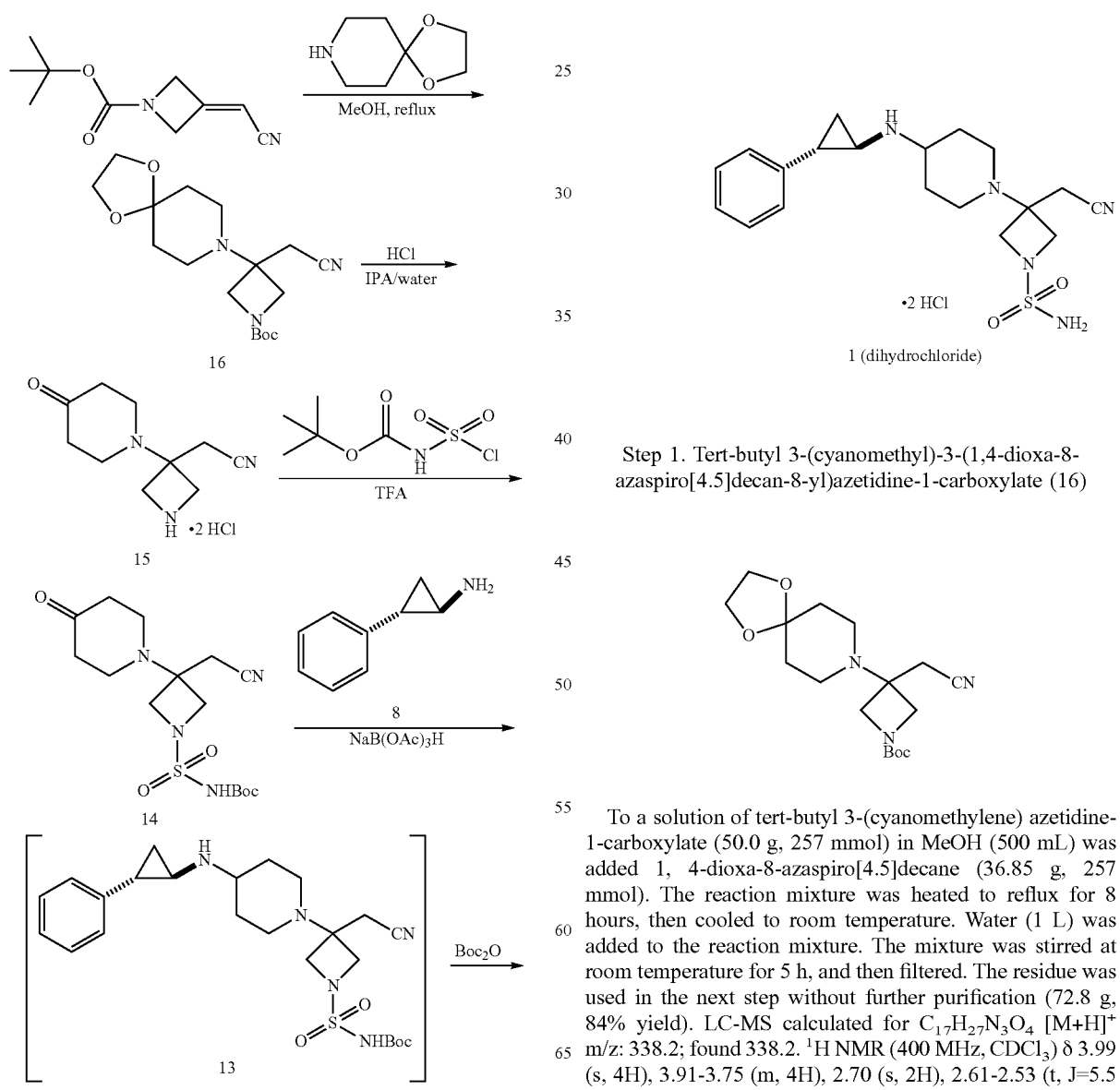

Step 1. Tert-butyl 3-(cyanomethyl)-3-(1,4-dioxa-8-azaspiro[4.5]decan-8-yl)azetidine-1-carboxylate (16)

To a solution of tert-butyl 3-(cyanomethylene) azetidine-1-carboxylate (50.0 g, 257 mmol) in MeOH (500 mL) was added 1, 4-dioxa-8-azaspiro[4.5]decane (36.85 g, 257 mmol). The reaction mixture was heated to reflux for 8 hours, then cooled to room temperature. Water (1 L) was added to the reaction mixture. The mixture was stirred at room temperature for 5 h, and then filtered. The residue was used in the next step without further purification (72.8 g, 84% yield). LC-MS calculated for $C_{17}H_{27}N_3O_4$ [M+H]$^+$ m/z: 338.2; found 338.2. $^1$H NMR (400 MHz, CDCl$_3$) δ 3.99 (s, 4H), 3.91-3.75 (m, 4H), 2.70 (s, 2H), 2.61-2.53 (t, J=5.5 Hz, 4H), 1.79-1.71 (t, J=5.5 Hz, 4H), 1.49 (s, 9H).

Step 2. 2-(3-(4-oxopiperidin-1-yl)azetidin-3-yl)acetonitrile dihydrochloride (15)

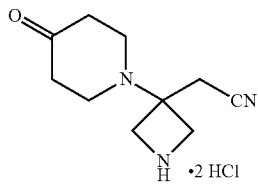 [SMILES: N#CCC1(N2CCC(=O)CC2)CNC1]

To a suspension of tert-butyl 3-(cyanomethyl)-3-(1,4-dioxa-8-azaspiro[4.5]decan-8-yl)azetidine-1-carboxylate (10.0 g) in a solution of 5.2 N HCl in isopropanol (60 mL) was added water (30 mL) at room temperature. The reaction mixture was heated to 60° C. for 30 minutes. The solution became cloudy, and solid precipitated out. After stirring for another 1.5 h, the reaction mixture was cooled to room temperature. Filtration and washing with isopropanol provided a solid. The solid was dried in a vacuum oven (50° C.) overnight to provide the title compound (6.18 g, 78%). LC-MS calculated for $C_{10}H_{17}Cl_2N_3O$ [M+H]+ m/z: 194.1; found 194.1. 1H NMR (400 MHz, DMSO) δ 9.60 (s, 1H), 9.46 (s, 1H), 4.08-3.97 (dt, J=13.1, 7.2 Hz, 2H), 3.93-3.81 (dd, J=18.8, 4.1 Hz, 2H), 3.22 (s, 2H), 2.87-2.79 (t, J=6.0 Hz, 4H), 2.43-2.35 (t, J=5.9 Hz, 4H).

Step 3. Tert-butyl((3-(cyanomethyl)-3-(4-oxopiperidin-1-yl)azetidin-1-yl)sulfonyl)carbamate (14)

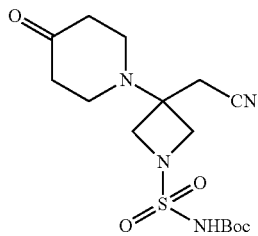 [SMILES: CC(C)(C)OC(=O)NS(=O)(=O)N1CC(CC#N)(N2CCC(=O)CC2)C1]

A stirring solution of tert-butyl alcohol (61.5 g, 830 mmol) in dichloromethane (330 mL, 6V) was cooled with ice/salt water bath. Sulfurisocyanatidic chloride (64 mL, 734 mmol) dissolved in DCM (330 mL, 6V) was slowly added with an addition funnel, holding the temperature between 1.5° C. and 5.5° C. The solution was stirred for 1 h at 3° C., providing a solution of tert-butyl chlorosulfonylcarbamate.

To a suspension of 2-(3-(4-oxopiperidin-1-yl)azetidin-3-yl)acetonitrile dihydrochloride (from Step 2) (169.8 g, 638 mmol) in dichloromethane (1698 mL, 10V) was added triethylamine (231 mL, 1660 mmol). After stirring for 30 minutes, the reaction mixture was cooled to 0° C. To this mixture was added the prepared solution of tert-butyl chlorosulfonylcarbamate with an addition funnel (2-13° C., controlled by the addition rate) slowly. The reaction mixture was stirred at 0° C. for 1 h after addition. The reaction mixture was diluted with dichloromethane (300 mL). The reaction mixture was partitioned between dichloromethane and 0.2N HCl in water (3.55 L). The organics were dried over MgSO4 and concentrated to give the title compound (235 g, 99%). LC-MS calculated for $C_{15}H_{24}N_{34}O_5S$ [M+H]+ m/z: 373.1; found 373.1. 1H NMR (400 MHz, CDCl3) δ 7.01 (s, 1H), 4.23 (d, J=8.1 Hz, 2H), 3.97 (d, J=8.2 Hz, 2H), 2.92-2.68 (m, 6H), 2.46 (t, J=5.9 Hz, 4H), 1.50 (s, 9H).

Step 4. Tert-butyl(1-(3-(cyanomethyl)-1-sulfamoylazetidin-3-yl)piperidin-4-yl)((1S,2S)-2-phenylcyclopropyl)carbamate (12)

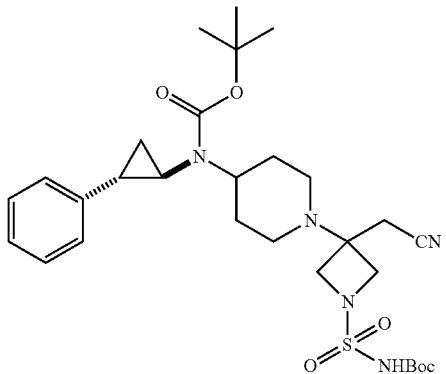

To a solution of tert-butyl ((3-(cyanomethyl)-3-(4-oxopiperidin-1-yl)azetidin-1-yl)sulfonyl)carbamate (24.96 g, 128 mmol) and (1R,2S)-2-phenylcyclopropan-1-amine (19.94 g, 141 mmol) in dichloromethane (340 ml) was added acetic acid (15.38 ml, 269 mmol) and the reaction mixture was stirred at room temperature for 1 h. After this time, the reaction mixture was cooled to 0° C. Sodium triacetoxyhydroborate (32.5 g, 153 mmol) was added in four portions over 30 min. The reaction mixture was stirred at 0° C. for 4 h, until the reaction was complete. 7% NaHCO3 in water (200 mL) was added. The mixture was stirred for 30 min, after which time the organic and aqueous phases were separated. The organic phase was dried with sodium sulfate, filtered, and returned to a round bottom flask. Di-tert-butyl dicarbonate (30.7 g, 141 mmol) was added, and the reaction mixture was heated to 40° C. The reaction mixture was stirred at 40° C. until complete. The reaction mixture was then cooled to room temperature. Water (200 mL) was added. The organic and aqueous phases were separated. The organic phase was dried with sodium sulfate, filtered, and concentrated to provide 50.8 g of oil of the title compound that was used without further purification. LC-MS calculated for $C_{29}H_{43}N_5O_6S$ [M+H]+ m/z: 590.3; found 590.3. 1H NMR (400 MHz, CDCl3) δ 7.35-7.26 (m, 2H), 7.18-7.08 (m, 3H), 4.18-4.09 (t, J=8.1 Hz, 2H), 3.98-3.88 (dd, J=7.7, 5.1 Hz, 2H), 3.77-3.63 (tq, J=12.5, 4.8, 4.4 Hz, 1H), 2.83-2.71 (m, 4H), 2.62-2.53 (m, 1H), 2.44-2.30 (tdd, J=11.0, 8.5, 2.4 Hz, 2H), 2.18-1.99 (m, 2H), 2.00-1.77 (m, 3H), 1.53 (s, 9H), 1.48-1.18 (m, 12H).

Step 5. 3-(Cyanomethyl)-3-(4-{[(1R,2S)-2-phenylcyclopropyl]amino}piperidin-1-yl)azetidine-1-sulfonamide dihydrochloride (1)

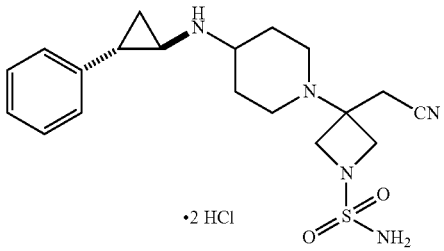

Tert-butyl (1-(1-(N-(tert-butoxycarbonyl)sulfamoyl)-3-(cyanomethyl)azetidin-3-yl)piperidin-4-yl)((1R,2S)-2-phenylcyclopropyl)carbamate (2.0 g, 4.08 mmol) was dissolved in methanol (6 mL, 3 V) and methanolic HCl (3.0 M, 12.0 mL). The reaction mixture was heated to 40° C. and stirred for 3 h, at which time the reaction was judged complete by HPLC. After cooling to room temperature, a white precipitate formed. MTBE (36 mL, 18 V) was added and the mixture was stirred at room temperature. Filtration provided the desired product (1.7 g, 3.68 mmol) in 90% yield. LC-MS calculated for $C_{19}H_{29}Cl_2N_5O_2S$ [M+H]$^+$ m/z: 390.1; found 390.1. $^1$H NMR (400 MHz, D$_2$O) δ 7.43-7.27 (m, 3H), 7.25-7.17 (m, 2H), 4.20-4.13 (d, J=9.8 Hz, 2H), 4.09-4.01 (d, J=9.8 Hz, 2H), 3.71-3.58 (tt, J=11.9, 4.2 Hz, 1H), 3.48-3.33 (m, 4H), 3.12-2.95 (dddt, J=23.8, 11.8, 8.0, 3.4 Hz, 3H), 2.59-2.39 (m, 3H), 2.08-1.96 (m, 2H), 1.60-1.43 (m, 2H).

Example 4

Preparation and Characterization of Form I 3-(Cyanomethyl)-3-(4-{[(1R,2S)-2-phenylcyclopropyl]amino}piperidin-1-yl)azetidine-1-sulfonamide dihydrochloride (15.68 g, 33.90 mmol) was dissolved in methanol (5000 mmol) while heating to reflux, and then polish filtrated. 2-Methoxy-2-methylpropane (2000 mmol) was then slowly added while solid crashed out and the mixture was stirred overnight. Solids were then collected by filtration and dried on the filter overnight to give Form I.

The solid product was confirmed as a crystalline solid having Form I according to XRPD analysis. The XRPD pattern of Form I is shown in FIG. 1 and the peak data is given below in Table 1.

TABLE 1

| XRPD Peak Data for Form I | | |
|---|---|---|
| 2-Theta | Height | I % |
| 3.8 | 71.0 | 15.4 |
| 5.9 | 461.0 | 100.0 |
| 7.1 | 77.0 | 16.7 |
| 9.9 | 44.0 | 9.5 |
| 12.5 | 36.0 | 7.8 |
| 13.2 | 50.0 | 10.8 |
| 15.1 | 63.0 | 13.7 |
| 15.9 | 39.0 | 8.5 |
| 16.9 | 80.0 | 17.4 |
| 18.2 | 107.0 | 23.2 |
| 20.3 | 52.0 | 11.3 |

TABLE 1-continued

| XRPD Peak Data for Form I | | |
|---|---|---|
| 2-Theta | Height | I % |
| 20.7 | 70.0 | 15.2 |
| 23.5 | 142.0 | 30.8 |
| 24.7 | 39.0 | 8.5 |
| 25.2 | 68.0 | 14.8 |
| 26.1 | 124.0 | 26.9 |
| 29.7 | 64.0 | 13.9 |
| 32.0 | 40.0 | 8.7 |

Form I exhibits a DSC thermogram having endotherm peaks at temperatures of about 80° C. and about 175° C. and an exotherm peak at a temperature of about 197° C. FIG. 2 shows a DSC thermogram of Form I. FIG. 3 shows a TGA thermogram of Form I.

Example 5

Preparation and Characterization of Form II 3-(Cyanomethyl)-3-(4-{[(1R,2S)-2-phenylcyclopropyl]amino}piperidin-1-yl)azetidine-1-sulfonamide dihydrochloride (532.9 g, 729.1 mmol; See Example 1) was mixed with 2-butanone (7223 mL). The mixture was heated to 55° C. (internal temperature set) to become a clear solution. The hot solution was polish filtered through an inline filter, and the clear solution was distilled off under vacuum to about 4 L volume while being heated at 55° C. To the solution was added heptane (4676 mL) while stirring. After the addition, the mixture was kept at 55° C. for 4 hours, then allowed to cool to room temperature. The mixture was stirred overnight. The solid was filtered and washed with a mixture of heptane (1000 mL) and 2-butanone (1000 mL). The product was dried on the filter overnight, and then under high vacuum at 50° C. overnight to give Form II.

The solid product was confirmed as a crystalline solid having Form II according to XRPD analysis. The XRPD pattern of Form II is shown in FIG. 4 and the peak data is given below in Table 2.

TABLE 2

| XRPD Peak Data for Form II | | |
|---|---|---|
| 2-Theta | Height | I % |
| 5.8 | 69.0 | 94.5 |
| 13.2 | 30.0 | 41.1 |
| 15.1 | 50.0 | 68.5 |
| 17.1 | 50.0 | 68.5 |
| 20.1 | 58.0 | 79.5 |
| 20.8 | 60.0 | 82.2 |
| 22.5 | 68.0 | 93.2 |
| 25.4 | 73.0 | 100.0 |
| 28.0 | 41.0 | 56.2 |
| 29.1 | 37.0 | 50.7 |

Form II exhibits a DSC thermogram having an exotherm peak at a temperature of about 198° C. FIG. 5 shows a DSC thermogram of Form I. FIG. 63 shows a TGA thermogram of Form I.

Example 6

Solubility Measurement

The solubility of Compound 1 di-HCl was measured at 25±1° C. and 50±1° C. according to the following procedures.

Solubility at 25±1° C.

Compound 1 di-HCl was added to 2 mL of a solvent listed in Table 3 at 25±1° C. until the solution became cloudy. Another 10 mg of Compound 1 di-HCl was then added. The mixture was agitated at 25±1° C. for 36 h. The supernatant was filtered using a syringe filter. The saturated solution was pipetted into an HPLC vial, which was diluted with acetonitrile. The solubility of Compound 1 di-HCl was calculated for each solvent. The calculated solubilities at 25±1° C. are shown in Table 3.

Solubility at 50±1° C.

Compound 1 di-HCl was added to 2 mL of a solvent listed in Table 3 at 50±1° C. until the solution became cloudy. Another 20-25 mg of Compound 1 di-HCl was then added. The mixture was agitated at 50±1° C. for 24 h. The supernatant was filtered using a warmed syringe filter at 50±1° C. The saturated solution was pipetted into an HPLC vial, which was diluted with acetonitrile. The solubility of Compound 1 di-HCl was calculated for each solvent. The calculated solubilities at 50±1° C. are shown in Table 3.

TABLE 3

Solubility of Compound 1 di-HCl in Various Solvents

| Solvent | Solubility at 25° C. (mg/mL) | Solubility at 50° C. (mg/mL) |
|---|---|---|
| MeCN | 0.61 | 6.29 |
| Chloroform | >50* | >50* |
| Dichloromethane | 0.00 | 0.06 |
| DMF | >50* | >50* |
| 1,4-Dioxane | 0.20 | 0.31 |
| Methanol | 32.32 | >50 |
| 2-Methoxyethanol | 45.92 | 48.27 |
| MIBK | 0.06 | 0.13 |
| Toluene | 0.00 | 0.00 |
| Hexane | 0.00 | 0.00 |
| THF | 0.04 | 0.09 |
| Acetone | 3.49 | 0.85 |
| n-BuOH | 1.31 | 2.34 |
| MTBE | 0.00 | 0.00 |
| DMSO | >50* | >50* |
| EtOH | 3.37 | 3.63 |
| EtOAc | 0.00 | 0.03 |
| Ethyl formate | 0.09 | 0.05 |
| Heptane | 0.00 | 0.00 |
| Isobutyl acetate | 0.00 | 0.00 |
| IPAc | 0.00 | 0.00 |
| 1-Propanol | 4.60 | 5.21 |
| IPA | 1.31 | 1.91 |
| Water | >50* | >50* |
| MEK | 0.16 | 0.16 |
| MeOH/water/ACN (6 v/1.5 v/3 v) | >50* | >50* |
| MeOH/water/ACN (5 v/2 v/3 v) | >50* | >50* |
| MeOH/water/ACN (6 v/1 v/3 v) | >50 | >50* |
| MeOH/water/ACN (6 v/0.5 v/3.5 v) | >50* | >50* |
| MeOH/ACN (10 v/3 v) | >50* | >50* |
| ACN/water (9:1) | >50* | >50* |
| 5% Water in ACN | >50 | 45.39 |
| 5% Water in MeOH | >50* | >50* |
| ACN:Water (4:1) | >50* | >50* |
| MeOH/Water/ACN (6.0/0.5/1.0) | >50* | >50* |

*by vision

Example 7

Phase Equilibration at 25±1° C. and 50±1° C.

Phase equilibration studies were designed to provide information on a predominant crystal form for phase identification. Based on its solubility in various solvent systems (Table 3), Compound 1 di-HCl was equilibrated in a representative group of solvents at 25±1° C. (Table 4) and 50±1° C. (Table 5). To the solvents listed in Table 4 (25±1° C.) and Table 5 (50±1° C.) was added Compound 1 di-HCl until a cloudy solution was obtained, then, about 15-20 mg of Compound 1 di-HCl was added to the cloudy solution. The mixture was stirred at 25±1° C. for 2 days and 50±1° C. for 1 day. The solid was filtered under nitrogen and analyzed by XRPD to give the results in Table 4 and Table 5.

Three new polymorphic forms were found by XRPD in the phase equilibration at 25±1° C. including Form III (1,4-dioxane, n-BuOH, EtOH, IPAc, and IPA), Form IV (toluene), and Form V (MTBE). Phase equilibration at 50±1° C. resulted in Form III (1,4-dioxane and MEK), Form IV (toluene), and Form V (MTBE).

TABLE 4

Crystal form for phase equilibration at 25 ± 1° C.

| Solvent | Solid State Form |
|---|---|
| Acetonitrile | N/A |
| Chloroform | N/A |
| DCM | II |
| 1,4-Dioxane | III |
| Methanol | N/A |
| 2-Methoxy-ethanol | N/A |
| MIBK | II |
| Toluene | IV |
| Hexane | II |
| THF | II |
| Acetone | II |
| n-BuOH | III |
| MTBE | V |
| EtOH | III |
| EtOAc | I |
| Ethyl formate | I |
| Heptane | II |
| Isobutyl acetate | II |
| IPAc | III |
| 1-Propanol | II |
| IPA | III |
| water | N/A |
| MEK | I |
| MeOH/water/ACN (6 v/1.5 v/3 v) | N/A |
| MeOH/water/ACN (5 v/2 v/3 v) | N/A |
| MeOH/water/ACN (6 v/1 v/3 v) | N/A |
| MeOH/water/ACN (6 v/0.5 v/3.5 v) | N/A |
| MeOH/ACN (10 v/3 v) | N/A |
| ACN/water (9:1) | N/A |
| Acetone/water (1:4) | II |
| 5% water in MeOH | N/A |
| ACN:water (4:1) | N/A |
| MeOH/water/ACN (6.0/0.5/1.0) | N/A |

N/A: Not available.
Ether clear solution/oil or the amount of the precipitate was too small to be analyzed by XRPD.

TABLE 5

Crystal form for phase equilibration at 50 ± 1° C.

| Solvent | Solid State Form |
|---|---|
| Acetonitrile | II |
| Chloroform | II |
| DCM | II |
| 1,4-Dioxane | III |
| Methanol | N/A |
| 2-Methoxy-ethanol | N/A |
| MIBK | II |
| Toluene | IV |
| Hexane | II |

TABLE 5-continued

Crystal form for phase equilibration at 50 ± 1° C.

| Solvent | Solid State Form |
|---|---|
| THF | II |
| Acetone | II |
| n-BuOH | II |
| MTBE | V |
| EtOH | II |
| EtOAc | I |
| Ethyl formate | I |
| Heptane | I |
| Isobutyl acetate | II |
| IPAc | II |
| 1-propanol | II |
| IPA | II |
| water | N/A |
| MEK | III |
| MeOH/water/ACN (6 v/1.5 v/3 v) | N/A |
| MeOH/water/ACN (5 v/2 v/3 v) | N/A |
| MeOH/water/ACN (6 v/1 v/3 v) | N/A |
| MeOH/water/ACN (6 v/0.5 v/3.5 v) | N/A |
| MeOH/ACN (10 v/3 v) | N/A |
| ACN/water (9:1) | N/A |
| 5% water in ACN | II |
| 5% water in MeOH | N/A |
| ACN:water (4:1) | N/A |
| MeOH/water/ACN (6.0/0.5/1.0) | N/A |

N/A: Not available.
Ether clear solution/oil or the amount of the precipitate was too small to be analyzed by XRPD.

Example 8

Evaporation at 25±1° C. and 50±1° C.

Evaporation studies were carried out to identify the predominant crystal form during uncontrolled precipitation. Experiments that did not result in any particulate solids (i.e. clear thin films and oils) were not studied further. XRPD was used to study the solid-state morphology of the crystalline forms of the evaporation samples at 25±1° C. and 50±1° C. The results are presented in Table 6 (25±1° C.) and Table 7 (50±1° C.).

The evaporation in the selected 19 solvents at 25±1° C. (Table 6) led to amorphous solid, oil or sticky solid. Evaporation in 22 solvents at 50±1° C. resulted in Form I, II, and amorphous solid as indicated in Table 7.

TABLE 6

Crystal form identification from evaporation at 25 ± 1° C.

| Solvent | Solid State Form |
|---|---|
| Acetonitrile | N/A |
| Methanol | Sticky solid |
| 2-Methoxyethanol | Sticky solid |
| Acetone | N/A |
| Solvent | Solid State Form |
| n-BuOH | N/A |
| EtOH | N/A |
| 1-Propanol | Sticky solid |
| IPA | N/A |
| water | Brown oil |
| MeOH/water/ACN (6 v/1.5 v/3 v) | Brown oil |
| MeOH/water/ACN (5 v/2 v/3 v) | Brown oil |
| MeOH/water/ACN (6 v/1 v/3 v) | Brown oil |
| MeOH/water/ACN (6 v/0.5 v/3.5 v) | Brown oil |
| MeOH/ACN (10 v/3 v) | Brown oil |

TABLE 6-continued

Crystal form identification from evaporation at 25 ± 1° C.

| Solvent | Solid State Form |
|---|---|
| ACN/water (9:1) | Brown oil |
| 5% water in ACN | Brown oil |
| 5% water in MeOH | Brown oil |
| ACN:water (4:1) | Brown oil |
| MeOH/water/ACN (6 v/0.5 v/1.0 v) | Brown oil |

N/A: Not available.
Ether clear solution or the amount of the precipitate was too small to be analyzed by XRPD.

TABLE 7

Crystal form identification from evaporation at 50 ± 1° C.

| Solvent | Solid State Form |
|---|---|
| Acetonitrile | N/A |
| Chloroform | Amorphous solid |
| DMF | Amorphous solid |
| Methanol | Amorphous solid |
| 2-Methoxyethanol | II |
| Acetone | N/A |
| n-BuOH | N/A |
| DMSO | N/A |
| EtOH | N/A |
| 1-Propanol | Amorphous solid |
| IPA | N/A |
| water | Amorphous solid |
| MeOH/water/ACN (6 v/1.5 v/3 v) | Amorphous solid |
| MeOH/water/ACN (5 v/2 v/3 v) | Amorphous solid |
| MeOH/water/ACN (6 v/1 v/3 v) | Amorphous solid |
| MeOH/water/ACN (6 v/0.5 v/3.5 v) | Amorphous solid |
| MeOH/ACN (10 v/3 v) | II |
| ACN/water (9:1) | Amorphous solid |
| 5% water in ACN | Sticky solid |
| 5% water in MeOH | Amorphous solid |
| ACN:water (4:1) | Amorphous solid |
| Solvent | Solid State Form |
| MeOH/water/ACN (6 v/0.5 v/1.0 v) | Amorphous solid |

N/A: Not available.
Ether clear solution or the amount of the precipitate was too small to be analyzed by XRPD.

Example 9

Anti-Solvent Addition

Saturated solution or nearly saturated solution of Compound 1 di-HCl was prepared by adding the compound (Compound 1 di-HCl Form I) to the solvents in Table 8 respectively. An anti-solvent was added to induce precipitation. MTBE, toluene and IPAc were selected as the anti-solvents. Experiments that did not produce any particulate solids on anti-solvent addition were not studied further, and all solids were filtered under nitrogen. The results are presented in

TABLE 8

Antisolvent Addition of Compound 1 di-HCl in Various Solvents

| Solvent (mL) | Anti-Solvent (mL) | Solid State Form |
|---|---|---|
| Chloroform (1.0) | MTBE (4.0) | II |

TABLE 8-continued

Antisolvent Addition of Compound 1 di-HCl in Various Solvents

| Solvent (mL) | Anti-Solvent (mL) | Solid State Form |
|---|---|---|
| Methanol (0.5) | MTBE (1.0) | III |
| Methanol (1.0) | Toluene (8.0) | Turbid solution |
| Methanol (1.0) | IPAc (7.0) | II |
| 2-Methoxy-ethanol (0.5) | MTBE (2.0) | II |
| 2-Methoxy-ethanol (1.0) | Toluene (7.0) | Clear solution |
| 2-Methoxy-ethanol (0.5) | IPAc (4.0) | II |
| MeOH/water/ACN (6 V/1.5 V/3 V, 1.0 mL)) | IPAc (12) | Sticky solid |
| MeOH/water/ACN (6 V/1.5 V/3 V, 1.0 mL) | MTBE (12) | Sticky solid |
| MeOH/water/ACN (5 V/2 V/3 V, 1 mL) | MTBE (10) | II (filtered under nitrogen) |
| MeOH/water/ACN (5 V/2 V/3 V, 1.0 mL) | IPAc (5.0) | Sticky solid |
| MeOH/water/ACN (6 V/1 V/4 V, 1 mL) | MTBE (5.0) | I ( stirred for 5 h, filtered under nitrogen)) |
| MeOH/water/ACN (6 V/1 V/4 V, 1.0 mL) | IPAc (12 mL) | II (filtered under nitrogen) |
| MeOH/water/ACN (6 V/0.5 V/3.5 V, 1.0 mL)) | MTBE (5.0) | II (stirred for 30 minutes to give good solid, filtered under nitrogen)) |
| MeOH/water/ACN (6 V/0.5 V/3.5 V, 1.0 mL)) | IPAc (7.0) | II (filtered under nitrogen) |
| MeOH/ACN (10 V/3.0 V, 1.0 mL)) | IPAc (7.0) | II (filtered under nitrogen) |
| MeOH/ACN (10 V/3.0 V, 1.0 mL) | MTBE (6.0) | Amorphous solid |
| MeOH/ACN (10 V/3.0 V, 1 mL)) | Toluene (7.0) | Turbid solution |
| ACN/water (9.0 V/1.0 V, 1.0 mL) | MTBE (5.0 mL) | N/A |
| ACN/water (9.0 V/1.0 V, 1.0 mL) | IPAc (7 mL) | N/A |
| 5% water in ACN (1.0 mL) | MTBE (10) | I |
| 5% water in CAN (1.0 mL) | IPAc (6.0 mL) | Sticky solid after being filtered |
| 5% water in MeOH (1.0 mL) | Toluene (7.0 mL) | N/A |
| 5% water in MeOH (0.5 mL) | MTBE (2.5) | II (Stirred for 30 minutes and filtered under nitrogen) |
| 5% water in MeOH, 1.0 mL) | IPAc (10) | Amorphous solid |
| MeOH/water/ACN (6 v/0.5 v/1.0, 1.0 ml) | MTBE (12) | Sticky solid |
| MeOH/water/ACN (6 v/0.5 v/1.0, 1.0 mL) | IPAc (12) | Sticky solid |

N/A: Not available.
Ether clear solution or the amount of the precipitate was too small to be analyzed by XRPD.

TABLE 9

Reverse addition of Compound 1 di-HCl in various solvents

| Solvent (mL) | Anti-Solvent (mL) | Solid State Form |
|---|---|---|
| Chloroform (1.0) | MTBE (5) | Amorphous solid (filtered under nitrogen) |
| Chloroform (1.0) | IPAc (5.0) | Turbid solution |
| Methanol (1.0) | MTBE (5) | Amorphous solid (filtered under nitrogen) |
| Methanol (1.0) | IPAc (5.0) | Clear solution |
| 2-Methoxy-ethanol (1.0) | MTBE (5.0) | Sticky solid |
| 2-Methoxy-ethanol (1.0) | Toluene (5.0) | Turbid solution |
| 2-Methoxy-ethanol (0.4) | IPAc (5.0) | Oil |
| MeOH/water/ACN (6 V/1.5 V/3 V) (1.0) | IPAc (5.0) | Turbid solution |
| MeOH/water/ACN (6 V/1.5 V/3 V, 1.0) | MTBE (5.0) | Turbid solution |
| MeOH/water/ACN (5 V/2 V/3 V, 1.0 mL) | MTBE (5.0) | Turbid solution |
| MeOH/water/ACN (5 V/2 V/3 V, 1.0 mL) | IPAc (5.0) | Turbid solution |
| MeOH/water/ACN (6 V/1 V/4 V, 0.2 mL) | MTBE (5.0) | Sticky solid |
| MeOH/water/ACN (6 V/1 V/4 V, 0.2 mL) | IPAc (5.0) | Amorphous solid (filtered under nitrogen) |
| MeOH/water/ACN (6 V/0.5 V/3.5 V, 1.0 mL) | MTBE (5.0) | Amorphous solid (filtered under nitrogen) |
| MeOH/water/ACN (6 V/0.5 V/3.5 V, 1.0 mL) | IPAc (5.0) | II + Amorphous solid (filtered under nitrogen) |
| MeOH/ACN (10 V/3.0 V, 1.0 mL) | IPAc (5.0) | II (filtered under nitrogen) |
| MeOH/ACN (10 V/3.0 V, 1.0 mL) | MTBE (5.0) | II (filtered under nitrogen) |
| MeOH/ACN (10 V/3.0 V, 1.0 mL) | Toluene (5.0) | Turbid solution |
| ACN/water (9.0 V/1.0 V) (0.2 mL) | MTBE (5.0) | Amorphous solid (filtered under nitrogen) |
| ACN/water (9.0 V/1.0 V) (0.2 mL) | IPAc (5.0) | Amorphous solid (filtered under nitrogen) |
| 5% water in ACN (0.8 mL) | MTBE (5.0) | Turbid solution |
| 5% water in MeOH (1.2 mL) | Toluene (5.0) | Oil |
| 5% water in MeOH (0.4 mL) | MTBE (5.0) | Amorphous solid (filtered under nitrogen) |
| 5% water in MeOH (0.2 mL) | IPAc (5.0) | Amorphous solid (filtered under nitrogen) |
| ACN/water (4.0 V/1.0 V, 0.6 mL) | Toluene (5.0) | Sticky solid |
| ACN/water (4.0 V/1.0, 1.0 mL) | MTBE (5.0) | Sticky solid |
| MeOH/water/ACN (6 v/0.5 v/1.0 v, 1 mL) | IPAc (7.0) | Sticky solid |

N/A: Not available.
Ether clear solution or the amount of the precipitate was too small to be analyzed by XRPD.

Example 10

Reverse Addition

Saturated solution and nearly saturated solution of Compound 1 di-HCl were prepared in the solvents listed in Table 9, and added to a larger volume of a miscible anti-solvent. MTBE, toluene and IPAc were selected as the anti-solvents. Experiments that did not produce any particulate solids upon addition to the anti-solvent were not studied further, and all solids were filtered under nitrogen.

Example 11

Quenching of Saturated Solution

Saturated solution and nearly saturated solution of Compound 1 di-HCl Form I prepared at about 30° C. were quenched to about −20° C. to induce precipitation of higher energy forms. Representative solvents in Table 10 were chosen based on solubility data measured at 25° C. The quenching of the saturated and nearly saturated solution for all of solvents has not resulted in any solid.

TABLE 10

Result for Compound 1 di-HCl Form I from quenching

| Solvent | Result |
|---|---|
| MeCN | Clear solution |
| Methanol | Clear solution |
| MeOH/water/ACN (6v/1.5v/3v) | Clear solution |
| MeOH/water/ACN (5v/2v/3v) | Clear solution |
| MeOH/water/ACN (6v/1v/3v) | Clear solution |
| MeOH/water/ACN (6v/0.5v/3.5v) | Clear solution |
| MeOH/ACN (10v/3v) | Clear solution |
| ACN/water (9:1) | Clear solution |
| 5% water in ACN | Clear solution |
| 5% water in MeOH | Clear solution |
| ACN:water (4:1) | Clear solution |
| MeOH/water/ACN (6.0/0.5/1.0) | Clear solution |

Example 12

Crystallization of Saturated Solution with Heating and Cooling Cycles

This experiment was designed to search further for a more stable form than Form I and Form II. Saturated and nearly saturated solutions of Compound 1 di-HCl Form I were prepared at 50° C., and cooled in a bath slowly by using a programmed circulating bath. To the clear solution (about 5 mL) was added about 20-30 mg Compound 1 di-HCl Form I to give slurry. The formed slurry was then heated to 50° C. over 2 hours and then cooled down to 5° C. over 2 hours. This process was repeated for 3 days and the solid was filtered under nitrogen for further analysis. The results are presented in Table 11.

TABLE 11

Crystallization of saturated solution of Compound 1 di-HCl with heating and cooling recycles

| Solvent | Form |
|---|---|
| 2-methoxyethanol | I |
| Acetone | I |
| n-BuOH | I |
| ethanol | I |
| Ethyl formate | I |
| 1-propanol | I |
| 2- propanol | II |
| MEK | I |
| 5% water in ACN | II |

Example 13

Preparation and Characterization of Form III

To about 3.5 mL of cloudy solutions of Compound 1 di-HCl prepared in 1,4-dioxane was added about 15-20 mg of Compound 1 di-HCl followed by stirring at 25±1° C. for 2 days, which was filtered under nitrogen and analyzed by XRPD as Form III. The XRPD pattern of Form III is shown in FIG. 7 and the peak data is given below in Table 12.

TABLE 12

XRPD Peak Data for Form III

| 2-Theta | Height | I % |
|---|---|---|
| 5.4 | 2179.0 | 78.8 |
| 6.7 | 93.0 | 3.4 |
| 16.4 | 60.0 | 2.2 |
| 16.8 | 350.0 | 12.7 |
| 18.2 | 82.0 | 3.0 |
| 19.5 | 57.0 | 2.1 |
| 21.9 | 2765.0 | 100.0 |
| 22.2 | 538.0 | 19.5 |
| 23.3 | 56.0 | 2.0 |
| 27.4 | 153.0 | 5.5 |
| 27.7 | 234.0 | 8.5 |
| 28.6 | 369.0 | 13.3 |
| 33.1 | 138.0 | 5.0 |
| 36.8 | 31.0 | 1.1 |
| 39.0 | 232.0 | 8.4 |
| 39.6 | 67.0 | 2.4 |

Example 14

Preparation and Characterization of Form IV

To about 3.5 mL of cloudy solutions of drug substance prepared in toluene was added about 15-20 mg of Compound 1 di-HCl followed by stirring at 25±1° C. for 2 days, which was filtered under nitrogen and analyzed by XRPD as Form IV. The XRPD pattern of Form IV is shown in FIG. 8 and the peak data is given below in Table 13.

TABLE 13

XRPD Data for Form IV

| 2-Theta | Height | I % |
|---|---|---|
| 5.8 | 32.0 | 40.0 |
| 17.4 | 64.0 | 80.0 |
| 18.3 | 38.0 | 47.5 |
| 20.9 | 79.0 | 98.8 |
| 21.4 | 54.0 | 67.5 |
| 22.5 | 76.0 | 95.0 |
| 24.2 | 57.0 | 71.3 |
| 25.6 | 44.0 | 55.0 |
| 26.9 | 80.0 | 100.0 |
| 29.2 | 44.0 | 55.0 |
| 30.5 | 42.0 | 52.5 |
| 39.7 | 30.0 | 37.5 |

Example 15

Preparation and Characterization of Form V

To about 3.5 mL of cloudy solutions of Compound 1 di-HCl prepared in MTBE was added about 15-20 mg of drug substance followed by stirring at 25±1° C. for 2 days, which was filtered under nitrogen and analyzed by XRPD as Form V. The XRPD pattern of Form V is shown in FIG. 9 and the peak data is given below in Table 14.

TABLE 14

XRPD Data for Form V

| 2-Theta | Height | I % |
|---|---|---|
| 4.1 | 60.0 | 34.9 |
| 5.4 | 172.0 | 100.0 |

TABLE 14-continued

XRPD Data for Form V

| 2-Theta | Height | I % |
|---|---|---|
| 6.8 | 41.0 | 23.8 |
| 13.1 | 52.0 | 30.2 |
| 15.2 | 62.0 | 36.0 |
| 16.7 | 54.0 | 31.4 |
| 17.3 | 37.0 | 21.5 |
| 20.5 | 45.0 | 26.2 |
| 21.7 | 78.0 | 45.3 |
| 25.6 | 68.0 | 39.5 |
| 31.9 | 35.0 | 20.3 |

Form V exhibits a DSC thermogram having an exotherm peak at a temperature of about 198° C. FIG. 10 shows a DSC thermogram of Form V. FIG. 11 shows a TGA thermogram of Form V.

Example 16

Stability Relationship Between Forms II-V

The transformation of Compound 1 di-HCl solid forms was evaluated in competitive slurry experiments in methanol at 23-25° C. and 65-75% humidity. The experiments were performed with a mixture of four polymorphs (Form II through Form V), according to the following procedure.

10.0 mg of Compound 1 di-HCl Form II was added to a saturated solution of Compound 1 di-HCl Form II in methanol (1.0 mL) and stirred to give a thin slurry. A mixture of Form III (10.29 mg), Form IV (10.39 mg), and Form V (10.95 mg) were added to the slurry. The mixture was stirred for 4 h at 25° C.

A portion of the mixture was filtered after 4 h. The filtered solids were analyzed by XRPD and determined to be Form II in addition to a minor amount of amorphous solid.

A portion of the mixture was filtered after 20 h. The filtered solids were analyzed by XRPD and determined to be Form II in addition to a minor amount of amorphous solid. The sample was then dried under vacuum at 46-48° C. for 36 h. The dried solids were analyzed by XRPD and determined to be Form II.

Form II was the most stable form among the forms identified.

Example 17

Conversion of Compound 1 di-HCl to Compound 1 (Free Base)

50 mL of H$_2$O was added to Compound 1 di-HCl (6500 mg) and allowed to slurry for 10 min to give a clear solution. An aqueous solution of NaHCO$_3$ (75 mL; 8.7% solution in water; 5.5 equiv) was added to the solution and stirred to give a slurry. The mixture was allowed to stir for 20 min. The mixture was filtered and the solids were washed with deionized water (4×40 mL) until the pH was about 6-7. The solids were air dried for 4 days to provide Compound 1 as the free base in 92.5% yield (5.05 g).

The solid product was confirmed as a crystalline solid according to XRPD analysis. The XRPD pattern of Compound 1 (free base) is shown in FIG. 37 and the peak data is given below in Table 15.

TABLE 15

XRPD Peak Data for Compound 1 (free base)

| 2-Theta | Height | I % |
|---|---|---|
| 4.2 | 767 | 100 |
| 21.7 | 78 | 10.2 |

Compound 1 (free base) exhibits a DSC thermogram having an endotherm peak at a temperature of about 159° C. FIG. 38 shows a DSC thermogram of Compound 1 (free base). FIG. 39 shows a TGA thermogram of Compound 1 (free base).

Example 18

Preparation and Characterization of Compound 1 Di-Mesylate

Compound 1 (50.03 mg, 0.128 mmol) was dissolved in 1.0 mL dichloromethane and 0.8 mL of methanol to give a clear solution. Methanesulfonic acid (0.32 mL, 1 M in IPA, 0.32 mmol, 2.5 eq) was added to the solution. The mixture was stirred at room temperature for 4 h to gibe a slurry. Dichloromethane was removed using rotary evaporation to give a slurry. The slurry was allowed to stir for 2 h. The slurry was filtered, and the solids were dried at 40-45° C. under vacuum overnight to provide Compound 1 di-mesylate as a crystalline solid (63.5 mg, 84.98%).

The solid product was confirmed as a crystalline solid according to XRPD analysis. The XRPD pattern of compound 1 di-mesylate is shown in FIG. 12 and the peak data is given below in Table 16.

TABLE 16

XRPD Peak Data for compound 1 di-mesylate

| 2-Theta | Height | I % |
|---|---|---|
| 3.9 | 59.0 | 34.3 |
| 5.8 | 172.0 | 100.0 |
| 11.8 | 47.0 | 27.3 |
| 14.3 | 35.0 | 20.3 |
| 15.8 | 59.0 | 34.3 |
| 19.1 | 69.0 | 40.1 |
| 20.2 | 50.0 | 29.1 |
| 21.9 | 154.0 | 89.5 |
| 22.8 | 53.0 | 30.8 |
| 25.2 | 61.0 | 35.5 |
| 25.9 | 43.0 | 25.0 |

Compound 1 di-mesylate exhibits a DSC thermogram having an endotherm peak at a temperature of about 201° C. FIG. 13 shows a DSC thermogram of Compound 1 di-mesylate. FIG. 14 shows a TGA thermogram of Compound 1 di-mesylate.

Example 19

Preparation of Compound 1 di-HCl Form I from Compound 1 (Free Base)

MeOH (2.0 mL) was added to 100 mg of Compound 1. A solution of HCl (0.67 mL, 1.0 M in isopropyl alcohol, 2.6 eq). The solution was stirred at room temperature for 3 h. MTBE (4 mL) was added and the mixture was allowed to stir for 3 h. The mixture was filtered, and the cake was dried at 40-45° C. under vacuum overnight to provide Compound 1 di-HCl Form I (99.5 mg, 83.81%). Characterization data for Form I is provided in Example 4.

Example 20

Preparation and Characterization of Compound 1 Malonate

Dichloromethane (1.0 mL) and IPA (1.0 mL) were added to Compound 1 (50.07 mg, 0.131 mmol). Malonic acid (34.12 mg, 0.32 mmol, 2.5 eq) was added and the solution was allowed to stir at room temperature for 5 h. Dichloromethane was removed at 40° C. to give a slurry. The slurry was allowed to stir for 2 h. The slurry was filtered and washed with MTBE (2.0 mL). The solids were dried at 40-45° C. under vacuum overnight to provide Compound 1 malonate (54.0 mg) in 85.11% yield.

Figure 15:
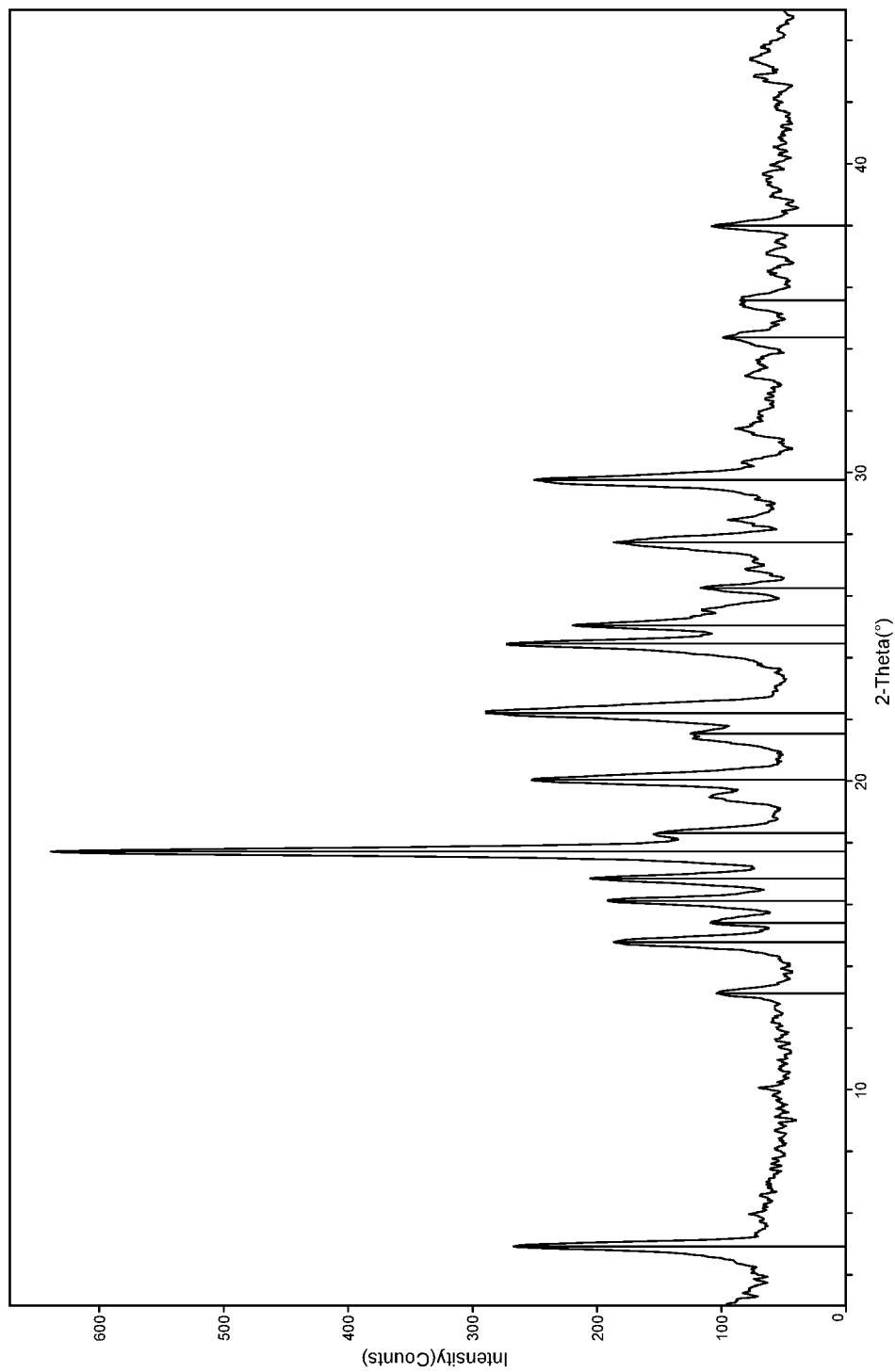
FIG. 15 shows an XRPD pattern of Compound 1 malonate.

The solid product was confirmed as a crystalline solid according to XRPD analysis. The XRPD pattern of Compound 1 malonate is shown in FIG. 15 and the peak data is given below in Table 17.

TABLE 17

XRPD Data for Compound 1 Malonate

| 2-Theta | Height | I % |
|---|---|---|
| 4.9 | 202.0 | 34.9 |
| 13.1 | 57.0 | 9.9 |
| 14.8 | 132.0 | 22.8 |
| 15.4 | 48.0 | 8.3 |
| 16.1 | 124.0 | 21.5 |
| 16.8 | 133.0 | 23.0 |
| 17.7 | 578.0 | 100.0 |
| 18.3 | 87.0 | 15.1 |
| 20.0 | 199.0 | 34.4 |
| 21.5 | 70.0 | 12.1 |
| 22.2 | 238.0 | 41.2 |
| 24.5 | 210.0 | 36.3 |
| 25.0 | 159.0 | 27.5 |
| 26.3 | 63.0 | 10.9 |
| 27.7 | 128.0 | 22.1 |
| 29.8 | 197.0 | 34.1 |
| 34.4 | 46.0 | 8.0 |
| 35.6 | 36.0 | 6.2 |
| 38.0 | 63.0 | 10.9 |

Compound 1 malonate exhibits a DSC thermogram having an endotherm peak at a temperature of about 147° C. FIG. 16 shows a DSC thermogram of Compound 1 malonate. FIG. 17 shows a TGA thermogram of Compound 1 malonate.

Example 21

Preparation and Characterization of Compound 1 Mono-HCl

Dichloromethane (1.8 mL) and IPA (1.8 mL) were added to 100 mg of Compound 1 (0.257 mmol). HCl (0.27 mL, 1 M in IPA, 0.27 mmol, 1.05 eq) was added to the solution. The solution was allowed to stir at room temperature for 2 h. Dichloromethane was removed at 40° C. to give a slurry. The slurry was stirred for 2 h, filtered, and washed with MTBE (2.0 mL). The solids were dried at 40-45° C. under vacuum overnight to provide Compound 1 mono-HCl (93.04 mg) in 85.07% yield.

The solid product was confirmed as a crystalline solid according to XRPD analysis. The XRPD pattern of Compound 1 mono-HCl is shown in FIG. 18 and the peak data is given below in Table 18.

TABLE 18

XRPD Data for Compound 1 mono-HCl

| 2-Theta | Height | I % |
|---|---|---|
| 10.3 | 305.0 | 49.1 |
| 11.4 | 100.0 | 16.1 |
| 12.1 | 93.0 | 15.0 |
| 12.8 | 251.0 | 40.4 |
| 14.2 | 122.0 | 19.6 |
| 15.6 | 570.0 | 91.8 |
| 16.4 | 621.0 | 100.0 |
| 16.9 | 56.0 | 9.0 |
| 18.4 | 152.0 | 24.5 |
| 19.3 | 397.0 | 63.9 |
| 21.5 | 574.0 | 92.4 |
| 22.8 | 331.0 | 53.3 |
| 23.5 | 202.0 | 32.5 |
| 24.2 | 259.0 | 41.7 |
| 25.3 | 200.0 | 32.2 |
| 25.7 | 438.0 | 70.5 |
| 27.2 | 274.0 | 44.1 |
| 28.1 | 80.0 | 12.9 |
| 29.6 | 113.0 | 18.2 |
| 30.8 | 129.0 | 20.8 |
| 31.9 | 154.0 | 24.8 |
| 32.4 | 134.0 | 21.6 |
| 33.0 | 74.0 | 11.9 |
| 34.5 | 80.0 | 12.9 |
| 36.4 | 143.0 | 23.0 |
| 37.2 | 79.0 | 12.7 |
| 39.7 | 47.0 | 7.6 |
| 40.6 | 90.0 | 14.5 |
| 41.5 | 33.0 | 5.3 |
| 43.9 | 63.0 | 10.1 |

Compound 1 mono-HCl exhibits a DSC thermogram having an exotherm peak at a temperature of about 178° C. and an endotherm peak at a temperature of about 204° C. FIG. 19 shows a DSC thermogram of Compound 1 mono-HCl. FIG. 20 shows a TGA thermogram of Compound 1 mono-HCl.

Example 22

Preparation and Characterization of Compound 1 Esylate

MeOH (0.5 mL) was added to Compound 1 (50.47 mg, 0.130 mmol). Ethanesulfonic acid (0.35 mL, 0.175 mmol, 1.35 eq, 0.5 M in IPA) was added and stirred for about 2 min to provide a clear solution. The solution was stirred for about 8 min to give a slurry. The slurry was then stirred for 3 h. The slurry was filtered, and the solids were dried at 40-45° C. under vacuum overnight to provide the Compound 1 esylate (52.0 mg) in 80.33% yield.

The solid product was confirmed as a crystalline solid according to XRPD analysis. The XRPD pattern of Compound 1 esylate is shown in FIG. 21 and the peak data is given below in Table 19.

TABLE 19

XRPD Data for Compound 1 Esylate.

| 2-Theta | Height | I % |
|---|---|---|
| 4.7 | 136.0 | 61.0 |
| 9.4 | 105.0 | 47.1 |
| 12.3 | 79.0 | 35.4 |
| 14.7 | 68.0 | 30.5 |
| 16.1 | 93.0 | 41.7 |
| 16.7 | 89.0 | 39.9 |
| 18.0 | 70.0 | 31.4 |

TABLE 19-continued

XRPD Data for Compound 1 Esylate.

| 2-Theta | Height | I % |
|---|---|---|
| 18.9 | 107.0 | 48.0 |
| 20.5 | 149.0 | 66.8 |
| 21.7 | 223.0 | 100.0 |
| 22.8 | 178.0 | 79.8 |
| 24.6 | 126.0 | 56.5 |
| 25.9 | 43.0 | 19.3 |
| 27.2 | 52.0 | 23.3 |
| 28.6 | 38.0 | 17.0 |
| 29.1 | 35.0 | 15.7 |
| 30.7 | 99.0 | 44.4 |
| 34.3 | 46.0 | 20.6 |
| 35.6 | 27.0 | 12.1 |
| 37.6 | 43.0 | 19.3 |
| 38.8 | 61.0 | 27.4 |
| 39.3 | 57.0 | 25.6 |
| 44.2 | 33.0 | 14.8 |

Compound 1 Esylate exhibits a DSC thermogram having an endotherm peak at a temperature of about 185° C. and an exotherm peak at a temperature of about 190° C. FIG. 22 shows a DSC thermogram of Compound 1 esylate. FIG. 23 shows a TGA thermogram of Compound 1 esylate.

Example 23

Preparation and Characterization of Compound 1 Maleate

MeOH (0.6 mL) was added to Compound 1 (51.05 mg, 0.133 mmol). Maleic acid (20.81 mg, 0.176 mmol, 1.34 eq, 98% purity) was added and stirred for two minutes to provide a clear solution. The solution was stirred at room temperature for 30 min. IPA (0.8 mL) was added and allowed to stir. Methanol was removed at 40-45° C. under vacuum unit the total volume was about 1.0-1.1 mL. The resulting cloudy solution was cooled to room temperature and IPA (0.6 mL) was added, resulting in a slurry. The slurry was stirred at 60° C. for 20 min, and then at room temperature for 3 h. The mixture was filtered, and the solids were dried at 40-45° C. under vacuum overnight to provide Compound 1 maleate (62.68 mg) in 94.59% yield.

Figure 24:
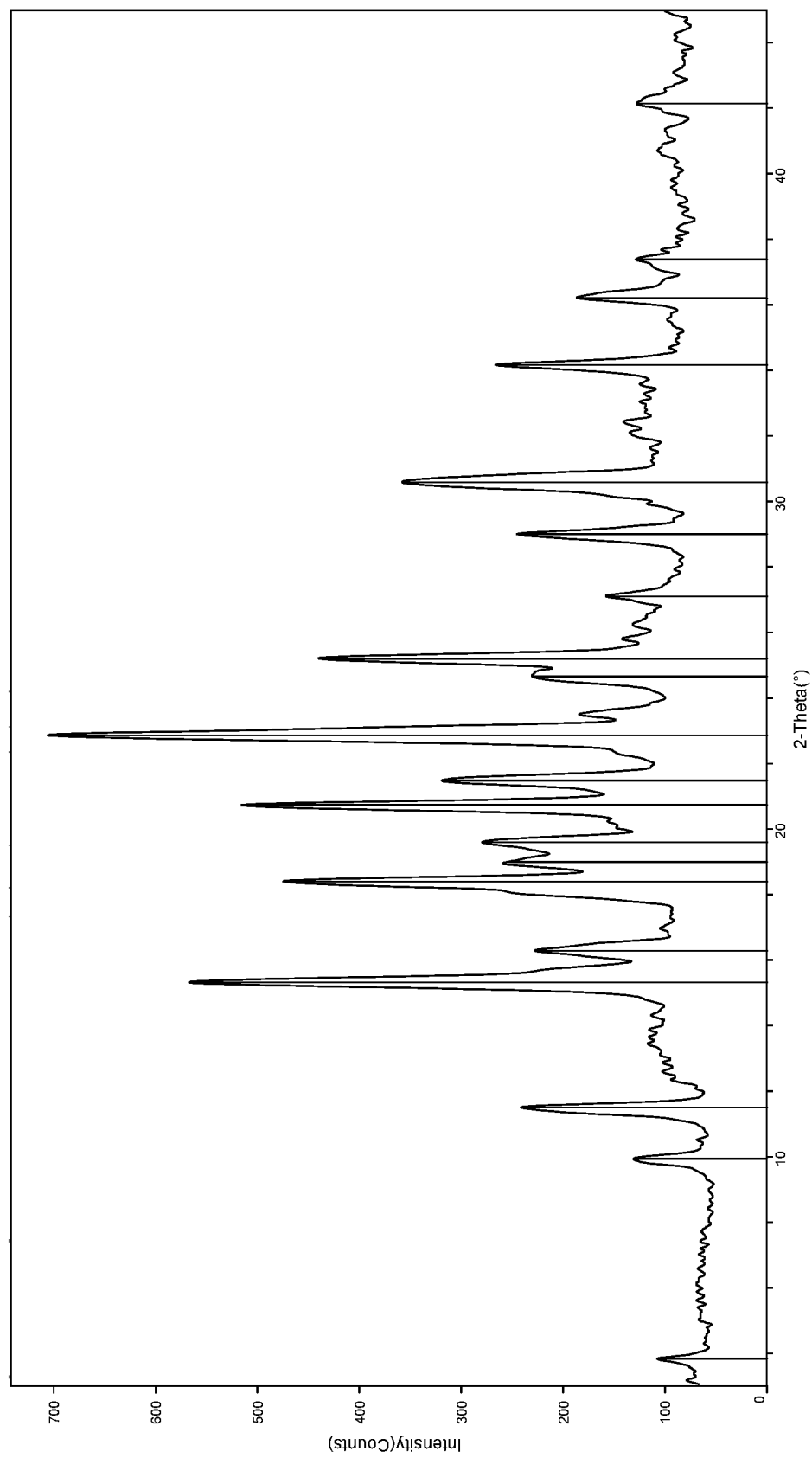
FIG. 24 shows an XRPD pattern of Compound 1 maleate.

The solid product was confirmed as a crystalline solid according to XRPD analysis. The XRPD pattern of Compound 1 maleate is shown in FIG. 24 and the peak data is given below in Table 20.

TABLE 20

XRPD Data for Compound 1 Maleate

| 2-Theta | Height | I % |
|---|---|---|
| 3.8 | 46.0 | 7.7 |
| 9.9 | 75.0 | 12.5 |
| 11.5 | 180.0 | 30.0 |
| 15.3 | 461.0 | 76.7 |
| 16.3 | 101.0 | 16.8 |
| 18.4 | 384.0 | 63.9 |
| 19.0 | 132.0 | 22.0 |
| 19.6 | 129.0 | 21.5 |
| 20.7 | 389.0 | 64.7 |
| 21.5 | 196.0 | 32.6 |
| 22.9 | 601.0 | 100.0 |
| 24.7 | 123.0 | 20.5 |
| 25.2 | 331.0 | 55.1 |
| 27.1 | 56.0 | 9.3 |
| 29.0 | 162.0 | 27.0 |
| 30.6 | 266.0 | 44.3 |

TABLE 20-continued

XRPD Data for Compound 1 Maleate

| 2-Theta | Height | I % |
|---|---|---|
| 34.2 | 167.0 | 27.8 |
| 36.2 | 100.0 | 16.6 |
| 37.4 | 44.0 | 7.3 |
| 42.1 | 49.0 | 8.2 |

Compound 1 maleate exhibits a DSC thermogram having an endotherm peak at a temperature of about 158° C. FIG. 25 shows a DSC thermogram of Compound 1 maleate. FIG. 26. shows a TGA thermogram of Compound 1 maleate.

Example 24

Preparation and Characterization of Compound 1 Camsylate (+)-(1S)-Camphorsulfonic acid (1.0 M in water, 0.14 mmol, 0.14 mL, 2.09 eq) was added dropwise to a solution of Compound 1 (26.10 mg, 0.067 mmol, 1.0 eq) in a mixture of dichloromethane (0.5 mL) and methanol (0.5 mL) to give Compound 1 camsylate.

The solid product was confirmed as a crystalline solid according to XRPD analysis. The XRPD pattern of Compound 1 camsylate is shown in FIG. 27 and the peak data is given below in Table 21.

TABLE 21

XRPD Data for Compound 1 Camsylate

| 2-Theta | Height | I % |
|---|---|---|
| 4.0 | 359.0 | 90.0 |
| 7.8 | 307.0 | 76.9 |
| 8.5 | 90.0 | 22.6 |
| 11.4 | 50.0 | 12.5 |
| 12.8 | 51.0 | 12.8 |
| 14.2 | 201.0 | 50.4 |
| 15.3 | 65.0 | 16.3 |
| 16.1 | 252.0 | 63.2 |
| 16.7 | 185.0 | 46.4 |
| 17.3 | 120.0 | 30.1 |
| 19.5 | 399.0 | 100.0 |
| 20.2 | 143.0 | 35.8 |
| 21.2 | 342.0 | 85.7 |
| 21.8 | 170.0 | 42.6 |
| 22.5 | 232.0 | 58.1 |
| 24.1 | 109.0 | 27.3 |
| 25.1 | 130.0 | 32.6 |
| 25.7 | 106.0 | 26.6 |
| 26.7 | 138.0 | 34.6 |
| 27.3 | 90.0 | 22.6 |
| 29.2 | 96.0 | 24.1 |
| 30.5 | 65.0 | 16.3 |
| 31.7 | 51.0 | 12.8 |
| 32.4 | 36.0 | 9.0 |
| 33.6 | 43.0 | 10.8 |
| 34.4 | 82.0 | 20.6 |
| 36.3 | 91.0 | 22.8 |
| 37.2 | 62.0 | 15.5 |
| 40.3 | 59.0 | 14.8 |
| 41.1 | 36.0 | 9.0 |
| 44.3 | 41.0 | 10.3 |

Compound 1 camsylate exhibits a DSC thermogram having an endotherm peak at a temperature of about 168° C. FIG. 28 shows a DSC thermogram of Compound 1 camsylate. FIG. 29 shows a TGA thermogram of Compound 1 camsylate.

Example 25

Preparation and Characterization of Compound 1 Isethionate

Isethionic acid (95% purity, 80% in water, 24.01 mg, 0.145 mmol, 2.16 eq) was added to a solution of Compound 1 (26.10 mg, 0.067 mmol, 1.0 eq) in a mixture of DCM (0.5 mL) and methanol (0.5 mL) and stirred to give Compound 1 isethionate.

Figure 30:
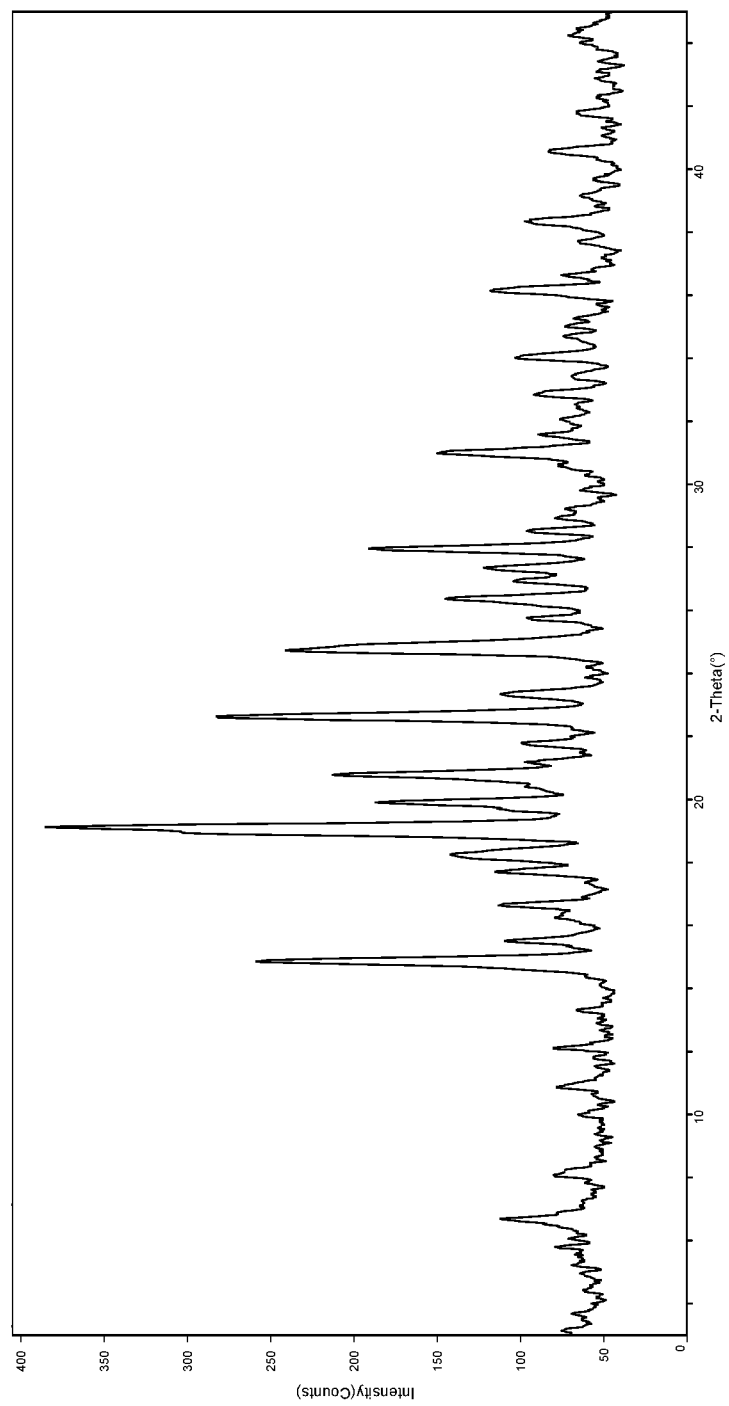
FIG. 30 shows an XRPD pattern of Compound 1 isethionate.

The solid product was confirmed as a crystalline solid according to XRPD analysis. The XRPD pattern of Compound 1 isethionate is shown in FIG. 30 and the peak data is given below in Table 22.

TABLE 22

XRPD Data for Compound 1 Isethionate

| 2-Theta | Height | I % |
|---|---|---|
| 6.7 | 55.0 | 17.5 |
| 14.9 | 210.0 | 66.9 |
| 15.5 | 53.0 | 16.9 |
| 16.7 | 58.0 | 18.5 |
| 17.7 | 57.0 | 18.2 |
| 18.2 | 77.0 | 24.5 |
| 19.1 | 314.0 | 100.0 |
| 19.9 | 110.0 | 35.0 |
| 20.8 | 143.0 | 45.5 |
| 21.8 | 39.0 | 12.4 |
| 22.6 | 226.0 | 72.0 |
| 23.3 | 58.0 | 18.5 |
| 24.8 | 175.0 | 55.7 |
| 25.8 | 40.0 | 12.7 |
| 26.4 | 86.0 | 27.4 |
| 27.4 | 61.0 | 19.4 |
| 28.0 | 131.0 | 41.7 |
| 31.0 | 97.0 | 30.9 |
| 32.9 | 29.0 | 9.2 |
| 34.1 | 49.0 | 15.6 |
| 36.1 | 71.0 | 22.6 |
| 38.4 | 52.0 | 16.6 |
| 40.6 | 41.0 | 13.1 |

Compound 1 isethionate exhibits a DSC thermogram having an endotherm peak at a temperature of about 169° C. and an exotherm peak at a temperature of about 212° C. FIG. 31 shows a DSC thermogram of Compound 1 isethionate. FIG. 32 shows a TGA thermogram of Compound 1 isethionate.

Example 26

Preparation and Characterization of Compound 1 1,2-Ethanedisulfonate 1,2-ethanedisulfonic acid (0.5 M in IPA, 0.14 mmol, 0.28 mL, 2.09 eq) was added to a solution of Compound 1 (26.10 mg, 0.067 mmol, 1.0 eq) in the mixture of DCM (0.5 mL) and methanol (0.5 mL) and stirred to give Compound 1 1,2-ethanedisulfonate as a solid.

The solid product was confirmed as a crystalline solid according to XRPD analysis. The XRPD pattern of Compound 1 1,2-ethanedisulfonate is shown in FIG. 33 and the peak data is given below in Table 23.

TABLE 23

XRPD Data for Compound 1 1,2-ethanedisulfonate

| 2-Theta | Height | I % |
|---|---|---|
| 7.9 | 286.0 | 42.8 |
| 10.5 | 255.0 | 38.1 |
| 11.9 | 33.0 | 4.9 |
| 12.9 | 120.0 | 17.9 |
| 15.7 | 107.0 | 16.0 |
| 16.8 | 42.0 | 6.3 |
| 17.6 | 72.0 | 10.8 |
| 18.4 | 566.0 | 84.6 |
| 19.4 | 47.0 | 7.0 |
| 20.3 | 152.0 | 22.7 |
| 21.0 | 235.0 | 35.1 |
| 21.9 | 104.0 | 15.5 |
| 22.9 | 78.0 | 11.7 |
| 23.7 | 669.0 | 100.0 |
| 25.0 | 204.0 | 30.5 |
| 25.8 | 140.0 | 20.9 |
| 27.1 | 44.0 | 6.6 |
| 29.0 | 43.0 | 6.4 |
| 29.7 | 34.0 | 5.1 |
| 32.4 | 43.0 | 6.4 |
| 35.6 | 77.0 | 11.5 |

Compound 1 1,2-ethanedisulfonate exhibits a DSC thermogram having an endotherm peak at a temperature of about 190° C. and an exotherm peak at a temperature of about 221° C. FIG. 34 shows a DSC thermogram of Compound 1 1,2-ethanedisulfonate.

Example 27

Preparation and Characterization of Compound 1 Mono-Mesylate

Methanesulfonic acid (1.0 M in IPA, 0.14 mmol, 0.14 mL, 2.09 eq) was added to a solution of Compound 1 (26.10 mg, 0.067 mmol, 1.0 eq) in the mixture of DCM (0.5 mL) and methanol (0.5 mL) and stirred to give Compound 1 mono-mesylate.

The solid product was confirmed as a crystalline solid according to XRPD analysis. The XRPD pattern of Compound 1 mono-mesylate is shown in FIG. 35 and the peak data is given below in Table 24.

TABLE 24

XRPD Data for Compound 1 Mono-Mesylate

| 2-Theta | Height | I % |
|---|---|---|
| 4.7 | 195.0 | 35.1 |
| 9.5 | 146.0 | 26.3 |
| 12.4 | 151.0 | 27.2 |
| 14.5 | 289.0 | 52.0 |
| 15.9 | 226.0 | 40.6 |
| 16.6 | 287.0 | 51.6 |
| 17.8 | 93.0 | 16.7 |
| 18.6 | 220.0 | 39.6 |
| 19.2 | 151.0 | 27.2 |
| 20.8 | 461.0 | 82.9 |
| 21.8 | 556.0 | 100.0 |
| 22.6 | 444.0 | 79.9 |
| 24.6 | 304.0 | 54.7 |
| 25.1 | 100.0 | 18.0 |
| 27.9 | 59.0 | 10.6 |
| 29.0 | 103.0 | 18.5 |
| 31.0 | 95.0 | 17.1 |
| 32.3 | 40.0 | 7.2 |
| 34.2 | 67.0 | 12.1 |
| 35.6 | 47.0 | 8.5 |

TABLE 24-continued

| XRPD Data for Compound 1 Mono-Mesylate | | |
|---|---|---|
| 2-Theta | Height | I % |
| 38.0 | 51.0 | 9.2 |
| 39.9 | 102.0 | 18.3 |

Compound 1 mono-mesylate exhibits a DSC thermogram having an endotherm peak at a temperature of about 187° C. FIG. 36 shows a DSC thermogram of Compound 1 mono-mesylate.

Example 28

Preparation of Compound 1 Sulfate

Sulfuric acid (1.0 M in IPA, fresh prepared, 0.14 mmol, 0.14 mL, 2.09 eq) was added dropwise to Compound 1 (26.10 mg, 0.067 mmol, 1.0 eq) in the mixture of DCM (0.5 mL) and methanol (0.5 mL) and stirred to give Compound 1 sulfate as an amorphous solid.

Example A

LSD1 Histone Demethylase Biochemical Assay

LANCE LSD1/KDM1A demethylase assay-10 µL of 1 nM LSD-1 enzyme (ENZO BML-SE544-0050) in the assay buffer (50 mM Tris, pH 7.5, 0.01% Tween-20, 25 mM NaCl, 5 mM DTT) were preincubated for 1 hour at 25° C. with 0.8 µL compound/DMSO dotted in black 384 well polystyrene plates. Reactions were started by addition of 10 µL of assay buffer containing 0.4 µM Biotin-labeled Histone H3 peptide substrate: ART-K(Me1)-QTARKSTGGKAPRKQLA-GGK (Biotin) SEQ ID NO:1 (AnaSpec 64355) and incubated for 1 hour at 25° C. Reactions were stopped by addition of 10 µL 1× LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). Compounds having an $IC_{50}$ of 1 µM or less were considered active.

Compound 1 has an $IC_{50}$ that is ≤100 nM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt which is a hydrochloric acid salt of a compound having the structure:

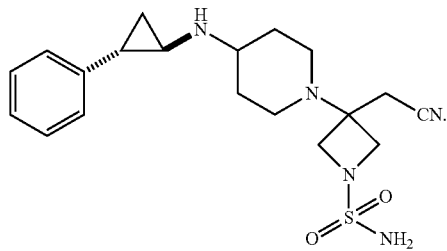

2. The salt of claim 1, wherein the salt is a solid form.

3. The salt of claim 1, wherein the salt is crystalline.

4. The salt of claim 1, wherein the hydrochloric acid salt is a mono-hydrochloric acid salt.

5. The salt of claim 1, wherein the hydrochloric acid salt is a di-hydrochloric acid salt.

6. The salt of claim 5, wherein the di-hydrochloric acid salt is a solid form, which is Form I.

7. The salt of claim 6, wherein Form I has an X-ray diffraction pattern comprising at least one characteristic peak in degrees 2θ selected from about 5.9°, about 7.1°, and about 9.9°.

8. The salt of claim 6, wherein Form I has an X-ray diffraction pattern comprising at least four characteristic peaks in degrees 2θ selected from about 5.9°, about 7.1°, about 9.9°, about 13.2°, about 15.1°, and about 18.2°.

9. The salt of claim 6, wherein Form I has an XRPD pattern with characteristic peaks substantially shown in FIG. 1.

10. The salt of claim 6, having a DSC thermogram characterized by endotherm peaks at temperatures of about 80° C. and about 175° C.

11. The salt of claim 6, having a DSC thermogram substantially as shown in FIG. 2.

12. The salt of claim 6, having a TGA thermogram substantially as shown in FIG. 3.

13. The salt of claim 5, wherein the di-hydrochloric acid salt is a solid form, which is Form II.

14. The salt of claim 13, wherein Form II has an X-ray diffraction pattern comprising at least one characteristic peak in degrees 2θ selected from about 5.8°, about 13.2°, and about 15.1°.

15. The salt of claim 13, wherein Form II has an X-ray diffraction pattern comprising at least four characteristic peaks in degrees 2θ selected from about 5.8°, about 13.2°, about 15.1°, about 17.1°, about 20.1° and about 20.8°.

16. The salt of claim 13, wherein Form II has an XRPD pattern with characteristic peaks substantially shown in FIG. 4.

17. The salt of claim 13, having a DSC thermogram having an exotherm peak at a temperature of about 198° C.

18. The salt of claim 13, having a DSC thermogram substantially as shown in FIG. 5.

19. The salt of claim 13, having a TGA thermogram substantially as shown in FIG. 6.

20. The salt of claim 5, wherein the di-hydrochloric acid salt is a solid form, which is Form III.

21. The salt of claim 20, wherein Form III has an X-ray diffraction pattern comprising at least four characteristic peaks in degrees 2θ selected from about 5.4°, about 16.8°, about 21.9°, about 27.7°, and about 28.6°.

22. The salt of claim 5, wherein the di-hydrochloric acid salt is a solid form, which is Form IV.

23. The salt of claim 22, wherein Form IV has an X-ray diffraction pattern comprising at least four characteristic peaks in degrees 2θ selected from about 5.8°, about 17.4°, about 18.3°, about 20.9°, about 22.5°, and about 26.9°.

24. The salt of claim 5, wherein the di-hydrochloric acid salt is a solid form, which is Form V.

25. The salt of claim 24, wherein Form V has an X-ray diffraction pattern comprising at least four characteristic peaks in degrees 2θ selected from about 5.4°, about 6.8°, about 13.1°, about 15.2, and about 21.7°.

26. The salt of claim 4, wherein the mono-hydrochloric acid salt is crystalline.

27. The salt of claim 26, wherein the mono-hydrochloric acid salt has an X-ray diffraction pattern comprising at least four characteristic peaks in degrees 2θ selected from about 10.3°, about 12.8°, about 15.6°, about 16.4°, about 21.5°, and about 25.7°.

28. A salt selected from:

3-(cyanomethyl)-3-(4-{[(1R,2 S)-2-phenylcyclopropyl]amino}piperidin-1-yl)azetidine-1-sulfonamide mono-methanesulfonic acid salt;

3-(cyanomethyl)-3-(4-{[(1R,2 S)-2-phenylcyclopropyl]amino}piperidin-1-yl)azetidine-1-sulfonamide di-methanesulfonic acid salt;

3-(cyanomethyl)-3-(4-{[(1R,2 S)-2-phenylcyclopropyl]amino}piperidin-1-yl)azetidine-1-sulfonamide mono-malonic acid salt;

3-(cyanomethyl)-3-(4-{[(1R,2 S)-2-phenylcyclopropyl]amino}piperidin-1-yl)azetidine-1-sulfonamide mono-ethanesulfonic acid salt;

3-(cyanomethyl)-3-(4-{[(1R,2 S)-2-phenylcyclopropyl]amino}piperidin-1-yl)azetidine-1-sulfonamide mono-maleic acid salt;

3-(cyanomethyl)-3-(4-{[(1R,2 S)-2-phenylcyclopropyl]amino}piperidin-1-yl)azetidine-1-sulfonamide mono-camphorsulfonic acid salt;

3-(cyanomethyl)-3-(4-{[(1R,2 S)-2-phenylcyclopropyl]amino}piperidin-1-yl)azetidine-1-sulfonamide mono-isethionic acid salt;

3-(cyanomethyl)-3-(4-{[(1R,2 S)-2-phenylcyclopropyl]amino}piperidin-1-yl)azetidine-1-sulfonamide mono-1,2-ethanedisulfonic acid salt; and 3-(cyanomethyl)-3-(4-{[(1R,2 S)-2-phenylcyclopropyl]amino}piperidin-1-yl)azetidine-1-sulfonamide sulfuric acid salt, or a hydrate or solvate thereof.

29. A pharmaceutical composition comprising a salt of claim 1, and a pharmaceutically acceptable carrier or excipient.

30. A pharmaceutical composition comprising a salt of claim 28 or a hydrate or solvate thereof, and a pharmaceutically acceptable carrier or excipient.

31. A solid oral dosage form comprising the pharmaceutical composition of claim 29.

32. A solid oral dosage form comprising the pharmaceutical composition of claim 31.

33. A method of inhibiting LSD1, said method comprising: contacting LSD1 with a salt of claim 1.

34. A method of inhibiting LSD1, said method comprising: contacting LSD1 with a salt of claim 28 or a hydrate or solvate thereof.

* * * * *

UNITED STATES PATENT AND TRADEMARK OFFICE
CERTIFICATE OF CORRECTION

PATENT NO. : 10,968,200 B2
APPLICATION NO. : 16/555907
DATED : April 6, 2021
INVENTOR(S) : Jia et al.

Page 1 of 2

It is certified that error appears in the above-identified patent and that said Letters Patent is hereby corrected as shown below:

In the Claims

Column 96, Line 63, Claim 25, delete "15.2," and insert -- 15.2°, --.

Column 97, Lines 5-7, Claim 28, delete "3-(cyanomethyl)-3-(4-{[(1R,2 S)-2-phenylcyclopropyl]amino}piperidin-1-yl)azetidine-1-sulfonamide mono-methanesulfonic acid salt" and insert -- 3-(cyanomethyl)-3-(4-{[(1R,2S)-2-phenylcyclopropyl]amino}piperidin-1-yl)azetidine-1-sulfonamide mono-methanesulfonic acid salt --;

Column 97, Lines 8-10, Claim 28, "3-(cyanomethyl)-3-(4-{[(1R,2 S)-2-phenylcyclopropyl]amino}piperidin-1-yl)azetidine-1-sulfonamide di-methanesulfonic acid salt" and insert -- 3-(cyanomethyl)-3-(4-{[(1R,2S)-2-phenylcyclopropyl]amino}piperidin-1-yl)azetidine-1-sulfonamide di-methanesulfonic acid salt --;

Column 97, Lines 11-13, Claim 28, delete "3-(cyanomethyl)-3-(4-{[(1R,2 S)-2-phenylcyclopropyl]amino}piperidin-1-yl)azetidine-1-sulfonamide mono-malonic acid salt" and insert -- 3-(cyanomethyl)-3-(4-{[(1R,2S)-2-phenylcyclopropyl]amino}piperidin-1-yl)azetidine-1-sulfonamide mono-malonic acid salt --;

Column 97, Lines 14-16, Claim 28, delete "3-(cyanomethyl)-3-(4-{[(1R,2 S)-2-phenylcyclopropyl]amino}piperidin-1-yl)azetidine-1-sulfonamide mono-ethanesulfonic acid salt" and insert -- 3-(cyanomethyl)-3-(4-{[(1R,2S)-2-phenylcyclopropyl]amino}piperidin-1-yl)azetidine-1-sulfonamide mono-ethanesulfonic acid salt --;

Column 97, Lines 17-19, Claim 28, delete "3-(cyanomethyl)-3-(4-{[(1R,2 S)-2-phenylcyclopropyl]amino}piperidin-1-yl)azetidine-1-sulfonamide mono-maleic acid salt" and insert -- 3-(cyanomethyl)-3-(4-{[(1R,2S)-2-phenylcyclopropyl]amino}piperidin-1-yl)azetidine-1-sulfonamide mono-maleic acid salt --;

Column 97, Lines 20-22, Claim 28, delete "3-(cyanomethyl)-3-(4-{[(1R,2 S)-2-phenylcyclopropyl]

Signed and Sealed this
Tenth Day of May, 2022

Katherine Kelly Vidal
*Director of the United States Patent and Trademark Office*

CERTIFICATE OF CORRECTION (continued)
U.S. Pat. No. 10,968,200 B2 amino}piperidin-1-yl)azetidine-1-sulfonamide mono-camphorsulfonic acid salt" and insert -- 3-(cyanomethyl)-3-(4-{[(1R,2S)-2-phenylcyclopropyl]amino}piperidin-1-yl)azetidine-1-sulfonamide mono-camphorsulfonic acid salt --;

Column 97, Lines 23-25, Claim 28, delete "3-(cyanomethyl)-3-(4-{[(1R,2 S)-2-phenylcyclopropyl]amino}piperidin-1-yl)azetidine-1-sulfonamide mono-isethionic acid salt" and insert -- 3-(cyanomethyl)-3-(4-{[(1R,2S)-2-phenylcyclopropyl]amino}piperidin-1-yl)azetidine-1-sulfonamide mono-isethionic acid salt --;

Column 98, Lines 1-3, Claim 28, delete "3-(cyanomethyl)-3-(4-{[(1R,2 S)-2-phenylcyclopropyl]amino}piperidin-1-yl)azetidine-1-sulfonamide mono-1,2-ethanedisulfonic acid salt" and insert -- 3-(cyanomethyl)-3-(4-{[(1R,2S)-2-phenylcyclopropyl]amino}piperidin-1-yl)azetidine-1-sulfonamide mono-1,2-ethanedisulfonic acid salt --;

Column 98, Lines 4-6, Claim 28, delete "3-(cyanomethyl)-3-(4-{[(1R,2 S)-2-phenylcyclopropyl]amino}piperidin-1-yl)azetidine-1-sulfonamide sulfuric acid salt" and insert -- 3-(cyanomethyl)-3-(4-{[(1R,2S)-2-phenylcyclopropyl]amino}piperidin-1-yl)azetidine-1-sulfonamide sulfuric acid salt --.

Column 98, Line 17, Claim 32, delete "31." and insert -- 30. --.